(12) United States Patent
Nadler et al.

(10) Patent No.: US 9,765,150 B2
(45) Date of Patent: *Sep. 19, 2017

(54) ANTIBODY POLYPEPTIDES THAT ANTAGONIZE CD40L

(71) Applicants: Bristol-Myers Squibb Company, Princeton, NJ (US); Domantis Limited, Brentford, Middlesex (GB)

(72) Inventors: Steven G. Nadler, Princeton, NJ (US); James K. Tamura, Yardley, PA (US); Laura Price, Langhorne, PA (US); Robert P. Rehfuss, North Wales, PA (US); Suzanne J. Suchard, Wilmington, DE (US); Anish Suri, Yardley, PA (US); James William Bryson, Langhorne, PA (US); Aaron Yamniuk, Lawrenceville, NJ (US); Steven Grant, Swaffham Prior (GB); Olga Ignatovich, Cambridge (GB); Philip Drew, Histon (GB)

(73) Assignees: Bristol-Myers Squibb Company, Princeton, NJ (US); Domantis Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/950,949

(22) Filed: Nov. 24, 2015

(65) Prior Publication Data
US 2016/0075790 A1    Mar. 17, 2016

Related U.S. Application Data

(63) Continuation of application No. 14/510,474, filed on Oct. 9, 2014, now Pat. No. 9,228,018, which is a continuation of application No. 13/650,493, filed on Oct. 12, 2012, now Pat. No. 8,895,010.

(60) Provisional application No. 61/546,800, filed on Oct. 13, 2011, provisional application No. 61/655,110, filed on Jun. 4, 2012.

(51) Int. Cl.
| A61K 39/395 | (2006.01) |
| C07K 16/28 | (2006.01) |
| A61K 45/06 | (2006.01) |
| C07K 16/46 | (2006.01) |
| C07K 16/18 | (2006.01) |
| A61K 39/00 | (2006.01) |
| A61K 38/00 | (2006.01) |

(52) U.S. Cl.
CPC ...... *C07K 16/2878* (2013.01); *A61K 39/3955* (2013.01); *A61K 45/06* (2013.01); *C07K 16/18* (2013.01); *C07K 16/283* (2013.01); *C07K 16/2833* (2013.01); *C07K 16/2875* (2013.01); *C07K 16/2896* (2013.01); *C07K 16/46* (2013.01); *C07K 16/468* (2013.01); *A61K 38/00* (2013.01); *A61K 2039/505* (2013.01); *A61K 2039/545* (2013.01); *C07K 2317/21* (2013.01); *C07K 2317/31* (2013.01); *C07K 2317/34* (2013.01); *C07K 2317/52* (2013.01); *C07K 2317/565* (2013.01); *C07K 2317/567* (2013.01); *C07K 2317/569* (2013.01); *C07K 2317/71* (2013.01); *C07K 2317/76* (2013.01); *C07K 2317/92* (2013.01); *C07K 2317/94* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| 5,876,950 | A | 3/1999 | Siadak et al. |
| 6,001,358 | A | 12/1999 | Black et al. |
| 7,094,874 | B2 | 8/2006 | Peach et al. |
| 7,482,327 | B2 | 1/2009 | Hagerty et al. |
| 8,895,010 | B2 | 11/2014 | Nadler et al. |
| 9,228,018 | B2 * | 1/2016 | Nadler ............... A61K 39/3955 |
| 2010/0166774 | A1 | 7/2010 | Dali et al. |

FOREIGN PATENT DOCUMENTS

| CL | 19900284 | 9/1999 |
| CL | 200100584 | 12/2001 |
| CL | 200700768 | 11/2007 |
| CL | 2007001335 | 1/2008 |

(Continued)

OTHER PUBLICATIONS

GenBank Accession No. CAJ90635.1 (2006).
Aruffo, et al., "The CD40 Ligand, gp39, Is Defective in Activated T Cells from Patients with X-Linked Hyper-Igm Syndorme," *Cell* (1993) 72:291-300.
Ashokkumar, et al., "Allospecific CD154+ T Cells Associate with Rejection Risk After Pediatric Liver Transplantation," *Amer. J. Transplantation* (2009) 9: 179-191.

(Continued)

*Primary Examiner* — Phillip Gambel
(74) *Attorney, Agent, or Firm* — Drinker Biddle & Reath LLP

(57) ABSTRACT

Antibody polypeptides that specifically bind human CD40L are provided. The antibody polypeptides do not activate platelets. The antibody polypeptides are useful in the treatment of diseases involving CD40L activation, such as graft-related diseases and autoimmune diseases. The antibody polypeptides may be domain antibodies (dAbs) comprising a single $V_H$ or $V_K$ domain. The half-life of the antibody polypeptides may be increased by modifying the antibody polypeptides to be dual specific reagents that can also bind human serum albumin (HSA) or another antigen.

37 Claims, 26 Drawing Sheets
(20 of 26 Drawing Sheet(s) Filed in Color)

(56) References Cited

FOREIGN PATENT DOCUMENTS

| | | |
|---|---|---|
| CL | 201202737 | 2/2013 |
| CL | 201303043 | 6/2014 |
| CL | 201301124 | 7/2014 |
| TW | 200911825 A | 3/2009 |
| WO | WO-9942075 A2 | 8/1999 |
| WO | WO-0168860 A1 | 9/2001 |
| WO | WO-2005003175 A2 | 1/2005 |
| WO | WO-2005035572 A2 | 4/2005 |
| WO | WO-2006030220 A1 | 3/2006 |
| WO | WO-2007129895 A2 | 11/2007 |
| WO | WO-2008118356 A2 | 10/2008 |
| WO | WO-2010023482 A2 | 3/2010 |
| WO | WO-2011123489 A2 | 10/2011 |
| WO | WO-2012065950 A1 | 5/2012 |
| WO | WO-2012115241 A1 | 8/2012 |
| WO | WO-2012145673 A1 | 10/2012 |
| WO | WO-2013118858 A1 | 8/2013 |

OTHER PUBLICATIONS

Ashokkumar, et al., Allospecific CD154+ T cells identify rejection-prone recipients after pediatric small-bowel transplantation, *Surgery* (2009) 146: 166-173.

Bartlett, et al., "Analysis of Intragraft Gene and Protein Expression of Costimulatory Molecules, CD80, CD86 and CD154, and Orthotopic Liver Transplant Recipients," *Amer. J. Transplantation* (2003) 3: 1363-1368.

Baumgart, et al., "Exaggerated inflammatory response of primary human myeloid dendritic cells to lipopolysaccharide in patients with inflammatory bowel disease," *Clinical and Experimental Immunology* (2009) 157: 423-436.

Biaconne, et al., "Expression of inducible lymphocyte costimulatory molecues in human renal allograft," *Nephrol. Diall. Translpant.* (1998) 13: 716-722.

Boumpas, et al., "A Short Course of BG9588 (Anti-CD40 Ligand Antibody) Improves Serologic Activity and Decreases Hematuria in Patients With Proliferative Lupus Glomerulonephritis," *Arthritis & Rheumatism* (2003), 48: 719-727.

Danese, et al., "Activated platelets are the source of elevated levels of soluble CD40 ligand and the circulation of inflammatory bowel disease patients," *Gut* (2003) 52: 1435-1441.

Grammer, et al., "Abnormal germinal center reactions in systemic lupus erythematosus demonstrated by blockade of CD154-CD40 interactions *J. Clin. Invest.* (2003) 112: 1506-1520.

Kasran, et al., "Safety and tolerability of antagonist anti-human CD40 Mab ch5D12 in patients with moderate to severe Crohn's disease," *Aliment. Pharmacol. Ther.* (2005) 22: 111-122.

Kawai, et al., "CD154 Blockade for Induction of Mixed Chimerism and Prolonged Renal Allograft Survival in Nonhuman Primates," *Amer. J. Transplantation* (2004) 4: 1391-1398.

Kenyon, et al., "Long-term survival and function of intrahepatic islet allografts in rhesus monkeys treated with humanized anti-CD154," *Proc. Natl. Acad. Sci. USA* (1999) 96: 8132-8137.

Kimura, et al., "Study of Plasma Levels of Soluble CD40 Ligand in Systemic Lupus Erythematosus Patients Who Have Undergone Plasmapheresis," *Therapeutic Apheriss and Dialysis* (2005) 9: 64-68.

Kirk, et al., "CTLA4-Ig and anti-CD40 ligand prevent renal allograft rejection in primates," *Proc. Natl. Acad. Sci. USA* (1997) 94: 8789-8794.

Komura, et al., "Elevated Circulating CD40 Concentrations in Patients with Systemic Sclerosis," *J. Reumatol.* (2004) 31: 514-519.

Ludwiczek, et al., "Plasma levels of soluble CD40 ligand are elevated in inflammatory bowel diseases," *Int. J. Colorectal Dis.* (2003) 18: 142-147.

Mach, et al., "Reduction of Atherosclerosis in mice by inhibition of CD40 signalling," *Nature* (1998) 394: 200-203.

Menchén, et al., "Matrix metalloproteinase 9 is involved in Crohn's disease associated platelet hyperactivation through th release of soluble CD40 ligand," *Gut* 58: (2009) 920-928.

Mirabet, et al., Platelet pro-aggregatory effects of CD40 monoclonal antibody, *Mol. Immunol.* (2008) 45: 937-44.

Montgomery, et al., "Combination Induction Thereapy With Monoclonal Antibodies Specific for CE80, CD86, and CD154 in Nonhuman Primate Renal Transplantation," *Transplantation* (2002) 74: 1365-1369.

Orozco, et al., "Association of CD40 with rheumatoid arthritis confirmed in a large UK case-control study," *Ann. Rheum. Dis.* (2010) 69: 813-816.

Patel, et al., "The effect of anti-CD40 ligand in immune thrombocytopenic purpura," *British J. Haematology* (2008) 141: 545-548.

Prahalad, et al., "Elevated serum levels of soluble CF154 in children with juvenile idiopathic arthritis," *Pediatric Rheumatology* (2008) 6: 1-8.

Preston, et al., "IDEC-131 (Anti-CD154), Sirolimus and Donor Specific Transfusion Facilitate Operational Tolerance in Non-Human Primates," *Amer. J. Transplantation* (2005) 5: 1032-1041.

Raychaudhuri, et al., "Common variants at CD40 and other loci confer risk of rheumatoid arthritis", *Nature Genetics* (2008) 40: 1216-1223.

Robles-Carrillo, et al., "Anti-CD40L Immune Complexes Potently Activate Platelets In Vitro and Cause Thrombosis in FCGRA2A Transgenic Mice," *The Journal of Immunology* (2010) 185: 1577-1583.

Schönbeck, et al., "Inhibition of CD40 signaling limits evolution of established atherosclerosis in mice," *Proc. Natl. Acad. Sci.* (2000) 97: 7458-7463.

Schuler, et al., "Efficacy and Safety of AB1793,A Novel Human Anti-Human CD154 Monoclonal Antibody, in Cynomolgus Monkey Renal Allotransplantation," *Transplantation* (2004) 77: 717-726.

Vakkalanka, et al., "Elevated Levels and Functional Capacity of Soluble CD40 Ligand in Systemi Lupus Erythematosus Sera,", *Arthritis & Rheumatism* (1999) 42: 871-881.

Xu, et al., "Effects of Dose and Duration of Anti-CD154 Antibody Therapy in Preventing Renal Allograft Rejection in a Nonhuman Primate Model," *Transplantation Proceedings* (2001) 33: 223-224.

Adams, et al., "Development of a Chimeric Anti-CD40 Monoclonal Antibody That Synergizes with LEA29Y to Prolong Islet Allograft Survival" (2005) J. Immunol. 174: 542-550.

Daoussis, et al., "Increased expression of CD154 (CD40L) on stimulated T-cells from patients with psoriatic arthritis", *Rheumatology* (2007) 46: 227-231.

Chapman, et al., "PEGylated antibodies and antibody fragments for improved therapy: a review," *Adv. Drug Deliv. Rev.* (2002) 54(4):531-545.

de Kruif, et al., "Rapid selection of cell subpopulation-specific human monoclonal antibodies from a synthetic phage antibody library", *Proc. Natl. Acad. Sci. USA* (1995) 92: 3938-3942.

Duffau, et al., "Platelet CD154 Potentiates Interferon-α Secretion by Plasmacytoid Dendritic Cells in Systemic Lupus Erythematosus", *Sci. Transl. Med.* (2010) 2: 47: 1-10 (2010).

Durie, et al., "Antibody to the Ligand of CD40, GP39, Blocks the Occurrence of the Acute and Chronic Forms of Graft-vs-Host Disease", *J. Clin. Invest.* (1994) 94: 1333-1338.

Ferroni, et al., "Contribution of Platelet-Derived CD40 Ligand to Inflammation, Thrombosis and Neoangiogenesis", *Curr. Med. Chem.* (2007) 14: 2170-2180.

Garcia, et al., "Monocytic suppressive cells mediate cardiovascular transplantation tolerance in mice", *J. Clin. Inv.* (2010) 120: 2486-2496.

Gilson, et al., "Anti-CD40 Monoclonal Antibody Synergizes with CTLA4-Ig in Promoting Long-Term Graft Survival in Murine Models of Transplantation", *J. Immunol.* (2009) 183: 1625-1635.

Harrison, et al., "Screening of Phage Antibody Libraries", *Meth. Enzymol.* (1996) 267: 83-109.

Hoogenboom, et al., "Multi-subunit proteins on the surface of filamentous phage: methodologies for displaying antibody (Fab) heavy and light chains", *Nucleic Acids Res.* (1991) 19:4133-4137.

Huang, et al., "The Effect of Anti-CD40 Ligand Antibody on B Cells in Human Systemic Lupus Erythematosus", *Arthritis & Reumatism* (2002) 46: 1554-1562.

(56) References Cited

OTHER PUBLICATIONS

Im, et al., "Blockade of CD40 Ligand Suppresses Chronic Experimental Myasthenia Gravis by Down-Regulation of Th1 Differentiation and Up-Regulation of CTLA-4", *J. Immunol.* (2001) 166: 6893-6898.

Kanmaz, et al., "Monotherapy With the Novel Human Anti-CD-154 Monoclonal Antibody ABI793 in Rhesus Monkey Renal Transplantation Model", *Transplantation* (2004) 77: 914-920.

Koyama, et al., "Thrombophilia Associated With Anti-CD154 Monoclonal Antibody Treatment and its Prophylaxis in Nonhuman Primates", Transplantation (2004) 77: 460-461.

Kuwana, et al., "T and B Cell Collaboration Is Essential for the Autoantibody Response to DNA Topoisomerase I in Systemic Sclerosis", *J. Immunol.* (1995) 155: 2703-2714.

Larsen, et al., "Rational Development of LEA29Y (belatacept), a High-Affinity Variant of CTLA4-Ig with Potent Immunosuppressive Properties", *Amer. J. Transplant.* (2005) 5: 443-453.

Lederer, et al., "Reduced CD40L Expression on ex vivo Activated CD4+ T-Lymphocytes from Patients with Excellent Renal Allograft Function Measured with a Rapid Whole Blood Flow Cytometry Procedure", *Int. Arch. Allergy Immunol.* (2004) 133: 276-284.

Marks, et al., "Human Antibody Fragments Specific for Human Blood Group Antigens from a Phage Display Library", *BioTechnology* (1993) 11: 1145-1149.

Oosterwegel, et al., "CTLA-4 and T cell activation", *Curr. Opin. Immunol.* (1999) 11: 294-300.

Reilly, et al., "Genetic Diversity in Human Fc Receptor II for Immunoglobulin G: Fcγ Receptor IIA Ligand-Binding Polymorphism", *Clin. Diagn. Lab. Immunol.* (1994) 1: 640-644.

Shi, et al., "Differential requirements for CD28 and CD40 ligand in the induction of experimental autoimmune myasthenia gravis", *Eur. J. Immunol.* (1998) 28: 3587-3593.

Tomiyama, et al., "Response of Human Platelets to Activating Monoclonal Antibodies: Importance of FcγRII (CD32) Phenotype and Level of Expression", *Blood* (1992) 80: 2261-2268.

Daley et al., "Fc-Disabled Anti-Mouse CD40L Antibodies Retain Efficacy in Promoting Transplantation Tolerance," American Journal of Transplantation, Nov. 1, 2008, vol. 8, No. 11, pp. 2265-2271.

Ge et al., "Functional expression of chimeric Fab of an anti-CD40L mAb: Vector design an culture condition optimization", Biomedicine & Pharmacotherapy, Sep. 17, 2010, vol. 65, No. 1, pp. 52-59.

Holt, et al., "Domain antibodies: proteins for therapy", Trends in Biotechnology, Nov. 1, 2003, vol. 21, No. 11, pp. 484-490.

Suri, et al., Investigative Studies Demonstrate Reduced Risk for Thromboembolism (TE) by BMS-986004, an Anti-CD40L Domain antibody, Session 71: Novel Approaches to Treatment & Monitoring of Allograft Injury, Jun. 6, 2012, Publication Page No. 518, XP002690660, Abstract.

International Search Report dated Mar. 12, 2013, issued in PCT Application No. PCT/US2012/059977 filed Oct. 12, 2012.

International Preliminary Report on Patentability and Written Opinion of the International Search Authority mailed Apr. 24, 2014 in PCT Application No. PCT/US2012/059977.

Borcherding et al., The CD40-CD40L pathway contributes to the proinflammatory function of intestinal epithelial cells in inflammatory bowel disease. Am J Pathol. (2010) 176(4):1816-27. {doi: 10.2353/ajpath.2010.090461. Epub Feb. 4, 2010.}.

Rudikoff et al., "Single amino acid substitution altering antigen-binding specificity," PNAS Immunology, vol. 79, pp. 1979-1983, Mar. 1982.

* cited by examiner

Domain antibody-[AS]-THTCPPCP...

CT-long

Domain antibody-[AST]-EPKSSDKTHTSPPSP ...

CT-short

Domain antibody-[AS]-THTSPPSP...

N297Qlong Fc

Domain antibody-[AST]-EPKSSDKTHTSPPSP...

N297Qshort Fc

Domain antibody-[AS]-THTSPPSP...

Osteonectin signal peptide sequence:

MRAWIFFLLCLAGRALA ^ EVQLLES...(start of Domain antibody)

FIG. 4

BMS2h-572-633-CT-L2

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSS\[AST\]EPKSSDKTHTSPPSPAPELLGGSSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

BMS2h-572-633-CT-S1

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSS\[AS\]THTSPPSPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

BMS2h-572-633-N297Q long Fc

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSS\[AST\]EPKSSDKTHTCPPCPAPELLGGPSVFLFPPKPKDTLMISRTPEVTCVVVDVSH
EDPEVKFNWYVDGVEVHNAKTKPREEQYQSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

BMS2h-572-633-N297Q short Fc

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSS\[AS\]THTCPPCPAPELLGGPSVFLFPPKPKDTLMISRTPEVTCVVVDVSHEDPEVKFN
WYVDGVEVHNAKTKPREEQYQSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

FIG. 14
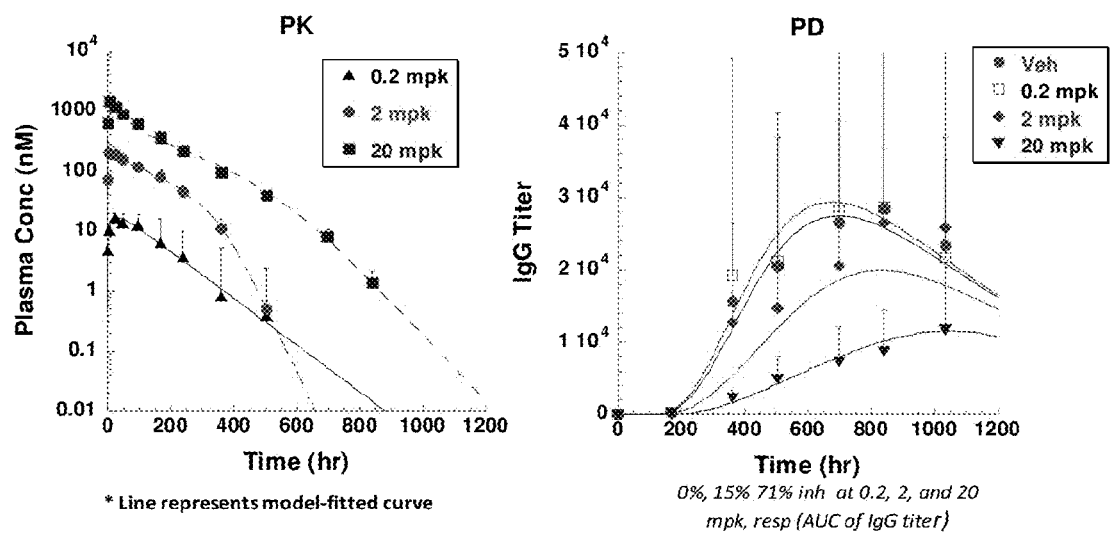
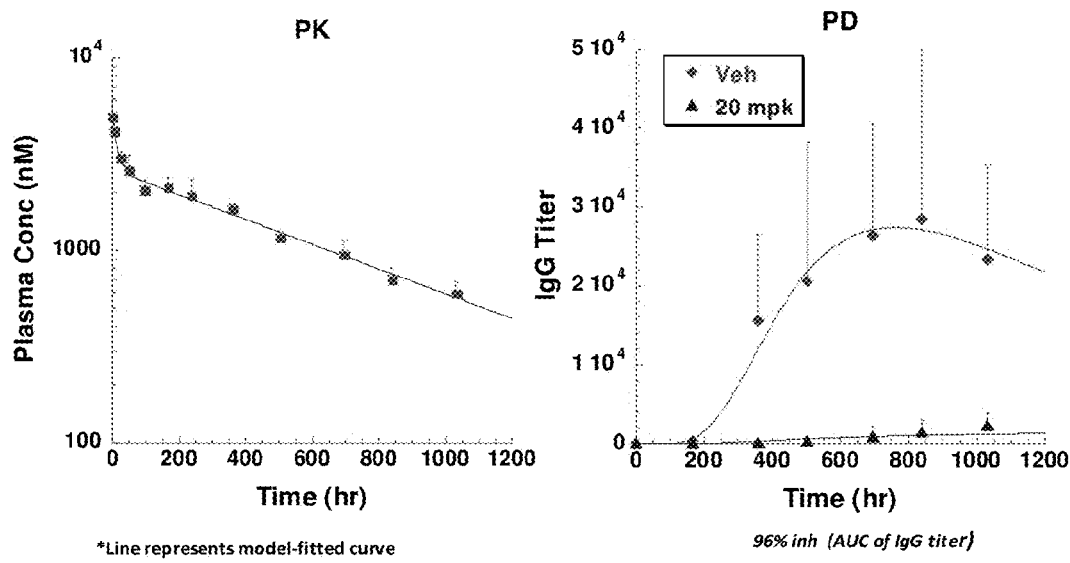

FIG. 21

|  | CDR1 | CDR2 |  |
|---|---|---|---|
| BMS2h-572-6   | EVQLLESGGGLVQPGGSLRLSCAASGFTFNWQLMGWVRQAPGKGLEWVSGIEGPGDVTYY | 60 |
| BMS2h-572-608 | EVQLLESGGGLVQPGGSLRLSCAASGFTFNWELMGWARQAPGKGLEWVSGIEGPGDVTYY | 60 |
| BMS2h-572-614 | EVQLLESGGGLVQPGGSLRLSCAASGFTFNWQLMGWVRQAPGKGLEWVSGIEGPGDVTYY | 60 |
| BMS2h-572-619 | EVQLLESGGGLVQPGGSLRLSCAASGFTFNWQLMGWVRQAPGKGLEWVSGIEGPGDVTYY | 60 |
| BMS2h-572-633 | EVQLLESGGGLVQPGGSLRLSCAASGFTFNWELMGWARQAPGKGLEWVSGIEGPGDVTYY | 60 |
| BMS2h-572-634 | EVQLLESGGGLVQPGGSLRLSCAASGFTFNWELMGWARQAPGKGLEWVSGIEGPGDVTYY | 60 |
| BMS2h-572-635 | EVQLLESGGGLVQPGGSLRLSCAASGFTFNWELMGWARQAPGKGLEWVSGIEGPGDVTYY | 60 |
|               | ************************************************************ |

CDR2                                                         CDR3

| BMS2h-572-6   | ADSVKGRFTISRDNSKNTLYLQMNSLRAEDTAVYYCVKVGKESNSDYRGQGTLVTVSS | 118 |
| BMS2h-572-608 | ADSVKGRFTISRDNSKNTLYLQMNSLRAEDTAVYYCVKVGKESNSDYRGQGTLVTVSS | 118 |
| BMS2h-572-614 | ADSVKGRFTISRDNSKNTLYLQMNSLRAEDTAVYYCVKVGKDAKSDYRGQGTLVTVSS | 118 |
| BMS2h-572-619 | ADSVKGRFTISRDNSKNTLYLQMNSLRAEDTAVYYCVKVGKDSRSDYRGQGTLVTVSS | 118 |
| BMS2h-572-633 | ADSVKGRFTISRDNSKNTLYLQMNSLRAEDTAVYYCVKVGKDAKSDYRGQGTLVTVSS | 118 |
| BMS2h-572-634 | ADSVKGRFTISRDNSKNTLYLQMNSLRAEDTAVYYCVKVGKDSRSDYRGQGTLVTVSS | 118 |
| BMS2h-572-635 | ADSVKGRFTISRDNSKNTLYLQMNSLRAEDTAVYYCVKVGKDSKSDYRGQGTLVTVSS | 118 |
|               | ********************************************************** |

FIG. 22

```
                              CDR1                                           CDR2
BMS2h-719-2    EVQLLESGGGLVQPGGSLRLSCAASGFTFKRYEMMWVRQAPGKGLEWVSSISSDGSFTYY 60
BMS2h-719-202  EVQLLESGGGLVQPGGSLRLSCAASGFTFKRYEMMWVRQAPGKGLEWVSSISSDGSFTYY 60
BMS2h-719-203  EVQLLESGGGLVQPGGSLRLSCAASGFTFNSYEMMWVRQAPGKGLEWVSSISSDGSFTYY 60
BMS2h-719-213  EVQLLESGGGLVQPGGSLRLSCAASGFTFKRYEMMWVRQAPGKGLEWVSSISSDGSFTYY 60
BMS2h-719-214  EVQLLESGGGLVQPGGSLRLSCAASGFTFKRYEMMWVRQAPGKGLEWVSSISSDGSFTYY 60
BMS2h-719-215  EVQLLESGGGLVQPGGSLRLSCAASGFTFKRYEMMWVRQAPGKGLEWVSSISSDGSFTYY 60
BMS2h-719-218  EVQLLESGGGLVQPGGSLRLSCAASGFTFKRYEMMWVRQAPGKGLEWVSSISSDGSFTYY 60
BMS2h-719-225  EVQLLESGGGLVQPGGSLRLSCAASGFTFNTYEMQWVRQAPGKGLEWVSSISSDGSFTYY 60
               *************************** ***  ***************************

CDR2                                       CDR3
BMS2h-719-2    ADSVKGRFTISRDNSKNTLYLQMNSLRAEDTAVYYCAEPFTEFDYWGHGTLVTVSS 116
BMS2h-719-202  ADSVKGRFTISRDNSKNTLYLQMNSLRAEDTAVYYCAEPFTEFDYWGHGTLVTVSS 116
BMS2h-719-203  ADSVKGRFTISRDNSKNTLYLQMNSLRAEDTAVYYCAEPFTEFDYWGHGTLVTVSS 116
BMS2h-719-213  ADSVKGRFTISRDNSKNTLYLQMNSLRAEDTAVYYCADPFTEMDYWGHGTLVTVSS 116
BMS2h-719-214  ADSVKGRFTISRDNSKNTLYLQMNSLRAEDTAVYYCADPFTEFDYWGHGTLVTVSS 116
BMS2h-719-215  ADSVKGRFTISRDNSKNTLYLQMNSLRAEDTAVYYCAEPFTELDYWGHGTLVTVSS 116
BMS2h-719-218  AESVKGRFTISRDNSKNTLYLQMNSLRAEDTAVYYCAEPFTEFDYWGHGTLVTVSS 116
BMS2h-719-225  ADSVKGRFTISRDNSKNTLYLQMNSLRAEDTAVYYCAEPFTEFDYWGHGTLVTVSS 116
               * ***************************** ***** **  ***************
```

FIG. 23

```
BMS2h-503-1    DIQMTQSPSSLSASVGDRVTITCRASHHIQRYLSWYQQKPGKAPKLLIIWGSQLQSGVPS 60
BMS2h-503-2    DIQMTQSPSSLSASVGDRVTITCRASHDIQRYLSWYQQKPGKAPKLLIIWGSQLQSGVPS 60
               *************************** *******************************

BMS2h-503-1    RFSGSGSGTDFTLTISSLQPEDFATYYCGQWAPPQTFGQGTKVEIKR 108
BMS2h-503-2    RFSGSGSGTDFTLTISSLQPEDFATYYCGQWAPPQTFGQGTKVEIKR 108
               ***********************************************
```

FIG. 24

```
BMS2h-116-1312    DIQMTQSPSSLSASVGDRVTITCRASQPIGPDLLWYQQKPGKAPKLLIYQTSILRSGVPS  60
BMS2h-116-1313    DIQMTQSPSSLSASVGDRVTITCRASQPIGPDLLWYQQKPGKAPKLLIYQTSILRSGVPS  60
BMS2h-116-1320    DIQMTQSPSSLSAYVGDRVTITCRASQPIGPDLLWYQQKPGKAPKLLIYQTSILRSGVPS  60
                  ************ ***********************************************

BMS2h-116-1312    RFSGSGSETDFTLTISNLQPEDLATYYCQQYWAFPVTFGKGTKVVIKR  108
BMS2h-116-1313    RFSGSGSETDFTLTISNLQPEDFATYYCQQYWAFPVTFGRGTKVVIKR  108
BMS2h-116-1320    RFSGSGSETDFTLTISNLQPEDFAKYYCQQYWAFPVTFGQGTKVVIKR  108
                  ********************** * ************** *******
```

ANTIBODY POLYPEPTIDES THAT ANTAGONIZE CD40L

REFERENCE TO RELATED APPLICATIONS

This application is a continuation of U.S. application Ser. No. 14/510,474, filed Oct. 9, 2014, now U.S. Pat. No. 9,228,018, issued Jan. 5, 2016, which is a continuation of U.S. application Ser. No. 13/650,493, filed Oct. 12, 2012, now U.S. Pat. No. 8,895,010, issued Nov. 25, 2015, which claims the benefit of U.S. Provisional Application No. 61/546,800, filed Oct. 13, 2011, and U.S. Provisional Application No. 61/655,110, filed Jun. 4, 2012, which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 23, 2015, is named 200896-0005-03-US_ST25.txt and is 1,222,204 bytes in size.

TECHNICAL FIELD

Antibodies and fragments thereof that target CD40L, compositions comprising the same, and methods of using the same for treatment of diseases involving CD40L activity are provided.

BACKGROUND

CD40 ligand (CD40L), also known as CD154, gp39, TNF-related activation protein (TRAP), 5c8 antigen, or T-BAM, is a trimeric transmembrane protein of the tumor necrosis factor (TNF) superfamily of molecules. CD40L is primarily expressed on activated T cells, as well as on activated leukocytes, eosinophils, basophils, natural killer cells, mast cells, and non-immune cells such as platelets and activated endothelial cells. CD40L also exists in soluble form (sCD40L) that is produced by microsomal stimulus-dependent cleavage of the membrane-bound CD40L. Most of sCD40L in circulation (>90%) is platelet-derived.

CD40L binds CD40, a type I transmembrane glycoprotein belonging to the TNF receptor (TNFR) family. Although all monomeric, dimeric, and trimeric forms of sCD40L can bind to CD40, the trimeric form of sCD40L has the most potent biological activity through oligomerization of cell surface CD40, a common feature of TNFR family. The highest expression of CD40 has been observed on antigen presenting cells (APCs), such as B cells, macrophages, and dendritic cells, while lower expression of this receptor is noted on a variety of other cell types, including stromal cells and thymic epithelium. The CD40-CD40L interaction is essential for normal T-B cell interactions, including increased co-stimulation, T-cell priming, cytokine production, antibody-class switching and affinity maturation, and antibody and autoantibody production.

The crucial role of CD40-CD40L interactions in immune and inflammatory responses has made them a promising target for treatment of pathological immuno-inflammatory processes. Blockade of CD40-CD40L interactions by means of specific CD40L monoclonal antibodies (mAbs) successfully prevents allograft rejection in primates and treats autoimmune diseases and atherosclerosis in animal models. Montgomery et al., *Transplantation* 74: 1365-1369 (2002).

In humans, two different anti-CD40L mAb clones have been used in clinical trials for treatment of different autoimmune diseases. Maribel et al., *Mol. Immunol.* 45: 937-44 (2008). Monoclonal antibodies, however, can display unusually high incidence of thromboembolic (TE) complications, such as atherothrombotic central nervous system events, myocardial infarction, pulmonary embolism, and deep vein thrombosis. For example, the usefulness of the anti-CD40L mAb clone hu5c8 (anti-CD40L mAb, Biogen) is limited by an unusually high incidence of TE complications. TE by these antibodies is thought to result from the formation of higher-order immune complexes (IC) of the mAbs with membrane-bound CD40L on platelets, or sCD40L shed from platelets, that can ligate and thereby aggregate neighboring platelets via their FcgRIIa receptors, resulting in thrombi formation. The risk of thromboembolism has led to a halt in all ongoing clinical trials. Boumpas et al., *Arthritis & Rheumatism* 48: 719-727 (2003).

SUMMARY

Anti-CD40L antibody antagonists that are less likely to cause platelet aggregation and thus cause thromboembolism are still needed in a clinical setting. Novel antibody polypeptides that specifically bind human CD40L are provided. The antibody polypeptides advantageously do not cause platelet aggregation. The antibody polypeptides are useful in the treatment of diseases involving CD40L activation, including autoimmune diseases, transplant rejection, and allergic responses. The antibody polypeptides comprise a variable domain. Exemplary antibody polypeptides are in the form of a domain antibody (dAb) that contains a single variable domain. Alternatively, the dAbs can be bi-specific reagents that comprise a second variable domain that can bind another antigen, such as human serum albumin (HSA), for example.

An antibody polypeptide is provided comprising a first variable domain that specifically binds human CD40L, wherein the first variable domain comprises the amino acid sequence of one of the variable domains selected from the BMS2h lineage. Further provided is an isolated antibody polypeptide comprising a first variable domain that specifically binds human CD40L, wherein CD40L comprises the amino acid sequence of SEQ ID NO: 1, wherein the amino acid sequence of the first variable domain comprises: (a) a CDR1 region which differs from the CDR1 region of BMS2h-572-633 by up to three amino acids, (b) a CDR2 region which differs from the CDR2 region of BMS2h-572-633 by up to three amino acids, (c) a CDR3 region which differs from the CDR3 region of BMS2h-572-633 by up to three amino acids, (d) a FR1 region which differs from the FR1 region of BMS2h-572-633 by up to three amino acids, (e) a FR2 region which differs from the FR2 region of BMS2h-572-633 by up to three amino acids, (f) a FR3 region which differs from the FR3 region of BMS2h-572-633 by up to three amino acids, and (g) a FR4 region which differs from the FR4 region of BMS2h-572-633 by up to three amino acids; and wherein the antibody polypeptide inhibits binding of CD40L to CD40 with an EC50 of 100 pM to 100 nM. Also provided is an antibody polypeptide, wherein the amino acid sequence of the first variable domain comprises: (a) a CDR1 region which differs from the CDR1 region of BMS2h-572-633 by up to three amino acids, (b) a CDR2 region which differs from the CDR2 region of BMS2h-572-633 by up to three amino acids, and (c) a CDR3 region which differs from the CDR3 region of BMS2h-572-633 by up to three amino acids. Alternatively, the amino acid sequence of the first variable domain can differ from the amino acid sequence of BMS2h-572-633 by up to and including 10 amino acids. Furthermore, the amino acid sequence of the first variable domain can differ from the amino acid sequence of BMS2h-572-633 by up to and including 5 amino acids. The amino acid sequence of the first variable domain can also differ from the amino acid sequence of BMS2h-572-633 by up to and including 2 amino acids. Alternatively, the first variable domain differs from the amino acid sequence of BMS2h-572-633 by 1 amino acid.

Also provided is an antibody polypeptide selected from the lineage group of BMS2h-572, wherein the amino acid sequence of the first variable domain further comprises: (a) a CDR1 region having a sequence Trp-$X_1$-Leu-Met-Gly (SEQ ID NO: 2), wherein $X_1$ is Glu or Gln; (b) a CDR2 region having a sequence Gly-Ile-Glu-Gly-Pro-Gly-Asp-Val-Thr-Tyr-Tyr-Ala-Asp-Ser-Val-Lys-Gly (SEQ ID NO: 3); and (c) a CDR3 region having a sequence Lys-$X_2$-$Y_2$-$Z_2$-Ser-Asp-Tyr (SEQ ID NO: 4), wherein $X_2$ is Asp or Glu, $Y_2$ is Ala or Ser, and $Z_2$ is Lys, Asn, or Arg. Also provided is the antibody polypeptide, wherein the amino acid sequence of the first variable domain further comprises: (a) a FR1 region having a sequence Glu-Val-Gln-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-Asn (SEQ ID NO: 5); (b) a FR2 region having a sequence Trp-$X_1$-Arg-Gln-Ala-Pro-Gly-Lys-Gly-Leu-Glu-Trp-Val-Ser (SEQ ID NO: 6), wherein $X_1$ is Ala or Val; (c) a FR3 region having a sequence Arg-Thr-Phe-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Val-Lys-Val-Gly (SEQ ID NO: 7); and (d) a FR4 region having a sequence Arg-Gly-Gln-Gly-Thr-Leu-Val-Thr-Val-Ser-Ser (SEQ ID NO: 8). Alternatively, the first variable domain of the antibody polypeptide can comprise the amino acid sequence of BMS2h-572-633.

Also provided is an antibody polypeptide selected from the lineage group of BMS2h-719, comprising a first variable domain with the following consensus sequence: Glu-Val-Gln-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-$X_1$-$Y_1$-Tyr-Glu-Met-$Z_1$-Trp-Val-Arg-Gln-Ala-Pro-Gly-Lys-Gly-Leu-Glu-Trp-Val-Ser-Ser-Ile-Ser-Ser-Asp-Gly-Ser-Phe-Thr-Tyr-Tyr-Ala-$A_1$-Ser-Val-Lys-Gly-Arg-Phe-Thr-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Ala-$B_1$-Pro-Phe-Thr-Glu-$C_1$-Asp-Tyr-Trp-Gly-His-Gly-Thr-Leu-Val-Thr-Val-Ser-Ser (SEQ ID NO: 9), wherein $X_1$ is Lys or Asn; $Y_1$ is Arg, Lys, Ser, or Thr; $Z_1$ is Met or Gln; $A_1$ is Asp or Glu; $B_1$ is Asp or Glu; and $C_1$ is Phe, Met, or Leu.

Also provided is an antibody polypeptide selected from the lineage group of BMS2h-503, comprising a first variable domain with the following consensus sequence: Asp-Ile-Gln-Met-Thr-Gln-Ser-Pro-Ser-Ser-Leu-Ser-Ala-Ser-Val-Gly-Asp-Arg-Val-Thr-Ile-Thr-Cys-Arg-Ala-Ser-His-$X_1$-Ile-Gln-Arg-Tyr-Leu-Ser-Trp-Tyr-Gln-Gln-Lys-Pro-Gly-Lys-Ala-Pro-Lys-Leu-Leu-Ile-Leu-Trp-Gly-Ser-Gln-Leu-Gln-Ser-Gly-Val-Pro-Ser-Arg-Phe-Ser-Gly-Ser-Gly-Ser-Gly-Thr-Asp-Phe-Thr-Leu-Thr-Ile-Ser-Ser-Leu-Gln-Pro-Glu-Asp- Phe-Ala-Thr-Tyr-Tyr-Cys-Gly-Gln-Trp-Trp-Ala-Pro-Pro-Gln-Thr-Phe-Gly-Gln-Gly-Thr-Lys-Val-Glu-Ile-Lys-Arg (SEQ ID NO: 10), wherein $X_1$ is His or Asp.

Also provided is an antibody polypeptide selected from the lineage group of BMS2h-116, comprising a first variable domain with the following consensus sequence: Asp-Ile-Gln-Met-Thr-Gln-Ser-Pro-Ser-Ser-Leu-Ser-Ala-$X_1$-Val-Gly-Asp-Arg-Val-Thr-Ile-Thr-Cys-Arg-Ala-Ser-Gln-Pro-Ile-Gly-Pro-Asp-Leu-Leu-Trp-Tyr-Gln-Gln-Lys-Pro-Gly-Lys-Ala-Pro-Lys-Leu-Leu-Ile-Tyr-Gln-Thr-Ser-Ile-Leu-Arg-Ser-Gly-Val-Pro-Ser-Arg-Phe-Ser-Gly-Ser-Gly-Ser-Glu- Thr-Asp-Phe-Thr-Leu-Thr-Ile-Ser-Asn-Leu-Gln-Pro-Glu-Asp-$Y_1$-Ala-$Z_1$-Tyr-Tyr-Cys-Gln-Gln-Tyr-Trp-Ala-Phe-Pro-Val-Thr-Phe-Gly-$A_1$-Gly-Thr-Lys-Val-Val-Ile-Lys-Arg (SEQ ID NO: 11), wherein $X_1$ is Ser or Tyr; $Y_1$ is Leu or Phe; $Z_1$ is Thr or Lys; and $A_1$ is Lys, Arg, or Gln.

Also provided is an antibody polypeptide comprising a first variable domain that specifically binds human CD40L, wherein the antibody polypeptide is a domain antibody (dAb). The antibody polypeptide can be a fusion polypeptide comprising the first variable domain and an Fc domain. Alternatively, the fusion polypeptide can comprise an IgG4 Fc domain. The fusion polypeptide also can comprise an IgG1 Fc domain. The fusion polypeptide can also comprise an IgG1 Fc domain. Alternatively, the fusion polypeptide can comprise a CT-Long domain. The fusion polypeptide can also comprise a CT-short domain. Alternatively, the fusion polypeptide can comprise a N297Q Long Fc domain. The fusion polypeptide can alternatively comprise a N297Q Short Fc domain.

Also provided is an antibody polypeptide comprising a first variable domain that specifically binds human CD40L, wherein the antibody polypeptide further comprises a second variable domain that specifically binds a second antigen, wherein the second antigen is an antigen other than human CD40L. The second antigen can be a cluster of differentiation (CD) molecule or a Major Histocompatibility Complex (MHC) Class II molecule. Alternatively, the second antigen can be serum albumin (SA).

Also provided is a nucleic acid encoding any of the antibody polypeptides provided herein. Further contemplated is a vector comprising the nucleic acid. An isolated host cell can comprise such vector.

A pharmaceutical composition is provided comprising a therapeutically-effective amount of the presently provided antibody polypeptide and a pharmaceutically acceptable carrier. The pharmaceutical composition can further comprise an immunosuppressive/immunomodulatory and/or anti-inflammatory agent.

A method of treating an immune disease in a patient in need of such treatment is provided comprising administering to the patient a therapeutically effective amount of the pharmaceutical composition described herein. An exemplary method administers the pharmaceutical composition in combination with an immunosuppressive/immunomodulatory and/or anti-inflammatory agent. The immune disease can be an autoimmune disease or a graft-related disease. Alternatively, the immune disease is a graft-related disease. Furthermore, the graft-related disease can comprise solid organ, tissue and/or cell transplant rejection. Alternatively, the graft-related disease is graft versus host disease (GVHD). The graft-related disease can further be an acute transplant rejection. Alternatively, the graft-related disease can be a chronic transplant rejection.

Also provided is the method of treating a graft-related disease, wherein the pharmaceutical composition is co-administered with a CTLA4 mutant molecule. The CTLA4 mutant molecule can be L104EA29Y-Ig (belatacept).

A method of treating an immune disease in a patient in need of such treatment is also provided comprising administering to the patient a therapeutically effective amount of the pharmaceutical composition provided herein, wherein the immune disease is selected from the group consisting of selected from the group consisting of Addison's disease, allergies, ankylo sing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, alcohol addiction, and drug addiction. Alternatively, the immune disease can be myasthenia gravis, idiopathic thrombocytopenic purpura, or systemic sclerosis.

Also provided is a use of an isolated antibody polypeptide disclosed herein for the preparation of a medicament for the treatment of a patient, wherein the patient has or is at risk of having an immune disease. Further provided is a use of an isolated antibody polypeptide disclosed herein for preparation of a medicament for alleviating at least one symptom of an immune disease in a patient in need thereof.

Further provided herein is an isolated antibody polypeptide comprising a first variable domain, wherein said antibody polypeptide specifically binds human CD40L, wherein CD40L comprises the amino acid sequence of SEQ ID NO: 1, wherein the antibody polypeptide competes with the binding of BMS2h-572-633, and wherein the antibody polypeptide inhibits binding of CD40L to CD40 with an EC50 of 100 pM to 100 nM. In one aspect, the first variable domain comprises the amino acid sequence of one of the antibody polypeptides selected from the lineage group consisting of BMS2h-572, BMS2h-719, BMS2h-503, and BMS2h-116. In another aspect, the first variable domain comprises an amino acid sequence at least 95% identical to BMS2h-572-6, BMS2h-572-608, BMS2h-572-614, BMS2h-572-619, BMS2h-572-633, BMS2h-572-634, BMS2h-572-635, BMS2h-719-2, BMS2h-719-202, BMS2h-719-203, BMS2h-719-213, BMS2h-719-214, BMS2h-719-215, BMS2h-719-218, BMS2h-719-225, BMS2h-503-1, BMS2h-503-2, BMS2h-116-1312, BMS2h-116-1313, or BMS2h-116-1320. In yet another aspect, the first variable domain comprises the amino acid sequence of BMS2h-572-6, BMS2h-572-608, BMS2h-572-614, BMS2h-572-619, BMS2h-572-633, BMS2h-572-634, BMS2h-572-635, BMS2h-719-2, BMS2h-719-202, BMS2h-719-203, BMS2h-719-213, BMS2h-719-214, BMS2h-719-215, BMS2h-719-218, BMS2h-719-225, BMS2h-503-1, BMS2h-503-2, BMS2h-116-1312, BMS2h-116-1313, or BMS2h-116-1320.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3 provides sequences (SEQ ID NOS 1356-1361, respectively, in order of appearance) of various Fc domains. Linker regions are shown in boxes.

FIG. 4 shows examples of various Fc-formatted domain antibodies (SEQ ID NOS 1362-1365, respectively, in order of appearance). Linker regions are indicated by boxes.

FIG. 14 demonstrates PK/PD modeling of BMS-986003 and 5c8-IgG1 plasma exposures and anti-KLH antibody response (IgG Titers).

FIGS. 21, 22, 23, and 24 show is ClustalW2 alignments of representative domain antibody polypeptides from lineages BMS2h-572, BMS2h-719, BMS2h-503, and BMS2h-116, respectively. FIG. 21 discloses SEQ ID NOS 243, 251, 257, 262 and 274-276, respectively, in order of appearance, FIG. 22 discloses SEQ ID NOS 352, 354-355 and 357-361, respectively, in order of appearance, FIG. 23 discloses SEQ ID NOS 1087-1088, respectively, in order of appearance, and FIG. 24 discloses SEQ ID NOS 970-971 and 974, respectively, in order of appearance.

DETAILED DESCRIPTION

Figures 1A, 1B:
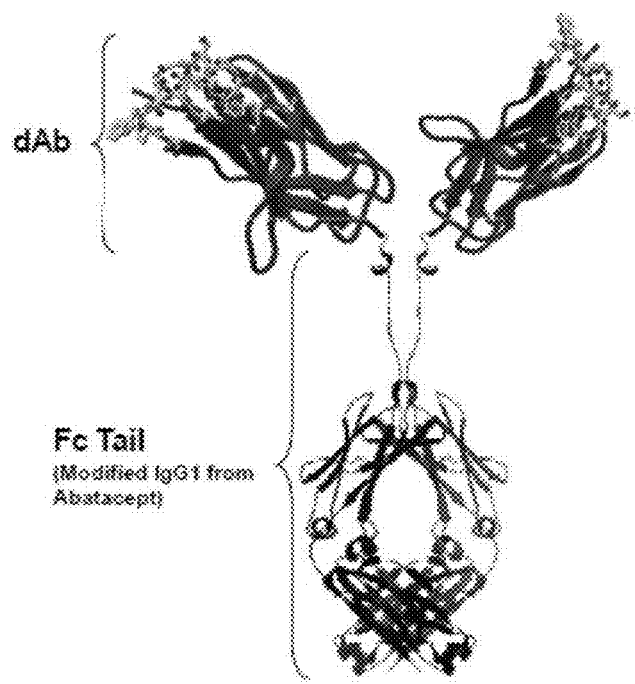
FIG. 1A depicts the domain antibody that comprises a $V_H$ variable domain BMS2h-572-633 fused to a modified Fc tail from Abatacept IgG1.
FIG. 1B shows the amino acid sequence (SEQ ID NO: 1355) of the variable domain BMS2h-572-633 (in blue). The Fc fusion protein is a dimer of molecular weight 77,984 Daltons, with each polypeptide chain consisting of 354 amino acids. The variable domain is fused by a linker (green) to the mutated Fc construct of human IgG1, wherein three cysteine residues (shown in purple) are substituted with serine, and one proline (shown in red) is substituted with a serine residue.
Figure 2:
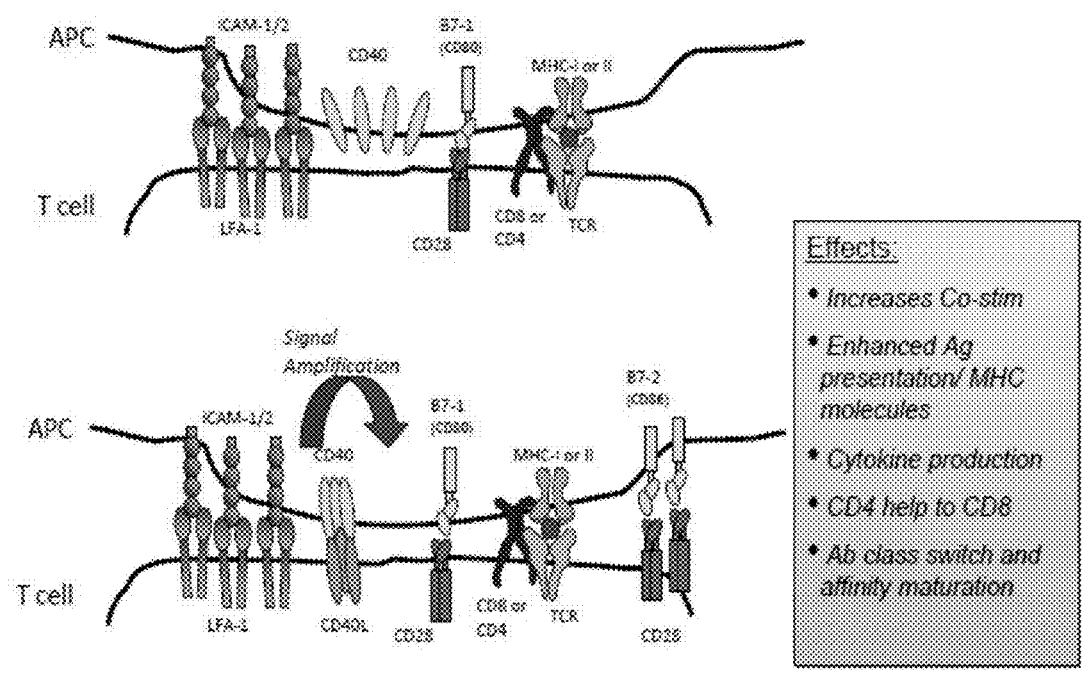
FIG. 2 depicts a working model for the CD40-40L pathway. The top panel demonstrates initial stages of an encounter between a T cell and an APC. The initial encounter driven by T cell receptor (TCR) engagement of pMHC complex (signal 1) coupled with an early CD28-CD80 interaction (signal 2) is sufficient for the cell surface expression of trimeric CD40L (bottom panel). Engagement of CD40 by CD40L results in numerous biological responses outlined in the grey box.

Antibody polypeptides that specifically bind to human CD40L are provided. The antibody polypeptides do not activate platelets, and the antibody polypeptides are useful in the treatment of diseases involving CD40L activation, such as graft-related diseases and autoimmune diseases. The antibody polypeptides may be selected using a primary screen that utilizes cell binding assays, followed by one or more rounds of error-prone or degenerate oligonucleotide-directed affinity maturation. As a result, a genus of antibody polypeptides that specifically bind CD40L are provided.

A "lineage" is a set of related antibody polypeptides that were prepared from a common precursor by error-prone or degenerate oligonucleotide-directed affinity maturation, as disclosed in the examples below, and that are expected to bind CD40L. The nomenclature of the antibody polypeptides is used to designate the various lineages. The nomenclature "BMS2h-572," for example, refers to antibody polypeptides of lineage 572, which were raised against human CD40L. "Lineage BMS2h-572" antibody polypeptides include BMS2h-572-1 through BMS2h-572-19, BMS2h-572-21 through BMS2h-572-24, BMS2h-572-601 through BMS2h-572-627, and BMS2h-572-630 through BMS2h-572-635.

Accordingly, in one aspect, an antibody polypeptide comprises a variable domain that specifically binds human CD40L, where the antibody polypeptide competes with the binding of any one of the domain antibodies (dAbs) listed in TABLE 1 or TABLE 3. For example, the antibody polypeptide may compete with a dAb selected from the 2h lineage. The dAb also may be selected from a lineage selected from the group consisting of BMS2h-116, BMS2h-503, BMS2h-572, and BMS2h-719, such as the dAb BMS2h-572-633, BMS2h-572-608, or BMS2h-572-614, for instance. In another aspect, an antibody polypeptide specifically binds human CD40L as any one of the dAbs listed in TABLE 1 and TABLE 3. For example, the antibody polypeptide may comprise a variable domain that specifically binds human CD40L as the dAb BMS2h-572-633, BMS2h-572-608, or BMS2h-572-614, for instance.

The antibody polypeptides may be a domain antibody containing a single variable domain. The antibody polypeptides also may comprise additional domains, such as an Fc domain. For instance, the antibody polypeptide may comprise a second variable domain that specifically binds human serum albumin (HSA). Such dual specific antibody polypeptides may have an increased half-life, for example.

As used herein, "specific binding" refers to the binding of an antigen by an antibody polypeptide with a dissociation constant ($K_d$) of about 1 μM or lower as measured, for example, by surface plasmon resonance (SPR). Suitable assay systems include the BIAcore™ surface plasmon resonance system and BIAcore™ kinetic evaluation software (e.g., version 2.1). The affinity or $K_d$ for a specific binding interaction may be about 1 μM or lower, about 500 nM or lower or about 300 nM or lower.

The term "about" will be understood by persons of ordinary skill in the art and will vary to some extent on the context in which it is used. Generally, about encompasses a range of values that are plus/minus 10% of a referenced value.

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

1. CD40L and CD40L Activities

Antibody polypeptides are provided that bind human CD40L. CD40L is also known as CD154, gp39, TNF-related activation protein (TRAP), 5c8 antigen, or T-BAM. Relevant structural information for human CD40L can be found, for example, at UniProt Accession Number P29965. "Human CD40L" refers to the CD40L comprising the following amino acid sequence:

```
                                         (SEQ ID NO: 1)
         10         20         30         40
MIETYNQTSP RSAATGLPIS MKIFMYLLTV FLITQMIGSA 50         60         70         80
LFAVYLHRRL DKIEDERNLH EDFVFMKTIQ RCNTGERSLS 90        100        110        120
LLNCEEIKSQ FEGFVKDIML NKEETKKENS FEMQKGDQNP 130        140        150        160
QIAAHVISEA SSKTTSVLQW AEKGYYTMSN NLVTLENGKQ 170        180        190        200
LTVKRQGLYY IYAQVTFCSN REASSQAPFI ASLCLKSPGR 210        220        230        240
FERILLRAAN THSSAKPCGQ QSIHLGGVFE LQPGASVFVN
```

-continued

```
         250        260
    VTDPSQVSHG TGFTSFGLLK L
```

CD40L has also been sequenced in *Sus scrofa, Mus musculus, Canis familiaris, Bos ffini, Macaca mulatta, Aotus tivirgatus, Callithrix jacchus, Cercocebus torquatus atys, Macaca nemestrina, Rattus norvegicus, Gallus gallus, Felis catus*, and *Sus scrofa*.

Binding of the present antibody polypeptides to CD40L antagonizes CD40L activity. "CD40L activities" include, but are not limited to, costimulation and activation an APC in association with T cell receptor stimulation by MHC molecules on the APC, secretion of all immunoglobulin isotypes in the presence of cytokines, stimulation of B cell proliferation, cytokine production, antibody class switching and affinity maturation. For example, patients with X-linked hyper-IgM syndrome express functional CD40 on their B cells, but their activated T cells have a defective CD40L protein, resulting in its inability to activate B cells and induce immunoglobulin isotype switching. Aruffo et al., *Cell* 72:291-300 (1993).

CD40L activities can be mediated by interaction with other molecules. "CD40 activities" include the functional interaction between CD40L and the following molecules: CD40 (CD40L receptor), α5β1 integrin, and αIIbβ3. For example, CD40L binds its receptor, CD40, which is expressed on a variety of APCs, such as B cells, macrophages, and dendritic cells, as well as on stromal cells, vascular endothelial cells, and platelets.

As used herein, the terms "activate," "activates," and "activated" refer to an increase in a given measurable CD40L activity by at least 10% relative to a reference, for example, at least 10%, 25%, 50%, 75%, or even 100%, or more. A CD40L activity is "antagonized" if the activity is reduced by at least 10%, and in an exemplary embodiment, at least 20%, 30%, 40%, 50%, 60%, 70%, 80%, 90%, 95%, 97%, or even 100% (i.e., no detectable activity), relative to the absence of the antagonist. For example, an antibody polypeptide may antagonize some or all CD40L activity. In one embodiment, the antibody polypeptide does not activate B cell proliferation. In another embodiment, the antibody polypeptide does not activate cytokine secretion by T cells or dendritic cells (DCs), where the cytokine is at least one cytokine selected from the group consisting of IL-2, IL-6, IL-10, IL-12, IL-13, IL-17, IL-23, TNF-α, and IFN-γ.

2. Antibody Polypeptides

The antibody polypeptides comprise a variable domain. In one embodiment, the antibody polypeptides are in the form of a dAb that contains a single variable domain. Antibody polypeptides may be full-length anti-CD40L immunoglobulin molecules comprising two heavy (H) chains and two light (L) chains interconnected by disulfide bonds. In this embodiment, the amino terminal portion of each chain includes a variable domain ($V_L$ or $V_H$) of about 100-120 amino acids. The complementarity determining regions (CDRs) contained therein are primarily responsible for antigen recognition, although framework residues can play a role in epitope binding. The carboxy-terminal "half" of each heavy chain defines a constant region (Fc) primarily responsible for effector function.

Antibody polypeptides also may be "fragments" comprising a portion of the full-length anti-CD40L immunoglobulin molecule that comprises a variable domain that specifically binds CD40L. Thus, the term "antibody polypeptides" includes an antigen-binding heavy chain, light chain, heavy chain-light chain dimer, Fab fragment, F(ab')$_2$ fragment, Fv fragment, single chain Fv (scFv), and dAb, for example. The term "antibody polypeptides" thus includes polypeptides made by recombinant engineering and expression, as well as monoclonal antibodies produced by natural recombination and secretion by hybridoma cell clones.

Light chains are classified as kappa (κ) or lambda (λ), and are characterized by a particular constant region, $C_L$, as known in the art. Heavy chains are classified as γ, μ, α, δ, or ε, and define the isotype of an antibody as IgG, IgM, IgA, IgD, or IgE, respectively. The heavy chain constant region is comprised of three domains (CH1, CH2, and CH3) for IgG, IgD, and IgA; and four domains (CH1, CH2, CH3, and CH4) for IgM and IgE. Anti-CD40L antibodies may have a heavy chain constant region selected from any of the immunoglobulin classes (IgA, IgD, IgG, IgM, and IgE).

Each light chain variable domain ($V_L$) and heavy chain variable domain ($V_H$) is composed of three CDRs and four framework regions (FRs), arranged from amino-terminus to carboxy-terminus in the following order: FR1, CDR1, FR2, CDR2, FR3, CDR3, and FR4. The three CDRs of the light chain are referred to as "LCDR1, LCDR2, and LCDR3" and the three CDRs of the heavy chain are referred to as "HCDR1, HCDR2, and HCDR3."

As used herein, the term "Fc domain" refers to the constant region antibody sequences comprising CH2 and CH3 constant domains as delimited according to Kabat et al., *Sequences of Immunological Interest*, 5$^{th}$ ed., U.S. Dept. Health & Human Services, Washington, D.C. (1991). The Fc domain may be derived from an IgG1 or an IgG4 Fc region, for example.

A variable domain may be fused to an Fc domain. Examples of various Fc-formatted domain antibodies and their potency are provided in TABLE 6. FIG. 3 provides sequences of various Fc domains provided herein. Linker regions are shown in boxes. As used in TABLE 6, "Fc" indicates that the dAb is fused to a human IgG1 short Fc. "CT Long Fc," also called CT-L2, refers to the Fc from CTLA4. The underlined S are cysteine-to-serine point mutations made to eliminate the disulfides in the Fc hinge. "CT Short," also called CT-S1, is shorter than CT Long by 7 amino acids. "N297Q Long Fc," also referred to as N297Q-L4, is the Fc domain of human IgG1 with a N297Q mutation made to eliminate the N-linked carbohydrate in the Fc. "N297Q Short Fc," also called N297Q-S3, is short than N297Q Long Fc by 7 amino acids, and is a human IgG1 with a N297Q point mutation made to eliminate the N-linked carbohydrate in the Fc domain. "CT-Fc SP5" is the CT Long Fc, where SP5 refers to the octeonectin signal peptide used for secretion from the mammalian expression host. Cleavage site is indicated by "^". FIG. 4 further provides examples of various Fc domain formats.

When a variable domain is fused to an Fc domain, the carboxyl terminus of the variable domain (either a $V_L$ or $V_H$ domain, including dAbs) may be linked or fused to the amino terminus of the Fc CH2 domain. Alternatively, the carboxyl terminus of the variable domain may be linked or fused to the amino terminus of a CH1 domain, which itself is fused to the Fc CH2 domain. The protein may comprise the hinge region between the CH1 and CH2 domains in whole or in part.

The CDRs contain most of the residues that form specific interactions with the antigen. In one embodiment, the variable domain of an antibody polypeptide comprises CDR1, CDR2, and CDR3 regions that have the same amino acid sequence as the CDR1, CDR2, and CDR3 regions of one of the dAbs listed in TABLE 1 or TABLE 3 or that each differ from the CDR1, CDR2, and CDR3 regions by one, two, or three amino acids. For example, the antibody polypeptide may comprise CDR1, CDR2, and CDR3 regions that have the same amino acid sequence as the CDR1, CDR2, and CDR3 regions of BMS2h-572-633, BMS2h-572-608, or BMS2h-572-614, for example.

A "domain antibody" (dAb) comprises a single variable ($V_L$ or $V_H$) domain that is capable of specifically and monovalently binding an antigen, such as CD40L. For example, a dAb may have a $V_{HH}$ structure, characteristic of a camelid dAb. A "$V_H$ domain" as used herein is meant to include a $V_{HH}$ structure. In another embodiment, the $V_H$ domains (including all features and combination of features presented as embodiments herein) are other than $V_{HH}$ domains. dAbs may form homo- or heterodimers in solution. While not limited by any particular theory, it is believed that the dAbs disclosed herein do not cause platelet aggregation, because the antibodies containing mutated Fc constructs do not bind FcγRIIa (also known as CD32a) on the platelet surface and do not activate platelets.

As used herein, the term "variable domain" refers to immunoglobulin variable domains defined by Kabat et al., Sequences of Immunological Interest, 5$^{th}$ ed., U.S. Dept. Health & Human Services, Washington, D.C. (1991). The numbering and positioning of CDR amino acid residues within the variable domains is in accordance with the well-known Kabat numbering convention.

The term "human," when applied to antibody polypeptides, means that the antibody polypeptide has a sequence, e.g., framework regions and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above. An "isolated" compound as used herein means that the compound is removed from at least one component with which the compound is naturally associated with in nature.

Antibody polypeptides can be administered to human patients while largely avoiding the anti-antibody immune response often provoked by the administration of antibodies from other species, e.g., mouse. For example, murine antibodies can be "humanized" by grafting murine CDRs onto a human variable domain FR, according to procedures well known in the art. Human antibodies as disclosed herein, however, can be produced without the need for genetic manipulation of a murine antibody sequence.

Variable domains may comprise one or more FR with the same amino acid sequence as a corresponding framework region encoded by a human germline antibody gene segment. For example, a domain antibody may comprise the $V_H$ germline gene segments DP47, DP45, or DP38, the $V_\kappa$ germline gene segment DPK9, the $J_H$ segment JH4b, or the $J_\kappa$ segment $J_\kappa 1$.

Changes may be made to antibody polypeptide sequences while retaining the ability to bind CD40L specifically. Specifically, the antibody polypeptides (e.g., a dAb) may comprise a variant variable domain that retains the function of specifically binding CD40L as the dAb BMS2h-572-633. In one embodiment, the variant variable domain may compete with BMS2h-572-633 for specific binding to CD40L. Error-prone affinity maturation, as disclosed in the examples below, provides one exemplary method for making and identifying antibody polypeptides with variant sequences that specifically bind CD40L.

For example, a variant variable domain may differ from one of the variable domains listed in TABLE 1 and TABLE 3 by up to 10 amino acids or any integral value between, where the variant variable domain specifically binds CD40L. Alternatively, the variant variable domain may have at least 90% sequence identity (e.g., at least 91%, 92%, 93%, 94%, 95%, 96%, 97%, 98%, or 99% sequence identity) relative to a sequence listed in the present Sequence Listing. Non-identical amino acid residues or amino acids that differ between two sequences may represent amino acid substitutions, additions, or deletions. Residues that differ between two sequences appear as non-identical positions, when the two sequences are aligned by any appropriate amino acid sequence alignment algorithm, such as BLAST.

In one embodiment, amino acid substitutions may be made to individual FR regions, such that a FR comprises 1, 2, 3, 4, or 5 amino acid differences relative to the amino acid sequence of the corresponding FR encoded by a human germline antibody gene segment. In another embodiment, the variant variable domain may contain one or two amino acid substitutions in a CDR. In other embodiments, amino acid substitutions to FR and CDR regions may be combined. Representative variable domains that specifically bind CD40L are listed in TABLE 1 and TABLE 3.

The information regarding the boundaries of the $V_L$ or $V_H$ domains of heavy and light chain genes may be used to design PCR primers to amplify the variable domain from a cloned heavy or light chain coding sequence encoding an antibody polypeptide known to bind CD40L. The amplified variable domain may be inserted into a suitable expression vector, e.g., pHEN-1 (Hoogenboom et al. (1991) Nucleic Acids Res. 19:4133-4137) and expressed, either alone or as a fusion with another polypeptide sequence, using techniques well known in the art. Based on the disclosed amino acid and polynucleotide sequences, the fusion protein can be produced and purified using only ordinary skill in any suitable mammalian host cell line, such as CHO, 293, COS, NSO, and the like, followed by purification using one or a combination of methods, including protein A affinity chromatography, ion exchange, reverse phase techniques, or the like.

In one aspect, the antibody polypeptide is a "dual specific" antibody polypeptide comprising a first variable domain that specifically binds human CD40L. Dual specific antibody polypeptides comprise a second variable domain that specifically binds a second antigen that is other than human CD40L.

In another embodiment, the second antigen may be a cell surface molecule of an immune effector cell or a soluble molecule such as a cytokine, for example. Binding of the dual specificity antibody polypeptide could be used to antagonize CD40L and antagonize a biological activity of the second antigen. Cell surface molecules of immune effector cells include the cluster of differentiation (CD) molecules. Representative CD markers are listed on the Internet at hypertext transfer protocol http://en.wikipedia.org/wiki/List_of human_clusters_of_differentiation (last modified on Aug. 8, 2012). Cell surface molecules of immune effector cells also include Major Histocompatibility Complex (MHC) Class II molecules. Antibodies against these cell surface molecules are known in the art and can be used a source of a variable domain to construct a dual specific antibody polypeptide.

In one embodiment, antibody polypeptides of a dual specific ligand may be linked by an "amino acid linker" or "linker." For example, a dAb may be fused to the N-terminus of an amino acid linker, and another dAb may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include (GGGGS)$_n$ (SEQ ID NO: 12), where n may be any integer between 1 and 5. Other suitable linker sequences may be selected from the group consisting of AS, AST, TVAAPS (SEQ ID NO: 13), TVA, and ASTSGPS (SEQ ID NO: 14).

The binding of the second antigen can increase the in vivo half-life of the antibody polypeptide. For example, the second variable domain of the dual specific antibody polypeptide may specifically bind serum albumin (SA), e.g., human serum albumin (HSA). The antibody polypeptide formatted to bind I can have an increased in vivo t-α ("alpha half-life") or t-β ("beta half-life") half-life relative to the same unformatted antibody polypeptide. The t-α and t-β half-lives measure how quickly a substance is distributed in and eliminated from the body. The linkage to I may be accomplished by fusion of the antibody polypeptide with a second variable domain capable of specifically binding I, for example. Anti-human serum albumin antibodies are well-known in the art. See, e.g., Abcam®, Human Serum Albumin antibodies ab10241, ab2406, and ab8940, available on the Internet at hypertext transfer protocol www.abcam.com/index.html, or GenWay, ALB antibody, available on the Internet at hypertext transfer protocol www.genwaybio.com. Variable domains that specifically bind I can be obtained from any of these antibodies, and then fused to an antibody polypeptide of the disclosure using recombinant techniques that are well known in the art.

Alternatively, the linking of the antibody polypeptide to I can be accomplished by directly fusing the antibody polypeptide sequence to an I coding sequence using techniques well known to the skilled artisan. The I coding sequences can be obtained by PCR using primers derived from the cDNA sequence available at GenBank Accession No. NM000477, for example.

In one embodiment, the tα-half-life of the I-linked domain antibody composition is increased by 10% or more. In another embodiment, the tα-half-life of the I-linked domain antibody composition is in the range of 0.25 hours to 6 hours. In another embodiment, the tβ-half-life of the I-linked domain antibody composition is increased by 10% or more. In another embodiment, the tβ-half-life of the I-linked domain antibody composition is in the range of 12 to 48 hours.

In another embodiment, an antibody polypeptide may be formatted to increase its in vivo half-life by PEGylation. In one embodiment, the PEG is covalently linked. In another embodiment, the PEG is linked to the antibody polypeptide at a cysteine or lysine residue. In yet another embodiment, the PEG-linked antibody polypeptide has a hydrodynamic size of at least 24 kD. In yet another embodiment, the total PEG size is from 20 to 60 kD, inclusive. In yet another embodiment, the PEG-linked domain antibody has a hydrodynamic size of at least 200 kD.

PEGylation can be achieved using several PEG attachment moieties including, but not limited to N-hydroxylsuccinimide active ester, succinimidyl propionate, maleimide, vinyl sulfone, or thiol. A PEG polymer can be linked to an antibody polypeptide at either a predetermined position, or can be randomly linked to the domain antibody molecule. PEGylation can also be mediated through a peptide linker attached to a domain antibody. That is, the PEG moiety can be attached to a peptide linker fused to an antibody polypeptide, where the linker provides the site (e.g., a free cysteine or lysine) for PEG attachment. Methods of PEGylating antibodies are well known in the art, as disclosed in Chapman, et al., "PEGylated antibodies and antibody fragments for improved therapy: a review," *Adv. Drug Deliv. Rev.* 54(4):531-45 (2002), for example.

Antibody polypeptides also may be designed to form a dimer, trimer, tetramer, or other multimer. Antibody polypeptides, e.g., dAbs, can be linked to form a multimer by several methods known in the art, including, but not limited to, expression of monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). In one embodiment, the multimer can bind a single molecule of CD40.

3. Pharmaceutical Compositions and Methods of Treatment

A pharmaceutical composition comprises a therapeutically-effective amount of one or more antibody polypeptides and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are well known in the art. See, e.g., Remington, THE SCIENCE AND PRACTICE OF PHARMACY, A. Gennaro, et al., eds., 21$^{st}$ ed., Mack Publishing Co. (2005).

The pharmaceutical composition further may comprise an immunosuppressive/immunomodulatory and/or anti-inflammatory agent. A method of treating an immune disease in a patient in need of such treatment may comprise administering to the patient a therapeutically effective amount of the pharmaceutical composition. Antagonizing CD40L-mediated T cell activation could inhibit undesired T cell responses occurring during autoimmunity, transplant rejection, or allergic responses, for example. Inhibiting CD40L-mediated T cell activation could moderate the progression and/or severity of these diseases.

As used herein, a "patient" means an animal, e.g. mammal, including humans. The patient may be diagnosed with an immune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to graft-related disease, inflammation, allergy, and autoimmune disease. The autoimmune disease may be selected from the group consisting of systemic lupus erythematosus, multiple sclerosis, rheumatoid arthritis, diabetes, psoriasis, scleroderma, atherosclerosis, inflammatory bowel disease, and ulcerative colitis.

Diseases that can be treated by administering the pharmaceutical composition may be selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, and vasculitis. Autoimmune-mediated conditions include, but are not limited to, conditions in which the tissue affected is the primary target, and in some cases, the secondary target. Such conditions include, but not limited to, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus' phenomenon, anaphylaxis, alcohol addiction, and drug addiction.

Preferred indications for administration of the present pharmaceutical compositions are, for example, immune thrombocytopenic purpura, systemic sclerosis, myasthenia gravis, allograft rejection, and graft-versus-host disease.

The pharmaceutical composition may be administered alone or in combination therapy, (i.e., simultaneously or sequentially) with an immunosuppressive/immunomodulatory and/or anti-inflammatory agent. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

For example, the disclosed pharmaceutical composition may be co-administered, concomitantly or sequentially, with a cytotoxic T-lymphocyte antigen 4 (CTLA4) mutant molecule, such as L104EA29Y-Ig (belatacept). CTLA4 binds to CD80 (B7-1) and CD86 (B7-2) with higher avidity than CD28, and it is transiently expressed on T cells following their activation, where it interrupts the interaction between CD28 and CD80/86. Oosterwegel et al., Curr. Opin. Immunol. 11: 294-300 (1999). This creates a negative feedback signal for T cell activation.

CTLA4 mutant molecules, including L104EA29Y-Ig, have increased binding avidity to CD80/86 compared to wild-type CTLA4. Intervention of the CD28-CD80/86 pathway by L104EA29Y-Ig has been successfully pursued, for example, to treat graft-related diseases in non-human primate transplant models, alone or in combination with other immunosuppressive agents. Larsen et al., Amer. J. Transplant. 5: 443 (2005). U.S. Patent Application number 2010/0166774 describes the structure of L104EA29Y-Ig, methods of producing it, and a formulation comprising a CTLA4 molecule; and the application is herein incorporated by reference. U.S. Pat. Nos. 7,094,874 and 7,482,327 further disclose administration (including co-administration with one or more other drugs) and dosage schedule of L104EA29Y-Ig, and the disclosures of these patents are herein incorporated by reference.

Any suitable method or route can be used to administer the antibody polypeptide or the pharmaceutical composition. Routes of administration include, for example, oral, intravenous, intraperitoneal, subcutaneous, or intramuscular administration. A therapeutically effective dose of administered antibody polypeptide(s) depends on numerous factors, including, for example, the type and severity of the immune disease being treated, the use of combination therapy, the route of administration of the antibody polypeptide(s) or pharmaceutical composition, and the weight of the patient. A non-limiting range for a therapeutically effective amount of a domain antibody is 0.1-20 mg/kg, and in an aspect, 1-10 mg/kg, relative to the body weight of the patient. The dose of antibody polypeptide(s) can be further guided by the amount of antibody polypeptide(s) required for CD40 antagonism in in vitro and/or in vivo models of disease states. Representative models are described below and in the examples.

4. In Vitro and In Vivo Models

The ability of antibody polypeptides of the disclosure to antagonize CD40L can be tested in one of several available in vitro or in vivo model systems. Appropriate human, animal, and cell model systems are described below. Further cell assay systems are described in the examples.

4.1. Immune Thrombocytopenic Purpura (ITP) In Vivo Model:

The potential role of CD40-CD40L in the pathogenesis of ITP is reported by Patel et al., British J. Haematology 141: 545-548 (2008). Antiplatelet autoantibodies in patients with ITP bind to circulating platelets and accelerate their destruction. The primary mechanism by which anti-CD40L antibodies are thought to increase the platelet count in ITP is by blocking T-cell based activation of autoreactive B cells that produce anti-platelet antibodies. Anti-CD40L antibodies may also block expression of CD40L on platelets, thus preventing autopresentation of platelet glycoprotein antigens to macrophages. Furthermore, anti-CD40L mAbs inhibit direct interactions between platelet CD40L and other cells, such as plasmacytoid dendritic cells (DCs), which have recently been implicated in driving the type 1 interferon (IFN) response in human lupus patients. Duffau et al., Sci. Transl. Med. 2: 47 (2010).

Patel et al. demonstrated efficacy of two humanized anti-CD40L monoclonal antibodies, hu5c8 and IDEC-131, in 46 human patients with chronic ITP refractory to conventional therapies. The patients had an overall 24% response rate, characterized by increased platelet counts. This demonstrated the potential role of CD40-CD40L in the pathogenesis of ITP.

4.2. Lupus In Vivo and In Vitro Models:

Glomerular and tubular CD40 expression is markedly upregulated in proliferative nephritis. Several studies have reported hyperexpression of CD40L by T cells and elevated soluble sCD40L concentrations in human lupus. Kimura et al., Therapeutic Apheriss and Dialysis 9: 64-68 (2005); Vakkalanka et al., Arthritis & Rheumatism 42: 871-881 (1999).

Systemic lupus erythematosus (SLE) is a chronic autoimmune disease characterized by the production of multiple autoantibodies and by B cell hyperactivity. Grammer et al., J. Clin. Invest. 112: 1506-1520 (2003) reports the results of treatment of patients with SLE with humanized anti-CD40L mAb 5c8 (BG9588). See also Huang et al., Arthritis &

*Reumatism* 46: 1554-1562 (2002). Grammer et al. report that CD19+ peripheral B cells were examined before and after treatment with the anti-CD40L mAb. Before treatment, SLE patients manifested activated B cells that expressed CD40L, CD69, CD38, CD5, and CD27. The activated B cells disappeared from the periphery during and post-treatment. Before treatment, active SLE patients had circulating CD38$^{bright}$ Ig-secreting cells that were not found in normal individuals. Disappearance of these plasma cells during treatment was associated with decreases in anti-double stranded DNA (anti-dsDNA) Ab levels, proteinuria, and SLE disease activity index. Consistent with this finding, peripheral B cells cultured in vitro spontaneously proliferated and secreted Ig in a manner that was inhibited by anti-CD40L mAb. The CD38+/++IgD+, CD38+++, and CD38+IgD− B cell subsets present in the peripheral blood of SLE patients also disappeared following treatment with the anti-CD40L mAb. Together, these results suggest that spontaneous CD40L-CD40 interactions in active SLE patients drive B cell activation, proliferation, and differentiation to autoantibody-secreting plasma cells that mediate proteinuria and disease activity.

Proliferative lupus glomerulonephritis is a protracted autoimmune disease with a waxing and waning course, characterized by increased level of anti-dsDNA antibodies, decreased serum C3 concentrations, and hematuria. Boumpas et al, *Arthritis & Rheumatism* 48: 719-727 (2003) report results of a phase II, multicenter, open-label study evaluating the toxicity and efficacy of BG9688, a humanized anti-CD40L monoclonal antibody, in patients with proliferative lupus glomerulonephritis. Although the study had to be terminated prematurely because of thromboembolic events occurring in patients in several BG9588 protocols, a short course of the anti-CD40L antibody treatment in patients with proliferative lupus nephritis reduced anti-dsDNA antibodies, increased C3 concentrations, and decreased hematuria, suggesting that the drug has immunomodulatory function.

4.3. Inflammatory Bowel Disease (IBD) In Vivo Models:

Crohn's disease (CD) and ulcerative colitis (UC) are IBDs that are characterized by leukocytic infiltrates in inflamed intestinal mucosa, which consists primarily of activated CD25+ cells, B cells, and macrophages. Ludwiczek et al., *Int. J. Colorectal Dis.* 18: 142-147 (2003) report that in CD patients, plasma levels of sCD40L were significantly higher than in healthy individuals. Moreover, CD patients with fistulas and/or abscesses had significantly higher levels of sCD40L than patients with uncomplicated CD. It has also been reported that the CD40-CD40L pathway contributes to the proinflammatory function of intestinal epithelial cells in IBD. Borcherding et al., *Am. J. Pathol.* 176: 1816-1827 (2010). Patients with CD also have an increased risk of systemic thromboembolism, and the hyperactive state of platelets from such patients likely results from the enhanced release of sCD40L as a consequence of their higher endogenous content of CD40L. Menchen et al., *Gut* 58: 920-928 (2009); see also Danese et al., *Gut* 52: 1435-1441 (2003).

Kasran et al., *Aliment. Pharmacol. Ther.* 22: 111-122 (2005) investigated the use of a chimeric anti-human CD40 mAb ch5D12 to treat Crohn's disease. The mAb was administered to 18 patients with moderate to severe CD in a single dose, open-label dose escalation phase I/IIa study. Of the 18 patients, 13 (or 72%) experienced a favorable response to the antibody infusion, and 4 patients (or 22%) experienced a remission. Treatment with the anti-CD40 mAb reduced microscopic disease activity and intensity of the lamina propria cell infiltrate, and the mAb was well tolerated.

4.4. Rheumatoid Arthritis (RA), Juvenile Idiopathic Arthritis (JIA), and Psoriatic Arthritis (PsA) In Vivo Models:

Rheumatoid arthritis is a systemic autoimmune disease with intra-articular inflammation as a dominant feature that affects up to 1% of the population. The disease can be subdivided clinically by the presence or absence of autoantibodies (antibodies to cyclic citrullinated peptide (CCP) or rheumatoid factor (RF), both of which are highly correlated to each other. Raychaudhuri et al., *Nature Genetics* 40: 1216-1223 (2008) reported that they conducted a meta-analysis of two published genome-wide association (GWA) studies totaling 3,393 cases and 12,462 controls, in order to identify RA risk loci in European populations. They genotyped 31 top-ranked short nucleotide polymorphisms (SNPs) not previously associated with RA in an independent replication of 3,929 autoantibody-positive RA cases and 5,807 matched controls from eight separate collections. They identified a common variant at the CD40 gene locus, which implied a central role for the CD40 signaling pathway in RA pathogenesis. The strong association of the CD40 gene with susceptibility to RA was robustly replicated in another study in a large UK cohort of 3,962 patients with RA. Orozso et al., *Ann. Rheum. Dis.* 69: 813-816 (2010).

A major role of CD40L has also been found in the pathogenesis of juvenile idiopathic arthritis (JIA). Prahalad et al., *Pediatric Rheumatology* 6: 1-8 (2008). JIA is a heterogeneous group of arthropathies of unknown etiology. It was found that sCD40L was significantly elevated in the serum of children with JIA, along with some cytokines. Logistic regression analysis suggested that sCD40L, as well as IL-6 and TNFα, were positively associated with JIA.

sCD40L was elevated in all JIA subtypes, with highest levels among more severe subtypes. These results implicated sCD40L as a potential biomarker for treatment and monitoring of patients with JIA.

It has also been demonstrated that activated T cells from patients with psoriatic arthritis (PsA), and particularly those with active disease, have a significantly increased expression of CD40L. Daoussis et al., *Rheumatology* 46: 227-231 (2007). These results indicate a role of the CD40-CD40L pathway in the pathogenesis of PsA and that a therapy selectively targeting CD40L could benefit PsA patients.

4.5. Systemic Sclerosis In Vivo Models:

Systemic sclerosis (SSc) is an autoimmune connective tissue disorder characterized by fibrous and vascular changes in the skin and internal visceral organs. In a study involving 52 Japanese patients with SSc, serum sCD40L levels were elevated when compared with healthy controls. Komura et al., *J. Reumatol.* 31: 514-519 (2004). Moreover, levels of sCD40L in patients with SSc were higher than in patients with systemic lupus erythematosus (SLE) who had elevated sCD40L levels compared to controls, and sCD40L levels correlated positively with C reactive peptide levels in SSc patients. It has also been reported that blockade of CD40L with anti-CD40L antibody in cultured T and B cells from SSc patients inhibited anti-topoisomerase I antibody production. Kuwana et al., *J. Immunol.* 155: 2703-2714 (1995). These results suggest that inhibition of CD40-CD40L interactions may be potential therapeutic targets in therapy of SSc as well as SLE.

4.6. Atherosclerosis In Vivo Models:

Several studies have suggested a role of CD40-CD40L signaling pathway during atherogenesis. Mach et al. demonstrated that in mice, treatment with monoclonal anti-CD40L antibody limited atherosclerosis in mice lacking receptor for low-density lipoprotein that had been fed a high-cholesterol diet for 12 weeks. Nature 394: 200-203

(1998). The antibody reduced the size of aortic atherosclerotic lesions by 59% and their lipid content by 79%. Additionally, atheroma of mice treated with anti-CD40L antibody contained significantly fewer macrophages and T lymphocytes, and exhibited decreased expression of vascular cell adhesion molecule-1.

Anti-CD40L antibody treatment of low-density lipoprotein receptor-deficient mice during the second half of a 26-week regimen of a high-cholesterol diet did not regress, but did significantly reduce further progression of established atherosclerotic lesions within the aortic arch and particularly the thoracic and abdominal aorta, as compared to control treatment. Schonbeck et al., *Proc. Natl. Acad. Sci.* 97: 7458-7463 (2000). Furthermore, anti-CD40L treatment changed the composition of atheroma in manners thought to favor plaque stability, e.g., reduced relative content of macrophages and lipid, as well as increased relative content of smooth muscle cells and collagen. These studies lend support to the importance of the CD40-CD40L signaling pathway in atherosclerosis and its complications, such as coronary artery disease.

4.7. Allograft Rejection In Vivo Models:

Targeting the CD40-CD40L pathway has long been of much interest for prevention of rejection of solid organ transplants (SOT), particularly in light of the promising data from numerous published transplant studies in non-human primates. It has been demonstrated that reduced CD40L expression on ex vivo activated CD4+ T lymphocytes correlates with excellent renal allograft function. Lederer et al., *Int. Arch. Allergy Immunol.* 133: 276-284 (2004). Furthermore, several studies have demonstrated that anti-CD40L mAbs can both prevent and reverse acute allograft rejection in primates. For example, Kirk et al., *Proc. Natl. Acad. Sci. USA* 94: 8789-8794 (1997) reported that, in rhesus monkeys transplanted with renal allografts, anti-CD40L mAb 5C8 alone or in combination with CTLA4-Ig significantly prolonged rejection-free survival. The CD40L-specific mAb hu5c8 alone also allowed for allogeneic islet engraftment and long-term insulin independence in rhesus monkeys that were transplanted an adequate number of viable pancreatic islets. Kenyon et al., *Proc. Natl. Acad. Sci. USA* 96: 8132-8137 (1999). Preston et al., *Amer. J. Transplantation* 5: 1032-1041 (2005) performed renal transplants in MHC-mismatched rhesus monkeys and treated the recipients with combinations of CD40L-specific mAb IDEC-131, and/or sirolimus, and/or pre-transplant donor-specific transfusion. IDEC-131 was highly effective in preventing renal allograft rejection in primates. In cynomolgus monkeys that underwent renal allotransplantation, treatment with anti-CD40L mAb ABI793 effectively prevented graft rejection. Schuler et al., *Transplantation* 77: 717-726 (2004). In addition to preventing allograft rejection, CD40L-specific mAbs induced donor specific tolerance in primate transplant models. Preston et al., *Amer. J. Transplantation* 5: 1032-1041 (2005); Kenyon et al., *Proc. Natl. Acad. Sci. USA* 96: 8132-8137 (1999).

In pediatric human patients that were undergoing acute graft rejection after liver or small-bowel transplantation, a correlation was observed between the expression of CD40L on CD8+ T cells and the risk of transplant rejection. Ashokkumar et al., *Amer. J. Transplantation* 9: 179-191 (2009) and Ashokkumar et al., *Surgery* 146: 166-173 (2009). Similarly, in adult patients that were undergoing allograft rejection following liver or renal transplantation, histological analysis demonstrated an association between CD40L expression and acute or chronic rejection. Bartlett et al., *Amer. J. Transplantation* 3: 1363-1368 (2003) and Biancone et al., *Nephrol. Diall. Translpant.* 13: 716-722 (1998).

Several studies support targeting CD40L over CD40 to achieve better efficacy in transplantation. For example, graft survival is longer and more durable when CD40L is selectively blocked, compared to CD40. Gilson et al., *J. Immunol.* 183: 1625-35 (2009). Furthermore, recent data suggest that CD40L blockade may enhance induction of Tregs and/or suppressor cells to promote graft survival. Garcia et al., *J. Clin. Inv.* 120: 2486-96 (2010). Also, blockade of CD40L, but not CD40, has demonstrated induction of long-lived immunological tolerance resulting in indefinite graft survival, particularly when combined with blockade of the B7 pathway. Kenyon et al., *Proc. Natl. Acad. Sci. USA* 96: 8132-8137 (1999); Kawai et al., *Amer. J. Transplantation* 4: 1391-1398 (2004); Preston et al., *Amer. J. Transplantation* 5: 1032-1041 (2005); Adams et al., *J. Immunol.* 174: 542-50 (2005). The synergy of blocking CD40-40L and B7-CD28 pathways in enhancing graft survival is especially important, because it presents the presently disclosed domain antibodies as a natural choice for combination with belatacept (CTLA4-Ig) for SOT.

4.8. Graft-Versus-Host Disease In Vivo Model:

Chronic and acute graft-versus-host disease (cGVHD and aGVHD) are complications that can occur after a stem cell or bone marrow transplant in which the transplanted donor cells attack the transplant recipient's body. Acute GVHD in humans takes place withing about 60 days post-transplantation and results in damage to the skin, liver, and gut by the action of cytolytic lymphocytes. Chronic GVHD occurs later and is a systemic autoimmune disease that affects primarily the skin, resulting in the polyclonal activation of B cells and the hyperproduction of Ig and autoantibodies.

CD40L-CD40 interactions appear to be critical in the development of both cGVHD and aGVHD. Durie et al., *J. Clin. Invest.* 94: 1333-1338 (1994). In a mouse in vivo model, anti-CD40L antibodies blocked the following cGVHD-associated phenomena: splenomegaly, in vitro polyclonal Ig production, elevated levels of serum IgE and serum anti-DNA autoantibodies, and the generation of anti-host cytotoxic T cells. Antibody production remained inhibited for extended periods of time after the end of anti-CD40L antibody administration. In mice with aGVHD, which is associated with the induction of a profound antiallogenic cytotoxic T cell (CTL) response, treatment with anti-CD40L prevented the generation of H-2b-derived CTL. The results of the study suggest that CD40L-CD40 interactions are critical in GVHD and that CD40L may be a valuable ligand for targeting immunotherapeutic agents to control GVHD.

4.9. Myasthenia Gravis In Vivo Model:

Myasthenia gravis (MG) and its animal model, experimental autoimmune MG (EAMG), are T-cell dependent autoimmune disorders caused by autoantibodies against the nicotinic acetylcholine receptors (AChR) at the neuromuscular junction of skeletal muscle. The role of CD40-CD40L in EAMG was shown in CD40L (CD40L−/−) knockout mice. Shi et al, *Eur. J. Immunol.* 28: 3587-3593 (1998). The CD40L knockout mice were completely resistant to EAMG induction and had diminished Th1 and Th2 responses as well as severely impaired T-cell dependent AChR-reactive B cell responses.

It has also been demonstrated that blockade of CD40L-CD40 signaling by anti-CD40L antibodies is capable of suppressing EAMG. Im et al., *J. Immunol.* 166: 6893-6898 (2001). Antibodies given to rats at the chronic stage of EAMG suppress the clinical progression of the autoimmune response and lead to a decrease in the AChR-specific humoral response and delayed-type hypersensitivity. The effect of anti-CD40L treatment during the chronic phase of EAMG is of particular relevance to human MG, which is a chronic disease. It suggests that antagonizing CD40L can be used for immunotherapy of MG and other antibody-mediated autoimmune diseases.

5. Thromboembolism

CD40-CD40L interactions on T and antigen presenting cells are important for adaptive immune responses, such as B-cell proliferation, immunoglobulin (Ig) production, upregulation of co-stimulatory activity (CD80, CD86), cytokine production, and Ig class-switching. The receptor and ligand are also expressed on platelets (off-target cell population), where CD40 is constitutively found on platelets, while CD40L is expressed on activated platelets and cleaved to sCD40L (>90% of circulating sCD40L is derived from platelets). Feroni et al., *Curr. Med. Chem.* 14: 2170-2180 (2007). At least three anti-CD40L monoclonal antibodies (mAb) caused TE in the clinic and/or nonclinical studies conducted in non-human primates (NHP). hu5c8 (BG9588) caused TE in multiple clinical trials (lupus and renal transplantation). Boumpas et al., *Arthritis & Rheumatism* 48: 719-727 (2003). IDEC131 caused TE in one patient in a Crohn's disease trial, leading to termination of ongoing trials at the time. Sidiropoulus & Boumpas, Lupus 13: 391-397 (2004). Both hu5c8 and ABI1793 (which binds CD40 at a different epitope from 5c8) caused TE/thrombosis in renal transplantation studies in cynomolgus or rhesus monkeys. Schuler et al., *Transplantation* 77: 717-726 (2004); Kanmaz et al., *Transplantation* 77: 914-920 (2004); Koyama et al., Transplantation 77: 460-461 (2004). In a non-published disclosure, Biogen reported a thrombosis incidence of ¼ and 6/12 in rhesus monkeys given 5 and 20 mg/kg weekly, respectively, for 6-months, but not in cynomolgus monkeys given 50 mg/kg at the same frequency and duration. The basis for the species difference is not clear.

Figure 10:
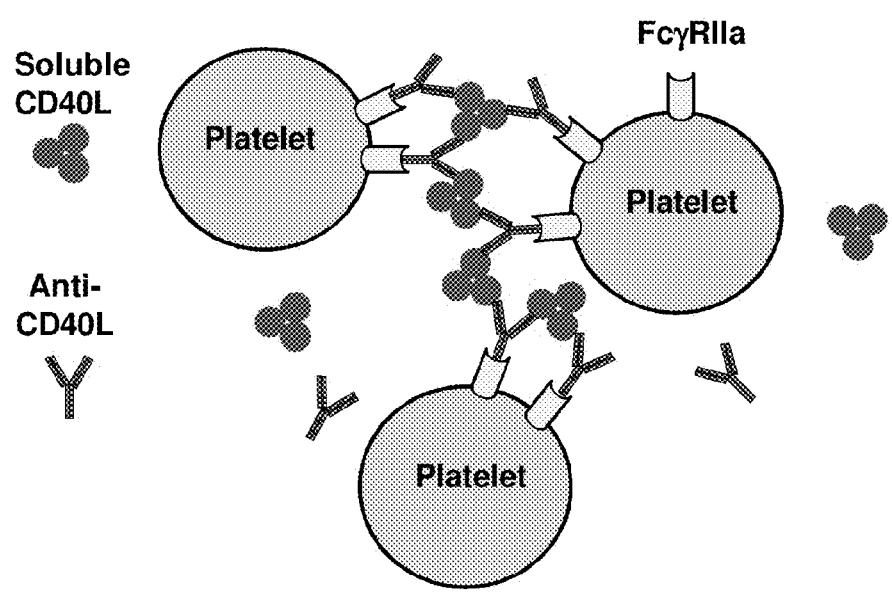
FIG. 10 provides a hypothetic model for anti-CD40 monoclonal antibody-mediated platelet aggregation.

One of the hypotheses is that the TE associated with administration of these antibodies is mediated by anti-CD40Lmab-CD40L immune complex (IC)-mediated cross linking of platelets, facilitated by IC binding to FcgRIIa, an IgG Fc receptor, causing activation and aggregation (FIG. 10). Blocking the interaction of Fc moiety of IgG with FcgRIIa is, therefore, expected to mitigate platelet cross linking and thrombosis. Approaches and methods developed to evaluate the risk for TE/thrombosis are described in Examples below.

EXAMPLES

TABLE 1 lists representative anti-human CD40L VH domain amino acid sequences useful for the disclosed antibody polypeptides. TABLE 2 discloses representative nucleic acids that encode the VH domain sequences listed in TABLE 1. TABLE 3 lists representative anti-human CD40L VK domain amino acid sequences useful for the antibody polypeptides of the present disclosure. TABLE 4 in turn discloses representative nucleic acids that encode the VK domain sequences listed in TABLE 3. As well known in the art, multiple codons can encode the same amino acid. Nucleic acids encoding a protein sequence thus include nucleic acids having codon degeneracy. The antibody polypeptides disclosed in TABLE 1 and TABLE 3 specifically bind CD40L. They were made using the reiterative initial/primary screening and affinity methodologies described in the examples that follow.

TABLE 1

Anti-human CD40L VH Domain Amino Acid Sequences

```
BMS2h-10 (SEQ ID NO: 15)
EVQLLESGGG LVQPGGSLRL SCAASGFTFI AYDMSWVRQA PGKGLEWVSW IDEWGLQTYY
ADSVKGRFTI SRDNSKNTLY LQMNSLRAED TAVYYCAKKT PEE------- FDYWGQGTLV TVSS

BMS2h-11 (SEQ ID NO: 16)
EVQLLESGGG LVQPGGSLRL SCAASGFTFG DYEMSWVRQA PGKGLEWVSG IDGEGSDTYY
ADSVKGRFTI SRDNSKNTLY LQMNSLRAED TAVYYCAKPG RS-------- FDYWGQGTLV TVSS

BMS2h-111 (SEQ ID NO: 17)
EVQLLESGGG LVQPGGSLRL SCAASGFTFE RYPMTWVRQA PGKGLEWVST IHGSGSATYY
ADSVKGRFTI SRDNSKNTLY LQMNSLRAED TAVYYCAKGP YTSRHNSLGH FDYWGQGTLV TVSS

BMS2h-112 (SEQ ID NO: 18)
EVQLLESGGG LVQPGGSLRL SCAASGFTFM DYPMGWVRQA PGKGLEWVSS IGPVGMSTYY
ADSVKGRFTI SRDNSKNTLY LQMNSLRAED TAVYYCAKYG GTSGRHNTK- FDYWGQGTLV TVSS

BMS2h-113 (SEQ ID NO: 19)
EVQLLESGGG LVQPGGSLRL SCAASGFTFT EYPMSWVRQA PGKGLEWVSV ISPLGFTTYY
ADSVKGRFTI SRDNSKNTLY LQMNSLRAED TAVYYCAKWT GGSGILNSS- FDYWGQGTLV TVSS

BMS2h-114 (SEQ ID NO: 20)
EVQLLESGGG LVQPGGSLRL SCAASGFRVS NYDLTWVRQA PGKGLEWVST ISATNGSTYY
ADSVKGRFTI SRDNSKNTLY LQMNSLRAED TAVYYCAAVT WWLLRHNDN- LGFWGQGTLV TVSS

BMS2h-115 (SEQ ID NO: 21)
EVQLLESGGG LVQPGGSLRL SCAASGFSIS YKNMAWVRQA PGKGLEWVSA IKAANGSTYY
ADSVKGRFTI SRDNSKNTLY LQMNSLRAED TAVYYCATGS QKKRTYT--- FDFWGQGTLV TVSS

BMS2h-12 (SEQ ID NO: 22)
EVQLLESGGG LVQPGGSLRL SCAASGFTFR LYEMAWVRQA PGKGLEWVSG IDILGSRTYY
ADSVKGRFTI SRDNSKNTLY LQMNSLRAED TAVYYCAKDL SWQG------ FDYWGQGTLV TVSS

BMS2h-120 (SEQ ID NO: 23)
EVQLLESGGG LVQPGGSLRL SCAASGFTFR SYTMGWVRQA PGKGLEWVSS INPMGYQTYY
ADSVKGRFTI SRDNSKNTLY LQMNSLRAED TAVYYCAKHG VGKGTKPHN FDYWGQGTLV TVSS
```

TABLE 1-continued

Anti-human CD40L VH Domain Amino Acid Sequences

BMS2h-121 (SEQ ID NO: 24)
EVQLLESGGG LVQPGGSLRL SCAASGFTFE LYRMSWVRQA PGKGLEWVSE ISGSGFPTYY
ADSVKGRFTI SRDNSKNTLY LQMNSLRAED TAVYYCAKSL HDKTQHHQE FDYWGQGTLV TVSS

BMS2h-123 (SEQ ID NO: 25)
EVQLLESGGG LVQPGGSLRL SCAASGFTFI EYPMSWVRQA PGKGLEWVSL ISPSGVFTYY
ADSVKGRFTI SRDNSKNTLY LQMNSLRAED TAVYYCAKGD ESST FDYWGQGTLV TVSS

BMS2h-124 (SEQ ID NO: 26)
EVQLLESGGG LVQPGGSLRL SCAASGFTFK RYDMDWVRQA PGKGLEWVST IGSSGYPTYY
ADSVKGRFTI SRDNSKNTLY LQMNSLRAED TAVYYCAERM PGYFPGFARQ FDYWGQGTLV TVSS

BMS2h-125 (SEQ ID NO: 27)
EVQLLESGGG LVQPGGSLRL SCAASGFTFW RYAMGWVRQA PGKGLEWVST INDEGRETYY
ADSVKGRFTI SRDNSKNTLY LQMNSLRAED TAVYYCAKKR VSSSVNAPYE FDYWGQGTLV TVSS

BMS2h-126 (SEQ ID NO: 28)
EVQLLESGGG LVQPGGSLRL SCAASGFTFA NYSMSWVRQA PGKGLEWVSS IDRLGTHTYY
ADSVKGRFTI SRDNSKNTLY LQMNSLRAED TAVYYCAKVL ADLIAGHAE FDYWGQGTLV TVSS

BMS2h-127 (SEQ ID NO: 29)
EVQLLESGGG LVQPGGSLRL SCAASGFTFP SYDMAWVRQA PGKGLEWVSG ISRSGSMTYY
ADSVKGRFTI SRDNSKNTLY LQMNSLRAED TAVYYCAKGV DAHVYYMEPF FDYWGQGTLV TVSS

BMS2h-128 (SEQ ID NO: 30)
EVQLLESGGG LVQPGGSLRL SCAASGFTFE RYQMAWVRQA PGKGLEWVST ISSDGGGTYY
ADSVKGRFTI SRDNSKNTLY LQMNSLRAED TAVYYCAKPG TV FDYWGQGTLV TVSS

BMS2h-129 (SEQ ID NO: 31)
EVQLLESGGG LVQPGGSLRL SCAASGFTFP KYEMAWVRQA PGKGLEWVSS IDGDGKSTYY
ADSVKGRFTI SRDNSKNTLY LQMNSLRAED TAVYYCAKPD QF FDYWGQGTLV TVSS

BMS2h-13 (SEQ ID NO: 32)
EVQLLESGGG LVQPGGSLRL SCAASGFTFS YYSMYWVRQA PGKGLEWVSS ISPFGWGTYY
ADSVKGRFTI SRDNSKDTLY LQMNSLRAED TAVYYCAKYG ETSGPISEN FDYWGQGTLV TVSS

BMS2h-130 (SEQ ID NO: 33)
EVQLLESGGG LVQPGGSLRL SCTASGFTFA GYQMSWVRQA PGKGLEWVSS ITNEGVSTYY
ADSVKGRFTI SRDNSKNTLY LQMNSLRAED TAVYYCAKPG KY FDYWGQGTLV TVSS

BMS2h-131 (SEQ ID NO: 34)
EVQLLESGGG LVQPGGSLRL SCAASGFTFG EYEMVWVRQA PGKGLEWVSS ITSDGLSTYY
ADSVKGRFTI SRDNSKNTLY LQMNSLRAED TAVYYCAKPG IRFDYWGQGTLV TVSS

BMS2h-132 (SEQ ID NO: 35)
EVQLLESGGG LVQPGGSLRL SCAASGFTFA DYDMAWVRQA PGKGLEWVSG IVDDGLMTYY
ADSVKGRFTI SRDNSKNTLY LQMNSLRAED TAVYYCAKPD VAFDYWGQGTLVTVSN

BMS2h-133 (SEQ ID NO: 36)
EVQLLESGGG LVQPGGSLRL SCAASGFTFI GYAMAWVRQA PGKGLEWVSS IGPLGATTYY
ADSVKGRFTI SRDNSKNTLY LQMNSLRAED TAVYYCAKLP AGTSSHSVDFDYWGQGTLV TVSS

BMS2h-134 (SEQ ID NO: 37)
EVQLLESGGG LVQPGGSLRL SCAASGFTFA DYEMTWVRQA PGKGLEWVSS ITSDGVSTYY
ADSVKGRFTI SRDNSKNTLY LQMNSLRAED TAVYYCAKPS VQ FDYWGQGTLV TVSS

BMS2h-135 (SEQ ID NO: 38)
EVQLLESGGG LVQPGGSLRL SCAASGFTFR RYVMGWVRQA PGKGLEWVSW IEADGRTTYY
ADSVKGRFTI SRDNSKNTLY LQMNSLRAED TAVYYCAKGL TDQHVIE FDYWGQGTLV TVSS

BMS2h-136 (SEQ ID NO: 39)
EVQLLESGGG LVQPGGSLRL SCAASGFTFD GYRMGWVRQA PGKGLEWVSS IAPDGNYTYY
ADSVKGRFTI SRDNSKNTLY LQMNSLRAED TAVYYCAKFW GMQFDYWGQGTLV TVSS

BMS2h-137 (SEQ ID NO: 40)
EVQLLESGGG LVQPGGSLRL SCAASGFTFA SYPMGWVRQA PGKGLEWVSS IGPIGFTTYY
ADSVKGRFTI SRDNSKNTLY LQMNSLRAED TAVYYCAEMK SPYKPQ---- FDYWGQGTLV TVSS

BMS2h-138 (SEQ ID NO: 41)
EVQLLESGGG LVQPGGSLRL SCAASGFTFL AYWMWVRQA PGKGLEWVSS ISPSGTHTYY
ADSVKGRFTI SRDNSKNTLY LQMNSLRVED TAVYYCAKYT EPGLGS---- FDYWGQGTLV TVSS

BMS2h-139 (SEQ ID NO: 42)
EVQLLESGGG LVQPGGSLRL SCAASGFTFS NYEMGWVRQA PGKGLEWVSV ISEVGSLTYY
ADSVKGRFTI SRDNSKNTLY LQMNSLRAED TAVYYCAKPH DSSIG----- FDYWGQGTLV TVSS

TABLE 1-continued

Anti-human CD40L VH Domain Amino Acid Sequences

BMS2h-14 (SEQ ID NO: 43)
EVQLLESGGG LVQPGGSLRL SCAASGFTFW SYDMTWVRQA PGKGLEWVSS IMASGDDTYY
ADSVKGRFTI SRDNSKNTLY LQMNSLRAED TAVYYCAKWD RD-------- FDYWGQGTLV TVSS

BMS2h-15 (SEQ ID NO: 44)
EVQLLESGGG LVQPGGSLRL SCAASGFTFE EYVMSWVRQA PGKGLEWVST ISPIGLTTYY
ADSVKGRFTI SRDNSKNTLY LQMNSLRAED TAVYYCAEFP LIILPD---- FDYWGQGTLV TVSS

BMS2h-16 (SEQ ID NO: 45)
EVQLLESGGG LVQPGGSLRL SCAASGFTFM EYAMIWVRQA PGKGLEWVSI ISPLGLSTYY
ADSVKGRFTI SRDNSKNTLY LQMNSLRAED TAVYYCAKYQ DSSDSQYTN- FDYWGQGTLV TVSS

BMS2h-17 (SEQ ID NO: 46)
EVQLLESGGG LVQPGGSLRL SCAASGFTFE DYGMGWARQA PGKGLEWVSS IGPLGLWTYY
ADSAKGRFTI SRDNSKNTLY LQMNSLRAED TAVYYCAKSP LEGLITN--- FDYWGQGTLV TVSS

BMS2h-176 (SEQ ID NO: 47)
EVQLLESGGG LVQPGGSLRL SCAASGFTFD AYEMGWVRQA PGKGLEWVSI IDWDGNSTYY
ADSVKGRFTI SRDNSKNTLY LQMNSLRAED TAVYYCAKPG DNVGI----- FDYWGQGTLV TVSS

BMS2h-177 (SEQ ID NO: 48)
EVQLLESGGG LVQPGGSLRL SCAASGFTFS NYYMVWVRQA PGKGLEWVSA IDEWGFATYY
ADSVKGRFTI SRDNSKNTLY LQMNSLRAED TAVYYCAKHW EFTSDTSR- FDYWGQGTLV TVSS

BMS2h-178 (SEQ ID NO: 49)
EVQLLESGGG LVQPGGSLRL SCAASGFTFE DFDMAWVRQA PGKGLEWVSS INDQGSLTYY
ADSVKGRFTI SRDNSKNTLY LQMNSLRAED TAVYYCAKPD QF-------- FDYWGQGTLV TVSS

BMS2h-179 (SEQ ID NO: 50)
EVQLLESGGG LVQPGGSLRL SCAASGFTFS AYDMMWVRQA PGKGLEWVSR ISPQGQRTYY
ADSVKGRFTI SRDNSKNTLY LQMNSLRAED TAVYYCAKIR GQSRIPMR- FDYWGQGTLV TVSS

BMS2h-18 (SEQ ID NO: 51)
EVQLLESGGG LVQPGGSLRL SCAASGFTFP EYDMTWVRQA PGKGLEWVSY ISSDGYSTYY
ADSVKGRFTI SRDNSKNTLY LQMNSLRAED TAVYYCAKPH GSPRE----- FDYWGQGTLV TVSS

BMS2h-180 (SEQ ID NO: 52)
EVQLLESGGG LVQPGGSLRL SCAASGFTFT DYEMGWVRQA PGKGLEWVST ITSLGESTYY
ADSVKGRFTI SRDNSKNTLY LQMNSLRAED TAVYYCAKPG RI-------- FDYWGQGTLV TVSS

BMS2h-181 (SEQ ID NO: 53)
EVQLLESGGG LVQPGGSLRL SCAASGFTFA FYPMMWVRQA PGKGLEWVSW IDATGTRTYY
ADSVKGRFTI SRDNSKNTLY LQMNSLRAED TAVYYCAEGN YGSSYTMGV- FDYWGQGTLV TVSS

BMS2h-182 (SEQ ID NO: 54)
EVQLLESGGG LVQPGGSLRL SCAASGFTFD EYPMYWVRQA PGKGLEWVSS IGPSGPNTYY
ADSVKGRFTI SRDNSKNTLY LQMNSLRAED TAVYYCAKSP YFDVIPSY- FDYWGQGTLV TVSS

BMS2h-183 (SEQ ID NO: 55)
EVQLLESGGG LVQPGGSLRL SCAASGFTFA DYGMGWVRQA PGKGLEWVSS IQSSGLRTYY
ADSVKGRFTI SRDNSKNTLY LQMNSLRAED TAVYYCAKRA NSRRG----- FDYWGQGTLV TVSS

BMS2h-184 (SEQ ID NO: 56)
EVQLLESGGG LVQPGGSLRL SCAASGFTFS DYEMMWVRQA PGKGLEWVSS ITSHGGSTYY
ADSVKGRFTI SRDNSKNTLY LQMNSLRAED TAVYYCAKPD KD-------- FDYWGQGTLV TVSS

BMS2h-185 (SEQ ID NO: 57)
EVQLLESGGG LVQPGGSLRL SCAASGFTFA HYPMSWVRQA PGKGLEWVSS IGRLGNRTYY
ADSVKGRFTI SRDNSKNTLY LQMNSLRAED TAVYYCAKRA TPVPIKGL- FDYWGQGTLV TVSS

BMS2h-186 (SEQ ID NO: 58)
EVQLLESGGG LVQPGGSLRL SCAASGLTFG RYEMAWVRQA PGKGLEWVSS IDSDGWVTYY
ADSVKGRFTI SRDNSKNTLY LQMNSLRAED TAVYYCAQPD SL-------- FDYWGQGTLV TVSS

BMS2h-187 (SEQ ID NO: 59)
EVQLLESGGG LVQPGGSLRL SCAASGFTFS SYSMVWVRQA PGKGLEWVSG INRGGTRTYY
ADSVKGRFTI SRDNSKNTLY LQMNSLRAED TAVYYCAKGW RRG------- FDYWGQGTLV TVSS

BMS2h-188 (SEQ ID NO: 60)
EVQLLESGGG LVQPGGSLRL SCAASGFTFT RYRMSWVRQA PGKGLEWVSG ISRDGYRTYY
ADSVKGRFTI SRDNSKNTLY LQMNSLRAED TAVYYCAKGM TAS------- FDYWGQGTLV TVSS

BMS2h-189 (SEQ ID NO: 61)
EVQLLESGGG LVQPGGSLRL SCAASGFTFQ MYPMGWVRQA PGKGLEWVSM IEPAGDLTYY
ADSVKGRFTI SRDNSKNTLY LQMNSLRAED TAVYYCAKYQ EQPW------ FDYWGQGTLV TVSS

TABLE 1-continued

Anti-human CD40L VH Domain Amino Acid Sequences

BMS2h-19 (SEQ ID NO: 62)
EVQLLESGGG LVQPGGSLRL SCAASGFPFP QYQMAWVRQA PGKGLEWVSM ITSDGLDTYY
ADSVKGRFTI SRDNSKNTLY LQMNSLRAED TAVYYCAKPE PL-------- FDYWGQGTLV TVSS

BMS2h-190 (SEQ ID NO: 63)
EVQLLESGGG LVQPGGSLRL SCAASGFTFS MYDMHWVRQA PGKGLEWVST ILSDGTDTYY
ADSVKGRFTI SRDNSKNTLY LQMNSLRAED TAVYYCAKYG AM-------- FDYWGQGTLV TVSS

BMS2h-191 (SEQ ID NO: 64)
EVQLLESGGG LVQPGGSLRL SCAASGFTFK LYPMTWVRQA PGKGLEWVSS IDAGGHETYY
ADSVKGRFTI SRDNSKNTLY LQMNSLRAED TAVYYCAKDW WDYL------ FDYWGQGTLV TVSS

BMS2h-192 (SEQ ID NO: 65)
EVQLLESGGG LVQPGGSLRL SCAASGFTFS RYPMSWVRQA PGKGLEWVSS INRSGMRTYY
ADSVKGRFTI SRDNSKNTLY LQMNSLRAED TAVYYCAEGH QAP------- FDYWGQGTLV TVSS

BMS2h-193 (SEQ ID NO: 66)
EVQLLESGGG LVQPGGSLRL SCAASGFTFT GYAMSWVRQA PGKGLEWVST INANGIRTYY
ADSVKGRFTI SRDNSKNTLY LQMNGLRAED TAVYYCAKGG VWRWGTGHK- FDYWGQGTLV TVSS

BMS2h-194 (SEQ ID NO: 67)
EVQLLESGGG LVQPGGSLRL SCAASGFTFK QYDMRWVRQA PGKGLEWVST ISQNGTKTYY
ADSVKGRFTI SRDNSKNTLY LQMNSLRAED TAVYYCAKSR TGRY------ FDYWGQGTLV TVSS

BMS2h-195 (SEQ ID NO: 68)
EVQLLESGGG LVQPGGSLRL SCAASGFTFG TYDMGWVRQA PGKGLEWVSR INWQGDRTYY
ADSVKGRFTI SRDNSKNTLY LQMNSLRAED TAVYYCAKAG FGHYVDGLG- FDYWGQGTLV TVSS

BMS2h-196 (SEQ ID NO: 69)
EVQLLESGGG LVQPGGSLRL SCAASGFTFS GYEMAWVRQA PGKGLEWVSS ITDMGDSTYY
ADSVKGRFTI SRDNSKNTLY LQMNSLRAED TAVYYCAKPG TA-------- FDYWGPGTLV TVSS

BMS2h-197 (SEQ ID NO: 70)
EVQLLESGGG LVQPGGSLRL SCAASGFTFA KYKMWWVRQA PGKGLEWVSS ITPKGHSTYY
ADSVKGRFTI SRDNSKNTLY LQMNSLRAED TAVYYCAKRP MTP------- FDYWGQGTLV TVSS

BMS2h-198 (SEQ ID NO: 71)
EVQLLESGGG LVQPGGSLRL SCAASGFTFE RYNMSWVRQA PGKGLEWVSS IRPRGGKTYY
ADSVKGRFTI SRDNSKNTLY LQMNSLRAED TAVYYCAKWR REGYTGSK-FDYWGQGTLV TVSS

BMS2h-199 (SEQ ID NO: 72)
EVQLLESGGG LVQPGGSLRL SCAASGFTFE RYGMTWVRQA PGKGLEWVSS IWPRGQKTYY
ADSVKGRFTI SRDNSKNTLY LQMNSLRAED TAVYYCAKGN SRYV------ FDYWGQGTLV TVSS

BMS2h-2 (SEQ ID NO: 73)
EVQLLESGGG LVQPGGSLRL SCAASGFTFS DYEMMWVRQA PGKGLEWVST ITSDGISTYY
ADSVKGRFTI FRDNSKNTLY LQMNSLRAED TAVYYCAKSG RF-------- FDYWGQGTLV TVSS

BMS2h-20 (SEQ ID NO: 74)
EVQLLESGGG LVQPGGSLRL SCAASGFTFS GYQMAWVRQA PGKGLEWVSG ISSEGLTTYY
ADSVKGRFTI SRDNSKNTLY LQMNSLRAED TAVYYCAKLG RR-------- FDYWGQGTLV TVSS

BMS2h-200 (SEQ ID NO: 75)
EVQLLESGGG LVQPGGSLRL SCAASGFTFT NYSMGWVRQA PGKGLEWVST IRPNGTKTYY
ADSVKGRFTI SRDNSKNTLY LQMNSLRAED TAVYYCAKRS SAHLQR---- FDYWGQGTLV TVSS

BMS2h-201 (SEQ ID NO: 76)
EVQLLESGGG LVQPGGSLRL SCAASGFTFG NYSMGWVRQA PGKGLEWVSS IGRHGGRTYY
ADSVKGRFTI SRDNSKNTLY LQMNSLRAED TAVYYCAKKG STYPR----- FDYWGQGTLV TVSS

BMS2h-202 (SEQ ID NO: 77)
EVQLLESGGG LVQPGGSLRL SCTASGFTFS HYEMGWVRQA PGKGLEWVSS IEPFGGGTYY
ADSVKGRFTI SRDNSKNTLY LQMNSLRAED TAVYYCAKVY PQGS------ FDYWGQGTLV TVSS

BMS2h-203 (SEQ ID NO: 78)
EVQLLESGGG LVQPGGSLRL SCAASGFTFS NYTMGWVRQA PGKGLEWVSS IRPDGKITYY
ADSVKGRFTI SRDNSKNTLY LQMNSLRAED TAVYYCAEVY SSCAMCTPLL FDYWGQGTLV TVSS

BMS2h-204 (SEQ ID NO: 79)
EVQLLESGGG LVQPGGSLRL SCAASGFTFK RYSMAWVRQA PGKGLEWVSD IGPRGFSTYY
ADSVKGRFTI SRDNSKNTLY LQMNSLRAED TAVYYCAKVG RGQRDTSQP- FDYWGQGTLV TVSS

BMS2h-205 (SEQ ID NO: 80)
EVQLLESGGG LVQPGGSLRL SCAASGFTFA SYQMAWVRQA PGKGLEWVSG ITSGGLSTYY
ADSVKGRFTI SRDNSKNTLY LQMNSLRAED TAVYYCAKPG RG-------- FDYWGQGTLV TVSS

TABLE 1-continued

Anti-human CD40L VH Domain Amino Acid Sequences

BMS2h-206 (SEQ ID NO: 81)
EVQLLESGGG LVQPGGSLRL SCAASGFTFA SYEMTWVRQA PGKGLEWVSG ISSDGLSTYY
ADSVKGRFTI SRDNSKNTLY LQMNSLRAED TAVYYCAKPG VL-------- FDYWGQGTLV TVSS

BMS2h-207 (SEQ ID NO: 82)
EVQLLESGGG LVQPGGSLRL SCAASGFTFD KYLMSWVRQA PGKGLEWVSG IEPLGDVTYY
ADSVKGRFTI SRDNSKNTLY LQMNSLRAED TAVYYCAKEA SGD------- FDYWGQGTLV TVSS

BMS2h-208 (SEQ ID NO: 83)
EVQLLESGGG LVQPGGSLRL SCAASGFTFT EYEMSWVRQA PGKGLEWVSS IDNVGSSTYY
ADSVKGRFTI SRDNSKNTLY LQMNSLRAED TAVYYCAKPG KL-------- FDYWGQGTLV TVSS

BMS2h-209 (SEQ ID NO: 84)
EVQLLESGGG LVQPGGSLRL SCAASGFTFA DYEMWWVRQA PGKGLEWVSA ISRQGFATYY
ADSVKGRFTI SRDNSKNTLY LQMNSLRAED TAVYYCAKDL ERDD------ FDYWGQGTLV TVSS

BMS2h-21 (SEQ ID NO: 85)
EVQLLESGGG LVQPGGSLRL SCAASGFTFA NYEMGWARQA PGKGLEWVSV ISEWGYSTYY
ADSAKGRFTI SRDNSKNTLY LQMNSLRAED TAVYYCAKLV GGTQYE---- FDYWGQGTLV TVSS

BMS2h-22 (SEQ ID NO: 86)
EVQLLESGGG LVQPGGSLRL SCAASGFTFH NYEMSWVRQA PGKGLEWVSS ISSGGSSTYY
ADSVKGRFTI SRDNSKNTLY LQMNSLRAED TAVYYCAKPG VK-------- FDYWGQGTLV TVSS

BMS2h-23 (SEQ ID NO: 87)
EVQLLESGGG LVQPGGSLRL SCAASGFTFG LYEMTWVRQA PGKGLEWVSS ITGDGISTYY
ADSVKGRFTI SRDNSRNTLY LQMNSLRAED TAVYYCAKAG RK-------- FDYWGQGTLV TVSS

BMS2h-24 (SEQ ID NO: 88)
EVQLLESGGG LVQPGGSLRL SCAASGFTFS NYQMAWVRQA PGKGLEWVSS ITSEGGSTYY
ADSVKGRFTI SRDNSKNTLY LQMNSLRAED TAVYYCAKPG KN-------- FDYWGQGTLV TVSS

BMS2h-24-1 (SEQ ID NO: 89)
EVQLLESGGG LVQPGGSLRL SCAASGFTFS DYQMAWVRQA PGKGLEWVSS ITSEGGSTYY
ADSVKGRFTI SRDNSKNTVY LQMNSLRAED TAVYYCAKPG KN-------- FDYWGQGTLV TVSS

BMS2h-25 (SEQ ID NO: 90)
EVQLLESGGG LVQPGGSLRL SCAASGFTFD NYEMTWVRQA PGKGLEWVST ITSQGTSTYY
ADSVKGRFTI SRDNSKNTLY LQMNSLRAED TAVYYCAKPD RS-------- FDYWGQGTLV TVSS

BMS2h-26 (SEQ ID NO: 91)
EVQLLESGGG LVQPGGSLRL SCAASGFTFR SYEMTWVRQA PGKGLEWVSS ITSDGGTTYY
ADSVKGRFTI SRDNSKNTLY LQMNSLRAED TAVYYCAKPD KT-------- FDYWGQGTLV TVSS

BMS2h-27 (SEQ ID NO: 92)
EVQLLESGGG LVQPGGSLRL SCAASGFTFN LYEMTWVRQA PGKGLEWVSS ITSDGVSTYY
ADSVKGRFTI SRDNSKNTLY LQMNSLRAED TAVYYCAKPD SP-------- FDYWGQGTLV TVSS

BMS2h-28 (SEQ ID NO: 93)
EVQLLESGGG LVQPGGSLRL SCAASGFTFG HYDMAWVRQA PGKGLEWVST ISDNGNGTYY
ADSVKGRFTI SRDNSKNTLY LQMNSLRAED TAVYYCAKPG RD-------- FDYWGQGTLV TVSS

BMS2h-29 (SEQ ID NO: 94)
EVQLLESGGG LVQPGGSLRL SCAASGFTFG RYQMAWVRQA PGKGLEWVSS ISSDGGGTYY
ADSVKGRFTI SRDNSKNTLY LQMNSLRAED TAVYYCAKPG RA-------- FDYWGQGTLV TVSS

BMS2h-30 (SEQ ID NO: 95)
EVQLLESGGG LVQPGGSLRL SCAASGFTFA RYQMAWVRQA PGKGLEWVST ISDDGDSTYY
ADSVKGRFTI SRDNSKNTLY LQMNSLRAED TAVYYCAKLD KL-------- FDYWGQGTLV TVSS

BMS2h-300 (SEQ ID NO: 96)
EVQLLESGGG LVQPGGSLRL SCAASGFTFD NDEMTWVRQA PGKGLEWVSA IDTTGGQTYY
ADSVKGRFTI SRDNSKNTLY LQMNSLRAED TAVYYCAKPG KE-------- FDYWGQGTLV TVSS

BMS2h-301 (SEQ ID NO: 97)
EVQLLESGGG LVQPGGSLRL SCAASGFTFG ESEMSWVRQA PGKGLEWVSS ILDEGSGTYY
ADSVKGRFTI SRDNSKNTLY LQMNSLRAED TAVYYCAKPD KD-------- FDYWGQGTLV TVSS

BMS2h-302 (SEQ ID NO: 98)
EVQLLESGGG LVQPGGSLRL SCAASGFTFG EEEMSWVRQA PGKGLEWVSA ITDDGDDTYY
ADSVKGRFTI SRDNSKNTLY LQMNSLRAED TAVYYCAKPN AGA------- FDYWGQGTLV TVSS

BMS2h-303 (SEQ ID NO: 99)
EVQLLESGGG LVQPGGSLRL SCAASGFTFE VYDMAWVRQA PGKGLEWVSG IVNDGSSTYY
ADSVKGRFTI SRDNSKNTLY LQMNSLRAED TAVYYCAKPD KD-------- FDYWGQGTLV TVSS

TABLE 1-continued

Anti-human CD40L VH Domain Amino Acid Sequences

```
BMS2h-304 (SEQ ID NO: 100)
EVQLLESGGG LVQPGGSLRL SCAASGFTFG NTEMTWVRQA PGKGLEWVSS IADDGSSTYY
ADSVKGRFTI SRDNSKNTLY LQMNSLRAED TAVYYCAKPG QA-------- FDYWGQGTLV TVSS

BMS2h-31 (SEQ ID NO: 101)
EVQLLESGGG LVQPGGSLRL SCAASGFTFE EYQMAWVRQA PGKGLEWVST ISDDGSSTYY
ADSVKGRFTI SRDNSKNTLY LQMNSLRAED TAVYYCAKPD LY-------- FDYWGQGTLV TVSS

BMS2h-32 (SEQ ID NO: 102)
EVQLLESGGG LVQPGGSLRL SCAASGFTFE VYQMGWVRQA PGKGLEWVSF IVPGGDLTYY
ADSVKGRFTI SRDNSKNTLY LQMNSLRAED TAVYYCAETW PE-------- FDYWGQGTLV TVSS

BMS2h-4 (SEQ ID NO: 103)
EVQLLESGGG LVQPGGSLRL SCAASGFTFD NYEMTWVRQA PGKGLEWVSS ITSDGTSTYY
ADSVKGRFTI SRDNSKNTLY LQMNSLRAED TAVYYCAKPN PP-------- FDYWGQGTLV TVSS

BMS2h-40 (SEQ ID NO: 104)
EVQLLESGGG LVQPGGSLRL SCAASGFTFK AYDMGWVRQA PGKGLEWVSQ IGRDGSFTYY
ADSVKGRFTI SRDNSKNTLY LQMNSLRAED TAVYYCAKPR RYAIF----- TFDRGQGTLV TVSS

BMS2h-400 (SEQ ID NO: 105)
EVQLLESGGG LVQPGGSLRL SCAASGFTFK QYPMVWVRQA PGKGLEWVST ISTNGVRTYY
ADSVKGRFTI SRDNSKNTLY LQMNSLRAED TAVYYCAKWT DIISSSE--- FDYWGQGTLV TVSS

BMS2h-401 (SEQ ID NO: 106)
EVQLLESGGG LVQPGGSLRL SCAASGFTFF NYDMSWVRQA PGKGLEWVSA ISGSGGSTYY
ADSVKGRFTI SRDNSKNTLY LQMNSLRAED TAVYYCAKVF VWSADIDFD- FDYWGQGTLV TVSS

BMS2h-402 (SEQ ID NO: 107)
EVQLLESGGG LVQPGGSLRL SCAASGFTFS WYDMSWVRQA PGKGLEWVSH IASWGGKTYY
ADSVKGRFTI SRDNSKNTLY LQMNSLRAED TAVYYCAKVT VKDGGYLMD- FDYWGQGTLV TVSS

BMS2h-403 (SEQ ID NO: 108)
EVQLLESGGG LVQPGGSLRL SCAASGFTFA EYAMAWVRQA PGKGLEWVSS IGRDGAVTYY
ADSVKGRFTI SRDNSKNTLY LQMNSLRAED TAVYYCAKWK AAKERGSW-FDYWGQGTLV TVSS

BMS2h-404 (SEQ ID NO: 109)
EVQLLESGGG LVQPGGSLRL SCAASGFTFQ AYQMQWVRQA PGKGLEWVST ISPNGLFTYY
ADSVKGRFTI SRDNSKNTLY LQMNSLRAED TAVYYCAKWL SS-------- FDYWGQGTLV TVSS

BMS2h-407 (SEQ ID NO: 110)
EVQLLESGGG LVQPGGSLRL SCAASGFTFA MYSMAWVRQA PGKGLEWVSG ISPRGVETYY
ADSVKGRFTI SRDNSKNTLY LQMNSLRAED TAVYYCAKTN WNGVDL---- FDYWGQGTLV TVSS

BMS2h-408 (SEQ ID NO: 111)
EVQLLESGGG LVQPGGSLRL SCAASGFTFP TYMMSWVRQA PGKGLEWVST INTNGRDTYY
ADSVKGRFTI SRDNSKNTLY LQMNSLRAED TAVYYCAKGD SNMSF----- FDYWGQGTLV TVSS

BMS2h-409 (SEQ ID NO: 112)
EVQLLESGGG LVQPGGSLRL SCAASGFTFE GYSMTWVRQA PGKGLEWVSS INASGTLTYY
ADSVKGRFTI SRDNSKNTLY LQMNSLRAED TAVYYCAKDG NRSEVF---- FDYWGQGTLV TVSS

BMS2h-41 (SEQ ID NO: 113)
EVQLLESGGG LVQPGGSLRL SCAASGFTFF EYEMTWVRQA PGKGLEWVSS IANDGSTTYY
ADSVKGRFTI SRDNSKNTLY LQMNSLRAED TAVYYCAKPD RQ-------- FDYWGQGTLV TVSS

BMS2h-410 (SEQ ID NO: 114)
EVQLLESGGG LVQPGGSLRL SCAASGFTFQ DYLMAWVRQA PGKGLEWVSE INQDGTVTYY
ADSVKGRFTI SRDNSKNTLY LQMNSLRAED TAVYYCAESS PY-------- FDYWGQGTLV TVSS

BMS2h-411 (SEQ ID NO: 115)
EVQLLESGGG LVQPGGSLRL SCAASGFTFD NYAMSWVRQA PGKGLEWVSS ISRDGHVTYY
ADSVKGRFTI SRDNSKNTLY LQMNSLRAED TAVYYCAKLS SKGGTFASS- FDYWGQGTLV TVSS

BMS2h-412 (SEQ ID NO: 116)
EVQLLESGGG LVQPGGSLRL SCAASGFTFS AVPMTWVRQA PGKGLEWVSA ITDDGLRTYY
ADSVKGRFTI SRDNSKNTLY LQMNSLRAED TAVYYCAKGH IYGDY----- FDYWGQGTLV TVSS

BMS2h-413 (SEQ ID NO: 117)
EVQLLESGGG LVQPGGSLRL SCAASGFTFE LYRMMWVRQA PGKGLEWVSA ISSDGDTTYY
ADSVKGRFTI SRDNSKNTLY LQMNSLRAED TAVYYCAEHW LGTTLSLRD- FDYWGQGTLV TVSS

BMS2h-414 (SEQ ID NO: 118)
EVQLLESGGG LVQPGGSLRL SCAASGFTFY RYTMAWVRQA PGKGLEWVSQ ISPRGNITYY
ADSVKGRFTI SRDNSKNTLY LQMNSLRAED TAVYYCAKSG VAGAESPEY- FDYWGQGTLV TVSS
```

TABLE 1-continued

Anti-human CD40L VH Domain Amino Acid Sequences

BMS2h-415 (SEQ ID NO: 119)
EVQLLESGGG LVQPGGSLRL SCAASGFTFL GYYMSWIRQA PGKGLEWVST IGPIGGGTYY
ADSVKGRFTI SRDNSKNTLY LQMNSLRAED TAVYYCAKSQ NIYGP----- FDYWGQGTLV TVSS

BMS2h-416 (SEQ ID NO: 120)
EVQLLESGGG LVQPGGSLRL SCAASGFTFE QYDMAWVRQA PGKGLEWVSE ISRDGGRTYY
ADSVKGRFTI SRDNSKNTLY LQMNSLRAED TAVYYCAEEY PY-------- FDYWGQGTLV TVSS

BMS2h-417 (SEQ ID NO: 121)
EVQLLESGGG LVQPGGSLRL SCAASGFTFP QYSMVWVRQA PGKGLEWVST ISPLGSSTYY
ADSVKGRFTI SRDNSKNTLY LQMNSLRAED TAVYYCAKMS KLLLSRE--- FDYWGQGTLV TVSS

BMS2h-418 (SEQ ID NO: 122)
EVQLLESGGG LVQPGGSLRL SCAASGFTFA MYSMAWVRQA PGKGLEWVSG ISPRGVETYY
ADSVKGRFTI SRDNSKNTLY LQMNSLRAED TAVYYCAKTN WNGVDL---- FDYWGQGTLV TVSS

BMS2h-419 (SEQ ID NO: 123)
EVQLLESGGG LVQPGGSLRL SCAASGFTFT RHGMAWVRQA PGKGLEWVST ITPTGNTTYY
ADSVKGRFTI SRDNSKNTLY LQMNSLRAED TAVYYCAKDA HDEGY----- FDYWGQGTLV TVSS

BMS2h-42 (SEQ ID NO: 124)
EVQLLESGGG LVQPGGSLRL SCAASGFTFG PYEMTWVRQA PGKGLEWVSS IVGDGLDTYY
ADSVKGRFTI SRDNSKNTLY LQMNSLRAED TAVYYCAKPD RV-------- FDYWGQGTLV TVSS

BMS2h-420 (SEQ ID NO: 125)
EVQLLESGGG LVQPGGSLRL SCAASGFTFG STPMMWVRQA PGKGLEWVSE IRDTGLATYY
ADSVKGRFTI SRDNSKNTLY LQMNSLRAED TAVYYCASVS ---------- FDYWGQGTLV TVSS

BMS2h-421 (SEQ ID NO: 126)
EVQLLESGGG LVQPGGSLRL SCAASGFTFH LGDMHWVRQA PGKGLEWVSS ISGTGHTTYY
ADSVKGRFTI SRDNSKNTLY LQMNSLRAED TAVYYCAKPM NDQG------ FDYWGQGTLV TVSS

BMS2h-422 (SEQ ID NO: 127)
EVQLLESGGG LVQPGGSLRL SCAASGFTFM DEDMLWVRQA PGKGLEWVSR INSLGTHTYY
ADSVKGRFTI SRDNSKNTLY LQMNSLRAED TAVYYCAKSF MM-------- FDYWGQGTLV TVSS

BMS2h-423 (SEQ ID NO: 128)
EVQLLESGGG LVQPGGSLRL SCAASGFTFR NYQMHWVRQA PGKGLEWVSG IDATGRATYY
ADSVKGRFTI SRDNSKNTLY LQMNSLRAED TAVYYCARST RS-------- FDYWGQGTLV TVSS

BMS2h-424 (SEQ ID NO: 129)
EVQLLESGGG LVQPGGSLRL SCAASGFTFT NADMVWVRQA PGKGLEWVSS ISGSGGSTYY
ADSVKGRFTI SRDNSKNTLY LQMNSLRAED TAVYYCAKGY LTSH------ FDYWGQGTLV TVSS

BMS2h-425 (SEQ ID NO: 130)
EVQLLESGGG LVQPGGSLRL SCAASGFTFR DYSMAWVRQA PGKGLEWVST ITPSGLTTYY
ADSVKGRFTI SRDNSKNTLY LQMNSLRAED TAVYYCAEWS QAVTRS---- FDYWGQGTLV TVSS

BMS2h-426 (SEQ ID NO: 131)
EVQLLESGGD LVQPGGSLRL SCAASGFTFS DEGMMWVRQA PGKGLEWVSE INQQGSATYY
ADSVKGRFTI SRDNSKNTLY LQMNSLRAED TAVYYCAKTI GM-------- FDYWGQGTLV TVSS

BMS2h-427 (SEQ ID NO: 132)
EVQLLESGGG LVQPGGSLRL SCAASGFTFT DQPMVWVRQA PGKGLEWVSS IGARGGPTYY
ADSVKGRFTV SRDNSKNTLY LQMNSLRAED TAVYYCAKWF DIIAWDPFS- FDYWGQGTLV TVSS

BMS2h-428 (SEQ ID NO: 133)
EVQLLESGGG LVQPGGSLRL SCAASGFTFN QYPMMWVRQA PGKGLEWVSS ITPSGFLTYY
ADSVKGRFTI SRDNSKNTLY LQMNSLRAED TAVYYCAEWN PFITT----- FDYWGQGTLV TVSS

BMS2h-429 (SEQ ID NO: 134)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKFD YSLR------ FDYWGQGTLV TVSS

BMS2h-43 (SEQ ID NO: 135)
EVQLLESGGG LVQPGGSLRL SCAASGFTFA SYEMAWVRQA PGKGLEWVSS IGSDGGPTYY
ADSVKGRFTI SRDNSKNTLY LQMNSLRAED SAVYYCAKPD RA-------- FDYWGQGTLV TVSS

BMS2h-430 (SEQ ID NO: 136)
EVQLLESGGG LVQPGGSLRL SCAASGFTFS AEQMTWARQA PGKGLEWVST ITPHGDSTYY
ADSVKGRFTI SRDNSKNTLY LQMNSLRAED TAVYYCAKWR TLVDWPTSES FDYWGQGTLV TVSS

BMS2h-44 (SEQ ID NO: 137)
EVQLLESGGG LVQPGGSLRL SCAASGFTFT SYEMGWVRQA PGKGLEWVSS IEPTGITTYY
ADSVKGRFTI SRDNSKNTLY LQMNSLRAED TAVYYCAKPH FTELG----- FDYWGQGTLV TVSS

TABLE 1-continued

Anti-human CD40L VH Domain Amino Acid Sequences

```
BMS2h-449 (SEQ ID NO: 138)
EVQLLESGGG LVQPGGSLRL SCAASGFTFE GEQMAWVRQA PGKGLEWVST ITLPGPYTFY
ADSVKGRFTI SRDNSKNTLY LQMNSLRAED TAVYYCAKGN GTF------- FDYWGQGTLV TVSS

BMS2h-45 (SEQ ID NO: 139)
EVQLLESGGG LVQPGGSLRL SCAASGFTFG NYAMAWVRQA PGKGLEWVSK IGAQGLHTYY
AGSVKGRFTI SRDNSKNTLY LQMNSLRAED TAVYYCAKQT TMDYER---- FDYWGQGTLV TVSS

BMS2h-450 (SEQ ID NO: 140)
EVQLLESGGG LVQPGGSLRL SCAASGFTFD EVDMSWVRQA PGKGLEWVSA IGNNGLKTYY
ADSVKGRFTI SRDNSKNTLY LQMNSLRAED TAVYYCAKSA LSYRPPV--- FDYWGQGTLV TVSS

BMS2h-451 (SEQ ID NO: 141)
EVQLLESGGG LVQPGGSLRL SCAASGFTFQ DDTMSWVRQA PGKGLEWVST ITLKGPSTYY
ADSVKGRFTI SRDNSKNTLY LQMNSLRAED TAVYYCAKSR DGLY------ FDYWGQGTLV TVSS

BMS2h-452 (SEQ ID NO: 142)
EVQLLESGGG LVQPGGSLRL SCAASGFTFA SSPMAWVRQA PGKGLEWVSS IGRDGSTTYY
ADSVKGRFTI SRDNSKNTLY LQMNSLRAED TAVYYCAKPS PYRR------ FDYWGQGTLV TVSS

BMS2h-453 (SEQ ID NO: 143)
EVQLLESGGG LVQPGGSLRL SCAASGFTFT DYSMVWVRQA PGKGLEWVST IVSHGGTTYY
ADSVKGRFTI SRDNSKNTLY LQMNSLRAED TAVYYCAKGK GYNAQY---- FDYWGQGTLV TVSS

BMS2h-454 (SEQ ID NO: 144)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKFD YSLR------ FDYWGQGTLV TVSS

BMS2h-455 (SEQ ID NO: 145)
EVQLLESGGG LVQPGGSLRL SCAASGFTFN DYDMIWVRQA PGKGLEWVST ISSHGDSTYY
ADSVKGRFTI SRDNSKNTLY LQMNSLRAED TAVYYCAKGD VF-------- FDYWGQGTLV TVSS

BMS2h-456 (SEQ ID NO: 146)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAEWS DS-------- FDYRGQGTLV TVSS

BMS2h-457 (SEQ ID NO: 147)
EVQLLESGGG LVQPGGSLRL SCAASGFTFA DYEMAWVRQA PGKGLEWVSG IQSNGNITYY
ADSVKGRFTI SRDNSKNTLY LQMNSLRAED TAVYYCAKAN SQVEY----- FDYWGQGTLV TVSS

BMS2h-458 (SEQ ID NO: 148)
EVQLLESGGG LVQPGGSLRL SCAASGFTFG VEPMSWVRQA PGKGLEWVSN IGRDGSMTYY
ADSVKGRFTI SRDNSKNTLY LQMNSLRAED TAVYYCAKLG KHGT------ FDYWGQGTLV TVSS

BMS2h-459 (SEQ ID NO: 149)
EVQLLESGGG LVQPGGSLRL SCAASGFTFP EYRMMWVRQA PGKGLEWVSW IDERGSLTYY
ADSVKGRFTI SRDNSKNTLY LQMNSLRAED TAVYYCAKRR KGTKQ----- FDYWGQGTLV TVSS

BMS2h-46 (SEQ ID NO: 150)
EVQLLESGGG LVQPGGSLRL SCAASGFTFE LYAMAWVRQA PGKGLEWVSG IGAVGETTYY
ADSVKGRFTI SRDNSKNTLY LQMNSLRAED TAVYYCAKEA NNLSDNLV-FDYWGQGTLV TVSS

BMS2h-460 (SEQ ID NO: 151)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKWS VEW------- FDYWGQGTLV TVSS

BMS2h-461 (SEQ ID NO: 152)
EVQLLESGGG LVQPGGSLRL SCAASGFTFN SYTMNWVRQA PGKGLEWVSS INPWGSRTYY
ADSVKGRFTI SRDNSKNTLY LQMNSLRAED TAVYYCAKGL VL-------- FDYWGQGTLV TVSS

BMS2h-462 (SEQ ID NO: 153)
EVQLLESGGG LVQPGGSLRL SCAASGFTFD GDMMSWVRQA PGKGLEWVSS ITQLGSRTYY
ADSVKGRFTI SRDNSKNTLY LQMNSLRAED TAVYYCAKQN WRTLT----- FDYWGQGTLV TVSS

BMS2h-463 (SEQ ID NO: 154)
EVQLLESGGG LVQPGGSLRL SCAASGFTFN AYGMMWVRQA PGKGLEWVSS ILSDGVITYY
ADSVKGRFTI SRDNSKNTLY LQMNSLRAED TAVYYCAKSA RGANF----- FDYWGQGTLV TVSS

BMS2h-464 (SEQ ID NO: 155)
EVQLLESGGG LVQPGGSLRL SCAASGFTFG HYMMVWVRQA PGKGLEWVSS ITPHGTSTYY
ADSVKGRFTI SRDNSKNTLY LQMNSLRAED TAVYYCAEFN AIFSEA---- FDYWGQGTLV TVSS

BMS2h-465 (SEQ ID NO: 156)
EVQLLESGGG LVQPGGSLRL SCAASGFTFR DYSMAWVRQA PGKGLEWVST ITPSGLTTYY
ADSVKGRFTI SRDNSKNTLY LQMNSLRAED TAVYYCAEWS QAVTRS---- FDYWGQGTLV TVSS
```

TABLE 1-continued

Anti-human CD40L VH Domain Amino Acid Sequences

BMS2h-466 (SEQ ID NO: 157)
EVQLLESGGG LVQPGGSLRL SCAASGFTFD LYAMAWVRQA PGKGLEWVSM IGRDGRFTYY
ADSVKGRFTI SRDNSKNTLY LQMNSLRAED TAVYYCAKLA GSLRGR---- FDYWGQGTLV TVSS

BMS2h-467 (SEQ ID NO: 158)
EVQLLESGGG LVQPGGSLRL SCAASGFTFN KASMGWVRQA PGKGLEWVST ITPHGSSTYY
ADSVKGRFTI SRDNSKNTLY LQMNSLRAED TAVYYCAKQR WGVE------ FDYWGQGTLV TVSS

BMS2h-468 (SEQ ID NO: 159)
EVQLLESGGG LVQPGGSLRL SCAASGFTFQ GYSMGWVRQA PGKGLEWVSS IAGRGGVTYY
ADSVKGRFTI SRDNSKNTLY LQMNSLRAED TAVYYCAKGL YIYHSL---- FDYWGQGTLV TVSS

BMS2h-469 (SEQ ID NO: 160)
EVQLLESGGG LVQPGGSLRL SCAASGFTFP GMEMSWVRQA PGKGLEWVSA ITGTGSTTYY
ADSVKGRFTI SRDNSKNTLY LQMNSLRAED TAVYYCAKGY HP-------- FDYWGQGTLV TVSS

BMS2h-470 (SEQ ID NO: 161)
EVQLLESGGG LVQPGGSLRL SCAASGFTFP MVAMSWVRQA PGKGLEWVSS IARDGNVTYY
ADSVKGRFTI SRDNSKNTLY LQMNSLRAED AAVYYCAKVS PTG------- FDYWGQGTLV TVSS

BMS2h-471 (SEQ ID NO: 162)
EVQLLESGGG LVQPGGSLRL SCAASGFTFG HQDMSWVRQA PGKGLEWVSG ITDDGESTYY
ADSVKGRFTI SRDNSKNTLY LQMNSLRAED TAVYYCAKGD YD-------- FDYWGQGTLV
TVSS

BMS2h-472 (SEQ ID NO: 163)
EVQLLESGGG LVQPGGSLRL SCAASGFTFG EYNMMWVRQA PGKGLEWVSQ ITRDGSRTYY
ADSVRGRFTI SRDNSRNTLY LQMNSLRAED SAVYYCAKLS NIG------- FDYWGQGTLV TVSS

BMS2h-473 (SEQ ID NO: 164)
EVQLLESGGG LVQPGGSLRL SCAASGFTFS DYSMIWARQA PGKGLEWVSS ITPYGSYTYY
ADSVKGRFTI SRDNSKNTLY LQMNSLRAED TAVYYCAKTD YL-------- FDYWGQGTLV TVSS

BMS2h-474 (SEQ ID NO: 165)
EVQLLESGGG LVQPGGSLRL SCAASGFTFD TYSMMWVRQA PGKGLEWVST ITPYGSSTYY
ADSVKGRFTI SRDNSKNTLY LQMNSLRAED TAVYYCAKWG LV-------- FDYWGQGTLV TVSS

BMS2h-475 (SEQ ID NO: 166)
EVQLLESGGG LVQPGGSLRL SCAASGFTFT TGPMMWVRQA PGKGLEWVSA IGIGGDTTYY
ADSVKGRFTI SRDNSKNTLY LQMNSLRAED TAVYYCAKLT PSNQ------ FDYWGQGTLV TVSS

BMS2h-476 (SEQ ID NO: 167)
EVQLLESGGG LVQPGGSLRL SCAASGFTFK QYQMMWVRQA PGKGLEWVSS ITPSGFLTYY
ADSVKGRFTI SRDNSKNTLY LQMNSLRAED TAVYYCAEWN PFIST----- FDYWGQGTLV TVSS

BMS2h-477 (SEQ ID NO: 168)
EVQLLESGGG LVQPGGSLRL SCAASGFTFP NYDMVWVRQA PGKGLEWVSS ISALGNVTYY
ADSVKGRFTI SRDNSKNTLY LQTNSLRAED TAVYYCAKWR SAITGN----
FDYWGQGTLV TVSS

BMS2h-478 (SEQ ID NO: 169)
EVQLLESGGG LVQPGGSLRL SCAASGFTFK EYQMSWVRQA PGKGLEWVST ISPSGMNTYY
ADSVKGRFTI SRDNSKNTLY LQMNSLRAED TAVYYCAEWR SVVRPWPGV- FDYWGQGTLV TVSS

BMS2h-479 (SEQ ID NO: 170)
EVQLLESGGG LVQPGGSLRL SCAASGFTFD DESMAWVRQA PGKGLEWVSS ITPHGTFTYY
ADSVKGRFTI SRDNSKNTLY LQMNSLRAED TAVYYCAKLH LKLYESH--- FDYWGQGTLV TVSS

BMS2h-480 (SEQ ID NO: 171)
EVQLLESGGG LVQPGGSLRL SCAASGFTFE GGEMGWVRQA PGKGLEWVSM IPMDGSATYY
ADSVKGRFTI SRDNSKNTLY LQMNSLRAED TAVYYCAKAG ST-------- FDYWGQGTLV TVSS

BMS2h-481 (SEQ ID NO: 172)
EVQLLESGGG LVQPGGSLRL SCAASGFTFD FMPMAWVRQA PGKGLEWVSS IGRDGAYTYY
ADSVKGRFTI SRDNSKNTLY LQMNSLRAED TAVYYCAKLA SPAQ------ FDYWGQGTLV TVSS

BMS2h-482 (SEQ ID NO: 173)
EVQLLESGGG LVQPGGSLRL SCAASGFTFG DEPMLWVRQA PGKGLEWVSS IGGTGTTTYY
ADSVKGRFTI SRDNSKNTLY LQMNSLRAED TAVYYCAKGN QGDFINR--- FHYWGQGTLV TVSS

BMS2h-483 (SEQ ID NO: 174)
EVQLLESGGG LVQPGGSLRL SCAASGFTFH AYNMAWVRQA PGKGLEWVST ISPRGSYTYY
ADSVKGRFTI SRDNSKNTLY LQMNSLRAED TAVYYCAKWP PPSSH----- FDYWGQGTLV TVSS

BMS2h-5 (SEQ ID NO: 175)
EVQLLESGGG LVQPGGSLRL SCAASGFTFD GYEMAWVRQA PGKGLEWVSS ITSDGTSTYY
ADSVKGRFTI SRDNSKNTLY LQMNSLRAED TAVYYCAKPG LR-------- FDYWGQGTLV TVSS

TABLE 1-continued

Anti-human CD40L VH Domain Amino Acid Sequences

BMS2h-505 (SEQ ID NO: 176)
EVQLLESGGG LVQPGGSLRL SCAASGFTFE GYMMYWVHQA PGKGLEWVSS ISPQGHFTYY
ADSVKGRFTI SRDNSKNTLY LQMNSLRAED TAVYYCAELR ELPRL----- FDYWGQGTLV TVSS

BMS2h-506 (SEQ ID NO: 177)
EVQLLESGGG LVQPGGSLRL SCAASGFTFS SYAMGWVRQA PGKGLEWVSS IDASGGPTYY
ADSVKGRFTI SRDNSKNTLY LQMNSLRAED TAVYYCAKAN GKKFPFTKY- FDYWGQGTLV TVSS

BMS2h-507 (SEQ ID NO: 178)
EVQLLESGGG LVQPGGSLRL SCAASGFTFP SVHMAWVRQA PGKGLEWVSG INLTGVDTYY
ADSVKGRFTI SRDNSKNTLY LQMNSLRAED TAVYYCAKSA TTRQAHPLY- FDYWGQGTLV TVSS

BMS2h-515 (SEQ ID NO: 179)
EVQLLESGGG LVQPGGSLRL SCAASGFTFK EGEMYWVRQA PGKGLEWVST ISTNGLTTYY
ADSVKGRFTI SRDNSKNTLY LQMNSLRAED TAVYYCAKST RDLG------ FAYWGQGTLV TVSS

BMS2h-516 (SEQ ID NO: 180)
EVQLLESGGG LVQPGGSLRL SCAASGFTFE EYEMAWARQA PGKGLEWVSF ISPRGHFTYY
ADSVKGRFTI SRDNSKNTLY LQMNSLRAED TAVYYCAKPA KT-------- FDYWGQGTLV TVSS

BMS2h-517 (SEQ ID NO: 181)
EVQLLESGGG LVQPGGSLRL SCAASGFTFD TYEMLWVRQA PGKGLEWVSR ISVDGSITYY
ADSVKGRFTI SRDNSKNTLY LQMNSLRAED TAVYYCAKTR MR-------- FDYWGQGTLV TVSS

BMS2h-518 (SEQ ID NO: 182)
EVQLLESGGG LVQPGGSLRL SCAASGFTFS SYAMSWVRQA PGKGLEWVSN ISRDGSKTYY
ADSVKGRFTI SRDNSKNTLY LQMNSLRAED TAVYYCAEAQ SGGLRSGLTT FDYWGQGTLV TVSS

BMS2h-519 (SEQ ID NO: 183)
EVQLLESGGG LVQPGGSLRL SCADSGFTFS SYAMSWVRQA PGKGLEWVSS IGRDGAYTYY
ADSVKGRFTI SRDNSKNTLY LQMNSLRAED TAVYYCAKAG PKGIA----- FDYWGQGTLV TVSS

BMS2h-520 (SEQ ID NO: 184)
EVQLLESGGG LVQPGGSLRL SCAASGFTFS PHAMAWVRQA PGKGLEWVSG IDGGGSMTYY
ADSVKGRFTI SRDNSKNTLY LQMNSLRAED TAVYYCAKSD PP-------- FDYWGQGTLV TVSS

BMS2h-521 (SEQ ID NO: 185)
EVQLLESGGG LVQPGGSLRL SCAASGFTFH AGEMHWVRQA PGKGLEWVSS ITLPGDMTYY
ADSVKGRFTI SRDNSKNTLY LQMNSLRAED TAVYYCAKPN TGYT------ FDYWGQGTLV TVSS

BMS2h-522 (SEQ ID NO: 186)
EVQLLESGGG LVQPGGSLRL SCAASGFTFG NYGMSWVRQA PGKGLEWVSS ISWDGSLTYY
ADSVKGRFTI SRDNSKNTLY LQMNSLRAED TAVYYCAQNT RL-------- FDYWGQGTLV TVSS

BMS2h-523 (SEQ ID NO: 187)
EVQLLESGGG LVQPGGSLRL SCAASGFTFH DADMLWVRQA PGKGLEWVSG ILSPGEDTYY
ADSVKGRFTI SRDNSKNTLY LQMNSLRAED TAVYYCAKFG LP-------- FDYWGQGTLV TVSS

BMS2h-524 (SEQ ID NO: 188)
EVQLLESGGG LVQPGGSLRL SCAASGFTFR TDQMNWVRQA PGKGLEWVSS ISPSGAYTYY
ADSVKGRFTI SRDNSKNTLY LQMNSLRAED TAVYYCAKGL GA-------- FDYWGQGTLV TVSS

BMS2h-525 (SEQ ID NO: 189)
EVQLLESGGG LVQPGGSLRL SCAASGFIFE QYQMVWVRQA PGKGLEWVSW ISPDGTHTYY
ADSVKGRFTI SRDNSKNTLY LQMNSLRAED TAVYYCAKFS LRKMEK---- FDYWGQGTLV TVSS

BMS2h-526 (SEQ ID NO: 190)
EVQLLESGGG LVQPGGSLRL SCAASGFTFQ DEQMAWVRQA PGKGLEWVSS IASDGMSTYY
ADSVKGRFTI SRDNSKNTLY LQMNSLRAED TAVYYCAQPG KN-------- FDHWGQGTLV TVSS

BMS2h-527 (SEQ ID NO: 191)
EVQLLESGGG LVQPGGSLRL SCAASGFTFS DYAMSWVRQA PGKGLEWVSS ITTGGERTYY
ADSVKGRFTI SRDNSKNTLY LQMNSLRAED TAVYYCAKRW NLYTES---- FDYWGQGTLV TVSS

BMS2h-528 (SEQ ID NO: 192)
EVQLLESGGG LVQPGGSLRL SCAASGFTFG GQPMDWVRQA PGKGLEWVSS IAPDGIHTYY
ADSVKGRFTI SRDNSKNTLY LQMNSLRAED TAVYYCAKNL GQG------- FDYWGQGTLV TVSS

BMS2h-529 (SEQ ID NO: 193)
EVQLLESGGG LVQPGGSLRL SCAASGFTFE RYQMTWVRQA PGKGLEWVSS ISPSGTFTYY
ADSVKGRFTI SRDNSKNTLY LQMNSLRAED TAVYYCAEWK AL-------- FDYWGQGTLV TVSS

BMS2h-530 (SEQ ID NO: 194)
EVQLLESGGG LVQPGGSLRL SCAASGFTFP HSTMYWVRQA PGKGLEWVSL ILPSGSRTYY
ADSVKGRFTI SRDNSKNTLY LQMNSLRAED TAVYYCAKFS DER------- FDYWGQGTLV TVSS

TABLE 1-continued

Anti-human CD40L VH Domain Amino Acid Sequences

BMS2h-531 (SEQ ID NO: 195)
EVQLSESGGG LVQPGGSLRL SCAASGFTFG DGNMDWVRQA PGKGLEWVSG ISSDGVTTYY
ADSVKGRFTI SRDNSKNTLY LQMNSLRAED TAVYYCAKDR GQG------- FDYWGQGTLV TVSS

BMS2h-532 (SEQ ID NO: 196)
EVQLLESGGG LVQPGGSLRL SCAASGFTFD DYMMWVRQA PGKGLEWVSS ISPHGVYTYY
ADSVKGRFTI SRDNSKNTLY LQMNSLRAED TAVYYCAKWL HT-------- FDYWGQGTLV TVSS

BMS2h-533 (SEQ ID NO: 197)
EVQLLESGGG LVQPGGSLRL SCAASGFTFS NYTMAWGRQA PGKGLEWVSF IAGPGNYTYY
ADSVKGRFTI SRDNSKNTLY LQMNSLRAED TAVYYCAKPG STATYNNGQ- FDYWGQGTLV TVSS

BMS2h-534 (SEQ ID NO: 198)
EVQLLESGGG LVQPGGSLRL SCAASGFTFT EYSMVWVRQA PGKGLEWVSS ISGSGRVTYY
ADSVKGRFTI SRDNSKNTLY LQMNSLRAED TAVYYCAKWL KLVRAPNP- FDYWGQGTLV TVSS

BMS2h-535 (SEQ ID NO: 199)
EVQLLESGGG LVQPGGSLRL SCAASGFTFS NYQMAWVRQA PGKGLEWVSG ISKTGHSTYY
ADSVKGRFTI SRDNSRNTLY LQMNSLRAED TAVYYCAKAS HSLGPL---- FDYWGQGTLV TVSS

BMS2h-54 (SEQ ID NO: 200)
EVQLLESGGG LVQPGGSLRL SCAASGFTFT AYRMAWVRQA PGKGLEWVSW ISPSGSGTYY
ADSVKGRFTI SRDNSKNTLY LQMNSLRAED TAVYYCAKTL TDSPSGHYE- FDYWGQGTLV TVSS

BMS2h-55 (SEQ ID NO: 201)
EVQLLESGGG LVQPGGSLRL SCAASGFTFA RYEMGWVRQA PGKGLEWVSR ITAQGLGTYY
ADSVKGRFTI SRDNSKNTLY LQMNSLRAED TAVYYCAKYL TDFSSGHQE- FDYWGQGTLV TVSS

BMS2h-553 (SEQ ID NO: 202)
EVQLLESGGG LVQPGGSLRL SCAASGFTFD DYGMSWVRQV PGKGLEWVSG ISHNGMLTYY
ADSVKGRFTI SRDNSKNTLY LQMNSLRAED TAVYYCAKYW PSTSWETD- FDYWGQGTLV TVSS

BMS2h-554 (SEQ ID NO: 203)
EVQLLESGGG SVQPGGSLRL SCAASGFTFG NEPMAWVRQA PGKGLEWVSS IEMQGKNTYY
ADSVKGRFTI SRDNSKNTLY LQMNSLRAED TAVYYCAKDR GQG------- FDYWGQGTLV TVSS

BMS2h-555 (SEQ ID NO: 204)
EVQLLESGGG LVQPGGSLRL SCAASGFTFG EEEMSWVRQA PGKGLEWVSC IDNLGSPTYY
ADSVKGRFTI SRDNSKNTLY LQMNSLRAED AAVYYCAKTI SHQYDR---- FDYWGQGTLV TVSS

BMS2h-556 (SEQ ID NO: 205)
EVQLLESGGG LVQPGGSLRL SCAASGFTFG EEEMSWVRQA PGKGLEWVSS IDEGGRWTYY
ADSVKGRFTI SRDNSKNTLY LQMNSLRAED TAVYYCAKWT PHKQLS---- FDYWGQGTLV TVSS

BMS2h-557 (SEQ ID NO: 206)
EVQLLESGGG LVQPGGSLRL SCAASGFSFA DEYMVWARQA PGKGLEWVSE IDPLGTGTYY
ADSVKGRFTI SRDNSKNTLY LQMNSLRAED TAVYYCAKYG TA-------- FDYWGQGTLV TVSS

BMS2h-558 (SEQ ID NO: 207)
EVQLLESGGG LVQPGGSLRL SCAASGFTFS THDMMWVRQA PGKGLEWVSS ISDDGISTYY
ADSVKGRFTI SRDNSKNTLY LQMNSLRAED TAVYYCAKPD MSLIE----- FDYWGQGTLV TVSS

BMS2h-559 (SEQ ID NO: 208)
EVQLLESGGG LVQPGGSLRL SCAASGFTFD GTPMVWVRQA PGKGLEWVSG ISGDGRNTYY
ADSVKGRFTI SRDNSKNTLY LQMNSLRAED TAVYYCAEPY ALTSSKP--- FDYWGQGTLV TVSS

BMS2h-56 (SEQ ID NO: 209)
EVQLLESGGG LVQPGGSLRL SCAASGFTFN DYTMGWVRQA PGKGLEWVSW IHGTGGQTYY
ADSVKGRFTI SRDNSKNTLY LQMNSLRAED TAVYYCAKAL ADRSGGVVE- FDYWGQGTLV TVSS

BMS2h-560 (SEQ ID NO: 210)
EVQLLESGGG LVQPGGSLRL SCAASGFTFE AETMAWVRQA PGKGLEWVSC ISNDGNTTYY
ADSVKGRFTI SRDNSKNTLY LQMNSLRAED TAVYYCAKES LISPGL---- FDYWGQGTLV TVSS

BMS2h-561 (SEQ ID NO: 211)
EVQLLESGGG LVQPGGSLRL SCAASGFTFT GEYMNWVRQA PGKGLEWVST INETGYMTYY
ADSVKGRFTI SRDNSKNTLY LQMNSLRAED TAVYYCAKLS TRGVP----- FDYWGQGTLV TVSS

BMS2h-562 (SEQ ID NO: 212)
EVQLLESGGG LVQPGGSLRL SCAASGFTFR SYDMGWVRQA PGKGLEWVST ISPMGVFTYY
ADSVKGRFTI SRDNSKNTLY LQMNSLRAED TAVYYCAKSN QHADP----- FDYWGQGTLV TVSS

BMS2h-563 (SEQ ID NO: 213)
EVQLLESGGG LVQPGGSLRL SCAASGFTFS DYDMGWVRQA PGKGLEWVSS ISPMGTFTYY
ADSVKGRFTI SRDNSKNTLY LQMNSLRAED TAVYYCAKAA LTEPM----- FDYWGQGTLV TVSS

TABLE 1-continued

Anti-human CD40L VH Domain Amino Acid Sequences

BMS2h-564 (SEQ ID NO: 214)
EVQLLESGGG LVQPGGSLRL SCAASGFTFR DYDMGWVRQA PGKGLEWVST ISPLGHFTYY
ADSVKGRSTI SRDNSKNTLY LQMNSLRAED TAVYYCAKAE EA-------- FDYWGQGTLV TVSS

BMS2h-565 (SEQ ID NO: 215)
EVQLLESGGG LVQPGGSLRL SCAASGFAFP RYGMTWVRQA PGKGLEWVSN IDQFGMKTYY
ADSVKGRFTI SRDNSKNTLY LQMNSLRAED TAVYYCAEEY AS-------- FDYWGQGTLV TVSS

BMS2h-566 (SEQ ID NO: 216)
EVQLLESGGG LVQPGGSLRL SCAASGFTFD KYDMGWVRQA PGKGLEWVST ISPMGVFTYY
ADSVKGRFTI SRDNSKNTLY LQMNSLRAED TAVYYCAKGR GNTSD----- FDYWGQGTLV TVSS

BMS2h-567 (SEQ ID NO: 217)
EVQLLESGGG LVQPGGSLRL SCAASGFTFS NYDMAWVRQA PGKGLEWVST ISGAGHFTYY
ADSVKGRFTI SRDNSKNTLY LQMNSLRAED TAVYYCAKSF PRDE------ FDYWGQGTLV TVSS

BMS2h-568 (SEQ ID NO: 218)
EVQLLESGGG LVQPGGSLRL SCAASGFTFP KYEMRWVRQA PGKGLEWVSE IGLDGSPTYY
ADSVKGRFTI SRDNSKNTLY LQMNSLRAED TAVYYCAKLG DPNG------ FDYWGQGTLV TVSS

BMS2h-569 (SEQ ID NO: 219)
EVQLLESGGG LVQPGGSLRL SCAASGFTFP TSEMDWVRQA PGKGLEWVSG IGPDGLTTYY
ADSVKGRFTI SRDNSKNTLY LQMNSLRAED TAVYYCAKHA DW-------- FDYWGQGTLV TVSS

BMS2h-57 (SEQ ID NO: 220)
EVQLLESGGG LVQPGGSLRL SCAASGFTFS EYDMYWVRQA PGKGLEWVSW IDTDGGDTYY
ADSVKGRFTI SRDNSKNTLY LQMNSLRAED TAVYYCAKPG LK-------- FDYWGQGTLV TVSS

BMS2h-570 (SEQ ID NO: 221)
EVQLLESGGG LVQPGGSLRL SCTASGFTFE NASMQWVRQA PGKGLEWVSS IEGQGNATYY
ADSVKGRFTI SRDNSKNTLY LQMNSLRAED TAVYYCAKSS SWS------- FDYWGQGTLV TVSS

BMS2h-571 (SEQ ID NO: 222)
EVQLLESGGG LVQPGGSLRL SCAASGFTFT RNEMGWVRQA PGKGLEWVST ITPTGTFTYY
ADSVKGRFTI SRDNSKNTLY LQMNSLRAED TAVYYCAKTD PGNRY----- FDYWGQGTLV TVSS

BMS2h-572 (SEQ ID NO: 223)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-1 (SEQ ID NO: 224)
EVQLLESGGG LVQPGGSLRL SCAASGFTFN WQLMGWFRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-10 (SEQ ID NO: 225)
EVQLLESGGG LVQPGGSLRL SCAASGFTFN WQLMGWVRQA PGKGLEWVSG IEGPGDVTYY
ADSVKGRFTV SRDNSKNTLY LQMNSLRAED TAVYYCAKVG KESN------ SDYRGQGTLV TVSS

BMS2h-572-11 (SEQ ID NO: 226)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESN------ SDYRGQGTQV TVSS

BMS2h-572-12 (SEQ ID NO: 227)
EVQLLESGGG LVQPGGSLRL SCAASGFTFN WQLMGWARQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-13 (SEQ ID NO: 228)
EVQLLESGGG LVQPGGSLRL SCAASGFTFN WQLMGWARQA PGKGLEWVSG IEGPGDVTYY
ADSVKDRFTI SRDNSKNTLY LLMNSLRAED TAVYYCAKVG KESN------ FDYWGQGTLV TVSS

BMS2h-572-14 (SEQ ID NO: 229)
EVQLLESGGG LVQPGGSLRL SCAASGFTFN WQLMGWVRQA PGKGLEWVSG IEGPGDVTYY
ADSVKGRFTI SRDNTKNTLY LQMNSLRAED TAVYYCVKVG KESN------ SDYRGQGTLV TVSS

BMS2h-572-15 (SEQ ID NO: 230)
EVRLLESGGG LVQPGGSLRL SCAASGFNFN WQLMGWIRQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-16 (SEQ ID NO: 231)
EVQLLESGGG LVRPGGSLRL SCVASGFTFN WQLMGWVRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-17 (SEQ ID NO: 232)
EVQLLESGGG LVQTGGSLRL SCAASGFTYN WQLMGWVRQA PGKGLEWVSG IEGPGDVTYY
ADSVKGRFTI SRDNSKNTLY LQMNSLRADD TAVYYCVKVG KESN------ FDYRGHGTLV TVSS

TABLE 1-continued

Anti-human CD40L VH Domain Amino Acid Sequences

BMS2h-572-18 (SEQ ID NO: 233)
EVQLLESGGG LVQPGGSLRL SCAASGFTFN WQLMGWVRKA PGKGLEWVSG IEGPGDVTYY
ADSVKGRFTI SRDNSKNTLY LQMNSLRAED TAVYYCAKVG KESN------ FDYRGQGTLV TVSS

BMS2h-572-19 (SEQ ID NO: 234)
EVQLLESGGG LVQPGGSLRL SCAASGFTFN WQLMGWVRQA PGKGLEWVSG IEGPGDVTYY
ADSVKGRFTI SRDNTKNTLY LQMNSLRAED TAVYYCAKVG KESN------ FDYRGQGTLV TVSS

BMS2h-572-2 (SEQ ID NO: 235)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESK------ FDYLGQGTLV TVSS

BMS2h-572-21 (SEQ ID NO: 236)
EVQLLESGGG LVQPGGSLRL SCAASGFTFN WQLMGWVRQA PGKGLEWVSG IEGPGDVTYY
AESVKGRFTI SRDNSKNTLY LQMNSLRAED TAVYYCAKVG KESN------ LDYRGQGTLV TVSS

BMS2h-572-22 (SEQ ID NO: 237)
EVQLFESGGG SVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-23 (SEQ ID NO: 238)
EVQLLESGGG LVQPGGSLRL TCAASGFTFN WQLMGWVRQA PGKGLEWVSG IEGPGDVTYY
ADSVKGRFII SRDNSKNTLY LQMNSLRAED TAVYYCAKVG KESN------ SDYRGQGTLV TVSS

BMS2h-572-24 (SEQ ID NO: 239)
EVQLLESGGG LVQPGGSLRL SCAASGFTFN WQLMGWVRQA PGKGLEWVSG IEGPGDVTYY
ADSVKGRFTI SRDNSTNTLY LQMNSLRAED TAVYYCAKVG KESE------ FDYRGQGTLV TVSS

BMS2h-572-3 (SEQ ID NO: 240)
EVRLLESGGG LVQPGGSLRL SCAASGFTFN WQLMGWVRQA PGKGLEWVSG IEGPGDVTYY
ADSVKGRFTI TRDNSKNTLY LQMNSLRAED TAVYYCVKVG KESN------ LDYRGQGTLV TVSS

BMS2h-572-4 (SEQ ID NO: 241)
EVQLLVSGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-5 (SEQ ID NO: 242)
EVQLLVSGGG LVQPGGSLRL SCAASGFTFN WQLMGWVRQA PGKGLEWVSG IEGPGDVTYY
ADSVKGRFTI SRDNSKNMLY LQMNGLRAED TAVYYCAKVG KESN------ FDYRGQGTLV TVSS

BMS2h-572-6 (SEQ ID NO: 243)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-601 (SEQ ID NO: 244)
EVQLLESGGG LVQPGGSLRL SCAASGFTFK WQLMGWARQA PGKGLEWVSG IEGPGDVTYY
ADPVKGRFTI SRDNSKNTLY LQMNSLRAED TAVYYCVKVG KESN------ SDYRGQGTLV TVSS

BMS2h-572-602 (SEQ ID NO: 245)
EVQLLESGGG LVQPGGSLRL SCAASGFTFK WHLMGWVRQA PGKGLEWVSG IEGPGDVTYY
ADSVKGRFTI SRDNSKNTLY LQMNSLRAED TAVYYCVKVG KESS------ SDYRGQGTLV TVSS

BMS2h-572-603 (SEQ ID NO: 246)
EVQLLESGGG LVQPGGSLRL SCAASGFTFN WHLMAWARQA PGKGLEWVSG IEGPGDVTYY
ADSVKGRFTI SRDNSKNTLY LQMNSLRAED TAVYYCVKVG KESN------ SDYRGQGTLV
TVSS

BMS2h-572-604 (SEQ ID NO: 247)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-605 (SEQ ID NO: 248)
EVQLLESGGG LVQPGGSLRL SCAASGFTFK WQLMAWARQA PGKGLEWVSG IEGPGDITYY
ADSVKGRFTI SRDNSKNTLY LQMNSLRAED TAVYYCVKVG KESN------ SDYRGQGTLV TVSS

BMS2h-572-606 (SEQ ID NO: 249)
EVQLLESGGG LVQPGGSLRL SCAASGFTFN WHLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-607 (SEQ ID NO: 250)
EVQLLESGGG LVQPGGSLRL SCAASGFTFK WQLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-608 (SEQ ID NO: 251)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KESN------ SDYRGQGTLV TVSS

TABLE 1-continued

Anti-human CD40L VH Domain Amino Acid Sequences

BMS2h-572-609 (SEQ ID NO: 252)
EVQLLESGGG LVQPGGSLRL SCAASGFTFN WQLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-610 (SEQ ID NO: 253)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-611 (SEQ ID NO: 254)
EVQLLESGGG LVQPGGSLRL SCAASGFTFN WQLMGWVRRA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-612 (SEQ ID NO: 255)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSN------ SDYRGQGTLV TVSS

BMS2h-572-613 (SEQ ID NO: 256)
EVQLLESGGG LAQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-614 (SEQ ID NO: 257)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDAK------ SDYRGQGTLV TVSS

BMS2h-572-615 (SEQ ID NO: 258)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDKN------ SDYRGQGTLV TVSS

BMS2h-572-616 (SEQ ID NO: 259)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESK------ SDYRGQGTLV TVSS

BMS2h-572-617 (SEQ ID NO: 260)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG RDSK------ SDYRGQGTLV TVSS

BMS2h-572-618 (SEQ ID NO: 261)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KYSN------ SDYRGQGTLV TVSS

BMS2h-572-619 (SEQ ID NO: 262)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-620 (SEQ ID NO: 263)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDDS------ SDYRGQGTLV TVSS

BMS2h-572-621 (SEQ ID NO: 264)
EVQLLEFGGG LVQPGGSLRF SCAASGFTFN WQLMGWFRQA PGKGLEWVSG IEGPGDVTYY
ADSVKGRFTI SRDNSKNTLY LQMNSLRAED TAVYYCVKVG RDSN------ SDYRGQGTLV TVSS

BMS2h-572-622 (SEQ ID NO: 265)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDST------ SDYRGQGTLV TVSS

BMS2h-572-623 (SEQ ID NO: 266)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESS------ SDYRGQGTLV TVSS

BMS2h-572-624 (SEQ ID NO: 267)
EVQLLESGGG LVQPGGSLRL SCAASGFTFN WQLMGWVRQA PGKGLEWVSG IEGPGDVTYY
ADSVKGRFTI FRDNSKNTLY LQMNSLRAED TAVYYCVKVG KDSA------ SDYRGQGTLV TVSS

BMS2h-572-625 (SEQ ID NO: 268)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG NDSY------ SDYRGQGTLV TVSS

BMS2h-572-626 (SEQ ID NO: 269)
EVQLLESGGG LVQPGGSLRL SCAASGFTFN WQLMGWVRQA PGKGLEWVSG IEGPGDVTYY
ADSVKGRFTI SRDNSKNTLY LQMNGLRAED TAVYYCVKVG KDSS------ SDYRGQGTLV TVSS

BMS2h-572-627 (SEQ ID NO: 270)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAIYYCVKVG KDSA------ SDYRGQGTLV TVSS

TABLE 1-continued

Anti-human CD40L VH Domain Amino Acid Sequences

BMS2h-572-630 (SEQ ID NO: 271)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KDAK------ SDYRGQGTLV TVSS

BMS2h-572-631 (SEQ ID NO: 272)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-632 (SEQ ID NO: 273)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-633 (SEQ ID NO: 274)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDAK------ SDYRGQGTLV TVSS

BMS2h-572-634 (SEQ ID NO: 275)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-635 (SEQ ID NO: 276)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-7 (SEQ ID NO: 277)
EVQLLESGGG LVQPGGSLRL SCAASGFTFN WQLMGWARQA PGKGLEWVSG IEGPGDVTYY
ADSVKGRFTI SRDNSKNTLY LQMNSLRAED SAVYYCAKVG KESN------ FDYLGQGTLV TVSS

BMS2h-572-8 (SEQ ID NO: 278)
EVQLLESGGG LVQPGGSLRL SCVASGFTFN WQLMGWVRQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-9 (SEQ ID NO: 279)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ SDYRGQGTLV TVSS

BMS2h-573 (SEQ ID NO: 280)
EVQLLESGGG LVQPGGSLRL SCAASGFTFS GWEMGWVRQA PGKGLEWVSS IDESGLNTYY
ADSVKGRFTI SRDNSKNTLY LQMNSLRAED TAVYYCAEGA PQYQIT---- FDYWGQGTLV TVSS

BMS2h-574 (SEQ ID NO: 281)
EVQLLESGGG LVQPGGSLRL SCAASGFTFP NYGMYWVRQA PGKGLEWVSY ISRRGLLTYY
ADSVKGRFTI SRDNSKNTLY LQMNSLRAED TAVYYCAKTS HYMNNG---- FDYWGQGTLV TVSS

BMS2h-575 (SEQ ID NO: 282)
EVQLLESGGG LVQPGGSLRL SCAASGFTFV DYTMAWVRQA PGKGLEWVSS ISPIGTFTYY
ADSVKGRFTI SRDNSKNTLY LQMNSLRAED TAVYYCAKDP YGMEDGLTW- FDYWGQGTLV TVSS

BMS2h-576 (SEQ ID NO: 283)
EVQLLESGGG LVQPGGSLRL SCAASGFTFD AYDMQWVRQA PGKGLEWVST ITSEGLSTYY
ADSVKGRFTI SRDNSKNTLY LQMNSLRAED TAVYYCAKPS DL-------- FDYWGQGTLV TVSS

BMS2h-577 (SEQ ID NO: 284)
EVQLLESGGG LVQPGGSLRL SCAASGFTFD GYDMGWVRQA PGKGLEWVST ISRGGWFTYY
ADSVKGRFTI SRDNSKNTLY LQMNSLRAED TAVYYCAKGT SQSSTGS--- FDYWGQGTLV TVSS

BMS2h-578 (SEQ ID NO: 285)
EVQLLESGGG LVQPGGSLRL SCAASGFTFR RYDMLWARQA PGKGLEWVSE ISPTGALTYY
ADSVKGRFTI SRDNSKNTLY LQMNSLRAED TAVYYCAKLG ST-------- FDYWGQGTLV TVSS

BMS2h-579 (SEQ ID NO: 286)
EVQLLESGGG LVQPGGSLRL SCAASGFTFF PYYMSWVRQA PGKGLEWVSS ISGTGGLTYY
ADSVKGRFTI SRDNSKNTLY LQMNSLRAED TAVYYCAKTT QNATL----- FDYWGQGTLV TVSS

BMS2h-58 (SEQ ID NO: 287)
EVQLLESGGG LVQPGGSLRL SCAASGFTFE VYTMAWVRQA PGKGLEWVST IDESGRDTYY
ADSVKGRFTI SRDNSKNTLY LQMNSLRAED TAVYYCAKPG VW-------- FDYWGQGTLV TVSS

BMS2h-580 (SEQ ID NO: 288)
EVQLLESGGG LVQPGGSLRL SCAASGFTFA FYKMGWVRQA PGKGLEWVST ITPKGHHTYY
ADSVKGRFTI SRDNSKNTLY LQMNSLRAED TAVYYCAKVF KGKGWTRPSG FDYWGQGTLV TVSS

BMS2h-581 (SEQ ID NO: 289)
EVQLLESGGG LVQPGGSLRL SCAASGFTFN EYSMMWVRQA PGKGLEWVSS IGRRGWLTYY
ADSVKGRFTI SRDNSKNTLY LQMNSLRAED TAVYYCAKAV LLDSTK---- FDYWGQGTLV TVSS

TABLE 1-continued

Anti-human CD40L VH Domain Amino Acid Sequences

```
BMS2h-582 (SEQ ID NO: 290)
EVQLLESGGG LVQPGGSLRL SCAASGFTFD EYPMTWVRQA PGKGLEWVST ISARGPFTYY
ADSVKGRFTI SRDNSKNTLY LQMNSLRAED TAVYYCAKGR HWLRNGR--- FDYWGQGTLV TVSS

BMS2h-583 (SEQ ID NO: 291)
EVQLLESGGG LVQPGGSLRL SCAASGFTFG MQSMQWVRQA PGKGLEWVSS ITDDGTSTYY
ADSVKGRFTI SRDNSKNTLY LQMNSLRAED TAVYYCAKPD RV-------- FDYWGQGTLV TVSS

BMS2h-584 (SEQ ID NO: 292)
EVQLLESGGG LVQPGGSLRL SCAASGFTFG AADMQWVRQA PGKGLEWVSL ITNDGISTYY
ADSVKGRFTI SRDNSKNTLY LQMNSLRAED TAVYYCAKAG DR-------- FDYWGQGTLV TVSS

BMS2h-586 (SEQ ID NO: 293)
EVQLLESGGG LVQPGGSLRL SCAASGFTFN KYRMQWVRQA PGKGLEWVSS IDSSGELTYY
ADSVKGRFTI SRDNSKNTLY LQMNSLRAED TAVYYCAEEV PMGNQTF--- FDYWGQGTLV TVSS

BMS2h-587 (SEQ ID NO: 294)
EVQLLESGGG LVQPGGSLRL SCAASGFTFT DYTMGWVRQA PGKGLEWVSS ITSQGAFTYY
ADSVKGRFTI SRDNSKNTLY LQMNSLRAED TAVYYCAKAT GTDSS----- FDYWGQGTLV TVSS

BMS2h-588 (SEQ ID NO: 295)
EVQLLESGGG LVQPGGSLRL SCAASGFTFE DYEMSWVRQA PGKGLEWVSC IGPGGKPTYY
ADSVKGRFTI SRDNSKNTLY LQMNSLRAED TAVYYCAKVD GH-------- FDYWGQGTLV TVSS

BMS2h-589 (SEQ ID NO: 296)
EVQLLESGGG LVQPGGSLRL SCAASGFTFS QYDMGWVRQA PGKGLEWVST ISSRGWLTYY
ADSVKGRFTI SRDNSKNTLY LQMNSLRAED TAVYYCAKGP GGRRR----- FDYWGQGTLV TVSS

BMS2h-59 (SEQ ID NO: 297)
EVQLLESGGG LVQPGGSLRL SCAASGFTFL DYAMGWVRQA PGKGLEWVST ISPMGMGTYY
ADSVKGRFTI SRDNSKNTLY LQMNSLRAED TAVYYCAKSS AISFTSDISN FDYWGQGTLV TVSS

BMS2h-590 (SEQ ID NO: 298)
EVQLLESGGG LVQPGGSLRL SCAASGFTFS DYPMSWVRQA PGKGLEWVSS ISWSGFQTYY
ADSVKGRFTI SRDNSKNTLY LQMNSLRAED TAVYYCAKPG VARMPTGIA- FDYWGQGTLV TVSS

BMS2h-591 (SEQ ID NO: 299)
EVQLLESGGG LVQPGGSLRL SCAASGFTFS AYEMQWVRQA PGKGLEWVSS IDSAGTFTYY
ADSVKGRFTI SRDNSKNTLY LQMNSLRAED TAVYYCAEPF GM-------- FDYWGQGTLV TVSS

BMS2h-592 (SEQ ID NO: 300)
EVQLLESGGG LVQPGGSLRL SCAASGFTFS EYPMKWVRQA PGKGLEWVST IDRQGDRTYY
ADSVKGRFTI SRDNSKNTLY LQMNSLRAED TAVYYCAKTV RRGLPRPSRY FDYWGQGTLV TVSS

BMS2h-593 (SEQ ID NO: 301)
EVQLLESGGG LVQPGGSLRL SCAASGFTFS DYDMGWVRQA PGKGLEWVSS ISPMGTFTYY
ADSVKGRFTI SRDNSKNTLY LQMNSLRAED TAVYYCAKGL SVYSGLD--- FDYWGQGTLV TVSS

BMS2h-594 (SEQ ID NO: 302)
EVQLLESGGG LVQPGGSLRL SCAASGFTFS HYDMGWVRQA PGKGLEWVSD IDYIGKTTYY
ADSVKGRFTI SRDNSKNTLY LQMNSLRAED TAVYYCAKAS DEVGVNTSK- FDYWGQGTLV TVSS

BMS2h-595 (SEQ ID NO: 303)
EVQLLESGGG LVQPGGSLRL SCAASGFTFA RYDMGWVRQA PGKGLEWVST ISPTGVLTYY
ADSVKGRFTI SRDNSKNTLY LQMNSLRAED TAVYYCAKGF ED-------- FDYWGQGTLV TVSS

BMS2h-596 (SEQ ID NO: 304)
EVQLLESGGG LVQPGGSLRL SCAASGFTFE AYPMSWVRQA PGKGLEWVSL ISHTGHATYY
ADSVKGRFTI SRDNSKNTLY LQMNSLRAED TAVYYCAKGH WP-------- FDYRGQGTLI TVSS

BMS2h-597 (SEQ ID NO: 305)
EVQLLESGGG LVQPGGSLRL SCAASGFTFE DEWMSWVRQA PGKGLEWVSD ISPGGWTTYY
ADSVKGRFTI SRDNSKNTLY LQMNSLRAED TAVYYCAKGY RPFDE----- FDYWGQGTLV TVSS

BMS2h-598 (SEQ ID NO: 306)
EVQLLESGGG LVQPGGSLRL SCAASGVTFD AIEMSWVRQA PGKGLEWVSS ISRHGEYTYY
ADSVKGRFTI SRDNSKNTLY LQMNSLRAED TAVYYCAEDA WSRH------ FDYWGQGTLV TVSS

BMS2h-599 (SEQ ID NO: 307)
EVQLLESGGG LVQPGGSLRL SCAASGFTFD STDMSWVRQA PGKGLEWVSG ILDNGSNTYY
ADSVKGRFTI SRDNSKNMLY LQMNSLRAED TAVYYCAKGA RD-------- FDYWGQGTLV TVSS

BMS2h-600 (SEQ ID NO: 308)
EVQLLESGGG LVQPGGSLRL SCAASGFTFG RQSMQWVRQA PGKGLEWVSS IDDDGFSTYY
ADSVKGRFTI SRDNSKNTLY LQMNSLRAED TAVYYCAKGD PWG------- FDYWGQGTLV TVSS
```

TABLE 1-continued

Anti-human CD40L VH Domain Amino Acid Sequences

```
BMS2h-601 (SEQ ID NO: 309)
EVQLLESGGG LVQPGGSLRL SCTASGFTFS DTQMAWVRQA PGKGLEWVSG IDDGGVSTYY
ADSVKGRFTI SRDNSKNTLY LQMNSLRAED TAVYYCAKPD RH-------- FDYWGQGTLV TVSS

BMS2h-602 (SEQ ID NO: 310)
EVQLLESGGG LVQPGGSLRL SCAASGFTFG STTMGWVRQA PGKGLEWVSV ISDDGGFTYY
ADSVKGRFTI SRDNSRNTLY LQMNSLRAED TAVYYCAKVD GYGV------ FDYWGQGTLV TVSS

BMS2h-603 (SEQ ID NO: 311)
EVQLLESGGG LVQPGGSLRL SCAASGFTFR SGDMNWVRQA PGKGLEWVST ITNDGTSTYY
ADSVKGRFTI SRDNSKNTLY LQMNSLRAED TAVYYCAKSD SD-------- FDYWGQGTLV TVSS

BMS2h-61 (SEQ ID NO: 312)
EVQLLESGGG LVQPGGSLRL SCAASGFTFA AYAMTWVRQA PGKGLEWVSY ISPNGTATYY
ADSVKGRFTI SRDNSKNTLY LQMNSLRAED TAVYYCAEYV GMRWNS---- FDYWGQGTLV TVSS

BMS2h-62 (SEQ ID NO: 313)
EVQLLESGGG LVQPGGSLRL SCAASGFTFS SYEMAWVRQA PGKGLEWVSS ITSLGTSTYY
ADSVKGRFTI SRDNSKNTLY LQMNSLRAED TAVYYCAKPG RK-------- FDYWGQGTLV TVSS

BMS2h-65 (SEQ ID NO: 314)
EVQLLESGGG LVQPGGSLRL SCAASGFTFN EYEMTWVRQA PGKGLEWVST ITSEGSGTYY
ADSVKGRFTI SRDNSKNTLY LQMNSLRAED TAVYYCAKPN GK-------- FDYWGQGTLV TVSS

BMS2h-66 (SEQ ID NO: 315)
EVQLLESGGG LVQPGGSLRL SCAASGFTFS DYEMLWVRQA PGKGLEWVST ITSEGHSTYY
ADSVKGRFTI SRDNSKNTLY LQMNSLRAED TAVYYCAKPG TS-------- FDYWGQGTLV TVSS

BMS2h-67 (SEQ ID NO: 316)
EVQLLESGGG LVQPGGSLRL SCAASGFTFS DYEMSWVRQA PGKGLEWVST IDSDGSFTYY
ADSVKGRFTI SRDNSKNTLY LQMNSLRAED TAVYYCAKPG VK-------- FDYWGQGTLV TVSS

BMS2h-68 (SEQ ID NO: 317)
EVQLLESGGG LVQPGGSLRL SCAASGFTFK DYEMTWVRQA PGKGLEWVSS ISSTGQSTYY
ADSVKGRFTI SRDNSKNTLY LQMNSLRAED TAVYYCAKPN NK-------- FDYWGQGTLV TVSS

BMS2h-69 (SEQ ID NO: 318)
EVQLLESGGG LVQPGGSLRL SCAASGFTFL DYGMAWVRQA PGKGLEWVSA ISPLGLSTYY
ADSVKSRFTI SRDNSKNTLY LQMNSLRAED TAVYYCAKEV RVGRGVHPPK FDYWGQGTLV TVSS

BMS2h-7 (SEQ ID NO: 319)
EVQLLESGGG LVQPGGSLRL SCAASGFTFN LYEMTWVRQA PGKGLEWVSS ITSDGVSTYY
ADSVKGRFTI SRDNSKNTLY LQMNSLRAED TAVYYCAKAG VI-------- FDYWGQGTLV TVSS

BMS2h-70 (SEQ ID NO: 320)
EVQLLESGGG LVQPGGSLRL SCAASGFTFE NYAMSWVRQA PGKGLEWVST IAPLGVPTYY
ADSVKGRFTI SRDNSKNTLY LQMNSLRAED TAVYYCAKKK VGAWLQSRS- FDYWGQGTLV TVSS

BMS2h-701 (SEQ ID NO: 321)
EVQLLESGGG LVQPGGSLRL SCAASGFTFM DYEMHWVRQA PGKGLEWVST IGASGHYTYY
ADSVKGRFTI SRDNSKNTLY LQMNSLRAED TAVYYCAKYL DMLLFG---- FDYWGQGTLV TVSS

BMS2h-702 (SEQ ID NO: 322)
EVQLLESGGG LVQPGGSLRL SCAASGFTFA EYEMMWARQA PGKGLEWVSR IAGNGSRTYY
ADSVKGRFTI SRDNSKNTLY LQMNSLRAED TAVYYCAIML SH-------- FDYWGQGTLV TVSS

BMS2h-703 (SEQ ID NO: 323)
EVQLLESGGG LVQPGGSLRL SCAASGFTFY NYDMSWVRQA PGKGLEWVSG IDSMGLVTYY
ADSVKGRFTI SRDNSKNTLY LQMNSLRAED TAVYYCAKGS NASDWVV--- FDYWGQGTLV TVSS

BMS2h-704 (SEQ ID NO: 324)
EVQLLESGGG LVQPGGSLRL SCAASGFTFA SYHMTWVRQA PGKGLEWVSS IADTGDRTYY
ADSVKGRFTI SRDNSKNTLY LQMNSLRAED TAVYYCAKLR GMARVWG--- FDYWGQGTLV TVSS

BMS2h-705 (SEQ ID NO: 325)
EVQLLESGGG LVQPGGSLRL SCAASGFTFS YYDMMWVRQA PGKGLEWISS ISDRGLQTYY
ADSVKGRFTI SRDNSKNTLY LQMNSLRAED TAVYYCAKFT EIPLDWLEV- FDYWGQGTLV TVSS

BMS2h-706 (SEQ ID NO: 326)
EVQLLESGGG LVQPGGSLRL SCAASGFTFG SYKMLWVRQA PGKGLEWVSS ITNSGTETYY
ADSVKGRFTI SRDNSKNTLY LQMNSLRAED TAVYYCAKSM YPDLEIVH-FDYWGQGTLV TVSS

BMS2h-707 (SEQ ID NO: 327)
EVQLLESGGG LVQPGGSLRL SCAASGFTFE TYRMSWVRQA PGKGLEWVSA IDQEGSATYY
ADSVKGRFTI SRDNSKNTLY LQMNSLRAED TAVYYCAKNS GTRPGLR--- FDYWGQGTLV TVSS
```

TABLE 1-continued

Anti-human CD40L VH Domain Amino Acid Sequences

```
BMS2h-708 (SEQ ID NO: 328)
EVQLLESGGG LVQPGGSLRL SCAASGFTFS SYDMLWVRQA PGKGLEWVSR IDASGYFTYY
ADSVKGRFTI SRDNSKNTLY LQMNSLRAED TAVYYCAQLL KLSLNPN--- FDYWGQGTLV TVSS

BMS2h-709 (SEQ ID NO: 329)
EVQLLESGGG LVQPGGSLRL SCAASGFTFS SYAMSWVRQA PGKGLEWVSS IHNTGLSTYY
ADSVKGRFTI SRDNSKNTLY LQMNSLRAED TAVYYCAKGT QHRFVV---- FDYWGQGTLV TVSS

BMS2h-71 (SEQ ID NO: 330)
EVQLLESGGG LVQPGGSLRL SCAASGFTFE GYPMSWVRQA PGKGLEWVST ISPLGPDTYY
ADSVKGRFTI SRDNSKNTLY LQMNSLRAED TAVYYCAKLL MGEYLNSRT- FDYWGQGTLV TVSS

BMS2h-710 (SEQ ID NO: 331)
EVQLLESGGG LVQPGGSLRL SCAASGFTFN TYSMSWVRQA PGKGLEWVSW IDADGWVTYY
ADSVKGRFTI SRDNSKNTLY LQMNSLRAED TAVYYCAQTG HT-------- FDYWGQGTLV TVSS

BMS2h-711 (SEQ ID NO: 332)
EVQLLESGGG LVQPGGSLRL SCAASGFTFT DGEMGWARQA PGKGLEWVSR IVDPGDSTYY
ADSVKGRFTI SRDNSKNTLY LQMNSLRAED TAVYYCAKAG DQ-------- FDYWGQGTLV TVSS

BMS2h-712 (SEQ ID NO: 333)
EVQLLESGGG LVQPGGSLRL SCAASGFTFP EYEMKWVRQA PGKGLEWVST ITPSGGHTYY
ADSVKGRFTI SRDNSKNTLY LQMNSLRAED AAVYYCAIPL SS-------- FDYWGRGTLV TVSS

BMS2h-713 (SEQ ID NO: 334)
EVQLLESGGG LVQPGGSLRL SCAASGFTFS NYVMIWVRQA PGKGLEWVSL INGAGDMTYY
ADSVKGRFTI SRDNSKNTLY LQMNSLRAED TAVYYCAEGG ARSFGVPPN- FDYWGQGTLV TVSS

BMS2h-714 (SEQ ID NO: 335)
EVQLLESGGG LVQPGGSLRL SCAASGFTFT DGEMGWARQA PGKGLEWVSR IVDPGDSTYY
ADSVKGRFTI SRDNSKNTLY LQMNSLRAED TAVYYCAKAG DQ-------- FDYWGQGTLV TVSS

BMS2h-715 (SEQ ID NO: 336)
EVQLLESGGG LVQPGGSLRL SCVASGFTFT LYNMSWVRQA PGKGLEWVSV ISSKGDSTYY
ADSVKGRFTI SRDNSKNTLY LQMNSLRAED TAVYYCAQTS SV-------- FDYWGQGTLV TVSS

BMS2h-716 (SEQ ID NO: 337)
EVQLLESGGG LVQPGGSLRL SCAASGFTFE AYYMSWVRQA PGKGLEWVSG IVNNGLLTYY
ADSVKGRFTI SRDNSKNMLY LQMNSLRAED TAVYYCAKSA VHPSYRAEL- FDYWGQGTLV TVSS

BMS2h-717 (SEQ ID NO: 338)
EVQLLESGGG LVQPGGSLRL SCAASGFTFS SYEMAWVRQA PGKGLEWVSR IEPDGSNTYY
ADSVKGRFTI SRDNSKNTLY LQMNSLRAED TAVYYCAKGP DNFTM----- FDYWGQGTLV TVSS

BMS2h-718 (SEQ ID NO: 339)
EVQLLESGGG LVQPGGSLRL SCAASGFTFN KYMMGWVRQA PGKGLEWVSS IDSLGHYTYY
ADSVKGRFTI SRDNSKNTLY LQMNSLRAED TAVYYCAEAE FP-------- FDYWGQGTLV TVSS

BMS2h-719 (SEQ ID NO: 340)
EVQLLESGGG LVQPGGSLRL SCAASGFTFK RYEMTWVRQA PGKGLEWVSS ISSDGSFTYY
ADSVKGRFTI SRDNSKNTLY LQMNSLRAED TAVYYCAEPF TE-------- FDYWGQGTLV TVSS

BMS2h-719-1 (SEQ ID NO: 341)
EVQLLESGGG MVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTQV TVSS

BMS2h-719-10 (SEQ ID NO: 342)
EVQLLESGGG MVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTLV TVSS

BMS2h-719-11 (SEQ ID NO: 343)
EVQLLESGGG LVQPGGSLRL SCAASGFTFK RYEMMWVRKA PGKGLEWVSS ISSDGSFTYY
ADSVKGRFTI SRDNSENTLY LQMNSLRAED TAVYYCADPF TE-------- FDYWGQGTLV TVSS

BMS2h-719-12 (SEQ ID NO: 344)
EVQLLESGGG LVQPGGSLRL SCAASGFTFK RYEMMWVRQA PGKGLEWVSS ISSDGSFTYY
ADSVKGRFTV SRDNSKNTLY LQMNSLRAED TAVYYCADPF TE-------- FDYWGQGTLV TVSS

BMS2h-719-13 (SEQ ID NO: 345)
EVQLLESGGG LVQPGGSLRL SCAASGFTFK RYEMMWVRQA PGKGLEWVSS ISSDGSFTYY
ADSVKGRFTI SRDNTKNTLY LQMNSLRAED TAVYYCADPF TE-------- LDYWGHGTLV TVSS

BMS2h-719-14 (SEQ ID NO: 346)
EVQLLESGGG LVRPGGSLRL SCAASGFTFK RYEMMWVRQA PGKGLEWVSS ISSDGSFTYY
ADSVKGRFTI SRDNSKNTLY LQMNSLRAED TAVYFCADPF TE-------- FDYWGQGTLV TVSS
```

TABLE 1-continued

Anti-human CD40L VH Domain Amino Acid Sequences

```
BMS2h-719-15 (SEQ ID NO: 347)
EVQLLESGGG LVQPGGSLRL SCAASGFAFK RYEMTWVRQA PGKGLEWVSS ISSDGSFTYY
ADSVKGRFTI SRDNSKNTLY LHMNSLRAED TAVYYCADPF TE-------- IDYWGQGTLV TVSS

BMS2h-719-16 (SEQ ID NO: 348)
EVQLLESGGG LVQPGGSLRL SCAASGFPFK RYEMTWVRQA PGKGLEWVSS ISSDGSFTYY
ADSVKGRFTI SRDNSKNTLY LQMNSLRAED TAVYYCAEPF TE-------- FDYRAQGTLV TVSS

BMS2h-719-17 (SEQ ID NO: 349)
EVQLLESGGG LVQPGGSLRL SCAASGFTFK RYEMSWVRQA PGKGLEWVSS ISSDGSFTYY
ADSVKGRFTI SRDNSKNTLY LQMNSLRAED TAVYYCADPF TE-------- IDYWGQGTQV TVSS

BMS2h-719-18 (SEQ ID NO: 350)
EVQLLESGGG LVHPGGSLRL SCAASGFTFK RYEMMWVRQA PGKGLEWVSS ISSDGSFTYY
ADSVKGRFTI SRDNSKNTLY LQMNSLRDED TAVYYCAEPF TE-------- FDYGGQGTLV TVSS

BMS2h-719-19 (SEQ ID NO: 351)
EVQLLESGGG WVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-2 (SEQ ID NO: 352)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-20 (SEQ ID NO: 353)
EVQLLESGGG LVQPGGSLRL SCAASGFTFK RYEMTWVRQA PGKGLEWVSS ISSDGSFTYY
ADSVKGRFTI SRDNSKNTLY LQMNSLRAED TAVYYCAEPF TE-------- IDYRGQGTLV TVSS

BMS2h-719-202 (SEQ ID NO: 354)
EVQLLESGGG LVQPGGSLRL SCAASGFTFK KYEMMWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-203 (SEQ ID NO: 355)
EVQLLESGGG LVQPGGSLRL SCAASGFTFN SYEMMWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-21 (SEQ ID NO: 356)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-213 (SEQ ID NO: 357)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- MDYWGHGTLV TVSS

BMS2h-719-214 (SEQ ID NO: 358)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGHGTLV TVSS

BMS2h-719-215 (SEQ ID NO: 359)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- LDYWGHGTLV TVSS

BMS2h-719-218 (SEQ ID NO: 360)
EVQLLESGGG LVQPGGSLRL SCAASGFTFK RYEMMWVRQA PGKGLEWVSS ISSDGSFTYY
AESVKGRFTI SRDNSKNTLY LQMNSLRAED TAVYYCAEPF TE-------- FDYWGHGTLV TVSS

BMS2h-719-225 (SEQ ID NO: 361)
EVQLLESGGG LVQPGGSLRL SCAASGFTFN TYEMQWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-226 (SEQ ID NO: 362)
EVQLLESGGG LVQPGGSLRL SCAASGFTFN KYEMMWARQA PGKGLEWVSS ISSDGSFTYY
ADSVKGRFTI SRDNSRNTLY LQMNSLRAED TAVYYCAEPF TE-------- FDYWGHGTLV TVSS

BMS2h-719-3 (SEQ ID NO: 363)
EVQLSESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-4 (SEQ ID NO: 364)
EVQLLESGGG LVQPGGSLRL SCAASGFTFK RYEMMWVRQT PGKGLEWVSS ISSDGSFTYY
ADSVKGRFTI SRDNSKNTLY LQMNSLRAED TAVYYCAEPF TE-------- FDYWGQGTLV TVSS

BMS2h-719-5 (SEQ ID NO: 365)
EVQLLESGGG LVQPGGSLRL SCAASGFTFK RYEMMWVRQA PGKGLEWVSS ISSDGSFTYY
ADSVKGRFTI SRDNSKNTLY LEMNSMRAED TAVYYCAEPF TE-------- FDNWGQGTLV TVSS
```

TABLE 1-continued

Anti-human CD40L VH Domain Amino Acid Sequences

BMS2h-719-6 (SEQ ID NO: 366)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTQV TVSS

BMS2h-719-7 (SEQ ID NO: 367)
EVQLLESGGG LVQPGGSLRL SCAASGFNFK RYEMTWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-8 (SEQ ID NO: 368)
EVQLLESGGD LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYRGQGTLV TVSS

BMS2h-719-9 (SEQ ID NO: 369)
EVQLLESGGG LVQPGGSLRL SCAASGFTFK RYEMSWVRQA PGKGLEWVSS ISSDGSFTYY
ADSVKGRFTI SRDNSKNTLY LQMNSLRAED TAVYYCAEPF TE-------- FDYWGRGTLV TVSS

BMS2h-72 (SEQ ID NO: 370)
EVQLLESGGG LVQPGGSLRL SCAASGFTFE AYPMSWVRQA PGKGLEWVSS ISPLGLWTYY
ADSVKGRFTI SRDNSKNTLY LQMNSLRAED TAVYYCAKLS AGAETHVYRL FDYWGQGTLV TVSS

BMS2h-720 (SEQ ID NO: 371)
EVQLLESGGG LVQPGGSLRL SCAASGFTFG NYEMMWVRQA PGKGLEWVSS IGVLGHTTYY
ADSVKGRFTI SRDNSKNTLY LQMNSLRAED TAVYYCAKLM SLRTFENL- FDYWGQGTLV TVSS

BMS2h-722 (SEQ ID NO: 372)
EVQLLESGGG LVQPGGSLRL SCAASGFTFT KYPMAWVRQA PGKGLEWVSG IDANGNRTYY
ADSVKGRFTI SRDNSKNTLY LQMNSLRAED TAVYYCAEGT WRRHFAI--- FDYWGQGTLV TVSS

BMS2h-723 (SEQ ID NO: 373)
EVQLLESGGG LVQPGGSLRL SCAASGFTFD LYDMMWVRQA PGKGLEWVSS ISDLGTLTYY
ADSVKGRFTI SRDNSKNTLY LQMNSLRAED TAVYYCAKNG FRVTSNDRR- FDYWGQGTLV TVSS

BMS2h-724 (SEQ ID NO: 374)
EVQLLESGGG LVQPGGSLRL SCAASGFTFT GGDMWWVRQA PGKGLEWVSM IEGGGVTTYY
ADSVKGRFTI SRDNSKNTLY LQMNSLRAED TAVYYCAELD LRTGQ----- FDYWGQGTLV TVSS

BMS2h-725 (SEQ ID NO: 375)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FDYWGQGTLV TVSS

BMS2h-725-1 (SEQ ID NO: 376)
EVQLLESGGG LVQPGGSLHL SCAASGFTFS AYTMGWVRQA PGKGLEWVSL IGDRGSWTYY
ADSVKGRFTI SRDNSKNTLY LQMNSLRAED TAVYFCADPS DPTK------ FDYWGQGTLV TVSS

BMS2h-725-10 (SEQ ID NO: 377)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTK------ FDYWGQGTLV TVSS

BMS2h-725-11 (SEQ ID NO: 378)
EVQLLESGGG LVQPGGSLRL SCAASGFTFS AYTMGWVRQA PGKGLEWVSL IGDRGSWTYY
ADSVKGRFTI SRDNSKNTLY LQMSSLRAED TAVYYCADPS DPTK------ FDYWGQGTLV TVSS

BMS2h-725-12 (SEQ ID NO: 379)
EVQLLESGGG LVQPGGSLRL SCAASGFTFP AYTMGWVRQA PGKGLEWVSL IGDRGSWTYY
ADSVKGRFTI SRDDSKNTLY LQMNSLRVED TAVYYCAEPS DPTM------ FVYWGQGTLV TVSS

BMS2h-725-13 (SEQ ID NO: 380)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTM------ FVYWGQGTLV TVSS

BMS2h-725-14 (SEQ ID NO: 381)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTM------ FDYWGQGTLV TVSS

BMS2h-725-15 (SEQ ID NO: 382)
EVQLLESGGG MVQPGGSLRL SCAASGFTFS AYTMGWVRQA PGKGLEWVSL IGDRGSWTYY
ADSVKGRFTI SRDNSKNTLY LQMNSMRAED TAVYYCADPS DPTK------ FDYWGQGTLV TVSS

BMS2h-725-16 (SEQ ID NO: 383)
EVQLLESGGG LVQPGGSLRL SCAASGFTFS AYTMGWVRQA PGKGLEWVTL IGDRGSWTYY
ADSVKGRFTI SRDNSKNTLY LQMNSLRAED TAVYYCAEPS DPTM------ FDYWGQGTLV TVSS

BMS2h-725-17 (SEQ ID NO: 384)
EVQLLESGGG LVQPGGSLRL SCAASGFTFT AYTMGWVRQA PGKGLEWVSL IGDRGSWTYY
ADSVKGRFTI SRDNSKNTLY LQMNSLRAED TAVYYCAEPS DPTK------ LDYWGQGTLV TVSS

TABLE 1-continued

Anti-human CD40L VH Domain Amino Acid Sequences

```
BMS2h-725-18 (SEQ ID NO: 385)
EVQLSESGGG LVQPGGSLRL TCAASGFTFS AYTMGWVRQA PGKGLEWVSL IGDRGSWTYY
ADSVKGRFTI SRDNSKNTLY LQMNSLRAED TAVYYCADPS DPTK------ FVYWGQGTLV TVSS

BMS2h-725-19 (SEQ ID NO: 386)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTK------ FVYWGQGTLV TVSS

BMS2h-725-2 (SEQ ID NO: 387)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FVYWGQGTPV TVSS

BMS2h-725-3 (SEQ ID NO: 388)
VQLLESGGG LVQPGGSLRL SCAASGFTFS AYTMGWVRQA PGKGLEWVSL IGDRGSWTYY
ADSVKGRFTI SRDNSRNMLY LQMKSLRAED TAVYYCADPS DPTK------ FVYWGQGTQV TVSS

BMS2h-725-4 (SEQ ID NO: 389)
EVQLLESGGG LVQPGGSLRL SCAASGFTFS AYTMGWVRQA PGKGLEWVSL IGDRGSWTYY
ADSVKGRFTI FRDNSKNTLY LQMNSLRAED TAVYYCADPS DPTK------ FVYWGQGTLV TVSS

BMS2h-725-5 (SEQ ID NO: 390)
EVQLLESGGG LLQPGGSLRL SCAASGFTFS DYTMGWVRQA PGKGLEWVSL IGDRGSWTYY
ADSVKGRFTI SRDNSKNTLY LQMNSLRAED TAVYYCAEPS DPTK------ FDYWGRGTLV TVSS

BMS2h-725-6 (SEQ ID NO: 391)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FVYWGQGTLV TVSS

BMS2h-725-7 (SEQ ID NO: 392)
EVQLLESGGG LVQPGGSLRL SCAASGFTFS AYTMGWVRQA PGKGLEWVSL IGDRGTWTYY
ADPVKGRFTI SRDNSKNTLY LQMNSLRAED TAVYYCADPS DPTK------ FDYWGQGTLV TVSS

BMS2h-725-8 (SEQ ID NO: 393)
EVQLLESGGG LVQPGGSLRL SCAASGFTFS AYTMGWVRQA PGKGLEWVSL IGDRGSWTYY
ADSVKGRFTV SRDNSKNTLY LQMNSLRAED TAVYYCAEPS DPTK------ FDYWGQGTLV TVSS

BMS2h-725-9 (SEQ ID NO: 394)
EVQLLESGGG LVQPGGSLRL SCAASGFTFS AYTMGWVRQA PGMGLEWVSL IGDRGSWTYY
ADSVKGRFTI SRDNSKNTLY LQMNSLRAED TAVYYCAEPS DPTK------ FDYWGQGTLV TVSS

BMS2h-726 (SEQ ID NO: 395)
EVQLLESGGG LVQPGGSLRL SCAASGFTFD NYKMYWVRQA PGKGLEWVSS ISEIGNLTYY
ADSVKGRFTI SRDNSKNTLY LQMNSLRAED TAVYYCAIAL TR-------- FDYWGQGTLV TVSS

BMS2h-727 (SEQ ID NO: 396)
EVQLLESGGG LVQPGGSLRL SCAASGFTFA SYRMYWVRQA PGKGLEWVSY IDPPGSRTYY
ADSVKGRFTI SRDNSKNTLY LQMNSLRAED TAVYYCAKSL NLSFPYIN-FDYWGQGTLV TVSS

BMS2h-728 (SEQ ID NO: 397)
EVQLLESGGG LVQPGGSLRL SCAASGFTFE RYEMLWVRQA PGKGLEWVSR ISHSGRTTYY
ADSVKGRFTI SRDNSKNTLY LQMNSLRAED TAVYYCAQLD GP-------- FDYWGQGTLV TVSS

BMS2h-729 (SEQ ID NO: 398)
EVQLLESGGG LVQPGGSLRL SCAASGFTFK RYYMDWVRQA PGKGLEWVSR INHNGSVTYY
ADSVKGRFTI SRDNSKNTLY LQMNSLRAED TAVYYCAKMP QGTSDWYY-FDYWGQGTLV TVSS

BMS2h-73 (SEQ ID NO: 399)
EVQLLESGGG LVQPGGSLRL SCAASGFTFS KYDMSWVRQA PGKGLEWVST ILEDGLTTYY
ADSVKGRFTI SRDNSKNTLY LQMNSLRAED TAVYYCAKPG RL-------- FDYWGQGTLV TVSS

BMS2h-74 (SEQ ID NO: 400)
EVQLLESGGG LVQPGGSLRL SCAASGFTFS DYPMTWVRQA PGKGLEWVST ILSPGTETYY
ADSVKGRFTI SRDNSKNTLY LQMNSLRAED TAVYYCAKAE KD-------- FDYWGQGTLV TVSS

BMS2h-741 (SEQ ID NO: 401)
EVQLLESGGG LVQPGGSLRL SCAASGFTFE GGEMGWVRQA PGKGLEWVSM IPMDGSATYY
ADSVKGRFTI SRDNSKNTLY LQMNSLRAED TAVYYCAKAG EV-------- FDYWGQGTLV TVSS

BMS2h-742 (SEQ ID NO: 402)
EVQLLESGGG LVQPGGSLRL SCAASGFTFR EYHMKWARQA PGKGLEWVSG ISRDGMNTYY
ADSVKGRFTI SRDNSKNTLY LQMNSLRAED TAVYYCAIQL AL-------- FDYWGQGTLV TVSS

BMS2h-743 (SEQ ID NO: 403)
EVQLLESGGG LVQPGGSLRL SCAASGFTFR DYEMLWARQA PGKGLEWVSG ILPSGGATYY
ADSVKGRFTI SRDNSKNTLY LQMNSLRAED TAVYYCAKAG SGNGPIL--- FDYWGQGTLV TVSS
```

TABLE 1-continued

Anti-human CD40L VH Domain Amino Acid Sequences

BMS2h-744 (SEQ ID NO: 404)
EVQLLESGGG LVQPGGSLRL SCAASGFTFK EHDMFWVRQA PGKGLEWVSG IGAEGVWTYY
ADSVKGRFTI SRDNSKNTLY LQMNSLRAED TAVYYCAEPT MSNGSQSR-FDYWGQGTLV TVSS

BMS2h-745 (SEQ ID NO: 405)
EVQLLESGGG LVQPGGSLRL SCAASGFTFD NTEMAWVRQA PGKGLEWVSG IIEDGNRTYY
ADSVKGRFTI SRDNSKNTLY LQMNSLRAED TAVYYCAKIR NLHWDVGRQ- FDYWGQGTLV TVSS

BMS2h-745-1 (SEQ ID NO: 406)
EVQLLESGGG LVQPGGSLRL SCAASGFTFD NTEMAWVRQA PGKGLEWVSG ITEDGNRTYY
ADSVKGRFTI SRDNSKNTLY LQMNSLRAED TAVYYCAKIR NLHWDVGRQ- FDYWGQGTLV TVSS

BMS2h-745-10 (SEQ ID NO: 407)
EVQLLESGGG LVQPGGSLRL SCAASGFTFD NTEMAWVRQA PGKGLEWVSG ITEDGNRTYY
ADSVKGRFTI SRDNSKNTLY LQMNNLRAED TAVYYCAKIR NLHWDVGRQ- FDYWGQGTLV TVSS

BMS2h-745-11 (SEQ ID NO: 408)
EVQLLESGGG LVQPGGSLRL SCAASGFTFD NTEMAWIRQA PGKGLEWVSG ITEDGNRTYY
ADSVKGRFTI SRDNFKNTLY LQMNSLRAED TAVYYCAKIR NLHWDVGRQ- FDYWGQGTLV TVSS

BMS2h-745-12 (SEQ ID NO: 409)
EVQLLESGGG LVQPGGSLRL SCAASGFTFD NTEMAWVRQA PGKGLEWVSG ITEDGNRTYY
ADSVKGRFTI SRDNSMNTLY LQMNSLRAED TAVYYCAKIR NLHWDVGRQ- FVYWGQGTLV TVSS

BMS2h-745-13 (SEQ ID NO: 410)
EVQLLESGGG LVQPGGSLRL SCAASGFTFD NTEMAWIRQA PGKGLEWVSG IIEDGNRTYY
ADSVKGRFTI SRDNSKNTLY LQMNSLRAED TAVYYCAKIR NLHWDVGRQ- FDYWGQGTLV TVSS

BMS2h-745-14 (SEQ ID NO: 411)
EVQLLESGGG LVQPGGSLRL SCAASGFTFD NTEMAWIRQA PGKGLEWVSG ITEDGNRTYY
ADSVKGRFTI SRDNSKNTLY LQMNSLRAED TAVYYCAKIR NLHWDVGRQ- FDYWGQGTLV TVSS

BMS2h-745-15 (SEQ ID NO: 412)
EVQLLESGGG LVQPGGSLRL SCAASGFTFD NTEMAWIRQA PGKGLEWVSG ITEDGNRTYY
ADSVKGRFTI SRDNSKNALY LQMNSLRAED TAVYYCAKIR NLHWDVGRQ- FDYWGLGTLV TVSS

BMS2h-745-16 (SEQ ID NO: 413)
EVQLLESGGG LVQPGGSLRL SCAASGFTFD NTEMAWVRQA PGKGLEWVSG ITEDGNRTYY
ADSVKGRFTI SRDNTKNTLY LQMNSLRAED TAVYYCAKIR NLHWDVGRQ- FVYWGQGTLV TVSS

BMS2h-745-17 (SEQ ID NO: 414)
EVQLLESGGG LVQPGGSLRL SCAASGFTFD NTEMAWIRQA PGKGLEWVSG IIEDGNRTYY
ADSVKGRFTI SRDNSKNRLY LQMNSLRAED TAVYYCAKIR NLHWDVGRQ- FDYWGQGTLV TVSS

BMS2h-745-18 (SEQ ID NO: 415)
EVQLLESGGG LVQPGGSLRL SCAASGFTFD NTEMAWVRQA PGKGLEWVSG ITEDGNRTYY
ADSVKGRFTI SRDNSKNTLY LQMNSLRAED TAVYHCAKIR NLHWDVGRQ- FDYWGQGTLV TVSS

BMS2h-745-19 (SEQ ID NO: 416)
EVQLLESGGG LVQPEGSLRL SCAASGFTFD NTEMAWVRQA PGKGLEWVSG IIEDGNRTYY
ADSVKGRFTI SRDNSKNTLY LQMNSLRAED TAVYYCAKIR NLHWDVGRQ- FDYWGQGTLV TVSS

BMS2h-745-2 (SEQ ID NO: 417)
EVQLLESGGG LVQPGGSLRL SCAASGFTFD NTEMAWVRQA PGKGLEWVSG ISEDGNRTYY
ADSVKGRFTI SRDNSKNTLY LQMNSLRAED SAVYYCAKIR NLHWDVGRQ- FVYWGQGTLV TVSS

BMS2h-745-3 (SEQ ID NO: 418)
EVQLLESGGG LVEPGGSLRL SCAASGFTFD NTEMAWVRQA PGKGLEWVSG ITEDGNRTYY
ADSVKGRFTI SRDNSKNTLY LQMSSLRAED TAVYYCAKIR NLHWDVGRQ- FDYWGQGTLV TVSS

BMS2h-745-4 (SEQ ID NO: 419)
EVQLLESGGG LVQPGGSLRL SCAASGFTFD NTEMAWVRQA PGKGLEWVSG ISEDGNRTYY
ADSVKGRFTI SRDNSKNTLY LQMNSLRAED TAVYHCAKIR NLHWDVGRQ- FDYWGQGTLV TVSS

BMS2h-745-5 (SEQ ID NO: 420)
EVQLLESGGG LVQPGGSLRL SCAASGFTFD NTEMAWVRQA PGKGLEWVSG ITEDGNRTYY
ADSVKGRFII SRDNSKNTLN LQMNSLRAED TAVYYCAKIR NLHWDVGRQ- FDYWGQGTLV TVSS

BMS2h-745-6 (SEQ ID NO: 421)
EVQLLESGGG LVQPGGSLRL SCAASGFTFD NTEMAWIRQA PGRGLEWVSG VTEDGNRTYY
ADSVKGRFTI SRDNSKNTLY LQMNSLRAED TAVYYCAKIR NLHWDVGRQ- FDYWGQGTLV TVSS

BMS2h-745-7 (SEQ ID NO: 422)
EVQLLESGGG LVQPGGSLRL SCEASGFTFD NTEMAWIRQA PGKGLEWVSG IIEDGNRTYY
ADSVKGRFTI SRDNTKNTLY LQMNSLRAED TAVYYCAKIR NLHWDVGRQ- FDYWGQGTLV TVSS

TABLE 1-continued

Anti-human CD40L VH Domain Amino Acid Sequences

BMS2h-745-8 (SEQ ID NO: 423)
EVQLLESGGG LVQPGGSLRL SCAASGFTFD NTEMAWIRQA PGKGLEWVSG ITEDGDRTYY
ADSVKGRFTI SRDNSKSSLY LQMNSLRAED TAVYYCAKIR NLHWDVGRQ- FDYWGQGTLV TVSS

BMS2h-745-9 (SEQ ID NO: 424)
EVQLLESGGG SVQPGGSLRL SCAASGFTFD NTEMAWVRQA PGKGLEWVSG ITEDGNRTYY
ADSVKGRFTI SRDNSKNTLY LQMNSLRAED TAVYYCAKIR NLHWDVGRQ- FVYWGQGTLV TVSS

BMS2h-746 (SEQ ID NO: 425)
EVQLLESGGG LVQPGGSLRL SCAASGFTFG SAEMGWVRQA PGKGLEWVSG ISRPGQVTYY
ADSVKGRFTI SRDNSKNTLY LQMNSLRAED TAVYYCAKIR NLHWDVGRQ- FDYWGQGTLV TVSS

BMS2h-747 (SEQ ID NO: 426)
EVQLLESGGG LVQPGGSLRL SCAASGFTFD DGTMGWARQA PGKGLEWVSL ILPSGSRTYY
ADSVKGRFTI SRDNSKNTLY LQMNSLRAED TAVYYCAKHS LTNRP----- FDYWGQGTLV TVSS

BMS2h-748 (SEQ ID NO: 427)
EVQLLESGGG LVQPGGSLRL SCAASGFTFS KYDMRWARQA PGKGLEWVSD IDAVGTRTYY
ADSVKGRFTI SRDNSKNTLY LQMNSLRAED TAVYYCAIPG GT-------- FDYWGQGTLV TVSS

BMS2h-749 (SEQ ID NO: 428)
EVQLLESGGG LVQPGGSLRL SCAASGFTFE MYGMMWARQA PGKGLEWVSS IEGAGHATYY
ADSVKGRFTI SRDNSKNTLY LQMNSLRAED TAVYYCAIVL GM-------- FDYWGQGTLV TVSS

BMS2h-75 (SEQ ID NO: 429)
EVQLLESGGG LVQPGGSLRL SCAASGFTFL QYPMGWVRQA PGKGLEWVST ISPVGLTTYY
ADSVKGRFTI SRDNSKNTLY LQMNSLRAED TAVYYCAKLF EGSRIQRDVG FDYWGQGTLV TVSS

BMS2h-750 (SEQ ID NO: 430)
EVQLLESGGG LVQPGGSLRL SCAASGFTFE KYQMGWARQA PGKGLEWVSS IRGSGLVTYY
ADSVKGRFTI SRDNSKNTLY LQMNSLRAED TAVYYCAKVH TTLHTEVIG- FDYWGQGTLV TVSS

BMS2h-751 (SEQ ID NO: 431)
EVQLLESGGG LVQPGGSLRL SCAASGFTFS QYTMYWARQA PGKGLEWVSE ISHSGSNTYY
ADSVKGRFTI SRDNSKNTLY LQMNSLRAED TAVYYCAISG LH-------- FDYWGQGTLV TVSS

BMS2h-752 (SEQ ID NO: 432)
EVQLLESGGG LVQPGGSLRL SCAASGFTFS DYAMAWVRQA PGKGLEWVSR IGVEGGDTYY
ADSVKGRFTI SRDNSKNTLY LQMNSLRAED TAVYYCAKLL RLYRLG---- FDYWGQGTLV TVSS

BMS2h-753 (SEQ ID NO: 433)
EVQLLESGGG LVQPGGSLRL SCAASGFTFA KYDMTWVRQA PGKGLEWVSK INSDGGLTYY
ADSVKGRFTI SRDNSKNTLY LQMNSLRAED TAVYYCAKGL HGRGFVI--- FDYWGQGTLV TVSS

BMS2h-754 (SEQ ID NO: 434)
EVQLLESGGG LVQPGGSLRL SCAASGFTFS RYDMVWVRQA PGKGLEWVSR INSMGLATYY
ADSVKGRFTI SRDNSKNTLY LQMNSLRAED TAVYYCAKDY SVAPHGYPLG FDYWGQGTLV TVSS

BMS2h-755 (SEQ ID NO: 435)
EVQLLESGGG LVQPGGSLRL SCAASGFTFK DYSMMWVRQA PGKGLEWVST ITDNGTSTYY
ADSVKGRFTI SRDNSKNTLY LQMNSLRAED TAVYYCAKHM SLATYLQF-FDYWGQGTLV TVSS

BMS2h-756 (SEQ ID NO: 436)
EVQLLESGGG LVQPGGSLRL SCAASGFTFM EYDMLWVRQA PGKALEWVSR ISSDGLWTYY
ADSVKGRFTI SRDNSKNTLY LQMNSLRAED TAVYYCAKGV SALAPFDIG- FDYWGQGTLV TVSS

BMS2h-757 (SEQ ID NO: 437)
EVQLLESGGG LVQPGGSLRL SCAASGFTFK EYNMAWVRQA PGKGLEWVSS INFAGRTTYY
ADSVKGRFTI SRDNSKNTLY LQMNSLRAED TAVYYCAKLS LPLDIFS--- FDYWGQGTLV TVSS

BMS2h-758 (SEQ ID NO: 438)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS GY-------- FDYWGQGTLV TVSS

BMS2h-758-1 (SEQ ID NO: 439)
EVQLLESGGG LVQPGGSLRL SCAASGFTFG DYGMNWVRQA PGKGLEWVSH ISSNGRFTYY
ADSVKGRFTI SRDNSKNMLY LRMNSLRAED TAVYYCAETS GY-------- YEYWGQGTLV TVSS

BMS2h-758-2 (SEQ ID NO: 440)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS GY-------- FEYWGQGTLV TVSS

BMS2h-758-3 (SEQ ID NO: 441)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS SY-------- FEYWGQGTLV TVSS

TABLE 1-continued

Anti-human CD40L VH Domain Amino Acid Sequences

```
BMS2h-758-4 (SEQ ID NO: 442)
EVQLLESGGG LVQPGGSLRL SCAASGFTFG DYGMNWVRQA PGKGLEWVSH ISSNGRFTYY
ADSVKGRFTI SRDNSKNTLF LQMNSLRAED TAVYYCAETS GY-------- YEYWGHGTLV TVSS

BMS2h-758-5 (SEQ ID NO: 443)
EVQLLESGGG LVQPGGSLRL SCAASGFAFG DYGMNWVRQA PGKGLEWVSH ISSNGRFTYY
ADSVKGRFTI SRDNSKNTLY LQMNSLRAED TAVYYCAETS GY-------- FEYWGQGTLV TVSS

BMS2h-758-6 (SEQ ID NO: 444)
EVQLLESGGG LVQPGGSLRL SCAASGFTFG DYGMNWVRQA PGKGLEWVSH ISSNGRFIYY
ADSVKGRFTI SRDNSKNTLY LQMNSLRAED TAVYYCAETS GY-------- FEYWGQGTLV TVSS

BMS2h-759 (SEQ ID NO: 445)
EVQLLESGGG LVQPGGSLRL SCAASGFTFR EYVMGWVRQA PGKGLEWVST INGLGNVTYY
ADSVKGRFTI SRDNTKNTLY LQMNSLRAEE TAVYYCAIQL PN-------- FDYWGQGTLV TVSS

BMS2h-760 (SEQ ID NO: 446)
EVQLLESGGG LVQPGGSLRL SCAASGFTFG NDGMWWVRQA PGKGLEWVSF INVDGRETYY
ADSVKGRFTI SRDNSKNTLY LQMNSLRAED TAVYYCAEWS PGRVQ----- FDYWGQGTLV TVSS

BMS2h-761 (SEQ ID NO: 447)
EVQLLESGGG LVQPGGSLRL SCAASGFTFG GWDMAWVRQA PGKGLEWVSS IAHEGGETYY
ADSVKGRFTI SRDNSKNTLY LQMNSLRAED TAVYYCAKYV PGSPL----- FDYWGQRTLV TVSS

BMS2h-762 (SEQ ID NO: 448)
EVQLLESGGG LVQPGGSLRL SCAASGFTFD QGWMYWVRQA PGKGLEWVSG IGSNGPRTSY
ADSVKGRFTI SRDNSKNTLY LQMNSLRAED TAVYYCAKSG EY-------- FDYWGQGTLV TVSS

BMS2h-763 (SEQ ID NO: 449)
EVQLLESGGG LVQPGGSLRL SCAASGFTFR QSDMWWVRQA PGKGLEWVSV IGNNGEFTYY
ADSVKGRFTI SRDNSKNTLY LQMNSLRAED TAVYYCAKDN WLL------- FDYWGQGTLV TVSS

BMS2h-764 (SEQ ID NO: 450)
EVQLLESGGG LVQPGGSLRL SCAASGFTFD LSTMYWVRQA PGKGLEWVST IGGDGSHTYY
ADSVKGRFTI SRDNSKNTLY LQMNSLRAED TAVYYCAEGT QY-------- FDYWGQGTLV TVSS

BMS2h-765 (SEQ ID NO: 451)
EVQLLESGGG LVQPGGSLRL SCAASGFTFS AYTMEWVRQA PGKGLEWVSS IGVTGYDTYY
ADSVKGRFTI SRDNSKNTLY LQMNSLRAED TAVYYCAKGG QG-------- FDYWGQGTLV TVSS

BMS2h-766 (SEQ ID NO: 452)
EVQLLESGGG LVQPGGSLRL SCAASGFTFG DYGMSWVRQA PGKGLEWVSY IDPLGRLTYY
ADSVKGRFTI SRDNSKNTLY LQMNSLRAED TAVYYCAEDL SSLQYGVSPN FDYWGQGTLV TVSS

BMS2h-767 (SEQ ID NO: 453)
EVQLLESGGG LVQPGGSLRL SCAASGFTFF HYSMSWVRQA PGKGLEWVSS IGPVGRETYY
ADSVKGRFTI SRDNSKNTLY LQMNSLRAED TAVYYCAKMI QSPLFKD--- FDYWGQGTLV TVSS

BMS2h-768 (SEQ ID NO: 454)
EVQLLESGGG LVQPGGSLRL SCAASGFTFE WYDMYWVRQA PGKGLEWVSR IDSGGNQTYY
ADSVKGRFTI SRDNSKNTLY LQMNSLRAED TAVYYCAEAS LWKWRL---- FDYWGQGTLV TVSS

BMS2h-77 (SEQ ID NO: 455)
EVQLLESGGG LVQPGGSLRL SCAASGFTFE EYGMAWVRQA PGKGLEWVST ISPLGISTYY
ADSVKGRFTI SRDNSKNTLY LQMNSLRAED TAVYYCAKHA TSQESLRS-FDYWGQGTLV TVSS

BMS2h-770 (SEQ ID NO: 456)
EVQLLESGGG LVQPGGSLRL SCAASGFTFS KYEMMWVRQA PGKGLEWVSA ISGSGGSTYY
ADSVKGRFTI SRDNSKNTLY LQMNSLRAED TAVYYCAKGP LPDAFWTRG- FDYWGQGTLV TVSS

BMS2h-771 (SEQ ID NO: 457)
EVQLLESGGG LVQPGGSLRL SCAASGFTFG TYSMAWVRQA PGKGLEWVST IDRHGLATYY
ADSVKGRFTI SRDNSKNTLY LQMNSLRAED TAVYYCAKTP GSSWQTV--- FGYWGQGTLV TVSS

BMS2h-772 (SEQ ID NO: 458)
EVQLLESGGG LVQPGGSLRL SCAASGFTFE SYPMGWVRQA PGKGLEWVSS IDHHGHSTYY
ADSAKGRFTI SRDNSKNTLY LQMNSLRAED TAVYYCAKLL RVSMIFG--- FDYWGQGTLV TVSS

BMS2h-773 (SEQ ID NO: 459)
EVQLLESGGG LVQPGGSLRL SCAASGFTFV QYGMSWVRQA PGKGLEWVSW ISSSGTYTYY
ADSVKGRFTI SRDNSKNTLY LQMNSLRAED TAVYYCAETS RM-------- FDYWGQGTLV TVSS

BMS2h-774 (SEQ ID NO: 460)
EVQLLESGGG LVQPGGSLRL SCAASGFTFR EYDMGWVRQA PGKGLEWVSL ISPPGRTTYY
ADSVKGRFTI SRDNSKNTLY LQMNSLRAED TAVYYCAKVV ILGYTNR--- FDYWGQGTLV TVSS
```

TABLE 1-continued

Anti-human CD40L VH Domain Amino Acid Sequences

BMS2h-775 (SEQ ID NO: 461)
EVQLLESGGG LVQPGGSLRL SCAASGFTFP NYGMLWVRQA PGKGLEWVSS INSSGMETYY
ADSVKGRFTI SRDNSKNTLY LQMNSLRAED TAVYYCAKFF RLNDHNSVFG FDYWGQGTLV TVSS

BMS2h-776 (SEQ ID NO: 462)
EVQLLESGGG LVQPGGSLRL SCAASGFTFK DYKMMWIRQA PGKGLEWVSS IVGSGSMTYY
ADSVKGRFTI SRDNSKNTLY LQMNSLRAED TAVYYCAKGP GY-------- FDYWGQGTLV TVSS

BMS2h-777 (SEQ ID NO: 463)
EVQLLESGGG LVQPGGSLRL SCAASGFTFH NYAMGWVRRA PGKGLEWVSS IDEHGTITYY
ADSVKGRFTI SRDNSKNTLY LQMNSLRAED TAVYYCAKDS LDRVWI---- FDYWGQGTLV TVSS

BMS2h-778 (SEQ ID NO: 464)
EVQLLESGGG LVQPGGSLRL SCAASGFTFA DYPMTWVRQA PGKGLEWVSS IYSAGSPTYY
ADSVKGRFTI SRDNSKNTLY LQMNSLRAED TAVYYCAKLY HREPILFG- FDYWGQGTLV TVSS

BMS2h-78 (SEQ ID NO: 465)
EVQLLESGGG LVQPGGSLRL SCAASGFTFE RYQMAWVRQA PGKGLEWVST ISSDGGGTYY
ADSVKGRFTI SRDNSKNTLY LQMNSLRAED TAVYYCAKPG HR-------- FDYWGQGTLV TVSS

BMS2h-780 (SEQ ID NO: 466)
EVQLLESGGG LVQPGGSLRL SCAASGFTFG SYTMMWVRQA PGKGLEWVSE IDRTGERTYY
ADSVKGRFTI SRDNSKNTLY LQMNSLRAED TAVYYCAEPG FASLP----- FDYWGQGTLV TVSS

BMS2h-781 (SEQ ID NO: 467)
EVQLLESGGG LVQPGGSLRL SCAASGFTFT DYTMYWVRQA PGKGLEWVSK ISPSGRSTYY
ADSVKGRFTI SRDNSKNTLY LQMNSLRAED TAVYYCAKDP FG-------- FDYWGQGTLV TVSS

BMS2h-782 (SEQ ID NO: 468)
EVQLLESGGG LVQPGGSLRL SCAASGFTFD DAEMFWVRQA PGKGLEWVSS IDARGLTTYY
ADPVKGRFTI SRDNSKNTLY LQMNSLRAED TAVYYCAEAT SAMYP----- FDYWGQGTLV TVSS

BMS2h-783 (SEQ ID NO: 469)
EVQLLESGGG LVQPGGSLRL SCAASGFTFR DYDMGWVRQA PGKGLEWVST ISPLGHFTYY
ADSVKGRFTI SRDNSKNTLY LQMNSLRAED TAVYYCAKSF FHEYTEG--- FDYWGQGTLV TVSS

BMS2h-784 (SEQ ID NO: 470)
EVQLLESGGG LVQPGGSLRL SCAASGFTFD RAGMGWVRQA PGKGLEWVSL IGRGGDITYY
ADSVKGRFTI SRDNSKNTLY LQMNSLRAED TAVYYCAKIR NLHWDVGRQ- FDYWGQGTLV TVSS

BMS2h-80 (SEQ ID NO: 471)
EVQLLESGGG LVQPGGSLRL SCAASGFTFG RYQMAWVRQA PGKGLEWVSS ISSDGGGTYY
ADSVKGRFTI SRDNSKNTLY LQMNSLRAED TAVYYCAKPS RR-------- FDYWGQGTLV TVSS

BMS2h-81 (SEQ ID NO: 472)
EVQLLESGGG LVQPGGFLRL SCAASGFTFE LYPMAWVRQA PGKGLEWVSS ISPVGFLTYY
ADSVKGRFTI SRDNSKNTLY LQMNSLRAED TAVYYCAKGH EGSYTPRSA- FDYWGQGTLV TVSS

BMS2h-82 (SEQ ID NO: 473)
EVQLLESGGG LVQPGGSLRL SCAASGFTFV AYPMAWVRQA PGKGLEWVST IAPLGGNTYY
ADSVKGRFTI SRDNSKNTLY LQMNSLRAED TAVYYCAKRP EGLQIDSQN- FDYWGQGTLV TVSS

BMS2h-83 (SEQ ID NO: 474)
EVQLLESGGG LVQPGGSLRL SCAASGFTFA LYQMAWVRQA PGKGLEWVSS IDSSGSDTYY
ADSVKGRFTI SRDNSKNTLY LQMNSLRAED TAVYYCAKPE RD-------- FDYWGQGTLV TVSS

BMS2h-84 (SEQ ID NO: 475)
EVQLLESGGG LVQPGGSLRL SCAASGFTFR QYQMAWARQA PGKGLEWVST IASDGVSTYY
ADSVKGRFTI SRDNSKNTLY LQMNSLRAED TAVYYCAKVG RD-------- FDYWGQGTLV TVSS

BMS2h-85 (SEQ ID NO: 476)
EVQLLESGGG LVQPGGSLRL SCAASGFTFE QYDMRWVRQA PGKGLEWVSW IDEAGHETYY
ADSVKGRFTI SRDNSRNTLY LQMNSLRAED TAVYYCAKGM DG-------- FDYWGQGTLV TVSS

BMS2h-92 (SEQ ID NO: 477)
EVQLLESGGG LVQPGGSLRL SCAASGFTFV DYPMGWVRQA PGKGLEWVST ISTGGFSTYY
ADSVKGRFTI SRDNSKNTLY LQMNSLRAED TAVYYCAKAR YYYLSQIKN- FDYWGQGTLV TVSS

BMS2h-93 (SEQ ID NO: 478)
EVQLLESGGG LVQPGGSLRL SCAASGFTFD IYGMTWVRQA PGKGLEWVSS ISPLGLVTYY
ADPVKGRFTI SRDNSKNTLY LQMNSLRAED TAVYYCAKLK EHGDVP---- FDYWGQGTLV TVSS

BMS2h-94 (SEQ ID NO: 479)
EVQLLESGGG LVQPGGSLRL SCAASGFTFE LYPMSWVRQA PGKGLEWVST ISPTGLLTYY
ADSVKGRFTI SRDNSKNTLY LQMNSLRAED TAVYYCAKFK RSGKTDDTN- FDYWGQGTLV TVSS

TABLE 1-continued

Anti-human CD40L VH Domain Amino Acid Sequences

BMS2h-95 (SEQ ID NO: 480)
EVQLLESGGG LVQPGGSLRL SCAASGFTFR EYDMLWVRQA PGKGLEWVST IVGDGNGTYY
ADSVKGRFTI SRDNSKNTLY LQMNSLRAED TAVYYCAKQD RQ-------- FDYWGQGTLV TVSS

BMS2h-97 (SEQ ID NO: 481)
EVQLLESGGG LVQPGGSLRL SCAASGFTFE EYGMSWVRQA PGKGLEWVST ISPIGVTTYY
ADSVKGRFTI SRDNSKNTLY LQMNSLRAED TAVYYCAKNA YDRKSN---- FDYWGQGTLV TVSS

BMS2h-98 (SEQ ID NO: 482)
EVQLLESGGG LVQPGGSLRL SCAASGFTFD RYVMVWVRQA PGKDLEWVSG ITPSGRRTYY
ADSVKGRFTI SRDNSKDTLY LQMNSLRAED TAVYYCAKVL GRHFDPLLPS FDYWGQGTLV TVSS

BMS2h-99 (SEQ ID NO: 483)
EVQLLESGGG LVQPGGSLRL SCAASGFTFE DYAMSWVRQA PGKGLEWVST ITPGFWTYY
ADSVKGRFTI SRDNSKNTLY LQMNSLRAED TAVYYCAKTS SGELQLVED-FDYWGQGTLV TVSS

TABLE 2

Human Anti-CD40L VH Domain Encoding Nucleotide Sequences

BMS2h-10 (SEQ ID NO: 484)
GAGGTGCAGCTGTTGGAGTCTGGGGGAGGCTTAGTACAGCCTGGGGGGTC
CCTGCGTCTCTCCTGTGCAGCCTCCGGATTCACCTTTATTGCTTATGATA
TGAGTTGGGTCCGCCAGGCTCCAGGGAAGGGTCTGGAGTGGGTCTCATGG
ATTGATGAGTGGGGTCTGCAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAAGACG
CCTGAGGAGTTTGACTACTGGGGTCAGGGAACCCTGGTCACCGTCTCGAG
C

BMS2h-11 (SEQ ID NO: 485)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTGATTATGAGA
TGAGTTGGGTCCGCCAGGCTCCAGGGAAGGGTCTAGAGTGGGTCTCAGGG
ATTGATGGTGAGGGTTCTGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACCGCT
AGGAGTTTTGACTACTGGGGTCAGGGAACCCTGGTCACCGTCTCGAGC

BMS2h-111 (SEQ ID NO: 486)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCGTTATCCTA
TGACGTGGGTCCGCCAGGCTCCAGGGAAGGGTCTAGAGTGGGTCTCAACG
ATTCATGGTTCTGGTAGTGCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGCCG
TATACTAGTCGGCATAATAGTCTTGGGCATTTTGACTACTGGGGTCAGGG
AACCCTGGTCACCGTCTCGAGC

BMS2h-112 (SEQ ID NO: 487)
GAGGTGCAGCTGTTGGAGTCTGGGGGAGGCTTGGTACAGCCTGGGGGGTC
CCTGCGTCTCTCCTGTGCAGCCTCCGGATTCACCTTTATGGATTATCCTA
TGGGGTGGGTCCGCCAGGCTCCAGGGAAGGGTCTAGAGTGGGTCTCATCT
ATTGGGCCTGTTGGTATGAGTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATATGGG
GGGACTAGTGGTAGGCATAATACTAAGTTTGACTACTGGGGTCAGGGAAC
CCTGGTCACCGTCTCGAGC

BMS2h-113 (SEQ ID NO: 488)
GAGGTGCAGCTGTTGGAGTCTGGGGGAGGCTTGGTACAGCCTGGGGGGTC
CCTGCGTCTCTCCTGTGCAGCCTCCGGATTCACCTTTACTGATATCCTA
TGAGTTGGGTCCGCCAGGCTCCAGGGAAGGGTCTAGAGTGGGTCTCAGTT
ATTTCTCCTCTTGGTTTTACGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATGGACT
GGTGGGAGTGGTATTTTGAATTCTTCTTTTGACTACTGGGGTCAGGGAAC
CCTGGTCACCGTCTCGAGC

BMS2h-114 (SEQ ID NO: 489)
GAGGTGCAGCTGTTGGAGTCTGGGGGAGGCTTGGTACAGCCTGGGGGGTC
CCTGCGTCTCTCCTGTGCAGCCTCCGGATTTAGGGTTAGCAATTACGATT
TGACCTGGGTCCGCCAGGCTCCAGGGAAGGGTCTAGAGTGGGTATCAACC
ATTAGTGCCACAAACGGTAGCACATACTACGCAGACTCCGTGAAGGGCCG
GTTCACCATCTCCCGTGACAATTCCAAGAACACGCTGTATCTGCAAATGA
ACAGCCTGCGTGCCGAGGACACCGCGGTATATTATTGCGCGGCAGTGACG
TGGTGGTTGCTCATAACGACAACTTGGGGTTTTGGGGTCAGGGAACC
CTGGTCACCGTCTCGAGC

BMS2h-115 (SEQ ID NO: 490)
GAGGTGCAGCTGTTGGAGTCTGGGGGAGGCTTGGTACAGCCTGGGGGGTC
CCTGCGTCTCTCCTGTGCAGCCTCCGGATTTAGCATTAGCTATAAGAATA
TGGCCTGGGTCCGCCAGGCTCCAGGGAAGGGTCTAGAGTGGGTATCAGCC
ATTAAGGCGGCAAACGGTAGCACATACTACGCAGACTCCGTGAAGGGCCG
GTTCACCATCTCCCGTGACAATTCCAAGAACACGCTGTATCTGCAAATGA
ACAGCCTGCGTGCCGAGGACACCGCGGTATATTATTGCGCGACAGGGAGT
CAGAAGAAGCGGACCTACACGTTCGACTTTTGGGGTCAGGGAACCCTGGT
CACCGTCTCGAGC

BMS2h-12 (SEQ ID NO: 491)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGTTGTATAGAGA
TGGCGTGGGTCCGCCAGGCTCCAGGGAAGGGTCTAGAGTGGGTCTCAGGG
ATTGATATTTTGGGTTCGAGGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGATCTG
TCGTGGCAGGGTTTTGACTACTGGGGTCAGGGAACCCTGGTCACCGTCTC
GAGC

BMS2h-120 (SEQ ID NO: 492)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGTCTTATACGA
TGGGTTGGGTCCGCCAGGCTCCAGGGAAGGGTCTAGAGTGGGTCTCATCT
ATTAATCCTATGGGTTATCAGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACATGGG
GTGGGGAAGGGTACTAAGCACATAATTTTGACTACTGGGGTCAGGGAAC
CCTGGTCACCGTCTCGAGC

BMS2h-121 (SEQ ID NO: 493)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCTGTATAGGA
TGTCTTGGGTCCGCCAGGCTCCAGGGAAGGGTCTAGAGTGGGTCTCAGAG
ATTAGTGGTAGTGGTTTTCCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAGTCTG
CATGATAAGACTCAGCATCATCAGGAGTTTGACTACTGGGGTCAGGGAAC
CCTGGTCACCGTCTCGAGC

BMS2h-123 (SEQ ID NO: 494)
GAGGTGCAGCTGTTGGAGTCTGGGGGAGGCTTGGTACAGCCTGGGGGGTC
CCTGCGTCTCTCCTGTGCAGCCTCCGGATTCACCTTTATTGAGTATCCTA
TGCGGTGGGTCCGCCAGGCTCCAGGGAAGGGTCTAGAGTGGGTCTCACTT
ATTTCTCCGTCTGGTGTGTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGGAT

TABLE 2-continued

Human Anti-CD40L VH Domain Encoding
Nucleotide Sequences

GAGTCTAGTACTTTTGACTACTGGGGTCAGGGAACCCTGGTCACCGTCTC
GAGC

BMS2h-124 (SEQ ID NO: 495)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGCGGTATGATA
TGGATTGGGTCCGCCAGGCTCCAGGGAAGGGTCTAGAGTGGGTCTCAACG
ATTGGGAGTTCGGGTTATCCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAAGGATG
CCTGGTTATTTTCCTGGGTTTGCTCGGCAGTTTGACTACTGGGGTCAGGG
AACCCTGGTCACCGTCTCGAGC

BMS2h-125 (SEQ ID NO: 496)
GAGGTGCAGCTGTTGGAGTCTGGGGGAGGCTTGGTACAGCCTGGGGGGTC
CCTGCGTCTCTCCTGTGCAGCCTCCGGATTCACCTTTGGCGGTATGCTA
TGGGGTGGGTCCGCCAGGCTCCAGGGAAGGGTCTAGAGTGGGTCTCAACG
ATTAATGATGAGGGTCGGGAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAGCGG
GTGTCTAGTTCTGTGAATGCTCCGTATGAGTTTGACTACTGGGGTCAGGG
AACCCTGGTCACCGTCTCGAGC

BMS2h-126 (SEQ ID NO: 497)
GAGGTGCAGCTGTTGGAGTCTGGGGGAGGCTTGGTACAGCCTGGGGGGTC
CCTGCGTCTCTCCTGTGCAGCCTCCGGATTCACCTTCCGGAATTATAGTA
TGAGTTGGGTCCGCCAGGCCCCAGGGAAGGGTCTAGAGTGGGTCTCATCG
ATTGATCGTCTTGGTACGCATACATACTACGCAGACTCCGTGAAGGGCCG
GTTCACCATCTCCCGCGACAATTCCAAGAATACGCTGTATCTGCAAATGA
ACAGCCTGCGTGCCGAGGACACCGCGGTATATTACTGTGCGAAAGTGCTG
GCTGATCTTATTGCTGGGCATGCGGAGTTTGACTACTGGGGTCAGGGAAC
CCTGGTCACCGTCTCGAGC

BMS2h-127 (SEQ ID NO: 498)
GAGGTGCAGCTGTTGGAGTCTGGGGGAGGCTTGGTACAGCCTGGGGGGTC
CCTGCGTCTCTCCTGTGCAGCCTCCGGATTCACCTTTCCGTCGTATGATA
TGGCGTGGGTCCGCCAGGCTCCAGGGAAGGGTCTAGAGTGGGTCTCAGGG
ATTTCGAGGTCTGGTTCTATGACATACTACGCAGACTCCGTGAAGGGCCG
GTTCACCATCTCCCGCGACAATTCCAAGAACACGCTGTATTTGCAAATGA
ACAGCCTGCGTGCCGAGGACACCGCGGTATATTACTGTGCGAAAGGTGTT
GATGCGCATGTTTATTATATGGAGCCTTTTTTTGACTACTGGGGTCAGGG
AACCCTGGTCACCGTCTCGAGC

BMS2h-128 (SEQ ID NO: 499)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGAGGTATCAGA
TGGCGTGGGTCCGCCAGGCTCCAGGGAAGGGTCTAGAGTGGGTCTCAACG
ATTAGTTCTGATGGTGGGGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGT
ACTGTTTTTGACTACTGGGGTCAGGGAACCCTGGTCACCGTCTCGAGC

BMS2h-129 (SEQ ID NO: 500)
GAGGTGCAGCTGTTGGAGTCTGGGGGAGGCTTGGTACAGCCTGGGGGGTC
CCTGCGTCTCTCCTGTGCAGCCTCCGGATTCACATTTGCGAAGTATGAGA
TGGCGTGGGTCCGCCAGGCTCCAGGGAAGGGTCTAGAGTGGGTCTCATCT
ATTGATGGTGATGGTAAGTCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCGGAT
CAGTTTTTTGACTACTGGGGTCAGGGAACCCTGGTCACCGTCTCGAGC

BMS2h-13 (SEQ ID NO: 501)
GAGGTGCAGCTGTTGGAGTCTGGGGGAGGCTTGGTACAGCCTGGGGGGTC
CCTGCGTCTCTCCTGTGCAGCCTCCGGATTCACCTTTCTTATTATTCGA
TGTATTGGGTCCGCCAGGCTCCAGGGAAGGGTCTAGAGTGGGTCTCATCG
ATTTCGCCTTTTGGTTGGGTACATACTACGCAGACTCCGTGAAGGGCCG
GTTCACCATCTCCCGCGACAATTCCAAGGACACGCTGTATCTGCAAATGA
ACAGCCTGCGTGCCGAGGACACCGCGGTATATTACTGTGCGAAATATGGG
GAGACGAGTGGTCCGATTTCTGAGAATTTTGACTACTGGGGTCAGGGAAC
CCTGGTCACCGTCTCGAGC

BMS2h-130 (SEQ ID NO: 502)
GAGGTGCAGCTGTTGGAGTCTGGGGGAGGCTTGGTACAGCCTGGGGGGTC
CCTGCGTCTCTCCTGTACAGCCTCCGGATTCACCTTTGCGGGTTATCAGA
TGTCGTGGGTCCGCCAGGCTCCAGGGAAGGGTCTAGAGTGGGTCTCAAGT
ATTACTAATGAGGGTGTTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGG
AAGTATTTTGACTACTGGGGTCAGGGAACCCTGGTCACCGTCTCGAGC

BMS2h-131 (SEQ ID NO: 503)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGAGTATGAGA
TGGTGTGGGTCCGCCAGGCTCCAGGGAAGGGTCTGGAGTGGGTCTCATCT
ATTACGTCGGATGGTCTGAGTACATACTACGCAGACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGAAAACCGGGT
ATTCGTTTTGACTACTGGGGTCAGGGAACCCTGGTCACCGTCTCGAGC

BMS2h-132 (SEQ ID NO: 504)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTGATTATGATA
TGGCTTGGGTCCGCCAGGCTCCAGGGAAGGGTCTAGAGTGGGTCTCAGGT
ATTGTTGATGATGGTCTTATGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACGGAT
GTTGCTTTTGACTACTGGGGTCAGGGGACCCTGGTCACCGTCTCGAAC

BMS2h-133 (SEQ ID NO: 505)
GAGGTGCAGCTGTTGGAGTCTGGGGGAGGCTTGGTACAGCCTGGGGGGTC
CCTGCGTCTCTCCTGTGCAGCCTCCGGATTCACCTTTATTGGTTATGCTA
TGGCGTGGGTCCGCCAGGCTCCAGGGAAGGGTCTAGAGTGGGTCTCAAGT
ATTGGTCCTTTGGGTGCGACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTGCCT
GCTGGTACGAGTAGTCATAGTGTGGATTTTGACTACTGGGGTCAGGGAAC
CCTGGTCACCGTCTCGAGC

BMS2h-134 (SEQ ID NO: 506)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGGATTATGAGA
TGACTTGGGTCCGCCAGGCTCCAGGGAAGGGTCTAGAGTGGGTCTCATCT
ATTACTAGTGATGGTGTTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGTCG
GTTCAGTTTGACTACTGGGGTCAGGGAACCCTGGTCACCGTCTCGAGC

BMS2h-135 (SEQ ID NO: 507)
GAGGTGCAGCTGTTGGAGTCTGGGGGAGGCTTGGTACAGCCTGGGGGGTC
CCTGCGTCTCTCCTGTGCAGCCTCCGGATTCACCTTTCGTAGGTATGTTA
TGGGGTGGGTCCGCCAGGCTCCAGGGAAGGGTCTAGAGTGGGTCTCATGG
ATTGAGGCTGATGGTCGTACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGCTT
ACGGATCAGCATGTTATTGAGTTTGACTACTGGGGTCAGGGAACCCTGGT
CACCGTCTCGAGC

BMS2h-136 (SEQ ID NO: 508)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGGTTATCGTA
TGGGGTGGGTCCGCCAGGCTCCAGGGAAGGGTCTAGAGTGGGTCTCATCG
ATTGCTCCGGATAATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTTTGG
GGGATGCAGTTTGACTACTGGGGTCAGGGAACCCTGGTCACCGTCTCGAG
C

BMS2h-137 (SEQ ID NO: 509)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTTCGTATCCGA
TGGGTTGGGTCCGCCAGGCTCCAGGGAAGGGTCTAGAGTGGGTCTCAAGT
ATTGGTCCTATTGGTTTTACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAATGAAG
TCGCCTTATAAGCCGCAGTTTGACTACTGGGGTCAGGGAACCCTGGTCAC
CGTCTCGAGC

BMS2h-138 (SEQ ID NO: 510)
GAGGTGCAGCTGTTGGAGTCTGGGGGAGGCTTGGTACAGCCTGGGGGGTC
CCTGCGTCTCTCCTGTGCAGCCTCCGGATTCACCTTTTTGGCTTATTGGA
TGGTTTGGGTCCGCCAGGCTCCAGGGAAGGGTCTAGAGTGGGTCTCATCT
ATTTCTCCGTCGGGTACGCATACATACTACGCAGACTCCGTGAAGGGCCG
GTTCACCATCTCCCGCGACAATTCCAAGAACACGCTGTATCTGCAAATGA
ACAGCCTGCGTGTCGAGGACACCGCGGTATATTACTGTGCGAAATATACT

TABLE 2-continued

Human Anti-CD40L VH Domain Encoding
Nucleotide Sequences

GAGCCGGGGTTGGGTTCTTTTGACTACTGGGGTCAGGGAACCCTGGTCAC
CGTCTCGAGC

BMS2h-139 (SEQ ID NO: 511)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGAATTATGAGA
TGGGGTGGGTCCGCCAGGCTCCAGGGAAGGGTCTAGAGTGGGTCTCAGTG
ATTTCTGAGGTGGGTTCTCTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTCAT
GATAGTTCGATTGGGTTTGACTACTGGGGTCAGGGAACCCTGGTCACCGT
CTCGAGC

BMS2h-14 (SEQ ID NO: 512)
GAGGTGCAGCTGTTGGAGTCTGGGGGAGGCTTGGTACAGCCTGGGGGGTC
CCTGCGTCTCTCCTGTGCAGCCTCCGGATTCACCTTTTGGTCTTATGATA
TGACGTGGGTCCGCCAGGCTCCAGGGAAGGGTCTAGAGTGGGTCTCATCT
ATTATGGCTTCGGGTGATGATACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATGGGAT
CGGGATTTTGACTACTGGGGTCAGGGAACCCTGGTCACCGTCTCGAGC

BMS2h-15 (SEQ ID NO: 513)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGAGTATGTTA
TGTCGTGGGTCCGCCAGGCTCCAGGGAAGGGTCTAGAGTGGGTCTCAACT
ATTTCTCCTATTGGTCTGACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAATTTCCT
TTGATTATTCTTCCTGATTTTGACTACTGGGGTCAGGGAACCCTGGTCAC
CGTCTCGAGC

BMS2h-16 (SEQ ID NO: 514)
GAGGTGCAGCTGTTGGAGTCTGGGGGAGGCCTGGTACAGCCTGGGGGGTC
CCTGCGTCTCTCCTGTGCAGCCTCCGGATTCACCTTTATGGAGTATGCGA
TGATTTGGGTCCGCCAGGCTCCAGGGAAGGGTCTAGAGTGGGTCTCAATT
ATTTCTCCGCTTGGTTTGTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATATCAG
GATTCGTCTGATAGTCAGTATACGAATTTTGACTACTGGGGTCAGGGAAC
CCTGGTCACCGTCTCGAGC

BMS2h-17 (SEQ ID NO: 515)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGATTATGGGA
TGGGGTGGGCCCGCCAGGCTCCAGGGAAGGGTCTAGAGTGGGTCTCAAGT
ATTGGTCCTCTGGGTCTTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCTCCG
CTTGAGGGTTTGATTACGAATTTTGACTACTGGGGTCAGGGAACCCTGGT
CACCGTCTCGAGC

BMS2h-176 (SEQ ID NO: 516)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGTATGATAGA
TGGGGTGGGTCCGCCAGGCTCCAGGGAAGGGTCTAGAGTGGGTCTCAATT
ATTGATTGGGATGGTAATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTGGG
GATAATGTTGGTATTTTTGACTACTGGGGTCAGGGAACCCTGGTCACCGT
CTCGAGC

BMS2h-177 (SEQ ID NO: 517)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAATTATTATA
TGGTGTGGGTCCGCCAGGCTCCAGGGAAGGGTCTAGAGTGGGTCTCAGCG
ATTGATGAGTGGGGTTTTGCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACATTGG
GAGTTTACGTCTGATCGTCGCGTTTTGACTACTGGGGTCAGGGAACCCT
GGTCACCGTCTCGAGC

BMS2h-178 (SEQ ID NO: 518)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGATTTTGATA
TGGCTTGGGTCCGCCAGGCTCCAGGGAAGGGTCTAGAGTGGGTCTCATCT
ATTAATGATCAGGGTTCTCTGACATACTACGCAGACTCCGTGAAGGGCCG

GTTCACCATCTCCCGCGACAATTCCAAGAACACGCTGTATCTGCAAATGA
ACAGCCTGCGTGCCGAGGACACCGCGGTATATTACTGTGCGAAACCGGAT
CAGTTTTTTGACTACTGGGGTCAGGGAACCCTGGTCACCGTCTCGAGC

BMS2h-179 (SEQ ID NO: 519)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGCTTATGATA
TGATGTGGGTCCGCCAGGCTCCAGGGAAGGGTCTAGAGTGGGTCTCACGG
ATTAGTCCTCAGGGTCAGCGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAATTCGT
GGGCAGTCGCGGATTCCTATGAGGTTTGACTACTGGGGTCAGGGAACCCT
GGTCACCGTCTCGAGC

BMS2h-18 (SEQ ID NO: 520)
GAGGTGCAGCTGTTGGAGTCTGGGGGAGGCTTGGTACAGCCTGGGGGGTC
CCTGCGTCTCTCCTGTGCAGCCTCCGGATTCACCTTTCCTGAGTATGATA
TGACGTGGGTCCGCCAGGCTCCAGGGAAGGGTCTGGAGTGGGTCTCATAT
ATTAGTTCTGATGGTTATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGCAT
GGGAGTCCGCGGGAGTTTGACTACTGGGGTCAGGGAACCCTGGTCACCGT
CTCGAGC

BMS2h-180 (SEQ ID NO: 521)
GAGGTGCAGCTGTTGGAGTCTGGGGGAGGCTTGGTACAGCCTGGGGGGTC
CCTGCGTCTCTCCTGTGCAGCCTCCGGATTCACCTTTACGGATTATGAGA
TGGGGTGGGTCCGCCAGGCTCCAGGGAAGGGTCTAGAGTGGGTCTCAACG
ATTACTAGTTTGGGTGAGAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGGT
CGTATTTTTGACTACTGGGGTCAGGGAACCCTGGTCACCGTCTCGAGC

BMS2h-181 (SEQ ID NO: 522)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTTTTTATCCTA
TGATGTGGGTCCGCCAGGCTCCAGGGAAGGGTCTAGAGTGGGTCTCATGG
ATTGATGCTACGGGTACGAGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGGTAAT
TATGGGAGTTCGTATACTATGGGGTTTTTGACTACTGGGGTCAGGGAAC
CCTGGTCACCGTCTCGAGC

BMS2h-182 (SEQ ID NO: 523)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGAGTATCCGA
TGTATTGGGTCCGCCAGGCTCCAGGGAAGGGTCTAGAGTGGGTCTCATCG
ATTGGTCCTTCTGGTCCGAATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCTCCG
TATTTTGATGTTATTCCTAGTTATTTTGACTACTGGGGTCAGGGAACCCT
GGTCACCGTCTCGAGC

BMS2h-183 (SEQ ID NO: 524)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGGATTACGTA
TGGGTTGGGTCCGCCAGGCTCCAGGGAAGGGTCTAGAGTGGGTCTCATCT
ATTCAGTCGTCGGGTTTGCGGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACGGGCT
AATTCTCGTAGGGGTTTTGACTACTGGGGTCAGGGAACCCTGGTCACCGT
CTCGAGC

BMS2h-184 (SEQ ID NO: 525)
GAGGTGCAGCTGTTGGAGTCTGGGGGAGGCTTGGTACAGCCTGGGGGGTC
CCTGCGTCTCTCCTGTGCAGCCTCCGGATTCACCTTTTCTGATTATGAGA
TGATGTGGGTCCGCCAGGCTCCAGGGAAGGGTCTAGAGTGGGTCTCATCT
ATTACTATGATGGTGGCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTGAT
AAGGATTTTGACTACTGGGGTCAGGGAACCCTGGTCACCGTCTCGAGC

BMS2h-185 (SEQ ID NO: 526)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGCATTATCCGA
TGTCGTGGGTCCGCCAGGCTCCAGGGAAGGGTCTAGAGTGGGTCTCATCG
ATTGGTAGGCTGGGTAATCGTACATACTACGCAGACTCCGTGAAGGGCCG

TABLE 2-continued

Human Anti-CD40L VH Domain Encoding Nucleotide Sequences

GTTCACCATCTCCCGCGACAATTCCAAGAACACGCTGTATCTGCAAATGA
ACAGCCTGCGTGCCGAGGACACCGCGGTATATTACTGTGCGAAACGTGCT
ACGCCTGTGCCGATTAAGGGTTTGTTTGACTACTGGGGTCAGGGAACCCT
GGTCACCGTCTCGAGC

BMS2h-186 (SEQ ID NO: 527)
GAGGTGCAGCTGTTGGAGTCTGGGGGAGGCTTGGTACAGCCTGGGGGGTC
CCTGCGTCTCTCCTGTGCAGCCTCCGGACTCACCTTTGGGAGGTATGAGA
TGGCGTGGGTCCGCCAGGCTCCAGGGAAGGGTCTAGAGTGGGTCTCAAGT
ATTGATTCGGATGGTTGGGTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGCAACCGGAT
TCGTTGTTTGACTACTGGGGTCAGGGAACCCTGGTCACCGTCTCGAGC

BMS2h-187 (SEQ ID NO: 528)
GAGGTGCAGCTGTTGGAGTCTGGGGGAGGCTTGGTACAGCCTGGGGGGTC
CCTGCGTCTCTCCTGTGCAGCCTCCGGATTCACCTTTTCTAGTTATTCTA
TGGTGTGGGTCCGCCAGGCTCCAGGGAAGGGTCTAGAGTGGGTCTCAAGT
ATTAATCGGGGTGGTACTCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTTGG
AGGAGGGGGTTTGACTACTGGGGTCAGGGAACCCTGGTCACCGTCTCGAG
C

BMS2h-188 (SEQ ID NO: 529)
GAGGTGCAGCTGTTGGAGTCTGGGGGAGGCTTGGTACAGCCTGGGGGGTC
CCTGCGTCTCTCCTGTGCAGCCTCCGGATTCACCTTTACGCGTTATAGGA
TGTCTTGGGTCCGCCAGGCTCCAGGGAAGGGTCTGGAGTGGGTCTCAGGG
ATTTCGAGGGATGGTTATCGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTATG
ACTGCGTCGTTTGACTACTGGGGTCAGGGAACCCTGGTCACCGTCTCGAG
C

BMS2h-189 (SEQ ID NO: 530)
GAGGTGCAGCTGTTGGAGTCTGGGGGAGGCTTGGTACAGCCTGGGGGGTC
CCTGCGTCTCTCCTGTGCAGCCTCCGGATTCACCTTTCAGATGTATCCGA
TGGGGTGGGTCCGCCAGGCTCCAGGGAAGGGTCTAGAGTGGGTCTCAATG
ATTGAGCCGGCTGGTGATCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATATCAG
GAGCAGCCTTGGTTTGACTACTGGGGTCAGGGAACCCTGGTCACCGTCTC
GAGC

BMS2h-19 (SEQ ID NO: 531)
GAGGTGCAGCTGTTGGAGTCTGGGGGAGGCTTGGTACAGCCTGGGGGGTC
CCTGCGTCTCTCCTGTGCAGCCTCCGGATTCCCCTTTCCGCAGTATCAGA
TGGCGTGGGTCCGCCAGGCTCCAGGGAAGGGTCTAGAGTGGGTCTCAATG
ATTACTTCTGATGGTCTTGATACATATTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTGAG
CCTCTTTTTGACTACTGGGGTCAGGGAACCCTGGTCACCGTCTCGAGC

BMS2h-190 (SEQ ID NO: 532)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTATGTATGATA
TGCATTGGGTCCGCCAGGCTCCAGGGAAGGGTCTAGAGTGGGTCTCAACG
ATTTTGTCTGATGGTACGGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATATGGG
GCTATGTTTGACTACTGGGGTCAGGGAACCCTGGTCACCGTCTCGAGC

BMS2h-191 (SEQ ID NO: 533)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGTTGTATCCGA
TGACGTGGGTCCGCCAGGCTCCAGGGAAGGGTCTAGAGTGGGTCTCATCT
ATTGATGCGGGGGGTCATGAGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGATTGG
TGGGATTATCGTTTGACTACTGGGGTCAGGGAACCCTGGTCACCGTCTC
GAGC

BMS2h-192 (SEQ ID NO: 534)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGCGGTATCCGA
TGAGTTGGGTCCGCCAGGCTCCAGGGAAGGGTCTAGAGTGGGTCTCATCT
ATTAATCGTTCGGGTATGCGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGGGCAT
CAGGCGCCGTTTGACTACTGGGGTCAGGGAACCCTGGTCACCGTCTCGAG
C

BMS2h-193 (SEQ ID NO: 535)
GAGGTGCAGCTGTTGGAGTCTGGGGGAGGCTTGGTACAGCCTGGGGGGTC
CCTGCGTCTCTCCTGTGCAGCCTCCGGATTCACCTTTACGGGGTATGCTA
TGTCTTGGGTCCGCCAGGCTCCAGGGAAGGGTCTAGAGTGGGTCTCAACT
ATTAATGCGAATGGTATTCGGACATACTACGCGACTCCGTGAAGGGCCG
GTTCACCATCTCCCGCGACAATTCCAAGAACACGCTGTATCTGCAAATGA
ACGGCCTGCGTGCCGAGGACACCGCGGTATATTACTGTGCGAAAGGGGG
GTTTGGAGGTGGGGACTGGGCATAAGTTTGACTACTGGGGTCAGGGAAC
CCTGGTCACCGTCTCGAGC

BMS2h-194 (SEQ ID NO: 536)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGCAGTATGATA
TGCGGTGGGTCCGCCAGGCTCCAGGGAAGGGTCTAGAGTGGGTCTCAACG
ATTTCGCAGAATGGTACTAAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCGAGG
ACTGGTAGGTATTTTGACTACTGGGGTCAGGGAACCCTGGTCACCGTCTC
GAGC

BMS2h-195 (SEQ ID NO: 537)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGACTTATGATA
TGGGGTGGGTCCGCCAGGCTCCAGGGAAGGGTCTAGAGTGGGTCTCAAGG
ATTATTGCAGGGTGATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGGGG
TTTGGTCATTATGTTGATGGTCTTGGGTTTGACTACTGGGGTCAGGGAAC
CCTGGTCACCGTCTCGAGC

BMS2h-196 (SEQ ID NO: 538)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGGGTATGAGA
TGGCGTGGGTCCGCCAGGCTCCAGGGAAGGGTCTAGAGTGGGTCTCATCT
ATTACTGATATGGGTGATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGGG
ACTGCGTTTGACTACTGGGGTCCGGGAACCCTGGTCACCGTCTCGAGC

BMS2h-197 (SEQ ID NO: 539)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGAAGTATAAGA
TGTGGTGGGTCCGCCAGGCTCCAGGGAAGGGTCTAGAGTGGGTCTCAAGT
ATTACTCCGAAGGGTCATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAAGGCCG
ATGACTCCGTTTGACTACTGGGGTCAGGGAACCCTGGTCACCGTCTCGAG
C

BMS2h-198 (SEQ ID NO: 540)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCGGTATAATA
TGTCTTGGGTCCGCCAGGCTCCAGGGAAGGGTCTAGAGTGGGTCTCATCT
ATTCGGCCGCGGGTGGGAAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGCGG
CGGGAGGGGTATACTGGTTCTAAGTTTGACTACTGGGGTCAGGGAACCCT
GGTCACCGTCTCGAGC

BMS2h-199 (SEQ ID NO: 541)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGAGGTATGGTA
TGACTTGGGTCCGCCAGGCTCCAGGGAAGGGTCTGGAGTGGGTCTCAAGT
ATTTGGCGAGGGGTCAGAAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGAAT
AGTGGTATGTTTTGACTACTGGGGTCAGGGAACCCTGGTCACCGTCTCG
AGC

BMS2h-2 (SEQ ID NO: 542)
GAGGTGCAGCTGTTGGAGTCTGGGGGAGGCTTGGTACAGCCTGGGGGGTC
CCTGCGTCTCTCCTGTGCAGCCTCCGGATTCACCTTTTCTGATTATGAGA

TABLE 2-continued

Human Anti-CD40L VH Domain Encoding
Nucleotide Sequences

TGATGTGGGTCCGCCAGGCTCCAGGGAAGGGTCTAGAGTGGGTCTCAACT
ATTACTTCGGATGGTATTTCTACATACTACGCAGACTCCGTGAAGGGCCG
GTTCACCATCTTCCGCGACAATTCCAAGAACACGCTGTATCTGCAAATGA
ACAGCCTGCGTGCCGAGGATACCGCGGTATATTACTGTGCGAAAAGTGGG
AGGTTTTTTGACTACTGGGGTCAGGGAACCCTGGTCACCGTCTCGAGC

BMS2h-20 (SEQ ID NO: 543)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGGTTATCAGA
TGGCTTGGGTCCGCCAGGCTCCAGGGAAGGGTCTAGAGTGGGTCTCAGGT
ATTAGTTCGGAGGGTCTTACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTGGGG
CGTAGGTTTGACTACTGGGGTCAGGGAACCCTGGTCACCGTCTCGAGC

BMS2h-200 (SEQ ID NO: 544)
GAGGTGCAGCTGTTGGAGTCTGGGGGAGGCTTGGTACAGCCTGGGGGGTC
CCTGCGTCTCTCCTGTGCAGCCTCCGGATTCACCTTTACTAATTATAGTA
TGGGTTGGGTCCGCCAGGCTCCAGGGAAGGGTCTAGAGTGGGTCTCAACT
ATTCGTCCTAATGGTACTAAGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACGGTCG
TCTGCGCATCTTCAGAGGTTTGACTACTGGGGTCAGGGAACCCTGGTCAC
CGTCTCGAGC

BMS2h-201 (SEQ ID NO: 545)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTAATTATTCGA
TGGGTTGGGTCCGCCAGGCTCCAGGGAAGGGTCTAGAGTGGGTCTCATCG
ATTGGTCGTCATGGTGGGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAAGGGG
AGTACTTATCCTAGGTTTGACTACTGGGGTCAGGGAACCCTGGTCACCGT
CTCGAGC

BMS2h-202 (SEQ ID NO: 546)
GAGGTGCAGCTGTTGGAGTCTGGGGGAGGCTTGGTACAGCCTGGGGGGTC
CCTGCGTCTCTCCTGTACAGCCTCCGGATTCACCTTTTCGCATTATGAGA
TGGGGTGGGTCCGCCAGGCTCCAGGGAAGGGTCTAGAGTGGGTCTCAAGT
ATTGAGCCTTTTGGTGGTGGGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGTGTAT
CCTCAGGGTTCTTTTGACTACTGGGGTCAGGGAACCCTGGTCACCGTCTC
GAGC

BMS2h-203 (SEQ ID NO: 547)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAATTATACTA
TGGGGTGGGTCCGTCAGGCTCCAGGGAAGGGTCTAGAGTGGGTCTCATCT
ATTCGGCCTGATGGTAAGATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGTTTAT
TCTTCGTGTGCGATGTGTACTCCGCTTTTGTTTGACTACTGGGGTCAGGG
AACCCTGGTCACCGTCTCGAGC

BMS2h-204 (SEQ ID NO: 548)
GAGGTGCAGCTGTTGGAGTCTGGGGGGGGCTTGGTACAGCCTGGGGGGTC
CCTGCGTCTCTCCTGTGCAGCCTCCGGATTCACCTTTAAGCGGTATTCGA
TGGCTGGGTCCGCCAGGCTCCAGGGAAGGGTCTAGAGTGGGTCTCAGAT
ATTGGGCGAGGGGTTTTCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTGGGT
CGTGGTCAGCGTGATACTAGTCAGCCGTTTGACTACTGGGGTCAGGGAAC
CCTGGTCACCGTCTCGAGC

BMS2h-205 (SEQ ID NO: 549)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTTCTTATCAGA
TGGCTTGGGTCCGCCAGGCTCCAGGGAAGGGTCTAGAGTGGGTCTCAGGG
ATTACTTCGGGTGGTCTTAGTACGTACACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGG
AGGGGTTTTGACTGGGGTCAGGGAACCCTGGTCACCGTCTCGAGC

BMS2h-206 (SEQ ID NO: 550)
GAGGTGCAGCTGTTGGAGTCTGGGGGAGGCTTGGTACAGCCTGGTGGGTC
CCTGCGTCTCTCCTGTGCAGCCTCCGGATTCACCTTTGCTTCTTATGAGA

TABLE 2-continued

Human Anti-CD40L VH Domain Encoding
Nucleotide Sequences

TGACTTGGGTCCGCCAGGCTCCAGGGAAGGGTCTAGAGTGGGTCTCAGGG
ATTTCTTCTGATGGTCTGTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGG
GTGTTGTTTGACTACTGGGGTCAGGGAACCCTGGTCACCGTCTCGAGC

BMS2h-207 (SEQ ID NO: 551)
GAGGTGCAGCTGTTGGAGTCTGGGGGAGGCTTGGTACAGCCTGGGGGGTC
CCTGCGTCTCTCCTGTGCAGCCTCTGGATTCACCTTTGATAAGTATTTGA
TGTCTGGGTCCGCCAGGCTCCAGGGAAGGGTCTGGAGTGGGTCTCAGGT
ATTGAGCCTCTGGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGAGGCT
TCGGGGGATTTTGACTACTGGGGTCAGGGAACCCTGGTCACCGTCTCGAGC

BMS2h-208 (SEQ ID NO: 552)
GAGGTGCAGCTGTTGGAGTCTGGGGGAGGCTTGGTACAGCCTGGGGGGTC
CCTGCGTCTCTCCTGTGCAGCCTCCGGGTTCACCTTTACTGAGTATGAGA
TGTCTTGGGTCCGCCAGGCTCCAGGGAAGGGTCTAGAGTGGGTCTCAAGT
ATTGATAATGTGGGTAGTAGTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTGGG
AAGCTTTTTGACTACTGGGGTCAGGGAACCCTGGTCACCGTCTCGAGC

BMS2h-209 (SEQ ID NO: 553)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTGATTATGAGA
TGTGGTGGGTCCGCCAGGCTCCAGGGAAGGGTCTAGAGTGGGTCTCAGCG
ATTTCTAGGCAGGGTTTTGCTACATACTACGCAGACTCCGTGAAAGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATCTG
GAGCGGGATGATTTTGACTACTGGGGTCAGGGAACCCTGGTCACCGTCTC
GAGC

BMS2h-21 (SEQ ID NO: 554)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGAATTATGAGA
TGGGGTGGGCCCGCCAGGCTCCAGGGAAGGGTCTAGAGTGGGTCTCAGTT
ATTTCTGAGTGGGGTTATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTGTG
GGTGGGACTCAGTATGAGTTTGACTACTGGGGTCAGGGAACCCTGGTCAC
CGTCTCGAGC

BMS2h-22 (SEQ ID NO: 555)
GAGGTGCAGCTGTTGGAGTCTGGGGGAGGCTTGGTACAGCCTGGGGGGTC
CCTGCGTCTCTCCTGTGCAGCCTCCGGATTCACCTTTCATAATTATGAGA
TGTCGTGGGTCCGCCAGGCTCCAGGGAAGGGTCTAGAGTGGGTCTCAAGT
ATTTCTTCGGGTGGTTCTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACGGGG
GTTAAGTTTGACTACTGGGGTCAGGGAACCCTGGTCACCGTCTCGAGC

BMS2h-23 (SEQ ID NO: 556)
GAGGTGCAGCTGTTGGAGTCCGGGGGAGGCTTGGTACAGCCTGGGGGGTC
CCTGCGTCTCTCCTGTGCAGCCTCCGGATTCACCTTTGGGCTGTATGAGA
TGACGTGGGTCCGCCAGGCTCCAGGGAAGGGTCTAGAGTGGGTCTCAAGT
ATTACGGGTGATGGTATTTGACATACTACGCAGACTCCGTGAAGGGCCG
GTTCACCATCTCCCGCGACAATTCCAGGACACGCTGTATCTGCAAATGA
ACAGCCTGCGTGCCGAGGACACCGCGGTATATTACTGTGCGAAAGCTGGG
AGGAAGTTTGACTACTGGGGTCAGGGAACCCTGGTCACCGTCTCGAGC

BMS2h-24 (SEQ ID NO: 557)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAATTATCAGA
TGGCGTGGGTCCGCCAGGCTCCAGGGAAGGGTCTAGAGTGGGTCTCAAGT
ATTACTAGGAGGGTGGTTCTACATACTACGCAGACTCCGTGAAGGGCCG
GTTCACCATCTCCCGCGACAATTCCAAGAACACACTGTATCTGCAAATGA
ACAGCCTGCGTGCCGAGGACACCGCGGTATATTACTGTGCGAAACCGGGT
AAGAATTTTGACTACTGGGGTCAGGGAACCCTGGTCACCGTCTCGAGC

BMS2h-24-1 (SEQ ID NO: 558)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGATTATCAGA
TGGCGTGGGTTCGCCAGGCTCCAGGGAAGGGACTAGAGTGGGTCTCAAGT
ATTACTAGTGAGGGTGGTTCGACATACTACGCAGACTCCGTGAAGGGCCG

TABLE 2-continued

Human Anti-CD40L VH Domain Encoding
Nucleotide Sequences

GTTCACCATCTCCCGCGACAATTCCAAGAACACAGTGTATCTGCAAATGA
ACAGCCTGCGTGCCGAGGACACCGCGGTATATTACTGTGCGAAACCGGGT
AAGAATTTCGACTACTGGGGTCAGGGAACCCTGGTCACCGTCTCGAGC

BMS2h-25 (SEQ ID NO: 559)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATTATGAGA
TGACGTGGGTCCGCCAGGCTCCAGGGAAGGGTCTAGAGTGGGTCTCAACT
ATTACGTCGCAGGGTACTAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGAT
CGTTCTTTTGACTACTGGGGTCAGGGAACCCTGGTCACCGTCTCGAGC

BMS2h-26 (SEQ ID NO: 560)
GAGGTGCAGCTGTTGGAGTCTGGGGGAGGCTTGGTACAGCCTGGGGGGTC
CCTGCGTCTCTCCTGTGCAGCCTCCGGATTCACCTTTCGTAGTTATGAGA
TGACTTGGGTCCGCCAGGCTCCAGGGAAGGGTCTGGAGTGGGTCTCATCT
ATTACGTCGGATGGTGGTACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGAT
AAGACGTTTGACTACTGGGGTCAGGGAACCCTGGTCACCGTCTCGAGC

BMS2h-27 (SEQ ID NO: 561)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTTGTATGAGA
TGACTTGGGTCCGCCAGGCTCCAGGGAAGGGTCTAGAGTGGGTCTCATCT
ATTACTAGTGATGGTGTTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGAT
TCTCCGTTTGACTACTGGGGTCAGGGAACCCTGGTCACCGTCTCGAGC

BMS2h-28 (SEQ ID NO: 562)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGCATTATGATA
TGGCTTGGGTCCGCCAGGCTCCAGGGAAGGGTCTAGAGTGGGTCTCAACT
ATTAGTGATAATGGTAATGGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGG
CGTGATTTTGACTACTGGGGTCAGGGAACCCTGGTCACCGTCTCGAGC

BMS2h-29 (SEQ ID NO: 563)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTCGTTATCGAA
TGGCTTGGGTCCGCCAGGCTCCAGGGAAGGGTCTAGAGTGGGTCTCATCT
ATTTCTTCTGATGGTGGGGGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTGGG
CGGGCGTTTGACTACTGGGGTCAGGGAACCCTGGTCACCGTCTCGAGC

BMS2h-30 (SEQ ID NO: 564)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGAGGTATCGAA
TGGCTTGGGTCCGCCAGGCTCCAGGGAAGGGTCTGGAGTGGGTCTCAACT
ATTTCTGATGATGGTGATTCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTGGAT
AAGTTGTTTGACTACTGGGGTCAGGGAACCCTGGTCACCGTCTCGAGC

BMS2h-300 (SEQ ID NO: 565)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATGATGAGA
TGACGTGGGTCCGCCAGGCTCCAGGGAAGGGTCTAGAGTGGGTCTCAGCT
ATTGATACGACGGGTGGGCAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGGT
AAGGAGTTTGACTACTGGGGTCAGGGAACCCTGGTCACCGTCTCGAGC

BMS2h-301 (SEQ ID NO: 566)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGAGAGTGAGA
TGAGTTGGGTCCGCCAGGCTCCAGGGAAGGGTCTAGAGTGGGTCTCAAGT
ATTCTTGATGAGGGTTCTGGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGAT
AAGGATTTTGACTACTGGGGTCAGGGAACCCTGGTCACCGTCTCGAGC

BMS2h-302 (SEQ ID NO: 567)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGAGGAGGAGA
TGAGTTGGGTCCGCCAGGCTCCAGGGAAGGGTCTAGAGTGGGTCTCAGCG
ATTACTGATGATGGTGATGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTAAT
GCGGGTGCTTTTGACTACTGGGGTCAGGGAACCCTGGTCACCGTCTCGAG
C

BMS2h-303 (SEQ ID NO: 568)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGTGTATGATA
TGGCTTGGGTCCGCCAGGCTCCAGGGAAGGGTCTAGAGTGGGTCTCAGGG
ATTGTTAATGATGGTTCTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGAT
AAGGATTTTGACTACTGGGGTCAGGGAACCCTGGTCACCGTCTCGAGC

BMS2h-304 (SEQ ID NO: 569)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTAATACGGAGA
TGACTTGGGTCCGCCAGGCTCCAGGGAAGGGTCTAGAGTGGGTCTCATCG
ATTGCGGATGATGGTTCTAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGGT
CAGGCTTTTGACTACTGGGGTCAGGGAACCCTGGTCACCGTCTCGAGC

BMS2h-31 (SEQ ID NO: 570)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGAGTATCAGA
TGGCGTGGGTCCGCCAGGCTCCAGGGAAGGGTCTAGAGTGGGTCTCAACG
ATTTCGGATGATGGTTCTTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGAT
CTTTATTTTGACTACTGGGGTCAGGGAACCCTGGTCACCGTCTCGAGC

BMS2h-32 (SEQ ID NO: 571)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGTGTATCAGA
TGGGTTGGGTCCGCCAGGCTCCAGGGAAGGGTCTAGAGTGGGTCTCATTT
ATTGTTGATGGTGATTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACGTGG
CCGGAGTTTGACTACTGGGGTCAGGGAACCCTGGTCACCGTCTCGAGC

BMS2h-4 (SEQ ID NO: 572)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATTATGAGA
TGACGTGGGTCCGCCAGGCTCCAGGGAAGGGTCTAGAGTGGGTCTCATCT
ATTACGAGTGATGGTACTTCGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTAAT
CCGCCGTTTGACTACTGGGGTCAGGGAACCCTGGTCACCGTCTCGAGC

BMS2h-40 (SEQ ID NO: 573)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGGCAGTATGATA
TGGGTTGGGTCCGCCAGGCTCCAGGGAAGGGTCTAGAGTGGGTCTCACAG
ATTGGGAGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTCGT
CGGTATGCTATTTTTACTTTTGATCGGGGTCAGGGAACCCTGGTCACCGT
CTCGAGC

BMS2h-400 (SEQ ID NO: 574)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGCAGTATCCGA
TGGTGTGGGTCCGCCAGGCTCCAGGGAAGGGTCTAGAGTGGGTCTCAACG
ATTTCTACTAATGGTGTGAGGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATGGACG
GATATTATTTCGTCTTCGGAGTTTGACTACTGGGGTCAGGGAACCCTGGT
CACCGTCTCGAGC

TABLE 2-continued

Human Anti-CD40L VH Domain Encoding Nucleotide Sequences

BMS2h-401 (SEQ ID NO: 575)
GAGGTGCAGCTGTTGGAGTCTGGGGGAGGCTTGGTACAGCCTGGGGGGTC
CCTGCGTCTCTCCTGTGCAGCCTCCGGATTCACCTTTTTTAATTATGATA
TGTCTTGGGTCCGCCAGGCTCCAGGGAAGGGTCTAGAGTGGGTCTCAGCT
ATTAGTGGTAGTGGTGGTAGCACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTTTT
GTGTGGTCGGCTGATATTGATTTTGATTTTGACTACTGGGGTCAGGGAAC
CCTGGTCACCGTCTCGAGC

BMS2h-402 (SEQ ID NO: 576)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTATGATA
TGAGTTGGGTCCGCCAGGCTCCAGGGAAGGGTCTAGAGTGGGTCTCACAT
ATTGCGAGTTGGGGTGGTAAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTGACG
GTGAAGGATGGGGGGTATCTGATGGATTTTGACTACTGGGGTCAGGGAAC
CCTGGTCACCGTCTCGAGC

BMS2h-403 (SEQ ID NO: 577)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTGAGTATGCTA
TGGCGTGGGTCCGCCAGGCTCCAGGGAAGGGTCTGGAGTGGGTCTCAAGT
ATTGGGCGGGATGGTGCGGTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGAAG
GCGGCGAAGGAGCGGGGTTCTTGGTTTGACTACTGGGGTCAGGGAACCCT
GGTCACCGTCTCGAGC

BMS2h-404 (SEQ ID NO: 578)
GAGGTGCAGCTGTTGGAGTCTGGGGGAGGCTTGGTACAGCCTGGGGGGTC
CCTGCGTCTCTCCTGTGCAGCCTCCGGATTCACCTTTTCAGGCTTATCGA
TGCAGTGGGTCCGCCAGGCTCCAGGGAAGGGTCTTGAGTGGGTCTCAACT
ATTAGTCCTAATGGTCTTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGTTG
AGTTCTTTTGACTACTGGGGTCAGGGAACCCTGGTCACCGTCTCGAGC

BMS2h-407 (SEQ ID NO: 579)
GAGGTGCAGCTGTTGGAGTCTGGGGGAGGCTTGGTACAGCCTGGGGGGTC
CCTGCGTCTCTCCTGTGCAGCCTCCGGATTCACCTTTGTGTATGTATTCGA
TGGCTTGGGTCCGCCAGGCTCCAGGGAAGGGTCTAGAGTGGGTCTCAGGT
ATTTCGCCTCGTGGTGTTGAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACTAAT
TGGAATGGTGTGGATCTGTTTGACTACTGGGGTCAGGGAACCCTGGTCAC
CGTCTCGAGC

BMS2h-408 (SEQ ID NO: 580)
GAGGTGCAGCTGTTGGAGTCTGGGGGAGGCTTGGTACAGCCTGGGGGGTC
CCTGCGTCTCTCCTGTGCAGCCTCCGGATTCACCTTTCCTACGTATATGA
TGAGTTGGGTCCGCCAGGCTCCAGGGAAGGGTCTAGAGTGGGTCTCAACT
ATTAATACGAATGGTCGTGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGAT
AGTAATATGTCGTTTTTTGACTACTGGGGTCAGGGAACCCTGGTCACCGT
CTCGAGC

BMS2h-409 (SEQ ID NO: 581)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGGTTATTCGA
TGACGTGGGTCCGCCAGGCTCCAGGGAAGGGTCTAGAGTGGGTCTCATCT
ATTAATGCGTCGGGTACTCTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATGGT
AATAGGTCTGAGGTTTTTTTTGACTACTGGGGTCAGGGAACCCTGGTCAC
CGTCTCGAGC

BMS2h-41 (SEQ ID NO: 582)
GAGGTGCAGCTGTTGGAGTCTGGGGGAGGCTTGGTACAGCCTGGGGGGTC
CCTGCGTCTCTCCTGTGCAGCCTCCGGATTCACCTTTTTTGAGTATGAGA
TGACGTGGGTCCGCCAGGCTCCAGGGAAGGGTCTAGAGTGGGTCTCATCT
ATTGCGAATGATGGTTCGACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGAT
CGGCAGTTTGACTACTGGGGTCAGGGAACCCTGGTCACCGTCTCGAGC

BMS2h-410 (SEQ ID NO: 583)
GAGGTGCAGCTGTTGGAGTCTGGGGGAGGCTTGGTACAGCCTGGGGGGTC
CCTGCGTCTCTCCTGTGCAGCCTCCGGATTCACCTTTCAGGATTATTTGA
TGGCGTGGGTCCGCCAGGCTCCAGGGAAGGGTCTAGAGTGGGTCTCAGAG
ATTAATCAGGATGGTACTGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAAGTTCT
CCGTATTTTGACTACTGGGGTCAGGGAACCCTGGTCACCGTCTCGAGC

BMS2h-411 (SEQ ID NO: 584)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATTATGCGA
TGTCGTGGGTCCGCCAGGCTCCAGGGAAGGGTCTAGAGTGGGTCTCATCT
ATTAGTCGGGATGGTCATGTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTTCT
TCTAAGGGGGGGACGTTTGCTAGTTCTTTTGACTACTGGGGTCAGGGAAC
CCTGGTCACCGTCTCGAGC

BMS2h-412 (SEQ ID NO: 585)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGCTGTTCCGA
TGACGTGGGTCCGCCAGGCTCCAGGGAAGGGTCTAGAGTGGGTCTCAGCG
ATTACGGATGATGGTCTTCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTCAT
ATTTTATGGGGATTATTTTGACTACTGGGGTCAGGGAACCCTGGTCACCGT
CTCGAGC

BMS2h-413 (SEQ ID NO: 586)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCTTTATAGGA
TGATGTGGGTCCGCCAGGCTCCAGGGAAGGGTCTAGAGTGGGTCTCAGCT
ATTAGTAGTGATGGTGATACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACATTGG
TTGGGTACTACGTTGTCTTTGAGGGATTTTGACTACTGGGGTCAGGGAAC
CCTGGTCACCGTCTCGAGC

BMS2h-414 (SEQ ID NO: 587)
GAGGTGCAGCTGTTGGAGTCTGGGGGAGGCTTGGTACAGCCTGGGGGGTC
CCTGCGTCTCTCCTGTGCAGCCTCCGGATTCACCTTTTATCGTTATACGA
TGGCGTGGGTCCGCCAGGCTCCAGGGAAGGGTCTAGAGTGGGTCTCACAG
ATTTTCTAGGGGTAATATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAGTGGT
GTGGCGGGGCGGAGTCGCCTGAGTATTTTGACTACTGGGGTCAGGGAAC
CCTGGTCACCGTCTCGAGC

BMS2h-415 (SEQ ID NO: 588)
GAGGTGCAGCTGTTGGAGTCTGGGGGAGGTTTGGTACAGCCTGGGGGGTC
CCTGCGTCTCTCCTGTGCAGCCTCCGGATTCACCTTTTGGGTTATTATA
TGAGTTGGATCCGCCAGGCTCCAGGGAAGGGTCTAGAGTGGGTCTCAACG
ATTGGGCCGATTGGTGGTGGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCTCAG
AATATTTATGGTCCTTTTGACTACTGGGGTCAGGGAACCCTGGTCACCGT
CTCGAGC

BMS2h-416 (SEQ ID NO: 589)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCAGTATGATA
TGGCTTGGGTCCGCCAGGCTCCAGGGAAGGGTCTAGAGTGGGTCTCAGAG
ATTAGTCGTGATGGTGGCGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGAGTAT
CCTTATTTTGACTACTGGGGTCAGGGAACCCTGGTCACCGTCTCGAGC

BMS2h-417 (SEQ ID NO: 590)
GAGGTGCAGCTGTTGGAGTCTGGGGGAGGCTTGGTACAGCCTGGGGGGTC
CCTGCGTCTCTCCTGTGCAGCCTCCGGATTCACCTTTCCGCAGTATAGTA
TGGTGTGGGTCCGCCAGGCTCCAGGGAAGGGTCTTGAGTGGGTCTCAACT
ATTTCGCCTCTGGGTTCTTCGACATACTACGCAGACTCCGTGAAGGGCCG
GTTCACCATCTCCCGCGACAATTCCAAGAACACGCTGTATCTGCAAATGA

TABLE 2-continued

Human Anti-CD40L VH Domain Encoding Nucleotide Sequences

ACAGCCTGCGTGCCGAGGATACCGCGGTATATTACTGTGCGAAAATGAGT
AAGTTGTTGCTGTCGAGGGAGTTTGACTACTGGGGTCAGGGAACCCTGGT
CACCGTCTCGAGC

BMS2h-418 (SEQ ID NO: 591)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTATGTATTCGA
TGGCTTGGGTCCGCCAGGCTCCAGGGAAGGGTCTAGAGTGGGTCTCAGGT
ATTTCGCCTCGTGGTGTTGAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACTAAT
TGGAATGGTGTGGATCTGTTTGACTACTGGGGTCAGGGAACCCTGGTCAC
CGTCTCGAGC

BMS2h-419 (SEQ ID NO: 592)
GAGGTGCAGCTGTTGGAGTCTGGGGGAGGCTTGGTACAGCCTGGGGGGTC
CCTGCGTCTCTCCTGTGCAGCCTCCGGATTCACCTTTACGCGTCATGGTA
TGGCGTGGGTCCGCCAGGCTCCAGGGAAGGGTCTAGAGTGGGTCTCAACG
ATTACGCCTACTGGTAATACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATGCT
CATGATGAGGGGTATTTTGACTACTGGGGTCAGGGAACCCTGGTCACCGT
CTCGAGC

BMS2h-42 (SEQ ID NO: 593)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTCCGTATGAGA
TGACTTGGGTCCGCCAGGCTCCAGGGAAGGGTCTAGAGTGGGTCTCATCG
ATTGTTGGTGATGGTCTGGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGAT
CGGGTTTTTGACTACTGGGGTCAGGGAACCCTGGTCACCGTCTCGAGC

BMS2h-420 (SEQ ID NO: 594)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTAGTACGCCTA
TGATGTGGGTCCGCCAGGCTCCAGGGAAGGGTCTAGAGTGGGTCTCAGAG
ATTAGGGATACGGGTCTGGCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAGTGTTTCG
TTTGACTACTGGGGTCAGGGAACCCTGGTCACCGTCTCGAGC

BMS2h-421 (SEQ ID NO: 595)
GAGGTGCAGCTGTTGGAGTCTGGGGGAGGCTTGGTACAGCCTGGGGGGTC
CCTGCGTCTCTCCTGTGCAGCCTCCGGATTCACCTTTCATCTGGGGATA
TGCATTGGGTCCGCCAGGCTCCAGGGAAGGGTCTAGAGTGGGTCTCATCG
ATTAGTGGGACGGGTCATACTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTATG
AATGATCAGGGGTTTGACTACTGGGGTCAGGGAACCCTGGTCACCGTCTC
GAGC

BMS2h-422 (SEQ ID NO: 596)
GAGGTGCAGCTGTTGGAGTCTGGGGGAGGCTTGGTACAGCCTGGGGGGTC
CCTGCGTCTCTCCTGTGCAGCCTCCGGATTCACCTTTATGGATGAGGATA
TGTTGTGGGTCCGCCAGGCTCCAGGGAAGGGTCTAGAGTGGGTCTCAAGG
ATTAATTCGCTGGGTACTCATACATACTACGCAGACTCCGTGAAGGGCCG
ATTCACCATCTCCCGCGACAATTCCAAGAACACGCTGTATCTGCAAATGA
ACAGCCTGCGTGCCGAGGATACCGCGGTATATTACTGTGCGAAATCGTTT
ATGATGTTTGACTACTGGGGTCAGGGAACCCTGGTCACCGTCTCGAGC

BMS2h-423 (SEQ ID NO: 597)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTTAATTATCGA
TGCATTGGGTCCGCCAGGCTCCAGGGAAGGGTCTAGAGTGGGTCTCAGGT
ATTGATGCGACTGGTCGGGCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAGATCTACT
AGGTCATTTGACTACTGGGGTCAGGGAACCCTGGTCACCGTCTCGAGC

BMS2h-424 (SEQ ID NO: 598)
GAGGTGCAGCTGTTGGAGTCTGGGGGAGGCTTGGTACAGCCTGGGGGGTC
CCTGCGTCTCTCCTGTGCAGCCTCCGGATTCACCTTTACGAATGCGGATA
TGGTGTGGGTCCGCCAGGCTCCAGGGAAGGGTCTAGAGTGGGTCTCAAGT
ATTAGTGGTAGTGGTGGTAGCACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTTAT
TTGACTTCGCATTTTGACTACTGGGGTCAGGGAACCCTGGTCACCGTCTC
GAGC

BMS2h-425 (SEQ ID NO: 599)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGGATTATTCTA
TGGCTTGGGTCCGCCAGGCTCCAGGGAAGGGTCTAGAGTGGGTCTCAACT
ATTACTCCGTCGGGTCTTACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAATGGTCT
CAGGCGGTTACTCGGTCTTTTGACTACTGGGGTCAGGGAACCCTGGTCAC
CGTCTCGAGC

BMS2h-426 (SEQ ID NO: 600)
GAGGTGCAGCTGTTGGAGTCTGGGGGAGACTTGGTACAGCCTGGGGGGTC
CCTGCGTCTCTCCTGTGCAGCCTCCGGATTCACCTTTTCTGATGAGGGTA
TGATGTGGGTCCGCCAGGCTCCAGGGAAGGGTCTAGAGTGGGTCTCAGAG
ATTAATGCGGGTTCGGCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACGATT
GGGATGTTTGACTACTGGGGTCAGGGAACCCTGGTCACCGTCTCGAGC

BMS2h-427 (SEQ ID NO: 601)
GAGGTGCAGCTGTTGGAGTCTGGGGGAGGCTTGGTACAGCCTGGGGGGTC
CCTGCGTCTCTCCTGTGCAGCCTCCGGATTCACCTTTACTGATCAGCCGA
TGGTGTGGGTCCGCCAGGCTCCAGGGAAGGGTCTAGAGTGGGTCTCATCG
ATTGGGGCGCGTGGTGGGCCTACATACTACGCAGACTCCGTGAAGGGCCG
GTTCACCGTCTCCCGCGACAATTCCAAGAACACGCTGTATCTGCAAATGA
ACAGCCTGCGTGCCGAGGACACCGCGGTATATTACTGTGCGAAATGGTTT
GATATTATTGCTTGGGATCCTTTTAGTTTTGACTACTGGGGTCAGGGAAC
CCTGGTCACCGTCTCGAGC

BMS2h-428 (SEQ ID NO: 602)
GAGGTGCAGCTGTTGGAGTCTGGGGGAGGCTTGGTACAGCCTGGGGGGTC
CCTGCGTCTCTCCTGTGCAGCCTCCGGATTCACCTTTAATCAGTATCCTA
TGATGTGGGTTCGCCAGGCTCCAGGGAAGGGTCTAGAGTGGGTCTCAAGT
ATTACTCCTTCTGTTTTTTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAATGGAAT
CCTTTTATTACTACGTTTGACTACTGGGGTCAGGGAACCCTGGTGACCGT
CTCGAGC

BMS2h-429 (SEQ ID NO: 603)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGCATCAGCAGA
TGGCGTGGGTCCGCCAGGCTCCAGGGAAGGGTCTAGAGTGGGTCTCAACT
ATTACTCCGAATGGTTATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTTGAT
TATTCGCTTCGTTTTGACTACTGGGGTCAGGGAACCCTGGTCACCGTCTC
GAGC

BMS2h-43 (SEQ ID NO: 604)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTTTTATGAGA
TGGCGTGGGTCCGCCAGGCTCCAGGGAAGGGTCTAGAGTGGGTCTCATCG
ATTGGTAGTGATGGTGGGCCGACATACTACGCAGACTCCGTGAAGGGCCG
GTTCACCATCTCCCGCGACAATTCCAAGAACACGCTGTATCTGCAAATGA
ACAGCCTGCGTGCCGAGGACTCCGCGGTATATTACTGTGCGAAACCTGAT
AGGGCTTTTGACTACTGGGGTCAGGGAACCCTGGTCACCGTCTCGAGC

BMS2h-430 (SEQ ID NO: 605)
GAGGTGCAGCTGTTGGAGTCTGGGGGAGGCTTGGTACAGCCTGGGGGGTC
CCTGCGTCTCTCCTGTGCAGCCTCCGGATTCACCTTTCTGCGGAGCAGA
TGACTTGGGTCCGCCAGGCTCCAGGGAAGGGTCTAGAGTGGGTCTCAACT
ATTACTCCGATGGTGATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGCGG
ACTTTGGTTGATTGGCTACGAGTGAGTCGTTTGACTACTGGGGTCAGGG
AACCCTGGTCACCGTCTCGAGC

BMS2h-44 (SEQ ID NO: 606)
GAGGTGCAGCTGTTGGAGTCTGGGGGAGGCTTGGTACAGCCTGGGGGGTC
CCTGCGTCTCTCCTGTGCAGCCTCCGGATTCACCTTTACGTCTTATGAGA
TGGGGTGGGTCCGCCAGGCTCCAGGGAAGGGTCTAGAGTGGGTCTCATCT
ATTGAGCCTACTGGTATTACGACATACTACGCAGACTCCGTGAAGGGCCG
GTTCACCATCTCCCGCGACAATTCCAAGAACACGCTGTATCTGCAAATGA

TABLE 2-continued

Human Anti-CD40L VH Domain Encoding Nucleotide Sequences

ACAGCCTGCGTGCCGAGGACACCGCGGTATATTACTGTGCGAAACCTCAT
TTTACTGAGCTTGGTTTTGACTACTGGGGTCAGGGAACCCTGGTCACCGT
CTCGAGC

BMS2h-449 (SEQ ID NO: 607)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGGGGAGCAGA
TGGCTTGGGTCCGCCAGGCTCCAGGGAAGGGTCTAGAGTGGGTCTCAACG
ATTACGCTGCCTGGTCCGTATACATTCTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGAAT
GGGACGTTTTTTGACTACTGGGGTCAGGGAACCCTGGTCACCGTCTCGAG
C

BMS2h-45 (SEQ ID NO: 608)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTAATTATGCGA
TGGCGTGGGTCCGCCAGGCTCCAGGGAAGGGTCTAGAGTGGGTCTCAAAG
ATTGGGGCGCAGGGTCTTCATACATACTACGCAGGCTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACAGACG
ACGATGGATTATGAGAGGTTTGACTACTGGGGTCAGGGAACCCTGGTCAC
CGTCTCGAGC

BMS2h-450 (SEQ ID NO: 609)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGAGGTTGATA
TGTCGTGGGTCCGCCAGGCTCCAGGGAAGGGTCTGGAGTGGGTCTCAGCT
ATTGGTAATAATGGTCTTAAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCGGCT
CTGTCGTATAGGCCTCCTGTTTTTGACTACTGGGGTCAGGGAACCCTGGT
CACCGTCTCGAGC

BMS2h-451 (SEQ ID NO: 610)
GAGGTGCAGCTGTTGGAGTCTGGGGGAGGCTTGGTACAGCCTGGGGGGTC
CCTGCGTCTCTCCTGTGCAGCCTCCGGATTCACCTTTCAGGATGATACTA
TGTCGTGGGTCCGCCAGGCTCCAGGGAAGGGTCTAGAGTGGGTCTCAACG
ATTACGCTTAAGGGTCCGTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCGAGG
GATGGGTTGTATTTTGACTACTGGGGTCAGGGAACCCTGGTCACCGTCTC
GAGC

BMS2h-452 (SEQ ID NO: 611)
GAGGTGCAGCTGTTGGAGTCTGGGGGAGGCTTGGTACAGCCTGGGGGGTC
CCTGCGTCTCTCCTGTGCAGCCTCCGGATTCACCTTTGTCGTCTCGA
TGGCTTGGGTCCGCCAGGCTCCAGGGAAGGGTCTAGAGTGGGTCTCAAGT
ATTGGTCGGATGGTAGTACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTTCG
CCTTATCGGCGGTTTGACTACTGGGGTCAGGGAACCCTGGTCACCGTCTC
GAGC

BMS2h-453 (SEQ ID NO: 612)
GAGGTGCAGCTGTTGGAGTCTGGGGGAGGCTTGGTACAGCCTGGGGGGTC
CCTGCGTCTCTCCTGTGCAGCCTCCGGATTCACCTTTACTGATTATTCGA
TGGTTTGGGTCCGCCAGGCTCCAGGGAAGGGTCTAGAGTGGGTCTCAACT
ATTGTGAGTCATGGTACTACATACTACGCAGACTCCGTGAAGGGCCG
ATTCACCATCTCCCGCGACAATTCCAAGAACACGCTGTATCTGCAAATGA
ACAGCCTGCGTGCCGAGGACACCGCGGTATATTACTGTGCGAAAGGTAAG
GGTTATAATGCGCAGTATTTTGACTACTGGGGTCAGGGAACCCTGGTCAC
CGTCTCGAGC

BMS2h-454 (SEQ ID NO: 613)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGCATCAGCAGA
TGGCGTGGGTCCGCCAGGCTCCAGGGAAGGGTCTAGAGTGGGTCTCAACT
ATTACTCCGAATGGTTATTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAATTTGAT
TATTCGCTTCGTTTGACTACTGGGGTCAGGGAACCCTGGTCACCGTCTC
GAGC

BMS2h-455 (SEQ ID NO: 614)
GAGGTGCAGCTGTTGGAGTCTGGGGGAGGCTTGGTACAGCCTGGGGGGTC
CCTGCGTCTCTCCTGTGCAGCCTCCGGATTCACCTTTAATGATTATGATA
TGATTTGGGTCCGCCAGGCTCCAGGGAAGGGTCTAGAGTGGGTCTCAACT
ATTAGTTCGCATGGTGATAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTGAT
GTTTTTTTTGACTACTGGGGTCAGGGAACCCTGGTCACCGTCTCGAGC

BMS2h-456 (SEQ ID NO: 615)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGCATCAGCAGA
TGGCGTGGGTCCGCCAGGCTCCAGGGAAGGGTCTAGAGTGGGTCTCAACT
ATTACTGAATGGTTATTATACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAATGGTCG
GATTCTTTTGACTACAGGGGTCAGGGAACCCTGGTCACCGTCTCGAGC

BMS2h-457 (SEQ ID NO: 616)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTGATTATGAA
TGGCTTGGGTCCGCCAGGCTCCAGGGAAGGGTCTAGAGTGGGTCTCAGGG
ATTCAGTCTAATGGTAATATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCTAAT
TCTCAGGTTGAGTATTTTGACTACTGGGGTCAGGGAACCCTGGTCACCGT
CTCGAGC

BMS2h-458 (SEQ ID NO: 617)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGTGGAGCCTA
TGTCTTGGGTCCGCCAGGCTCCAGGGAAGGGTCTAGAGTGGGTCTCAAAT
ATTGGTGTGATGTTCGATGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTGGGG
AAGCATGGTACTTTTGACTACTGGGGTCAGGGAACCCTGGTCACCGTCTC
GAGC

BMS2h-459 (SEQ ID NO: 618)
GAGGTGCAGCTGTTGGAGTCTGGGGGAGGCTTGGTACAGCCTGGGGGGTC
CCTGCGTCTCTCCTGTGCAGCCTCCGGATTCACCTTTCCGGAGTATCGGA
TGATGTGGGTCCGCCAGGCTCCAGGGAAGGGTCTGGAGTGGGTCTCATGG
ATTGATGAGCGGGGTTCGCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAGGCGG
AAGGGTACTAAGCAGTTTGACTACTGGGGTCAGGGAACCCTGGTCACCGT
CTCGAGC

BMS2h-46 (SEQ ID NO: 619)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGTTGTATGCTA
TGGCGTGGGTCCGCCAGGCTCCAGGGAAGGGTCTAGAGTGGGTCTCAGGT
ATTGGTGCTGTGGGTGAGACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGAGGCT
AATAATCTTTCTGATAATCTTGTGTTTGACTACTGGGGTCAGGGAACCCT
GGTCACCGTCTCGAGC

BMS2h-460 (SEQ ID NO: 620)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGCATCAGCAGA
TGGCGTGGGTCCGCCAGGCTCCAGGGAAGGGTCTAGAGTGGGTCTCAACT
ATTACCGAATGGTTATTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGTCG
GTTGAGTGGTTTGACTACTGGGGTCAGGGAACCCTGGTCACCGTCTCGAG
C

BMS2h-461 (SEQ ID NO: 621)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAGTTATACGA
TGAATTGGGTCCGCCAGGCTCCAGGGAAGGGTCTAGAGTGGGTCTCAAGT
ATTAATCCTTGGGGTAGTCGGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGGTCTG
GTGCTGTTTGACTACTGGGGTCAGGGAACCCTGGTCACCGTCTCGAGC

BMS2h-462 0 (SEQ ID NO: 622)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGGTGATATGA

TABLE 2-continued

Human Anti-CD40L VH Domain Encoding Nucleotide Sequences

TGTCTTGGGTCCGCCAGGCTCCAGGGAAGGGTCTAGAGTGGGTCTCATCG
ATTACTCAGCTTGGTAGTAGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACAGAAT
TGGCGGACTCTTACTTTTGACTACTGGGGTCAGGGAACCCTGGTCACCGT
CTCGAGC

BMS2h-463 (SEQ ID NO: 623)
GAGGTGCAGCTGTTGGAGTCTGGGGGAGGCTTGGTACAGCCTGGGGGGTC
CCTGCGTCTCTCCTGCGCAGCCTCCGGATTCACCTTTAATGCTTATGGGA
TGATGTGGGTCCGCCAGGCTCCAGGGAAGGGTCTAGAGTGGGTCTCATCT
ATTCTTTCTGATGGTGTTATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAGTGCT
CGGGGTGCGAATTTTTTTGACTACTGGGGTCAGGGAACCCTGGTCACCGT
CTCGAGC

BMS2h-464 (SEQ ID NO: 624)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGCATTATGATG
TGGTGTGGGTCCGCCAGGCTCCAGGGAAGGGTCTGGAGTGGGTCTCATCT
ATTACGCCTCATGGTACAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAATTTAAT
GCTATTTTTAGTGAGGCGTTTGACTACTGGGGTCAGGGAACCCTGGTCAC
CGTCTCGAGC

BMS2h-465 (SEQ ID NO: 625)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGGATTATTCTA
TGGCTTGGGTCCGCCAGGCTCCAGGGAAGGGTCTAGAGTGGGTCTCAACT
ATTACTCCGTCGGGTCTTACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAATGGTCT
CAGGCGGTTACTCGGTCTTTTGACTACTGGGGTCAGGGAACCCTGGTCAC
CGTCTCGAGC

BMS2h-466 (SEQ ID NO: 626)
GAGGTGCAGCTGTTGGAGTCTGGGGGAGGCTTGGTACAGCCTGGGGGGTC
CCTGCGTCTCTCCTGTGCAGCCTCCGGATTCACCTTTGATCTTTATGCGA
TGGCTTGGGTCCGCCAGGCTCCAGGGAAGGGTCTAGAGTGGGTCTCAATG
ATTGGGAGGGATGGTCGTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACGGCGGTATATTACTGTGCGAAATTGGCT
GGGTTCGCTGAGGGGTCGTTTTGACTACTGGGGTCAGGGAACCCTGGTCAC
CGTCTCGAGC

BMS2h-467 (SEQ ID NO: 627)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAAGGCTAGTA
TGGGTTGGGTCCGCCAGGCTCCAGGGAAGGGTCTAGAGTGGGTCTCAACT
ATTACGCCTCATGGTTCGTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACAGCGG
TGGGGTGTTGAGTTTGACTACTGGGGTCAGGGAACCCTGGTCACCGTCTC
GAGC

BMS2h-468 (SEQ ID NO: 628)
GAGGTGCAGCTGTTGGAGTCTGGGGGAGGCTTGGTACAGCCTGGGGGGTC
CCTGCGTCTCTCCTGTGCAGCCTCCGGATTCACCTTTCAGGGGTATAGTA
TGGGTTGGGTCCGCCAGGCTCCAGGGAAGGGTCTAGAGTGGGTCTCATCT
ATTGCTGGGCGTGGTGGTGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTTTG
TATATTTATCATAGTCTGTTTGACTACTGGGGTCAGGGAACCCTGGTCAC
CGTCTCGAGC

BMS2h-469 (SEQ ID NO: 629)
GAGGTGCAGCTGTTGGAGTCTGGGGGAGGCTTGGTACAGCCTGGGGGCTC
CCTGCGTCTCTCCTGCAGCCTCCGGATTCACCTTTCCTGGTATGGAGA
TGTCGTGGGTCCGCCAGGCTCCAGGGAAGGGTCTAGAGTGGGTCTCAGCT
ATTACTGGGACTGGTAGTACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTTAT
CATCCGTTTGACTACTGGGGTCAGGGAACCCTGGTCACCGTCTCGAGC

BMS2h-470 (SEQ ID NO: 630)
GAGGTGCAGCTGTTGGAGTCTGGGGGAGGCTTGGTACAGCCTGGGGGGTC
CCTGCGTCTCTCCTGTGCAGCCTCCGGATTCACCTTTCCGATGGTGCTA
TGTCTTGGGTCCGCCAGGCTCCAGGGAAGGGTCTAGAGTGGGTCTCATCT
ATTGCTCGGGATGGTAATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACGCCGCGGTATATTACTGTGCGAAAGTTTCG
CCGACTGGTTTTGACTACTGGGGTCAGGGAACCCTGGTCACCGTCTCGAG
C

BMS2h-471 (SEQ ID NO: 631)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGCATCAGGATA
TGTGTGGGTCCGCCAGGCTCCAGGGAAGGGTCTAGAGTGGGTCTCAGGG
ATTACGGATGATGGTGAGAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTGAT
TATGATTTTGACTACTGGGGTCAGGGAACCCTGGTCACCGTCTCGAGC

BMS2h-472 (SEQ ID NO: 632)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGAGTATAATA
TGATGTGGGTCCGCCAGGCTCCAGGGAAGGGTCTAGAGTGGGTCTCACAG
ATTACGAGGGATGGTTCTAGGACATACTACGCAGACTCCGTGAGGGGCCG
GTTCACCATCTCCCGCGACAATTCCAGGACACGCTGTATCTGCAAATGA
ACAGCCTGCGTGCCGAGGACTCCGCGGTATATTACTGTGCGAAACTGTCG
AATATTGGGTTTGACTACTGGGGTCAGGGAACCCTGGTCACCGTCTCGAG
C

BMS2h-473 (SEQ ID NO: 633)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGATTATTCTA
TGATTTGGGCCCGCCAGGCTCCAGGGAAGGGTCTAGAGTGGGTCTCATCG
ATTACGCCTATGGTTCTTATACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAACTGAT
TATTTGTTTGACTACTGGGGTCAGGGAACCCTGGTCACCGTCTCGAGC

BMS2h-474 (SEQ ID NO: 634)
GAGGTGCAGCTGTTGGAGTCTGGGGGAGGCTTGGTACAGCCTGGGGGGTC
CCTGCGTCTCTCCTGTGCAGCCTCCGGATTCACCTTTGATACGTATAGTA
TGATGTGGGTCCGCCAGGCTCCAGGGAAGGGTCTTGAGTGGGTCTCAACT
ATTACTCCTTATGGTAGTTCGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATGGGT
CTGGTGTTTGACTACTGGGGTCAGGGAACCCTGGTCACCGTCTCGAGC

BMS2h-475 (SEQ ID NO: 635)
GAGGTGCAGCTGTTGGAGTCTGGGGGAGGCTTGGTACAGCCTGGGGGGTC
CCTGCGACTCTCCTGTGCAGCCTCCGGATTCACCTTTACTACGGGTCCTA
TGATGTGGGTCCGCCAGGCTCCAGGGAAGGGTCTAGAGTGGGTCTCAGCG
ATTGGTATTGGGGGTGATACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTCTATTACTGTGCGAAATTGACT
CCGTCTAATCAGTTTGACTACTGGGGTCAGGGAACCCTGGTCACCGTCTC
GAGC

BMS2h-476 (SEQ ID NO: 636)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGCAGTATCAGA
TGATGTGGGTTCGCCAGGCTCCAGGGAAGGGTCTAGAGTGGGTCTCAAGT
ATTACTCCTTCTGGTTTTTTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAATGGAAT
CCTTTTATTAGTACGTTTGACTACTGGGGTCAGGGAACCCTGGTCACCGT
CTCGAGC

BMS2h-477 (SEQ ID NO: 637)
GAGGTGCAGCTGTTGGAGTCTGGGGGAGGCTTGGTACAGCCTGGGGGGTC
CCTGCGTCTCTCCTGTGCAGCCTCCGGATTCACCTTTCCTAATTATGATA
TGGTTTGGGTCCGGCAGGCTCCAGGGAAGGGTCTAGAGTGGGTCTCATCG
ATTTCTGCTTTGGGTAATGTTACATACTACGCAGACTCCGTGAAGGGCCG
GTTCACCATCTCCCGCGACAATTCCAAGAACACGCTGTATCTGCAAACGA
ACAGCCTGCGTGCCGAGGACACTGCGGTATATTACTGTGCGAAATGGCGT
AGTGCTATTACTGGTAATTTTGACTACTGGGGTCAGGGAACCCTGGTCAC
CGTCTCGAGC

TABLE 2-continued

Human Anti-CD40L VH Domain Encoding
Nucleotide Sequences

BMS2h-478 (SEQ ID NO: 638)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGGAGTATAGA
TGTCTTGGGTCCGCCAGGCTCCAGGGAAGGGTCTAGAGTGGGTCTCAACT
ATTTCGCCGTCGGGTATGAATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAATGGCGG
TCGGTTGTTCGTCCTTGGCCGGGTGTGTTTGACTACTGGGGTCAGGGAAC
CCTGGTCACCGTCTCGAGC

BMS2h-479 (SEQ ID NO: 639)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGATGAGAGTA
TGGCGTGGGTCCGCCAGGCTCCAGGGAAGGGTCTAGAGTGGGTCTCATCG
ATTACTCCTCATGGTACTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTCAT
CTTAAGTTGTATGAGTCTCATTTTGACTACTGGGGTCAGGGAACCCTGGT
CACCGTCTCGAGC

BMS2h-480 (SEQ ID NO: 640)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGGTGGTGAGA
TGGGTTGGGTCCGCCAGGCTCCAGGGAAGGGTCTAGAGTGGGTCTCAATG
ATTCCGATGGATGGTAGTGCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGGGG
AGTACGTTTGACTACTGGGGTCAGGGAACCCTGGTCACCGTCTCGAGC

BMS2h-481 (SEQ ID NO: 641)
GAGGTGCAGCTGTTGGAGTCTGGGGGAGGCTTGGTACAGCCTGGGGGGTC
CCTGCGTCTCTCCTGTGCAGCCTCCGGATTCACCTTTGATTTTATGCCGA
TGGCGTGGGTCCGCCAGGCTCCAGGGAAGGGTCTAGAGTGGGTCTCATCT
ATTGGGAGGGATGGTGCTTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTGCT
TCGCCGGCGCAGTTTGACTACTGGGGTCAGGGAACCCTGGTCACCGTCTC
GAGC

BMS2h-482 (SEQ ID NO: 642)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTGATGAGCCTA
TGCTGTGGGTCCGCCAGGCTCCAGGGAAGGGTCTAGAGTGGGTCTCATCT
ATTGGGGGTACGGGTACGACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTAAT
CAGGGTGATTTTATTAATCGGTTTCACTACTGGGGTCAGGGAACCCTGGT
CACCGTCTCGAGC

BMS2h-483 (SEQ ID NO: 643)
GAGGTGCAGCTGTTGGAGTCTGGGGGAGGCTTGGTACAGCCTGGGGGGTC
CCTGCGTCTCTCCTGTGCAGCCTCCGGATTCACCTTTCATGCGTATAATA
TGGCGTGGGTCCGCCAGGCTCCAGGGAAGGGTCTAGAGTGGGTCTCAACG
ATTTCTCCGCGGGGTTCTTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGCCG
CCGCCTTCGTCTCATTTTGACTACTGGGGTCAGGGAACCCTGGTCACCGT
CTCGAGC

BMS2h-5 (SEQ ID NO: 644)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGGGTATGAGA
TGGCGTGGGTCCGCCAGGCTCCAGGGAAGGGTCTAGAGTGGGTCTCATCT
ATTACGAGTGATGGTACGAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGG
CTGCGTTTTGACTACTGGGGTCAGGGAACCCTGGTCACCGTCTCGAGC

BMS2h-505 (SEQ ID NO: 645)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGGTTATATGA
TGTATTGGGTCCACCAGGCTCCGGGGAAGGGTCTAGAGTGGGTCTCATCT
ATTTCTCCTCAGGGTCATTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACTTCGT
GAGCTTCCTCGTCTGTTTGACTACTGGGGTCAGGGAACCCTGGTCACCGT
CTCGAGC

BMS2h-506 (SEQ ID NO: 646)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAGTTATGCTA
TGGGTTGGGTCCGCCAGGCTCCAGGGAAGGGTCTAGAGTGGGTCTCATCG
ATTGATGCGAGTGGTGGTCCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGAAT
GGGAAGAAGTTTCCTTTTACTAAGTATTTTGACTACTGGGGTCAGGGAAC
CCTGGTCACCGTCTCGAGC

BMS2h-507 (SEQ ID NO: 647)
GAGGTGCAGCTGTTGGAGTCTGGGGGAGGCTTGGTACAGCCTGGGGGGTC
CCTGCGTCTCTCCTGTGCAGCCTCCGGATTCACCTTTCCTAGTGTGCATA
TGGCGTGGGTCCGCCAGGCTCCAGGGAAGGGTCTAGAGTGGGTCTCAGGG
ATTAATCTGACGGGTGTTGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAGTGCT
ACTACTAGGCAGGCGCATCCGTTGTATTTTGACTACTGGGGTCAGGGAAC
CCTGGTCACCGTCTCGAGC

BMS2h-515 (SEQ ID NO: 648)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGGAGGGTGAGA
TGTATTGGGTCCGCCAGGCTCCAGGGAAGGGTCTAGAGTGGGTCTCAACG
ATTTCGACTAATGGTCTTACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCTACT
CGTGATCTGGGTTTTGCCTACTGGGGTCAGGGAACCCTGGTCACCGTCTC
GAGC

BMS2h-516 (SEQ ID NO: 649)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGAGTATGAGA
TGGCTTGGGCCCGCCAGGCTCCAGGGAAGGGTCTAGAGTGGGTCTCATTT
ATTTCTCCTCGTGGTCATTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGCT
AAGACTTTTGACTACTGGGGTCAGGGAACCCTGGTCACCGTCTCGAGC

BMS2h-517 (SEQ ID NO: 650)
GAGGTGCAGCTGTTGGAGTCTGGGGGAGGCTTGGTACAGCCTGGGGGGTC
CCTGCGTCTCTCCTGTGCAGCCTCCGGATTCACCTTTGATACGTATGAGA
TGCTTTGGGTCCGCCAGGCTCCAGGGAAGGGTCTAGAGTGGGTCTCACGT
ATTTTCTGATGGTAGTATTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAACGCGG
ATGCGTTTTGACTACTGGGGTCAGGGAACCCTGGTCACCGTCTCGAGC

BMS2h-518 (SEQ ID NO: 651)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTTCGTATGCTA
TGTCGTGGGTCCGCCAGGCTCCAGGGAAGGGTCTAGAGTGGGTCTCCAAT
ATTTCTCGTGATGGTTGTGAAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGCGCAG
TCTGGGGGCTTCGGTCGGTTTGACTACGTTTGACTACTGGGGTCAGGG
AACCCTGGTCACCGTCTCGAGC

BMS2h-519 (SEQ ID NO: 652)
GAGGTGCAGCTGTTGGAGTCTGGGGGAGGCTTGGTACAGCCTGGGGGGTC
CCTGCGTCTCTCCTGTGCAGACTCACCTTTAGCAGCTATGCCA
TGAGCTGGGTCCGCCAGGCTCCAGGGAAGGGTCTAGAGTGGGTCTCATCT
ATTGGGAGGGATGGTGCTTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGGGG
CCGAAGGGTATTGCGTTTGACTACTGGGGTCAGGGAACCCTGGTCACCGT
CTCGAGC

BMS2h-520 (SEQ ID NO: 653)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTCCGATGCTA
TGGCTTGGGTCCGCCAGGCTCCAGGGAAGGGTCTGGAGTGGGTCTCAGGT
ATTGATGGGGGGGTTCGATGACATACTACGCAGACTCCGTGAAGGGCCG
GTTCACCATCTCCCGCGACAATTCCAAGAACACGCTGTATCTGCAAATGA

TABLE 2-continued

Human Anti-CD40L VH Domain Encoding Nucleotide Sequences

ACAGCCTGCGTGCCGAGGACACCGCGGTATATTACTGTGCGAAATCGGAT
CCTCCGTTTGACTACTGGGGTCAGGGAACCCTGGTCACCGTCTCGAGC

BMS2h-521 (SEQ ID NO: 654)
GAGGTGCAGCTGTTGGAGTCTGGGGGAGGCTTGGTACAGCCTGGGGGGTC
CCTGCGTCTCTCCTGCGCAGCCTCCGGATTCACCTTTCATGCGGGGAGA
TGCATTGGGTCCGCCAGGCTCCAGGGAAGGGTCTAGAGTGGGTCTCATCG
ATTACGCTGCCTGGTGATATGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGAAT
ACTGGGTATACTTTTGACTACTGGGGTCAGGGAACCCTGGTCACCGTCTC
GAGC

BMS2h-522 (SEQ ID NO: 655)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGAATTATGGTA
TGTCGTGGGTCCGCCAGGCTCCAGGGAAGGGTCTAGAGTGGGTCTCAAGT
ATTTCGTGGGATGGTTCTCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGCAAAATACG
CGGCTTTTTGACTACTGGGGTCAGGGAACCCTGGTCACCGTCTCGAGC

BMS2h-523 (SEQ ID NO: 656)
GAGGTGCAGCTGTTGGAGTCTGGGGGAGGCTTGGTACAGCCTGGGGGGTC
CCTGCGTCTCTCCTGTGCAGCCTCCGGATTCACCTTTCATGATGCGGATA
TGCTGTGGGTCCGCCAGGCTCCAGGGAAGGGTCTAGAGTGGGTCTCAGGT
ATTTTGTCTCCGGGTGAGGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTTGGT
CTGCCGTTTGACTACTGGGGTCAGGGAACCCTGGTCACCGTCTCGAGC

BMS2h-524 (SEQ ID NO: 657)
GAGGTGCAGCTGTTGGAGTCTGGGGGAGGCTTGGTACAGCCTGGGGGGTC
CCTGCGTCTCTCCTGTGCAGCCTCCGGATTCACCTTTCGTACTGATCAGA
TGAATTGGGTCCGCCAGGCTCCAGGGAAGGGTCTAGAGTGGGTCTCAAGT
ATTTCTCCTAGTGGTGCGTATACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGGTCTT
GGTGCTTTTGACTACTGGGGTCAGGGAACCCTGGTCACCGTCTCGAGC

BMS2h-525 (SEQ ID NO: 658)
GAGGTGCAGCTGTTGGAGTCTGGGGGAGGCTTGGTACAGCCTGGGGGGTC
CCTGCGTCTCTCCTGTGCAGCCTCCGGATTCATCTTTGAGCAGTATCAGA
TGGTTTGGGTCCGCCAGGCTCCAGGGAAGGGTCTAGAGTGGGTCTCATGG
ATTTCGCCTGATGGTACGCATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTTAGT
TTGCGTAAGATGGAGAAGTTTGACTACTGGGGTCAGGGAACCCTGGTCAC
CGTCTCGAGC

BMS2h-526 (SEQ ID NO: 659)
GAGGTGCAGCTGTTGGAATCTGGGGGAGGCTTGGTACAGCCTGGGGGGTC
CCTGCGTCTCTCCTGTGCAGCCTCCGGATTCACCTTTCAGGATGAGCAGA
TGGCGTGGGTCCGCCAGGCTCCAGGGAAGGGTCTAGAGTGGGTCTCAAGT
ATTGCGTCTGATGGTATGTTACATACTACGCAGACTCCGTGAAGGGCCG
GTTCACCATCTCCCGCGACAATTCCAAGAACACGCTGTATCTGCAAATGA
ATAGCCTGCGTGCCGAGGACACCGCGGTATATTACTGTGCGCAACCTGGG
AAGAATTTTGACCACTGGGGTCAGGGAACCCTGGTCACCGTCTCGAGC

BMS2h-527 (SEQ ID NO: 660)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGATTATGCGA
TGAGTTGGGTCCGCCAGGCTCCAGGGAAGGGTCTAGAGTGGGTCTCATCG
ATTACTACTGGGGTGAGCATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTCTGAAACGTTGG
AATCTGTATACGGAGTCTTTTGACTACTGGGGTCAGGGAACCCTGGTCAC
CGTCTCGAGC

BMS2h-528 (SEQ ID NO: 661)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTGATTATGGAA
TGGATTGGGTCCGCCAGGCTCCAGGGAAGGGTCTAGAGTGGGTCTCATCT
ATTGCTCCTGATGGTATTCATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAATTTG
GGTCAGGGTTTTGACTACTGGGGTCAGGGAACCCTGGTCACCGTCTCGAG
C

BMS2h-529 (SEQ ID NO: 662)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCGGTATCAGA
TGACGTGGGTCCGCCAGGCTCCAGGGAAGGGTCTAGAGTGGGTCTCAAGT
ATTTCTCCTAGTGGTACGTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAATGGAAG
GCGCTTTTTGACTACTGGGGTCAGGGAACCCTGGTCACCGTCTCGAGC

BMS2h-530 (SEQ ID NO: 663)
GAGGTGCAGCTGTTGGAGTCTGGGGGAGGCTTGGTACAGCCTGGGGGGTC
CCTGCGTCTCTCCTGTGCAGCCTCCGGATTCACCTTTCCTCATTCGACTA
TGTATTGGGTCCGCCAGGCTCCAGGGAAGGGTCTAGAGTGGGTCTCACTT
ATTTTGCCGTCGGGTAGTCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTTTCT
GATGAGCGTTTTGACTACTGGGGTCAGGGAACCCTGGTCACCGTCTCGAG
C

BMS2h-531 (SEQ ID NO: 664)
GAGGTGCAGCTGTCGGAGTCTGGGGGAGGCTTGGTACAGCCTGGGGGGTC
CCTGCGTCTCTCCTGTGCAGCCTCCGGATTCACCTTTGGTGATGGGAATA
TGGATTGGGTCCGCCAGGCTCCAGGGAAGGGTCTAGAGTGGGTCTCAGGT
ATTTCTAGTGATGGTGTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATAGG
GGTCAGGGGTTTGACTACTGGGGTCAGGGAACCCTGGTCACCGTCTCGAG
C

BMS2h-532 (SEQ ID NO: 665)
GAGGTGCAGCTGTTGGAGTCTGGGGGAGGCTTGGTACAGCCTGGGGGGTC
CCTGCGTCTCTCCTGTGCAGCTTCCGGATTCACCTTTGATGATTATATGA
TGTGGTGGGTCCGCCAGGCTCCAGGGAAGGGTCTAGAGTGGGTCTCATCT
ATTAGTCCGCATGGTGTTTATACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAATGGTTG
CATACGTTTGACTACTGGGGTCAGGGAACCCTGGTCACCGTCTCGAGC

BMS2h-533 (SEQ ID NO: 666)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGAATTATACGA
TGGCTGTGGGCCGCCAGGCTCCAGGGAAGGGTCTAGAGTGGGTCTCATTT
ATTGCTGGTCCGGGTAATTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGG
AGTACTGCGACGTATAATAATGGTCAGTTTGACTACTGGGGTCAGGGAAC
CCTGGTCACCGTCTCGAGC

BMS2h-534 (SEQ ID NO: 667)
GAGGTGCAGCTGTTGGAGTCTGGGGGAGGCTTGGTACAGCCTGGGGGGTC
CCTGCGTCTCTCCTGTGCAGCCTCCGGATTCACCTTTACGGAGTATAGTA
TGGTGTGGGTCCGCCAGGCTCCAGGGAAGGGTCTGGAGTGGGTCTCATCT
ATTAGTGGAGTGGTCGTGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGCTT
AAGCTGGTTAGGGCTCCTAATCCGTTTGACTACTGGGGTCAGGGAACCCT
GGTCACCGTCTCGAGC

BMS2h-535 (SEQ ID NO: 668)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAATTATCAGA
TGGCGTGGGTCCGCCAGGCTCCAGGGAAGGGTCTAGAGTGGGTCTCAGGT
ATTTCTAAGACTGGTCATTCTACATACTACGCAGACTCCGTGAAGGGCCG
GTTCACCATCTCCCGCGACAATTCCAGGAACACGCTGTATCTGCAAATGA
ACAGCCTGCGTGCCGAGGACACCGCGGTATATTACTGTGCGAAAGCTTCG
CATTCGTTGGGGCCTCTTTTTGACTACTGGGGTCAGGGAACCCTGGTCAC
CGTCTCGAGC

BMS2h-54 (SEQ ID NO: 669)
GAGGTGCAGCTGTTGGAGTCTGGGGGAGGCTTGGTACAGCCTGGGGGGTC
CCTGCGTCTCTCCTGTGCAGCCTCCGGATTCACCTTTACGGCGTATAGGA
TGGCTTGGGTCCGCCAGGCTCCAGGGAAGGGTCTAGAGTGGGTCTCATGG
ATTTCGCCTTCGGTTCGGGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACTTTG

TABLE 2-continued

Human Anti-CD40L VH Domain Encoding
Nucleotide Sequences

ACGGATTCGCCGTCGGGGCATTATGAGTTTGACTACTGGGGTCAGGGAAC
CCTGGTCACCGTCTCGAGC

BMS2h-55 (SEQ ID NO: 670)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGCGGTATGAGA
TGGGGTGGGTCCGCCAGGCTCCAGGGAAGGGTCTAGAGTGGGTCTCACGG
ATTACTGCTCAGGGTCTTGGGACATACTACGCAGACTCCGTGAAGGGCCG
GTTCACCATCTCCCGCGACAACTCCAAGAACACGCTGTATCTGCAAATGA
ACAGCCTGCGTGCCGAGGATACCGCGGTATATTACTGTGCGAAATATCTT
ACTGATTTTAGTAGTGGGCATCAGGAGTTTGACTACTGGGGTCAGGGAAC
CCTGGTCACCGTCTCGAGC

BMS2h-553 (SEQ ID NO: 671)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGATTATGGTA
TGTCGTGGGTCCGCCAGGTTCCAGGGAAGGGTCTGGAGTGGGTCTCAGGT
ATTAGTCATAATGGTATGTTGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATATTGG
CCGTCTACTAGTTGGGAGACTGATTTTGACTACTGGGGTCAGGGAACCCT
GGTCACCGTCTCGAGC

BMS2h-554 (SEQ ID NO: 672)
GAGGTGCAGCTGTTGGAGTCTGGGGGAGGCTCGGTACAGCCTGGGGGGTC
CCTGCGTCTCTCCTGTGCAGCCTCCGGATTCACCTTTGGGAATGAGCCTA
TGGCTTGGGTCCGCCAGGCTCCAGGGAAGGGTCTAGAGTGGGTCTCAAGT
ATTGAGATGCAGGGTAAGAATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATAGG
GGTCAGGGGTTTGACTACTGGGGTCAGGGAACCCTGGTCACCGTCTCGAG
C

BMS2h-555 1 (SEQ ID NO: 673)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGAGGAGGAGA
TGAGTTGGGTCCGCCAGGCTCCAGGGAAGGGTCTAGAGTGGGTCTCATGT
ATTGATAATCTGGGTAGTCCTACATACTACGCAGACTCCGTGAAGGGCCG
GTTCACCATCTCCCGCGACAATTCCAAGAACACGCTGTATCTGCAAATGA
ACAGCCTGCGTGCCGAGGACGCCGCGGTATATTACTGTGCGAAAACGATT
TCTCATCAGTATGATAGGTTTGACTACTGGGGTCAGGGAACCCTGGTCAC
CGTCTCGAGC

BMS2h-556 (SEQ ID NO: 674)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGAGGAGGAGA
TGAGTTGGGTCCGCCAGGCTCCAGGGAAGGGTCTAGAGTGGGTCTCATGT
ATTGATGAGGGGGTCGGTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGACG
CCGCATAAGCAGTTGTCGTTTGACTACTGGGGTCAGGGAACCCTGGTCAC
CGTCTCGAGC

BMS2h-557 (SEQ ID NO: 675)
GAGGTGCAGCTGTTGGAGTCTGGGGGAGGCTTGGTACAGCCTGGGGGGTC
CCTGCGTCTCTCCTGTGCAGCCTCCGGATTCAGCTTTGCTGATGAGTATA
TGGTTTGGGCCCGCCAGGCTCCAGGGAAGGGTCTAGAGTGGGTCTCAGAG
ATTGATCCGTTGGGTACTGGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATATGGG
ACGGCTTTTGACTACTGGGGTCAGGGAACCCTGGTCACCGTCTCGAGC

BMS2h-558 (SEQ ID NO: 676)
GAGGTGCAGCTGTTGGAGTCTGGGGGAGGCTTGGTACAGCCTGGGGGGTC
CCTGCGCCTCTCCTGTGCAGCCTCCGGATTCACCTTTTCTACGCATGATA
TGATGTGGGTCCGCCAGGCTCCAGGGAAGGGTCTAGAGTGGGTCTCATCG
ATTTCTGATGATGGTATTAGTACATACTACGCAGACTCCGTGAAGGGCCG
GTTCACCATTTCCCGCGACAATTCCAAGAACACGCTGTATCTGCAAATGA
ACAGCCTGCGTGCCGAGGATACCGCGGTATATTACTGTGCGAAACCTGAT
ATGTCTCTTATTGAGTTTGACTACTGGGGTCAGGGAACCCTGGTCACCGT
CTCGAGC

BMS2h-559 (SEQ ID NO: 677)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGGTACTCCGA
TGGTTTGGGTCCGCCAGGCTCCAGGGAAGGGTCTAGAGTGGGTCTCAGGG
ATTAGTGGTGATGGTAGGAATACATACTACGCAGACTCCGTGAAGGGCCG

TABLE 2-continued

Human Anti-CD40L VH Domain Encoding
Nucleotide Sequences

GTTCACCATCTCCCGCGACAATTCCAAGAACACGCTGTATCTGCAAATGA
ACAGCCTGCGTGCCGAGGACACCGCGGTATATTACTGTGCGGAACCTTAT
GCGCTTACTTCGTCTAAGCCTTTTGACTACTGGGGTCAGGGAACCCTGGT
CACCGTCTCGAGC

BMS2h-56 (SEQ ID NO: 678)
GAGGTGCAGCTGTTGGAGTCTGGGGGAGGCTTGGTACAGCCTGGGGGGTC
CCTGCGTCTCTCCTGTGCAGCCTCCGGATTCACCTTTAATGATTATACTA
TGGGTTGGGTCCGCCAGGCTCCAGGGAAGGGTCTAGAGTGGGTCTCATGG
ATTCATGGGACTGGTGGTCAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCTTTG
GCTGATAGGAGTGGGGGGGTTGTTGAGTTTGACTACTGGGGTCAGGGAAC
CCTGGTCACCGTCTCGAGC

BMS2h-560 (SEQ ID NO: 679)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGCGGAGACGA
TGGCTTGGGTCCGCCAGGCTCCAGGGAAGGGTCTAGAGTGGGTCTCATGT
ATTAGTAATGATGGTAATACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGAGTCT
CTGATTAGTCCTGGTCTTTTTGACTACTGGGGTCAGGGAACCCTGGTCAC
CGTCTCGAGC

BMS2h-561 (SEQ ID NO: 680)
GAGGTGCAGCTGTTGGAGTCTGGGGGAGGCTTGGTACAGCCTGGGGGGTC
CCTGCGTCTCTCCTGTGCAGCCTCCGGATTCACCTTTACTGGTGAGTATA
TGAATTGGGTCCGCCAGGCTCCAGGGAAGGGTCTAGAGTGGGTCTCAACT
ATTAATGAGACTGGTTATATGACATACTACGCAGACTCCGTGAAGGGCCG
GTTCACCATCTCCCGCGACAATTCCAAGAACACGCTGTATCTGCAAATGA
ATAGCCTGCGTGCCGAGGACACCGCGGTATATTACTGTGCGAAACTTTCT
ACGAGGGGGTGCCTTTTGACTACTGGGGTCAGGGAACCCTGGTCACCGT
CTCGAGC

BMS2h-562 (SEQ ID NO: 681)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGTCGTATGATA
TGGGTTGGGTCCGCCAGGCTCCAGGGAAGGGTCTAGAGTGGGTCTCAACG
ATTTCGCCTATGGGTGTTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCTAAT
CAGCATGCTCATGATCCTTTTGACTACTGGGGTCAGGGAACCCTGGTCAC
CGTCTCGAGC

BMS2h-563 (SEQ ID NO: 682)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGATTATGATA
TGGGTTGGGTCCGCCAGGCTCCAGGGAAGGGTCTGGAGTGGGTCTCAAGT
ATTTCGCCTATGGGTACGTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCTGCT
TTGACTGAGCCTATGTTTGACTACTGGGGTCAGGGAACCCTGGTCACCGT
CTCGAGC

BMS2h-564 (SEQ ID NO: 683)
GAGGTGCAGCTGTTGGAGTCTGGGGGAGGCTTGGTACAGCCTGGGGGGTC
CCTGCGTCTCTCCTGTGCAGCCTCCGGATTCACCTTTCGTGATTATGATA
TGGGTTGGGTCCGCCAGGCTCCAGGGAAGGGTCTAGAGTGGGTCTCAACT
ATTTCTCCTCTTGGTCATTTTACATACTACGCAGACTCCGTGAAGGGCCG
GTCACCATCTCCCGCGACAATTCCAAGAACACGCTGTATCTGCAAATGA
ACAGCCTGCGTGCCGAGGATACCGCGGTATATTACTGTGCGAAAGCTGAG
GAGGCTTTTGACTACTGGGGTCAGGGAACCCTGGTCACCGTCTCGAGC

BMS2h-565 (SEQ ID NO: 684)
GAGGTGCAGCTGTTGGAGTCTGGGGGAGGCTTGGTACAGCCTGGGGGGTC
CCTGCGCCTCTCCTGTGCAGCCTCCGGATTCGCCTTTCCTAGGTATGGTA
TGACGTGGGTCCGCCAGGCTCCAGGGAAGGGTCTAGAGTGGGTCTCAACT
ATTGATCAGTTTGGTATGAAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAGAGTAT
GCTTCGTTTGACTACTGGGGTCAGGGAACCCTGGTCACCGTCTCGAGC

BMS2h-566 (SEQ ID NO: 685)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAAGTATGATA
TGGGTTGGGTCCGCCAGGCTCCAGGGAAGGGTCTAGAGTGGGTCTCAACG

TABLE 2-continued

Human Anti-CD40L VH Domain Encoding
Nucleotide Sequences

ATTTCGCCTATGGGTGTTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGCGG
GGTAATACTTCGGATTTTGACTACTGGGGTCAGGGAACCCTGGTCACCGT
CTCGAGC

BMS2h-567 (SEQ ID NO: 686)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAATTATGATA
TGGCGTGGGTCCGCCAGGCTCCAGGGAAGGGTCTAGAGTGGGTCTCAACT
ATTTCTGGGGCGGGTCATTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAGTTTT
CCGCGTGATGAGTTTGACTACTGGGGTCAGGGAACCCTGGTCACCGTCTC
GAGC

BMS2h-568 (SEQ ID NO: 687)
GAGGTGCAGCTGTTGGAGTCTGGGGGAGGCTTGGTACAGCCTGGGGGGTC
CCTGCGTCTCTCCTGTGCAGCCTCCGGATTCACCTTTCCGAAGTATGAGA
TGAGGTGGGTCCGCCAGGCTCCAGGGAAGGGTCTAGAGTGGGTCTCAGAG
ATTGGTCTGGATGGTTCGCCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTGGGG
GATCCGAATGGTTTTGACTACTGGGTCAGGGAACCCTGGTCACCGTCTC
GAGC

BMS2h-569 (SEQ ID NO: 688)
GAGGTGCAGCTGTTGGAGTCTGGGGGAGGCTTGGTACAGCCTGGGGGGTC
CCTGCGTCTCTCCTGTGCAGCCTCCGGATTCACCTTTCCGACTAGTGAGA
TGGATTGGGTCCGCCAGGCTCCAGGGAAGGGTCTGGAGTGGGTCTCATGG
ATTGGGCCTGATGGTTTGACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACATGCG
GATTGGTTTGACTACTGGGGTCAGGGAACCCTGGTCACCGTCTCGAGC

BMS2h-57 (SEQ ID NO: 689)
GAGGTGCAGCTGTTGGAGTCTGGGGGAGGCTTGGTACAGCCTGGGGGGTC
CCTGCGTCTCTCCTGTGCAGCCTCCGGATTCACCTTTTCTGAGTATGATA
TGTATTGGGTCCGCCAGGCTCCAGGGAAGGGTCTAGAGTGGGTCTCATGG
ATTGATACTGATGGTGGGGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGGT
CTGAAGTTTGACTACTGGGGTCAGGGAACCCTGGTCACCGTCTCGAGC

BMS2h-570 (SEQ ID NO: 690)
GAGGTGCAGCTGTTGGAGTCTGGGGGAGGCCTGGTACAGCCTGGGGGGTC
CCTGCGTCTCTCCTGTACAGCCTCCGGATTCACCTTTGAGAATGCTTCTA
TGCAGTGGGTCCGCCAGGCTCCAGGGAAGGGTCTAGAGTGGGTCTCATCT
ATTGAGGGCAGGGTAATGCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTCCA
TCTTGGTCTTTTGACTACTGGGGTCAGGGAACCCTGGTCACCGTCTCGAG
C

BMS2h-571 (SEQ ID NO: 691)
GAGGTGCAGCTGTTGGAGTCTGGGGGAGGCTTGGTACAGCCTGGGGGGTC
CCTGCGTCTCTCCTGTGCAGCCTCCGGATTCACCTTTACGCGTAATGAGA
TGGGGTGGGTCCGCCAGGCTCCAGGGAAGGGTCTAGAGTGGGTCTCAACT
ATTACGCGACTGGTACGTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACGGAT
CCTGGTAATAGGTATTTTGACTACTGGGGTCAGGGAACCCTGGTCACCGT
CTCGAGC

BMS2h-572 (SEQ ID NO: 692)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTTTGACTACCGGGGTCAGGGAACCCTGGTCACCGTCTC
GAGC

BMS2h-572-1 (SEQ ID NO: 693)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGTTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTTTGACTACCGGGGTCAGGGGACCCTGGTCACCGTCTC
GAGC

BMS2h-572-10 (SEQ ID NO: 694)
GAGGTGCAGCTGTTGGAGTCTGGTGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCGTCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTCTGACTACCGGGGTCAGGGAACCCTGGTCACCGTCTC
GAGC

BMS2h-572-11 (SEQ ID NO: 695)
GAGGTGCAGCTGTTGGAGTCTGGGGGAGGCTTGGTACAGCCTGGGGGGTC
CCTGCGTCTCTCCTGTGCAGCCTCAGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGATTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCAGGTCACCGTCTC
GAGC

BMS2h-572-12 (SEQ ID NO: 696)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGCCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTCTGACTACCGGGGTCAGGGAACCCTGGTCACCGTCTC
GAGC

BMS2h-572-13 (SEQ ID NO: 697)
GAGGTGCAGTTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGCCCGCCAGGCTCCAGGGAAGGGTCTAGAGTGGGTCTCAGGT
ATTGAGGGTCCTGGTGATGTTACATACTACGCAGACTCCGTGAAGGACCG
GTTCACCATCTCCCGCGACAATTCCAAGAACACGCTGTATCTGCTAATGA
ACAGCCTGCGTGCCGAGGACACCGCGGTATATTACTGTGCGAAAGTAGGG
AAGGAGAGTAATTTTGACTACTGGGGTCAGGGAACCCTGGTCACCGTCTC
GAGC

BMS2h-572-14 (SEQ ID NO: 698)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGC
ATTGAGGGTCCTGGTGATGTTACATACTACGCAGACTCAGTGAAGGGCCG
GTTCACCATCTCCCGCGACAATACCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTCTC
GAGC

BMS2h-572-15 (SEQ ID NO: 699)
GAGGTGCGGCTATTGGAGTCTGGGGGAGGCTTGGTACAGCCTGGGGGGTC
CCTGCGTCTCTCCTGTGCAGCCTCCGGATTCAACTTTAATTGGCAGCTGA
TGGGTTGGATCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCAGTATATTACTGTGCGAAAGTTGGG
AAGGAGAGTAATTCTGACTACCGGGGTCAGGGAACCCTGGTCACCGTCTC
GAGC

BMS2h-572-16 (SEQ ID NO: 700)
GAGGTGCAGCTGTTGGAGTCTGGGGGAGGCTTGGTACAGCCTGGGGGGTC
ACTGCGTCTCTCCTGTGTAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTTTGACTACCGGGGTCAGGGAACCCTGGTCACCGTCTC
GAGC

TABLE 2-continued

Human Anti-CD40L VH Domain Encoding
Nucleotide Sequences

BMS2h-572-17 (SEQ ID NO: 701)
GAGGTGCAGCTGTTGGAGTCTGGGGGAGGCTTGGTACAGACTGGGGGGTC
CCTGCGTCTCTCCTGTGCAGCCTCCGGATTCACCTATAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGATGACACCGCGGTATATTACTGTGTGAAAGTTGGG
AAGGAGAGTAATTTTGACTACCGGGGTCACGGAACCCTGGTCACCGTCTC
GAGC

BMS2h-572-18 (SEQ ID NO: 702)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAAGGCTCCTGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTTTGACTACCGGGGTCAGGGAACCCTGGTCACCGTCTC
GAGC

BMS2h-572-19 (SEQ ID NO: 703)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCCCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATACCAAGAACACGCTGTATCTGCAAATGA
ACAGCCTGCGTGCCGAGGACACCGCGGTATATTACTGTGTGAAAGTTGGG
AAGGAGAGTAATTTTGACTACCGGGGTCAGGGAACCCTGGTCACCGTCTC
GAGC

BMS2h-572-2 (SEQ ID NO: 704)
GAGGTGCAGCTGTTGGAGTCTGGGGGAGGCTTGGTACAGCCTGGGGGGTC
CCTGCGCCTCTCCTGTGCAGCCTCCGGATTCACCTTTAATTGGCAGCTGA
TGGGTTGGGTCCGCCAGGCTCCAGGGAAGGGTCTTGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAAGTTTGACTACCGGGTCAGGGAACCCTGGTCACCGTCTC
GAGC

BMS2h-572-21 (SEQ ID NO: 705)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGAATCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATCTTGACTACCGGGGTCAGGGAACCCTGGTCACCGTCTC
GAGC

BMS2h-572-22 (SEQ ID NO: 706)
GAGGTGCAGCTGTTTGAGTCTGGGGGAGGCTCGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTCTGACTACCGGGGTCAGGGGACCCTGGTCACCGTCTC
GAGC

BMS2h-572-23 (SEQ ID NO: 707)
GAGGTGCAGCTGTTGGAGTCTGGGGGAGGCTTGGTACAGCCTGGGGGGTC
CCTGCGTCTCACCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCATCATCTCCCGCGACAATTCCAAGAACACGCTATATCTGCAAATGA
ACAGCCTGCGTGCCGAGGACACCGCGGTATATTACTGTGCGAAAGTTGGG
AAGGAGAGTAATTCTGACTACCGGGGTCAGGGAACCCTGGTCACCGTCTC
GAGC

BMS2h-572-24 (SEQ ID NO: 708)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCGGACTCCGTGAAGGGCCG
GTTCACCATCTCCCGCGACAATTCACGAACACGCTGTATCTGCAAATGA
ACAGCCTGCGTGCCGAGGACACCGCGGTATATTACTGTGCGAAAGTTGGG
AAGGAGAGTGAATTTGACTACCGGGGTCAGGGAACCCTGGTCACCGTCTC
GAGC

BMS2h-572-3 (SEQ ID NO: 709)
GAGGTGCAGCTGTTGGAGTCTGGGGGAGGCTTGGTACAGCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCACCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATCTTGACTACCGGGGTCAGGGAACCCTGGTCACCGTCTC
GAGC

BMS2h-572-4 (SEQ ID NO: 710)
GAGGTGCAGCTGTTGGTGTCTGGGGGAGGCCTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTTTGACTACCGGGGTCAGGGAACCCTGGTCACCGTCTC
GAGC

BMS2h-572-5 (SEQ ID NO: 711)
GAGGTGCAGCTGTTGGTGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACATGCTGTATCTGCAAATGA
ACGGCCTGCGTGCCGAGGACACCGCGGTATATTACTGTGCGAAAGTTGGG
AAGGAGAGTAATTTTGACTACCGGGGTCAGGGAACCCTGGTCACCGTCTC
GAGC

BMS2h-572-6 (SEQ ID NO: 712)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-601 (SEQ ID NO: 713)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGTGGCAGCTCA
TGGGGTGGGCCCGGCAGGCTCCAGGGAAGGGTCTAGAGTGGGTCTCAGGT
ATTGAGGGTCCAGGTGATGTTACATACTACGCAGACCCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-602 (SEQ ID NO: 714)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGTGGCACCTGA
TGGGGTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAGTTCTGACTACCGGGGTCAGGGAACCCTGGTCACCGTATC
GAGC

BMS2h-572-603 (SEQ ID NO: 715)
GAGGTGCAGCTGTTGGAGTCTGGGGGAGGCTTGGTACAGCCTGGGGGGTC
CCTGCGTCTCTCCTGTGCAGCCTCCGGATTCACCTTTAACTGGCACCTGA
TGGCCTGGGCCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-604 (SEQ ID NO: 716)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGTGGCAGCTGA
TGGGCTGGGTCCGGCAGGCTCCAGGGAAGGGTCTCGAGTGGGTCTCAGGT

TABLE 2-continued

Human Anti-CD40L VH Domain Encoding
Nucleotide Sequences

ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-605 (SEQ ID NO: 717)
GAGGTGCAGCTGTTGGAGTCTGGGGGAGGCTTGGTGCAGCCTGGGGGGTC
CCTGCGTCTCTCCTGTGCAGCCTCCGGATTCACCTTTAAGTGGCAGCTGA
TGGCCTGGGCCCGGCAGGCTCCAGGGAAGGGTCTAGAGTGGGTCTCAGGT
ATTGAGGGTCCAGGTGATATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-606 (SEQ ID NO: 718)
GAGGTGCAGCTGTTGGAGTCTGGGGGAGGCTTGGTACAGCCTGGGGGGTC
CCTGCGTCTCTCCTGTGCAGCCTCCGGATTCACCTTTAACTGGCACTTGA
TGGGCTGGGCCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-607 (SEQ ID NO: 719)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGTGGCAGCTCA
TGGGGTGGGCCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-608 (SEQ ID NO: 720)
GAGGTGCAGCTGTTGGAGTCTGGGGGAGGCTTGGTACAGCCTGGGGGGTC
CCTGCGTCTCTCCTGTGCAGCCTCCGGATTCACCTTTAACTGGGAGCTGA
TGGGCTGGGCCCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-609 (SEQ ID NO: 721)
GAGGTGCAGCTGTTGGAGTCTGGGGGAGGCTTGGTACAGCCTGGGGGGTC
CCTGCGTCTCTCCTGTGCAGCCTCCGGATTCACCTTTAACTGGCAGCTCA
TGGGCTGGGCCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTTGGG
AAGGAGAGTAATTCTGACTACCGGGGTCAGGGAACCCTGGTCACCGTATC
GAGC

BMS2h-572-610 (SEQ ID NO: 722)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGC
AAGGACAGCAAGTCCGACTACCGGGGTCAGGGAACCCTGGTCACCGTATC
GAGC

BMS2h-572-611 (SEQ ID NO: 723)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTCGGG
AAGGACAGCAAGTCGGACTACCGGGGTCAGGGAACCCTGGTCACCGTATC
GAGC

TABLE 2-continued

Human Anti-CD40L VH Domain Encoding
Nucleotide Sequences

BMS2h-572-612 (SEQ ID NO: 724)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTCGGG
AAGGACAGCAACTCGGACTACCGGGGTCAGGGAACCCTGGTCACCGTATC
GAGC

BMS2h-572-613 (SEQ ID NO: 725)
GAGGTGCAGCTGTTGGAGTCTGGGGGAGGCTTGGCACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGC
AAGGACAGCAAGTCCGACTACCGGGGTCAGGGAACCCTGGTCACCGTATC
GAGC

BMS2h-572-614 (SEQ ID NO: 726)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGTGAAAGTGGGG
AAGGACGCCAAGTCGGACTACCGGGGTCAGGGAACCCTGGTCACCGTATC
GAGC

BMS2h-572-615 (SEQ ID NO: 727)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGCCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGTGAAAGTGGGG
AAGGACAAGAACTCGGACTACCGGGGTCAGGGAACCCTGGTCACCGTATC
GAGC

BMS2h-572-616 (SEQ ID NO: 728)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGTGAAAGTGGGG
AAGGAGAGCAAGTCCGACTACCGGGGTCAGGGAACCCTGGTCACCGTATC
GAGC

BMS2h-572-617 (SEQ ID NO: 729)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGTGAAAGTGGGG
AGGGACAGCAAGTCGGACTACCGGGGTCAGGGAACCCTGGTCACCGTATC
GAGC

BMS2h-572-618 (SEQ ID NO: 730)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGTGAAAGTCGGG
AAGTACAGCAACTCGGACTACCGGGGTCAGGGAACCCTGGTCACCGTATC
GAGC

BMS2h-572-619 (SEQ ID NO: 731)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA

TABLE 2-continued

Human Anti-CD40L VH Domain Encoding
Nucleotide Sequences

ACAGCCTGCGTGCCGAGGACACCGCGGTATATTACTGTGTGAAAGTGGGC
AAGGACAGCAGGTCGGACTACCGGGGTCAGGGAACCCTGGTCACCGTATC
GAGC

BMS2h-572-620 (SEQ ID NO: 732)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGG
AAGGACGACAGCTCGGACTACCGGGGTCAGGGAACCCTGGTCACCGTATC
GAGC

BMS2h-572-621 (SEQ ID NO: 733)
GAGGTGCAGCTGTTGGAGTTTGGGGGAGGCTTGGTACAGCCTGGGGGGTC
CTTGCGTTTTTCCTGTGCAGCTTCCGGATTCACCTTTAATTGGCAGCTGA
TGGGTTGTTCCGGCAGGCTCCAGGGAAGGGTTTAGAGTGGGTTTCAGGT
ATTGAGGGTCCAGGTGATGTTACATATTACGCAGATTCCGTGAAGGGCCG
GTTCACCATTTCCCGCGACAATTCCAAGAACACGCTGTATCTGCAAATGA
ACAGCTTGCGTGCCGAGGATACCGCGGTATATTACTGTGTGAAAGTGGGG
AGGGACAGCAATTCCGACTACCGGGGTCAGGGAACCCTGGTCACCGTATC
GAGC

BMS2h-572-622 (SEQ ID NO: 734)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGG
AAGGACAGCACCTCGGACTACCGGGGTCAGGGAACCCTGGTCACCGTATC
GAGC

BMS2h-572-623 (SEQ ID NO: 735)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGG
AAGGAGAGCAGCTCGGACTACCGGGGTCAGGGAACCCTGGTCACCGTATC
GAGC

BMS2h-572-624 (SEQ ID NO: 736)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTTCCGCGACAATTCCAAGAACACGCTGTATCTGCAAATGA
ACAGCCTGCGTGCCGAGGATACCGCGGTATATTACTGTGTGAAAGTGGGC
AAGGACAGCGCGTCCGACTACCGGGGTCAGGGAACCCTGGTCACCGTATC
GAGC

BMS2h-572-625 (SEQ ID NO: 737)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGTGAAAGTCGGC
AACGACAGCTACTCGGACTACCGGGGTCAGGGAACCCTGGTCACCGTATC
GAGC

BMS2h-572-626 (SEQ ID NO: 738)
GAGGTGCAGCTGTTGGAGTCTGGGGGAGGCTTGGTACAGCCTGGGGGGTC
CCTGCGTCTCTCCTGTGCAGCCTCTGGATTCACCTTTAATTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACGGCCTGCGTGCCGAGGACACCGCGGTATATTACTGTGTGAAAGTGGGG
AAGGACAGCAGCTCGGACTACCGGGGTCAGGGAACCCTGGTCACCGTATC
GAGC

BMS2h-572-627 (SEQ ID NO: 739)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA

TABLE 2-continued

Human Anti-CD40L VH Domain Encoding
Nucleotide Sequences

TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGATATATTACTGTGTGAAAGTGGGG
AAGGACAGCGCGTCGGACTACCGGGGTCAGGGAACCCTGGTCACCGTATC
GAGC

BMS2h-572-630 (SEQ ID NO: 740)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGTGGCAGCTGA
TGGGTTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGTGAAAGTGGGG
AAGGACGCCAAGTCGGACTACCGGGGTCAGGGAACCCTGGTCACCGTATC
GAGC

BMS2h-572-631 (SEQ ID NO: 741)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGTGGCAGCTGA
TGGGCTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGC
AAGGACAGCAGGTCGGACTACCGGGGTCAGGGAACCCTGGTCACCGTATC
GAGC

BMS2h-572-632 (SEQ ID NO: 742)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGTGGCAGCTGA
TGGGCTGGGTCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGC
AAGGACAGCAAGTCCGACTACCGGGGTCAGGGAACCCTGGTCACCGTATC
GAGC

BMS2h-572-633 (SEQ ID NO: 743)
GAGGTGCAGCTGTTGGAGTCTGGGGGAGGCTTGGTACAGCCTGGGGGGTC
CCTGCGTCTCTCCTGTGCAGCCTCCGGATTCACCTTTAACTGGGAGCTGA
TGGGCTGGGTCCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGTGAAATGGGGG
AAGGACGCCAAGTCGGACTACCGGGGTCAGGGAACCCTGGTCACCGTATC
GAGC

BMS2h-572-634 (SEQ ID NO: 744)
GAGGTGCAGCTGTTGGAGTCTGGGGGAGGCTTGGTACAGCCTGGGGGGTC
CCTGCGTCTCTCCTGTGCAGCCTCCGGATTCACCTTTAACTGGGAGCTGA
TGGGTTGGGCCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGC
AAGGACAGCAGGTCGGACTACCGGGGTCAGGGAACCCTGGTCACCGTATC
GAGC

BMS2h-572-635 (SEQ ID NO: 745)
GAGGTGCAGCTGTTGGAGTCTGGGGGAGGCTTGGTACAGCCTGGGGGGTC
CCTGCGTCTCTCCTGTGCAGCCTCCGGATTCACCTTTAACTGGGAGCTGA
TGGGCTGGGCCCGGCAGGCTCCAGGGAAGGGTCTAGAGTGGGTCTCAGGT
ATTGAGGGTCCAGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGTGAAAGTGGGC
AAGGACAGCAAGTCCGACTACCGGGGTCAGGGAACCCTGGTCACCGTATC
GAGC

BMS2h-572-7 (SEQ ID NO: 746)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGATGGGCCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTACAAATGA
ACAGCCTGCGTGCCGAGGACTCCGCGGTATATTACTGTGCGAAAGTTGGG
AAGGAGAGTAATTTTGACTACTGGGTCAGGGAACCCTGGTCACCGTCTC
GAGC

TABLE 2-continued

Human Anti-CD40L VH Domain Encoding
Nucleotide Sequences

BMS2h-572-8 (SEQ ID NO: 747)
GAGGTGCAGCTGTTGGAGTCTGGGGGAGGCTTGGTACAGCCTGGGGGGTC
CCTGCGTCTCTCCTGTGTAGCCTCCGGATTCACCTTTAATTGGCAGCTGA
TGGGTTGGGTCCGCCAGGCGCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTCGGG
AAGGAGAGTAATTCTGACTACCGGGGTCAGGGAACCCTGGTCACCGTTTC
GAGC

BMS2h-572-9 (SEQ ID NO: 748)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTGGCAGCTGA
TGGGTTGGGTCCGCCAGGCTCCAGGGAAGGGTCTAGAGTGGGTCTCAGGT
ATTGAGGGTCCTGGTGATGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGG
AAGGAGAGTAATTCTGACTACCGGGGTCAGGGAACCCTGGTCACCGTCTC
GAGC

BMS2h-573 (SEQ ID NO: 749)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGGGTGGGAGA
TGGGTTGGGTCCGCCAGGCTCCAGGGAAGGGTCTAGAGTGGGTCTCATCT
ATTGATGAGTCTGGTCTTAATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGGTGCG
CCGCAGTATCAGATTACATTTGACTACTGGGGTCAGGGAACCCTGGTCAC
CGTCTCGAGC

BMS2h-574 (SEQ ID NO: 750)
GAGGTGCAGCTGTTGGAGTCTGGGGGAGGCTTGGTACAGCCTGGGGGGTC
CCTGCGTCTCTCCTGTGCAGCCTCCGGATTCACCTTTCCTAATTATGGGA
TGTATTGGGTCCGCCAGGCTCCAGGGAAGGGTCTAGAGTGGGTCTCATAT
ATTTCGCGGAGGGGTTTGTTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACGTCG
CATTATATGAATAATGGGTTTGACTACTGGGGTCAGGGAACCCTGGTCAC
CGTCTCGAGC

BMS2h-575 (SEQ ID NO: 751)
GAGGTGCAGCTGTTGGAGTCTGGGGGAGGCTTGGTACAGCCTGGGGGGTC
CCTGCGTCTCTCCTGTGCAGCCTCCGGATTCACCTTTGGATTATACGA
TGGCTTGGGTCCGCCAGGCTCCAGGGAAGGGTCTGGAGTGGGTCTCATCT
ATTAGTCCGATTGGTACTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATCCT
TATGGGATGGAGGATGGTCGACGTGGTTTGACTACTGGGGTCAGGGAAC
CCTGGTCACCGTCTCGAGC

BMS2h-576 (SEQ ID NO: 752)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGCGTATGATA
TGCAGTGGGTCCGCCAGGCTCCAGGGAAGGGTCTGGAGTGGGTCTCAACG
ATTACGTCGGAGGGTCTTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTAGT
GATTTGTTTGACTACTGGGGTCAGGGAACCCTGGTCACCGTCTCGAGC

BMS2h-577 (SEQ ID NO: 753)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGGGTATGATA
TGGGTTGGGTCCGCCAGGCTCCAGGGAAGGGTCTAGAGTGGGTCTCAACT
ATTTCTCGTGGGGTTGGTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGACG
AGTCAGTCGTCTACGGGGAGTTTTGACTACTGGGGTCAGGGAACCCTGGT
CACCGTCTCGAGC

BMS2h-578 (SEQ ID NO: 754)
GAGGTGCAGCTGTTGGAGTCTGGGGGAGGCTTGGTACAGCCTGGGGGGTC
CCTGCGTCTCTCCTGTGCAGCCTCCGGATTCACCTTTCGTCGGTATGATA
TGCTTTGGGCCCGCCAGGCTCCAGGGAAGGGTCTAGAGTGGGTCTCAGAG
ATTTCGCCTACGGGTGCTCTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACTTGGT
TCGACTTTTGACTACTGGGGTCAGGGAACCCTGGTCACCGTCTCGAGC

BMS2h-579 (SEQ ID NO: 755)
GAGGTGCAGCTGTTGGAGTCTGGGGGAGGCTTGGTACAGCCTGGGGGGTC
CCTGCGTCTCTCCTGTGCAGCCTCCGGATTCACCTTTTTTCCGTATTATA
TGAGTTGGGTCCGCCAGGCTCCAGGGAAGGGTCTAGAGTGGGTCTCATCT
ATTTCGGGTACGGGTGGGCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACGACG
CAGAATGCGACGCTTTTTGACTACTGGGGTCAGGGAACCCTGGTCACCGT
CTCGAGC

BMS2h-58 (SEQ ID NO: 756)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGTTTATACTA
TGGCTGGGTCCGCCAGGCTCCAGGGAAGGGTCTGGAGTGGGTCTCAACG
ATTGATGAGTCTGGTCGTGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGGT
GTTTGGTTTGACTACTGGGGTCAGGGAACCCTGGTCACCGTCTCGAGC

BMS2h-580 (SEQ ID NO: 757)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTTTTATAAGA
TGGGGTGGGTCCGCCAGGCTCCAGGGAAGGGTCTAGAGTGGGTCTCAACG
ATTACTCCTAAGGGTCATCATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTTTT
AAGGGTAAGGGTTGGACTCGTCCGAGTGGGTTTGACTACTGGGTCAGGG
AACCCTGGTCACCGTCTCGAGC

BMS2h-581 (SEQ ID NO: 758)
GAGGTGCAGCTGTTGGAGTCTGGGGGAGGCTTGGTACAGCCTGGGGGGTC
CCTGCGTCTCTCCTGTGCAGCCTCCGGATTCACCTTTAATGAGTATAGTA
TGATGTGGGTCCGCCAGGCTCCAGGGAAGGGTCTAGAGTGGGTCTCATCT
ATTGGGAGGCGTGGTTGGCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCTGTG
CTGCTGGATTCTACTAAGTTTGACTACTGGGGTCAGGGAACCCTGGTCAC
CGTCTCGAGC

BMS2h-582 (SEQ ID NO: 759)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGAGTATCGA
TGACTTGGGTCCGCCAGGCTCCAGGGAAGGGTCTAGAGTGGGTCTCAACT
ATTTCTGCGCGTGGTCCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTAGG
CATTGTTCGTAATGGTCGTTTTGACTACTGGGGTCAGGGAACCCTGGT
CACCGTCTCGAGC

BMS2h-583 (SEQ ID NO: 760)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTATGCAGTCGA
TGCAGTGGGTCCGCCAGGCTCCAGGGAAGGGTCTAGAGTGGGTCTCAAGT
ATTACTGGTAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGAT
CGGGTTTTTGACTACTGGGGTCAGGGAACCCTGGTCACCGTCTCGAGC

BMS2h-584 (SEQ ID NO: 761)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGCGGCTGATA
TGCAGTGGGTCCGCCAGGCTCCAGGGAAGGGTCTAGAGTGGGTCTCACTG
ATTACTAATGATGATATTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGGGT
GATCGTTTTGACTACTGGGGTCAGGGAACCCTGGTCACCGTCTCGAGC

BMS2h-586 (SEQ ID NO: 762)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAAGTATAGGA
TGCATGGGTCCGCCAGGCTCCAGGGAAGGGTCTAGAGTGGGTCTCAAGT
ATTGATAGTTCTGGTGAGCTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGAGGTT
CCGATGGGGAATCAGACTTTTTTTGACTACTGGGGTCAGGGAACCCTGGT
CACCGTCTCGAGC

TABLE 2-continued

Human Anti-CD40L VH Domain Encoding
Nucleotide Sequences

BMS2h-587 (SEQ ID NO: 763)
GAGGTGCAGCTGTTGGAGTCTGGGGGAGGCTTGGTACAGCCTGGGGGGTC
CCTGCGTCTCTCCTGTGCAGCCTCCGGATTCACCTTTACTGATTATACTA
TGGGGTGGGTCCGCCAGGCTCCAGGGAAGGGTCTAGAGTGGGTCTCATCG
ATTACGTCTCAGGGTGCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCTACG
GGTACGGATTCGTCGTTTGACTACTGGGGTCAGGGAACCCTGGTCACCGT
CTCGAGC

BMS2h-588 (SEQ ID NO: 764)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGATTATGAGA
TGTCTTGGGTCCGCCAGGCTCCAGGGAAGGGTCTGGAGTGGGTCTCATGT
ATTGGGCCGGGGGGTAAGCCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTGGAT
GGGCATTTTGACTACTGGGGTCAGGGAACCCTGGTCACCGTCTCGAGC

BMS2h-589 (SEQ ID NO: 765)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTCAGTATGATA
TGGGGTGGGTCCGCCAGGCTCCAGGGAAGGGTCTAGAGTGGGTCTCAACG
ATTTCTTCGAGGGGTTGGCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTCCG
GGGGGTCGTCGGCGGTTTGACTACTGGGGTCAGGGAACCCTGGTCACCGT
CTCGAGC

BMS2h-59 (SEQ ID NO: 766)
GAGGTGCAGCTGTTGGAGTCTGGGGGAGGCTTGGTACAGCCTGGGGGGTC
CCTGCGTCTCTCCTGTGCAGCCTCCGGATTCACCTTTCTGGATTATGCGA
TGGGTTGGGTCCGCCAGGCTCCAGGGAAGGGTCTGGAGTGGGTCTCAACT
ATTTCTCCGATGGGTATGGGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCGAGT
GCTATTTCGTTTACTTCTGATATTTCTAATTTTGACTACTGGGGTCAGGG
AACCCTGGTCACCGTCTCGAGC

BMS2h-590 (SEQ ID NO: 767)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGATTATCCGA
TGTCTTGGGTCCGCCAGGCTCCAGGGAAGGGTCTAGAGTGGGTCTCAAGT
ATTTCTTGGTCTGGTTTTCAGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACCTGGT
GTTGCGAGGATGCCTACTGGGATTGCTTTTGACTACTGGGGTCAGGGAAC
CCTGGTCACCGTCTCGAGC

BMS2h-591 (SEQ ID NO: 768)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGCTTATGAGA
TGCAGTGGGTCCGCCAGGCTCCAGGGAAGGGTCTAGAGTGGGTCTCATCT
ATTGATAGTGCTGGTACTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTCTATTACTGTGCGGAACCTTTT
GGGATGTTTGACTACTGGGGTCAGGGAACCCTGGTCACCGTCTCGAGC

BMS2h-592 (SEQ ID NO: 769)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGAGTATCCGA
TGAAGTGGGTCCGCCAGGCTCCAGGGAAGGGTCTAGAGTGGGTCTCAACG
ATTGATCGGCAGGGTGATCGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACGGTG
CGGAGGGGTCTTCCTCGTCCGAGTCGTTATTTTGACTACTGGGGTCAGGG
AACCCTGGTCACCGTCTCGAGC

BMS2h-593 (SEQ ID NO: 770)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGATTATGATA
TGGGTTGGGTCCGCCAGGCTCCAGGGAAGGGTCTGGAGTGGGTCTCAAGT
ATTTCGCCTATGGGTACGTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTCTG
AGTGTGTATTCGGGTCTTGATTTTGACTACTGGGGTCAGGGAACCCTGGT
CACCGTCTCGAGC

BMS2h-594 (SEQ ID NO: 771)
GAGGTGCAGCTGTTGGAGTCTGGGGGAGGCCTGGTACAGCCTGGGGGGTC
CCTGCGTCTCTCCTGCGCAGCCTCCGGATTCACCTTTTCTCATTATGATA
TGGGTTGGGTCCGCCAGGCTCCAGGGAAGGGTCTGGAGTGGGTCTCAGAT
ATTGATTATATTGGTAAGACTACATACTACGCAGACTCCGTGAAGGGCCG
GTTCACCATCTCTCGCGACAATTCCAAGAACACGCTGTATCTGCAAATGA
ACAGCCTGCGTGCCGAGGACACCGCGGTATATTACTGTGCGAAAGCTTCG
GATGAGGTGGGTGTTAATACTTCCAAGTTTGACTACTGGGGTCAGGGAAC
CCTGGTCACCGTCTCGAGC

BMS2h-595 (SEQ ID NO: 772)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGCGGTATGATA
TGGGGTGGGTCCGCCAGGCTCCAGGGAAGGGTCTAGAGTGGGTCTCAACT
ATTTTCTCCTACTGGTGTTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTTTT
GAGGATTTTGACTACTGGGGTCAGGGAACCCTGGTCACCGTCTCGAGC

BMS2h-596 (SEQ ID NO: 773)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGCTTATCCGA
TGAGTTGGGTCCGCCAGGCTCCAGGGAAGGGTCTAGAGTGGGTCTCACTG
ATTTCTCATACGGGTCATGCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGCAT
TGGCCTTTTGACTACCGGGTCAGGGAACCCTGATCACCGTCTCGAGC

BMS2h-597 0 (SEQ ID NO: 774)
GAGGTGCAGCTGTTGGAGTCTGGGGGAGGCTTGGTACAGCCAGGGGGGTC
CCTGCGCCTCTCCTGTGCAGCCTCCGGATTCACCTTTGAGGATGAGTGGA
TGAGTTGGGTCCGCCAGGCTCCAGGGAAGGGTCTAGAGTGGGTCTCAGAT
ATTAGCCGGGTGGTTGGACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTTAT
CGTCCGTTTGATGAGTTTGACTACTGGGGTCAGGGAACCCTGGTCACCGT
CTCGAGC

BMS2h-598 (SEQ ID NO: 775)
GAGGTGCAGCTGTTGGAGTCTGGGGGAGGCTTGGTACAGCCTGGGGGGTC
CCTGCGTCTCTCCTGTGCAGCCTCCGGAGTCACCTTTGATGCTATTGAGA
TGTCTTGGGTCCGCCAGGCTCCAGGGAAGGGTCTGGAGTGGGTCTCATCG
ATTTCGCGTCATGGTGAGTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGATGCT
TGGTCTCGGCATTTTGACTACTGGGGTCAGGGAACCCTGGTCACCGTCTC
GAGC

BMS2h-599 (SEQ ID NO: 776)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAGTACGGATA
TGAGTTGGGTCCGCCAGGCTCCAGGGAAGGGTCTAGAGTGGGTCTCAGGT
ATTTTGGATAATGGTAGTAATACATACTACGCAGACTCCGTGAAGGGCCG
GTTCACCATCTCCCGCGACAATTCCAAGAACATGCTGTATCTGCAAATGA
ATAGCCTGCGTGCCGAGGATACCGCGGTATATTACTGTGCGAAAGGGGCG
AGGGATTTTGACTACTGGGGTCAGGGAACCCTGGTCACCGTCTCGAGC

BMS2h-600 (SEQ ID NO: 777)
GAGGTGCAGCTGTTGGAGTCTGGGGGAGGCTTGGTACAGCCTGGGGGGTC
CCTGCGTCTCTCCTGTGCAGCTTCCGGATTCACCTTTGGTAGGCAGAGTA
TGCAGTGGGTCCGCCAGGCTCCAGGGAAGGGTCTAGAGTGGGTCTCAAGT
ATTGATAGTGGTTTTTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGGAT
CCGTGGGGTTTTGACTACTGGGGTCAGGGAACCCTGGTCACCGTCTCGAG
C

BMS2h-601 (SEQ ID NO: 778)
GAGGTGCAGCTGTTGGAGTCTGGGGGAGGCTTGGTACAGCCTGGGGGGTC
CCTGCGTCTCTCCTGTACAGCCTCCGGATTCACCTTTAGTGATACGAGA
TGGCGTGGGTCCGCCAGGCTCCAGGGAAGGGTCTAGAGTGGGTCTCAGGT
ATTGATGATGGGGGTGTGAGTACATACTACGCAGACTCCGTGAAGGGCCG
GTTCACCATCTCCCGCGACAATTCCAAGAACACGCTGTATCTGCAAATGA

TABLE 2-continued

Human Anti-CD40L VH Domain Encoding Nucleotide Sequences

ACAGCCTGCGTGCCGAGGACACCGCGGTATATTACTGTGCGAAACCGGAT
CGTCATTTTGACTACTGGGGTCAGGGAACCCTGGTCACCGTCTCGAGC

BMS2h-602 (SEQ ID NO: 779)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGAGTACGACGA
TGGGGTGGGTCCGCCAGGCTCCAGGGAAGGGTCTGGAGTGGGTCTCAGTG
ATTTCGGATGATGGTGGTTTTACATACTACGCAGACTCCGTGAAGGGCCG
GTTCACCATCTCCCGCGACAATTCCAGGAACACGCTGTATCTGCAAATGA
ACAGCCTGCGTGCCGAGGACACCGCGGTATATTACTGTGCGAAAGTTGAT
GGTTATGGTGTTTTTGACTACTGGGGTCAGGGAACCCTGGTCACCGTCTC
GAGC

BMS2h-603 (SEQ ID NO: 780)
GAGGTGCAGCTGTTGGAGTCTGGGGGAGGCTTGGTACAGCCTGGGGGGTC
CCTGCGTCTCTCCTGTGCAGCCTCCGGATTCACCTTTCGGAGTGGGGATA
TGAATTGGGTCCGCCAGGCTCCAGGGAAGGGTCTAGAGTGGGTCTCAACT
ATTACGAATGATGGTACGTTCTACATACTACGCAGACTCCGTGAAGGGCCG
GTTCACCATCTCCCGCGACAATTCCAAGAATACGCTGTATCTGCAAATGA
ACAGCCTGCGTGCCGAGGACACCGCGGTATATTACTGTGCGAAATCTGAT
TCTGATTTTGACTACTGGGGTCAGGGAACCCTGGTCACCGTCTCGAGC

BMS2h-61 (SEQ ID NO: 781)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTGCTTATGCTA
TGACGTGGGTCCGCCAGGCTCCAGGGAAGGGTCTAGAGTGGGTCTCATAT
ATTAGTCCGAATGGTACGGCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAATATGTG
GGGATGCGTTGGAATTCTTTTGACTACTGGGGTCAGGGAACCCTGGTCAC
CGTCTCGAGC

BMS2h-62 (SEQ ID NO: 782)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGAGTTATGAGA
TGGCTTGGGTCCGCCAGGCTCCAGGGAAGGGTCTAGAGTGGGTCTCATCT
ATTACGAGTCTTGGTACTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACGGGT
AGGAAGTTTGACTACTGGGGTCAGGGAACCCTGGTCACCGTCTCGAGC

BMS2h-65 (SEQ ID NO: 783)
GAGGTGCAGCTGTTGGAGTCTGGGGGAGGCTTGGTACAGCCTGGGGGGTC
CCTGCGTCTCTCCTGTGCAGCCTCCGGATTCACCTTTAATGAGTATGAGA
TGACGTGGGTCCGCCAGGCTCCAGGGAAGGGTCTAGAGTGGGTCTCAACG
ATTACTAGTGAGGGTAGTGGGACATACTACGCAGACTCCGTAAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTAAT
GGTAAGTTTGACTACTGGGGTCAGGGAACCCTGGTCACCGTCTCGAGC

BMS2h-66 (SEQ ID NO: 784)
GAGGTGCAGCTGTTGGAGTCTGGGGGAGGCTTGGTACAGCCTGGGGGGTC
CCTGCGTCTCTCCTGTGCAGCCTCCGGATTCACCTTTTCTGATTATGAGA
TGTTGTGGGTCCGCCAGGCTCCAGGGAAGGGTCTGGAGTGGGTCTCAACT
ATTACTAGTGAGGGTCATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGGG
ACTTCGTTTGACTACTGGGGTCAGGGAACCCTGGTCACCGTCTCGAGC

BMS2h-67 (SEQ ID NO: 785)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTGATTATGAGA
TGATTCTGGGTCCGCCAGGCTCCAGGGAAGGGTCTAGAGTGGGTCTCAACG
ATTGATTCGATGGTAGTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGT
GTGAAGTTTGACTACTGGGGTCAGGGAACCCTGGTCACCGTCTCGAGC

BMS2h-68 (SEQ ID NO: 786)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGGATTATGAGA
TGACTTGGGTCCGCCAGGCTCCAGGGAAGGGTCTAGAGTGGGTCTCATCT
ATTTCTTCTACTGGTCAGTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGT
AATAAGTTTGACTACTGGGGTCAGGGAACCCTGGTCACCGTCTCGAGC

BMS2h-69 (SEQ ID NO: 787)
GAGGTGCAGCTGTTGGAGTCTGGGGGAGGCTTGGTACAGCCTGGGGGGTC
CCTGCGTCTCTCCTGTGCAGCCTCCGGATTCACCTTTCTTGATTATGGTA
TGGCTTGGGTCCGCCAGGCTCCAGGGAAGGGTCTAGAGTGGGTCTCAGCT
ATTTCGCCTCTTGGTCTTAGTACATACTACGCAGACTCCGTGAAGAGCCG
GTTCACCATCTCCCGCGACAATTCCAAGAACACGCTGTATCTGCAAATGA
ACAGCCTGCGTGCCGAGGATACCGCGGTATATTACTGTGCGAAAGAGGTG
AGGGTGGGTAGGGGTGTTCATCCTCCGAAGTTTGACTACTGGGGTCAGGG
AACCCTGGTCACCGTCTCGAGC

BMS2h-7 (SEQ ID NO: 788)
GAGGTGCAGCTGTTGGAGTCTGGGGGAGGCTTGGTACAGCCTGGGGGGTC
CCTGCGTCTCTCCTGTGCAGCCTCCGGATTCACCTTTAATTTGTATGAGA
TGACTTGGGTCCGCCAGGCTCCAGGGAAGGGTCTAGAGTGGGTCTCATCT
ATTACTAGTGATGGTGTTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCTGGG
GTGATTTTGACTACTGGGGTCAGGGAACCCTGGTCACCGTCTCGAGC

BMS2h-70 (SEQ ID NO: 789)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGAATTATGCTA
TGTCGTGGGTCCGCCAGGCTCCAGGGAAGGGTCTAGAGTGGGTCTCAACG
ATTGCTCCGCTGGGTGTTCCGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAAAGAAG
GTTGGGGCTGGCTGCAGTCGCGGAGTTTTGACTACTGGGGTCAGGGAAC
CCTGGTCACCGTCTCGAGC

BMS2h-701 (SEQ ID NO: 790)
GAGGTGCAGCTGTTGGAGTCTGGGGGAGGCTTGGTACAGCCTGGGGGGTC
CCTGCGTCTCTCCTGTGCAGCCTCCGGATTCACCTTTATGGATTATGAGA
TGCATTGGGTCCGCCAGGCTCCAGGGAAGGGTCTAGAGTGGGTCTCAACG
ATTGGTGCTTCTGGTCATTATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATATCTT
GATATGCTGCTGTTTGGGTTTGACTACTGGGGTCAGGGAACCCTGGTCAC
CGTCTCGAGC

BMS2h-702 (SEQ ID NO: 791)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTGAGTATGAGA
TGATGTGGGTCCGCCAGGCTCCAGGGAAGGGTCTAGAGTGGGTCTCACGT
ATTGCTGGTAATGGTTCTCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATAATGCTT
TCTCATTTTGACTACTGGGGTCAGGGAACCCTGGTCACCGTCTCGAGC

BMS2h-703 (SEQ ID NO: 792)
GAGGTGCAGCTGTTGGAGTCTGGGGGAGGCTTGGTACAGCCTGGGGGGTC
CCTGCGTCTCTCCTGTGCAGCCTCCGGATTCACCTTTTATAATTATGATA
TGAGTTGGGTCCGCCAGGCTCCAGGGAAGGGTCTAGAGTGGGTCTCAGGT
ATTGATTCGATGGGTCTTGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGGGTCT
AATGCGAGTGATTGGGTTGTTTTTGACTACTGGGGTCAGGGAACCCTGGT
CACCGTCTCGAGC

BMS2h-704 (SEQ ID NO: 793)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGTCGTATCATA
TGACTTGGGTCCGCCAGGCTCCAGGGAAGGGTCTAGAGTGGGTCTCATCG
ATTGCGGATACGGGTGATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACTGCGGTATATTACTGTGCGAAATTGCGT
GGGATGGCTCGGGTTTGGGGGTTTGACTACTGGGGTCAGGGAACCCTGGT
CACCGTCTCGAGC

BMS2h-705 (SEQ ID NO: 794)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTTATTATGATA
TGATGTGGGTCCGCCAGGCTCCAGGGAAGGGTCTAGAGTGGGATCTCATCT
ATTTCGGATCGTGGTCTTCAGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATTTACG
GAGATTCCGTTGGATTGGTGGAGGTGTTTGACTACTGGGGTCAGGGAAC
CCTGGTCACCGTCTCGAGC

TABLE 2-continued

Human Anti-CD40L VH Domain Encoding
Nucleotide Sequences

BMS2h-706 (SEQ ID NO: 795)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGAGTTATAAGA
TGTTTGGGTCCGCCAGGCTCCAGGGAAGGGTCTAGAGTGGGTCTCATCG
ATTACTAATTCTGGTACTGAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCGATG
TATCCGGATTTGGAGATTGTGCATTTTGACTACTGGGGTCAGGGAACCCT
GGTCACCGTCTCGAGC

BMS2h-707 (SEQ ID NO: 796)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGACTTATCGTA
TGAGTTGGGTCCGCCAGGCTCAGGGAAGGGTCTAGAGTGGGTCTCAGCT
ATTGATCAGGAGGGTTCTGCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAAATAGT
GGGACGAGGCCGGGGCTTCGGTTTGACTACTGGGGTCAGGGAACCCTGGT
CACCGTCTCGAGC

BMS2h-708 (SEQ ID NO: 797)
GAGGTGCAGCTGTTGGAGTCTGGGGGAGGCTTGGTACAGCCTGGGGGGTC
CCTGCGCCTCTCCTGTGCAGCCTCCGGATTCACCTTTAGTAGTTATGATA
TGCTTTGGGTCCGCCAGGCTCCAGGGAAGGGTCTAGAGTGGGTCTCACGG
ATTGATGCGAGTGGTTATTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGCAATTGTTG
AAGCTGTCGTTGAATCCTAATTTTGACTACTGGGGTCAGGGAACCCTGGT
CACCGTCTCGAGC

BMS2h-709 1 (SEQ ID NO: 798)
GAGGTGCAGCTGTTGGAGTCTGGGGGAGGCTTGGTACAGCCTGGGGGGTC
CCTGCGTCTCTCCTGTGCAGCCTCCGGATTCACCTTTAGCAGCTATGCCA
TGAGCTGGGTCCGCCAGGCTCCAGGGAAGGGTCTAGAGTGGGTCTCATCG
ATTCATAATACTGGTTTGTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGACT
CAGCATCGTTTTGTTGTTTTTGACTACTGGGGTCAGGGAACCCTGGTCAC
CGTCTCGAGC

BMS2h-71 (SEQ ID NO: 799)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGGTTATCCTA
TGTCGTGGGTCCGCCAGGCTCCAGGGAAGGGTCTAGAGTGGGTCTCAACT
ATTAGTCCTTTGGGTCCTGATACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACTGTTG
ATGGGGGAGTATTTGAATTCTAGGACGTTTGACTACTGGGGTCAGGGAAC
CCTGGTCACCGTCTCGAGC

BMS2h-710 (SEQ ID NO: 800)
GAGGTGCAGCTGTTGGAGTCTGGGGGAGGCTTGGTACAGCCTGGGGGGTC
CCTGCGTCTCTCCTGTGCAGCCTCCGGATTCACCTTTAATACGTATAGTA
TGTCTTGGGTCCGCCAGGCTCCAGGGAAGGGTCTAGAGTGGGTCTCATGG
ATTGATGCTGATGGTTGGGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGCAAACTGGG
CATACGTTTGACTACTGGGGTCAGGGAACCCTGGTCACCGTCTCGAGC

BMS2h-711 (SEQ ID NO: 801)
GAGGTGCAGCTGTTGGAGTCTGGGGGAGGCTTGGTACAGCCTGGGGGGTC
CCTGCGTCTCTCCTGTGCAGCCTCCGGATTCACCTTTACGGATGGGAGA
TGGGTTGGGCCGCCAGGCTCCAGGGAAGGGTCTAGAGTGGGTCTCAAGG
ATTGTGGATCCTGGTGATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGGGT
GATCAGTTTGACTACTGGGGTCAGGGAACCCTGGTCACCGTCTCGAGC

BMS2h-712 (SEQ ID NO: 802)
GAGGTGCAGCTGTTGGAGTCTGGGGGAGGCTTGGTACAGCCTGGGGGGTC
CCTGCGTCTCTCCTGTGCAGCCTCCGGATTCACCTTTCCTGAGTATGAGA
TGAAGTGGGTCCGCCAGGCTCCAGGGAAGGGTCTAGAGTGGGTCTCAACT
ATTACTCCGTCGGGTGGTCATACATACTACGCAGACTCCGTGAAGGGCCG
GTTCACCATCTCCCGCGACAATTCCAAGAACACGCTGTATCTGCAAATGA
ACAGCCTGCGTGCCGAGGACGCCGCGGTATATTACTGTGCGATACCTCTT
TCTAGTTTTGACTACTGGGGTCGGGGAACCCTGGTCACCGTCTCGAGC

BMS2h-713 (SEQ ID NO: 803)
GAGGTGCAGCTGTTGGAGTCTGGGGGAGGCTTGGTACAGCCTGGGGGGTC
CCTGCGTCTCTCCTGTGCAGCCTCCGGATTCACCTTTTCTAATTATGTGA
TGATTTGGGTCCGCCAGGCTCCAGGGAAGGGTCTAGAGTGGGTCTCACTT
ATTAATGGTGCTGGTGATATGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGGGGGT
GCGCGTTCGTTTGGGGTTCCGCCTAATTTTGACTACTGGGGTCAGGGAAC
CCTGGTCACCGTCTCGAGC

BMS2h-714 (SEQ ID NO: 804)
GAGGTGCAGCTGTTGGAGTCTGGGGGAGGCTTGGTACAGCCTGGGGGGTC
CCTGCGTCTCTCCTGTGCAGCCTCCGGATTCACCTTTACGGATGGGAGA
TGGGTTGGGCCGCCAGGCTCCAGGGAAGGGTCTAGAGTGGGTCTCAAGG
ATTGTGGATCCTGGTGATTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGGGT
GATCAGTTTGACTACTGGGGTCAGGGAACCCTGGTCACCGTCTCGAGC

BMS2h-715 (SEQ ID NO: 805)
GAGGTGCAGCTGTTGGAGTCTGGGGGAGGCTTGGTACAGCCTGGGGGGTC
CCTGCGTCTCTCCTGTGTAGCCTCCGGATTCACCTTTACGCTGTATAATA
TGTCTTGGGTCCGCCAGGCTCCAGGGAAGGGTCTGGAGTGGGTCTCAGTT
ATTTCTAGTAAGGGTGATAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGCAAACGAGT
AGTGTTTTTGACTACTGGGGTCAGGGAACCCTGGTCACCGTCTCGAGC

BMS2h-716 (SEQ ID NO: 806)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGCGTATTATA
TGAGTTGGGTCCGCCAGGCTCCAGGGAAGGGTCTAGAGTGGGTCTCAGGT
ATTGTTAATAATGGTTTGTTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCGGCT
GTTCATCCTTCGTATAGGGCGGAGTTGTTCGACTACTGGGGTCAGGGAAC
CCTGGTCACCGTCTCGAGC

BMS2h-717 (SEQ ID NO: 807)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTTCGTATGAGA
TGGCGTGGGTCCGCCAGGCTCCAGGGAAGGGTCTAGAGTGGGTCTCACGT
ATTGAGCCTGATGGTAGTAATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTCCG
GATAATTTTACTATGTTTGACTACTGGGGTCAGGGAACCCTGGTCACCGT
CTCGAGC

BMS2h-718 (SEQ ID NO: 808)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAAGTATATGA
TGGGGTGGGTCCGCCAGGCTCCAGGGAAGGGTCTAGAGTGGGTCTCATCT
ATTGATAGTCTTGGTCATTATACATACTACGCAGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGCGGAG
TTTCCGTTTGACTACTGGGGTCAGGGAACCCTGGTCACCGTCTCGAGC

BMS2h-719 (SEQ ID NO: 809)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGACGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCAGGGAACCCTGGTCACCGTCTCGAGC

BMS2h-719-1 (SEQ ID NO: 810)
GAGGTGCAGCTGTTGGAGTCTGGGGGAGGCATGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCAGGGAACCCAGGTCACCGTCTCGAGC

TABLE 2-continued

Human Anti-CD40L VH Domain Encoding Nucleotide Sequences

BMS2h-719-10 (SEQ ID NO: 811)
GAGGTGCAGCTGTTGGAGTCTGGGGGAGGCATGGTGCAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCAGGGAACCCTGGTCACCGTCTCGAGC

BMS2h-719-11 (SEQ ID NO: 812)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCAAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCGAGAACACGCTGTATCTGCAAATGA
ACAGCCTGCGTGCCGAGGATACCGCGGTATATTACTGTGCGGATCCGTTT
ACTGAGTTTGACTATTGGGGTCAGGGTACCCTGGTCACCGTCTCGAGC

BMS2h-719-12 (SEQ ID NO: 813)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCGTCTCCCGCGACAATTCCAAGAACACGCTGTATCTGCAAATGA
ACAGCCTGCGTGCCGAGGATACCGCGGTATATTACTGTGCGGACCCGTTT
ACTGAGTTTGACTACTGGGGTCAGGGAACCCTGGTCACCGTCTCGAGC

BMS2h-719-13 (SEQ ID NO: 814)
GAGGTGCAGCTGTTGGAGTCTGCGGGAGGCTTGGTACAGCCTGGGGGGTC
CCTGCGTCTCTCGTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATACCAAGAACACGCTGTATCTACAGATGA
ACAGCCTGCGTGCCGAGGATACCGCGGTATATTACTGTGCGGACCCGTTT
ACTGAGCTTGACTACTGGGGTCATGGAACCCTGGTCACCGTCTCGAGC

BMS2h-719-14 (SEQ ID NO: 815)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTTCTGTGCAGATCCGTTT
ACTGAGTTTGACTACTGGGGTCAGGGAACCCTGGTCACCGTCTCGAGC

BMS2h-719-15 (SEQ ID NO: 816)
GAGGTGCAGCTGTTGGAGTCTGGGGGAGGCTTGGTACAGCCTGGGGGGTC
CCTGCGTCTCTCCTGTGCAGCCTCCGGATTCGCCTTTAAGAGGTATGAGA
TGACATGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCATATGA
ACAGCCTGCGTGCCGAGGATACCGCGGTATATTACTGTGCGGATCCGTTT
ACTGAGATTGACTACTGGGGTCAGGGAACCCTGGTCACCGTCTCGAGC

BMS2h-719-16 (SEQ ID NO: 817)
GAGGTGCAGCTGTTGGAGTCTGGGGGAGGCTTGGTACAGCCTGGGGGGTC
CCTGCGTCTCTCCTGTGCAGCCTCCGGATTCCCCTTTAAGAGGTATGAGA
TGACGTGGGTCCGCCAGGCTCCAGGGAAGGGTCTGGAGTGGTCGTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACCGGGCTCAGGGAACCCTGGTCACCGTCTCGAGC

BMS2h-719-17 (SEQ ID NO: 818)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGTCGTGGGTCCGCCAGGCTCCAGGGAAGGGTCTGGAGTGGGTCTTCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGATCCGTTT
ACTGAGATTGACTACTGGGGTCAGGGAACCCAGGTCACCGTCTCGAGC

BMS2h-719-18 (SEQ ID NO: 819)
GAGGTGCAGCTGTTGGAGTCTGGGGGAGGCTTGGTACATCCTGGGGGGTC
CCTGCGTCTCTCCTGTGCAGCTTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGACGAGGATACCGCGGTATATTACTGTGCGGAACCGTTT
ACTGAGTTTGACTACGGGGTCAGGGAACCCTGGTCACCGTCTCGAGC

BMS2h-719-19 (SEQ ID NO: 820)
GAGGTGCAGCTGTTGGAGTCTGGGGGAGGCTGGGTACAGCCTGGGGGGTC
CCTGCGTCTCTCCTGTGCAGCCTCAGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGATCCGTTT
ACTGAGTTTGACTACTGGGGTCAGGGAACCCTGGTCACCGTCTCGAGC

BMS2h-719-2 (SEQ ID NO: 821)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-20 (SEQ ID NO: 822)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGACGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACTCTGTATCTGCAAATGA
ACAGCCTGCGTGCCGAGGATACCGCGGTATATTACTGTGCGGAACCGTTT
ACTGAGATTGACTACCGGGGTCAGGGAACCCTGGTCACCGTCTCGAGC

BMS2h-719-202 (SEQ ID NO: 823)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAAGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-203 (SEQ ID NO: 824)
GAGGTGCAGCTGTTGGAGTCTGGGGGAGGCTTGGTACAGCCTGGGGGGTC
CCTGCGTCTCTCCTGTGCAGCCTCCGGATTCACCTTTAACAGCTATGAGA
TGATGTGGGTCCGCCAGGCTCCAGGGAAGGGTCTAGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-21 (SEQ ID NO: 825)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGATCCATTT
ACTGAGTTTGACTACTGGGGTCAGGGAACCCTGGTCACCGTCTCGAGC

BMS2h-719-213 (SEQ ID NO: 826)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGACCCGTTC
ACGGAGATGGACTACTGGGGTCATGGAACCCTGGTCACCGTCTCGAGC

BMS2h-719-214 (SEQ ID NO: 827)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGACCCGTTC
ACGGAGTTCGACTACTGGGGTCATGGAACCCTGGTCACCGTCTCGAGC

TABLE 2-continued

Human Anti-CD40L VH Domain Encoding
Nucleotide Sequences

BMS2h-719-215 (SEQ ID NO: 828)
GAGGTGCAGCTGTTGGAGTCTGGGGGAGGCTTGGTACAGCCTGGGGGGTC
CCTGCGTCTATCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAGCCGTTC
ACGGAGTTGGACTACTGGGGTCATGGAACCCTGGTCACCGTCTCGAGC

BMS2h-719-218 (SEQ ID NO: 829)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCCCCAGGGAAGGGTCTGGAGTGGGTCTCATCG
ATTTCGTCCGACGGTTCCTTCACGTACTACGCCGAGTCGGTCAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-225 (SEQ ID NO: 830)
GAGGTGCAGCTGTTGGAGTCTGGGGGAGGCTTGGTACAGCCTGGGGGGTC
CCTGCGTCTCTCCTGTGCAGCCTCCGGATTCACCTTTAACACGTATGAGA
TGCAGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-226 (SEQ ID NO: 831)
GAGGTGCAGCTGTTGGAGTCTGGGGGAGGCTTGGTACAGCCTGGGGGGTC
CCTGCGTCTCTCCTGTGCAGCCTCCGGATTCACCTTTAACAAGTATGAGA
TGATGTGGGCCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAGGAACACGCTGTATCTGCAAATGA
ACAGCCTGCGTGCCGAGGATACCGCGGTATATTACTGTGCGGAACCGTTT
ACTGAGTTTGACTACTGGGGTCATGGAACCCTGGTCACCGTCTCGAGC

BMS2h-719-3 (SEQ ID NO: 832)
GAGGTGCAGCTGTCGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAATACGCTGTATCTGCAAATGA
ACAGCCTGCGTGCCGAGGATACCGCGGTATATTACTGTGCGGATCCGTTT
ACTGAGTTTGACTACTGGGGTCAGGGAACCCTGGTCACCGTCTCGAGC

BMS2h-719-4 (SEQ ID NO: 833)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGACTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCCAGTATATTACTGTGCGGAACCGTTT
ACTGAGTTTGACTACTGGGGTCAGGGAACCCTGGTCACCGTCTCAAGC

BMS2h-719-5 (SEQ ID NO: 834)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGAAATGA
ACAGCATGCGTGCCGAGGATACCGCGGTATATTACTGTGCGGAACCGTTT
ACTGAGTTTGACAACTGGGGTCAGGGAACCCTCGTCACCGTCTCGAGC

BMS2h-719-6 (SEQ ID NO: 835)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCAGAACCGTTT
ACTGAGTTTGACTACTGGGGTCAGGGAACCCAGGTCACCGTCTCGAGC

BMS2h-719-7 (SEQ ID NO: 836)
GAGGTGCAGCTGTTGGAGTCTGGGGGAGGCTTGGTACAGCCTGGGGGGTC
CCTGCGTCTCTCCTGTGCAGCCTCCGGATTCAACTTTAAGAGGTATGAGA
TGACGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG

TABLE 2-continued

Human Anti-CD40L VH Domain Encoding
Nucleotide Sequences

GTTCACCATCTCCCGCGACAATTCCAAGAACACGCTGTATCTGCAAATGA
ACAGCCTGCGTGCCGAGGATACCGCGGTATATTACTGTGCAGACCCGTTT
ACTGAGTTTGACTACTGGGGTCAGGGAACCCTGGTCACCGTCTCGAGC

BMS2h-719-8 (SEQ ID NO: 837)
GAGGTGCAGCTGTTGGAGTCTGGGGGAGACTTGGTACAGCCTGGGGGGTC
CCTGCGTCTCTCCTGTGCAGCCTCCGGATTCACCTTTAAGAGGTATGAGA
TGATGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCACGCGACAATTCCAAGAACACGCTGTATCTGCAAATGA
ACAGCCTGCGTGCCGAGGATACCGCGGTATATTACTGTGCGGAACCGTTT
ACTGAGTTTGACTACAGGGGTCAGGGAACCCTGGTCACCGTCTCGAGC

BMS2h-719-9 (SEQ ID NO: 838)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATGAGA
TGTCGTGGGTCCGCCAGGCTCCAGGGAAGGGTCTGGAGTGGGTCTCATCT
ATTTCGTCGGATGGTTCTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAACCGTTT
ACTGAGTTTGACTACTGGGGTCGGGGAACCCTGGTCACCGTCTCGAGC

BMS2h-72 (SEQ ID NO: 839)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGCGTATCCTA
TGTCGTGGGTCCGCCAGGCTCCAGGGAAGGGTCTAGAGTGGGTCTCAAGT
ATTTCCCCTCTTGGTTTGTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTAGT
GCTGGGGCGGAGACTCATGTTTATCGGCTTTTTGACTACTGGGGTCAGGG
AACCCTGGTCACCGTCTCGAGC

BMS2h-720 (SEQ ID NO: 840)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTAATTATGAGA
TGATGTGGGTCCGCCAGGCTCCAGGGAAGGGTCTAGAGTGGGTCTCATCT
ATTGGGGTGTTGGGTCATACGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACTTATG
TCGTTGAGGCAGTTTGAGAATCTTTTTGACTACTGGGGTCAGGGAACCCT
GGTCACCGTCTCGAGC

BMS2h-722 (SEQ ID NO: 841)
GAGGTGCAGCTGTTGGAGTCTGGGGGAGGCTTGGTACAGCCTGGGGGGTC
CCTGCGTCTCTCCTGTGCAGCCTCCGGATTCACCTTTACGAAGTATCCTA
TGGCTTGGGTCCGCCAGGCTCCAGGGAAGGGTCTAGAGTGGGTCTCAGGT
ATTGATGCTAATGGTAATAGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGGGACT
TGGCGTAGGCATTTTGCGATTTTTGACTACTGGGGTCAGGGAACCCTGGT
CACCGTCTCGAGC

BMS2h-723 (SEQ ID NO: 842)
GAGGTGCAGCTGTTGGAGTCTGGGGGAGGCTTGGTACAGCCTGGGGGGTC
CCTGCGTCTCTCCTGTGCAGCCTCCGGATTCACCTTTGATCTGTATGATA
TGATGTGGGTCCGCCAGGCTCCAGGGAAGGGTCTAGAGTGGGTCTCATCT
ATTTCTGATCTGGGTACGCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAATGGT
TTTAGGGTTACGAGTAATGATCGTAGGTTTGACTACTGGGGTCAGGGAAC
CCTGGTCACCGTCTCGAGC

BMS2h-724 (SEQ ID NO: 843)
GAGGTGCAGCTGTTGGAGTCTGGGGGAGGCTTGGTACAGCCTGGGGGGTC
CCTGCGTCTCTCCTGTGCAGCCTCCGGATTCACCTTTACTGGTGGGATA
TGTGGTGGGTCCGCCAGGCTCCAGGGAAGGGTCTAGAGTGGGTCTCAATG
ATTGAGGGTGGTGGTGTGACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACTTGAT
CTTCGGACGGGTCAGTTTGACTACTGGGGTCAGGGAACCCTGGTCACCGT
CTCGAGC

BMS2h-725 (SEQ ID NO: 844)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG

TABLE 2-continued

Human Anti-CD40L VH Domain Encoding
Nucleotide Sequences

GTTCACCATCTCCCGCGACAATTCCAAGAACACGCTGTATCTGCAAATGA
ACAGCCTGCGTGCCGAGGACACCGCGGTATATTACTGTGCGGAACCGTCG
GATCCTACTAAGTTTGACTACTGGGGTCAGGGAACCCTGGTCACCGTCTC
GAGC

BMS2h-725-1 (SEQ ID NO: 845)
GAGGTGCAGCTGTTGGAGTCTGGGGGAGGCTTGGTACAGCCTGGGGGGTC
CCTGCATCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTTCTGTGCGGATCCGTCG
GATCCTACTAAGTTTGACTACTGGGGTCAGGGAACCCTGGTCACCGTCTC
GAGC

BMS2h-725-10 (SEQ ID NO: 846)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGTGACAATTCCAAGAACACGCTGTATCTGCAAATGA
ACAGCCTGCGTGCCGAGGACACCGCGGTATATTACTGTGCGGATCCGTCG
GATCCTACTAAGTTTGACTACTGGGGTCAGGGAACCCTGGTCACCGTCTC
GAGC

BMS2h-725-11 (SEQ ID NO: 847)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
GCAGCCTGCGTGCCGAGGACACCGCGGTATATTACTGTGCGGATCCGTCG
GATCCTACTAAGTTTGACTACTGGGGTCAGGGAACCCTGGTCACCGTCTC
GAGC

BMS2h-725-12 (SEQ ID NO: 848)
GAGGTGCAGCTGTTGGAGTCTGGGGGTGGCTTGGTACAGCCTGGGGGGTC
CCTGCGTCTCTCCTGTGCAGCCTCCGGATTCACCTTTCCCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGCGACGATTCCAAGAACACGCTGTATCTGCAAATGA
ACAGCCTGCGTGTCGAGGACACCGCGGTATATTACTGTGCGGAACCGTCG
GATCCTACTATGTTTGTCTACTGGGGTCAGGGAACCCTTGTCACCGTCTC
GAGC

BMS2h-725-13 (SEQ ID NO: 849)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGCTGGGTCCGCCAGGCTCCAGGGAAGGGTCTGGAGTGGGTCTCTCTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACCGTCG
GATCCTACTATGTTTGTCTACTGGGGTCAGGGAACCCTGGTCACCGTCTC
GAGC

BMS2h-725-14 (SEQ ID NO: 850)
GAGGTGCAGCTGTTGGAGTCTGGGGGAGGCTTGGTACAGCCTGGGGGGTC
CCTGCGTCTCTCCTGTGCAGCATCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGTGACAATTCCAAGAACACGCTGTATCTGCAAATGA
ACAGCCTGCGTGCCGAGGACACCGCGGTATATTACTGTGCGGATCCGTCA
GATCCTACTATGTTTGACTACTGGGGTCAGGGAACCCTGGTCACCGTCTC
GAGC

BMS2h-725-15 (SEQ ID NO: 851)
GAGGTGCAGCTGTTGGAGTCTGGGGGGGGCATGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
ACAGCATGCGTGCCGAGGACACCGCGGTATATTACTGTGCGGATCCGTCG
GATCCTACTAAGTTTGACTACTGGGGTCAGGGAACCCTGGTCACCGTCTC
GAGC

BMS2h-725-16 (SEQ ID NO: 852)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCACACTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACCGTCG
GATCCTACTATGTTTGACTACTGGGGTCAGGGAACCCTGGTCACCGTCTC
GAGC

BMS2h-725-17 (SEQ ID NO: 853)
GAGGTGCAGCTGTTGGAGTCTGGGGGAGGCTTGGTGCAGCCTGGGGGGTC
CCTGCGTCTCTCCTGTGCAGCCTCCGGATTCACCTTTACGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGCGACAATTCCAAGAACACACTGTATCTGCAAATGA
ACAGCCTGCGTGCCGAGGACACCGCGGTATATTACTGCGCGGAACCGTCG
GATCCTACTAAGTTAGACTACTGGGGTCAGGGAACCCTGGTCACCGTCTC
GAGC

BMS2h-725-18 (SEQ ID NO: 854)
GAGGTGCAGCTGTCGGAGTCTGGGGGAGGCTTGGTACAGCCTGGGGGGTC
CCTGCGTCTCACCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGATCCGTCG
GATCCTACTAAGTTTGTCTACTGGGGTCAGGGAACCCTGGTCACCGTCTC
GAGC

BMS2h-725-19 (SEQ ID NO: 855)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCAGATCCGTCG
GATCCTACTAAGTTTGTCTACTGGGGTCAGGGAACCCTGGTCACCGTCTC
GAGC

BMS2h-725-2 (SEQ ID NO: 856)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGTTCTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGCGCGGAACCGTCG
GATCCTACTAAGTTTGTCTACTGGGGTCAGGGAACCCCGGTCACCGTCTC
GAGC

BMS2h-725-3 (SEQ ID NO: 857)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCGCTT
ATTGGGGATCGTGGTTCTTGGACATACTACGCAGACTCCGTGAAGGGCCG
GTTCACCATCTCCCGCGACAATTCCAGGAACATGCTGTATCTGCAAATGA
AAAGCCTGCGTGCCGAGGACACCGCGGTATATTACTGCGCGGATCCGTCG
GATCCTACTAAGTTTGTCTACTGGGGTCAAGGAACCCAGGTCACCGTCTC
GAGC

BMS2h-725-4 (SEQ ID NO: 858)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATTCTTCCGCGACAATTCCAAGAACACGCTGTATCTGCAAATGA
ACAGCCTGCGTGCCGAGGACACCGCGGTATATTACTGTGCGGATCCGTCG
GATCCTACTAAGTTTGTCTACTGGGGTCAGGGAACCCTGGTCACCGTCTC
GAGC

BMS2h-725-5 (SEQ ID NO: 859)
GAGGTGCAGCTGTTGGAGTCTGGGGGAGGCTTGTTACAGCCTGGGGGGTC
CCTGCGTCTCTCCTGTGCAGCCTCCGGATTCACCTTTTCGGATTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACCGTCG
GATCCTACTAAGTTCGACTACTGGGGTCGGGGAACCCTGGTCACCGTCTC
GAGC

TABLE 2-continued

Human Anti-CD40L VH Domain Encoding Nucleotide Sequences

BMS2h-725-6 (SEQ ID NO: 860)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCATCTCACGCGACAATTCCAAGAACACGCTGTATCTGCAAATGA
ACAGCCTGCGTGCCGAGGACACCGCGGTATATTACTGTGCGGAACCGTCC
GATCCTACTAAGTTTGTCTACTGGGGTCAGGGAACCCTGGTCACCGTCTC
GAGC

BMS2h-725-7 (SEQ ID NO: 861)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTACTTGGACATATTACGCAGACCCCGTGAAGGGCCG
GTTCACCATCTCCCGCGACAATTCCAAGAACACACTGTATCTGCAAATGA
ACAGCCTGCGTGCCGAGGACACTGCGGTATATTATTGTGCGGATCCGTCG
GATCCTACTAAGTTTGACTACTGGGGTCAGGGAACCCTGGTCACCGTCTC
GAGC

BMS2h-725-8 (SEQ ID NO: 862)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGAAGGGTCTGGAGTGGGTCTCACTT
ATTGGGGATCGTGGTTCTTGGACATACTACGCAGACTCCGTGAAGGGCCG
GTTCACCGTCTCCCGCGACAATTCCAAGAACACGCTGTATCTGCAAATGA
ACAGCCTGCGTGCCGAGGACACCGCGGTATATTACTGTGCGGAACCGTCG
GATCCTACTAAGTTTGACTACTGGGGTCAGGGAACCCTGGTCACCGTCTC
GAGC

BMS2h-725-9 (SEQ ID NO: 863)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCTTATACTA
TGGGTTGGGTCCGCCAGGCTCCAGGGATGGGTCTGGAGTGGGTCTCACTT
ATTGGGGATCGTGGTTCTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACCGTCG
GATCCTACTAAGTTTGACTACTGGGGTCAGGGAACCCTGGTCACCGTCTC
GAGC

BMS2h-726 (SEQ ID NO: 864)
GAGGTGCAGCTGTTGGAGTCTGGGGGAGGCTTGGTACAGCCCGGGGGGTC
CCTGCGTCTCTCCTGTGCAGCCTCCGGATTCACCTTTGATAATTATAAGA
TGTATTGGGTCCGCCAGGCTCCAGGGAAGGGTCTGGAGTGGGTCTCAAGT
ATTTCGGAGATAGGTAATCTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATAGCTCTG
ACGCGTTTTGACTACTGGGGTCAGGGAACCCTGGTCACCGTCTCGAGC

BMS2h-727 (SEQ ID NO: 865)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGAGTTATCGTA
TGTATTGGGTCCGCCAGGCTCCAGGGAAGGGTCTGGAGTGGGTCTCATAT
ATTGATCCGCCGGGTAGTCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAAGTTTG
AATTTGTCGTTTCCTTATATTAATTTTGACTACTGGGGTCAGGGAACCCT
GGTCACCGTCTCGAGC

BMS2h-728 (SEQ ID NO: 866)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCGGTATGAGA
TGCTGTGGGTCCGCCAGGCTCCAGGGAAGGGTCTGGAGTGGGTCTCACGT
ATTTCTCATTCGGGTCGGACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGCAATTGGAT
GGTCCGTTTGACTACTGGGGTCAGGGAACCCTGGTCACCGTCTCGAGC

BMS2h-729 (SEQ ID NO: 867)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGAGGTATTATA
TGGATTGGGTCCGCCAGGCTCCAGGGAAGGGTCTAGAGTGGGTCTCAAGG
ATTAATCATAATGGTTCTGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAATGCCG
CAGGGTACTTCTGATTGGTATTATTTTGACTACTGGGGTCAGGGAACCCT
GGTCACCGTCTCGAGC

BMS2h-73 (SEQ ID NO: 868)
GAGGTGCAGCTGTTGGAGTCTGGGGGAGGCTTGGTACAGCCTGGGGGGTC
CCTGCGTCTCTCCTGTGCAGCCTCCGGATTCACCTTTTCTAAGTATGATA
TGTCTTGGGTCCGCCAGGCTCCAGGGAAGGGTCTAGAGTGGGTCTCAACT
ATTCTGGAGGATGGTCTGACTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGGGG
CGTTTGTTTGACTACTGGGGTCAGGGAACCCTGGTCACCGTCTCGAGC

BMS2h-74 (SEQ ID NO: 869)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGATTATCCTA
TGACGTGGGTCCGCCAGGCTCCAGGGAAGGGTCTGGAGTGGGTCTCAACT
ATTCTGTCTCCGGGTACGGAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCTGAG
AAGGATTTTGACTACTGGGGTCAGGGAACCCTGGTCACCGTCTCGAGC

BMS2h-741 (SEQ ID NO: 870)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGGTGGTGAGA
TGGGTTGGGTCCGCCAGGCTCCAGGGAAGGGTCTAGAGTGGGTCTCAATG
ATTCCGATGGATGGTAGTGCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGGGT
GAGGTGTTTGACTACTGGGGTCAGGGAACCCTGGTCACCGTCTCGAGC

BMS2h-742 (SEQ ID NO: 871)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGGAGTATCATA
TGAAGTGGGCCCGCCAGGCTCCAGGGAAGGGTCTAGAGTGGGTCTCAGGG
ATTAGTAGGGATGGTATGAATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATACAGCTT
GCTTTGTTTGACTACTGGGGTCAGGGAACCCTGGTCACCGTCTCGAGC

BMS2h-743 (SEQ ID NO: 872)
GAGGTGCAGCTGTTGGAGTCTGGGGGAGGCTTGGTACAGCCTGGGGGGTC
CCTGCGTCTCTCCTGTGCAGCCTCCGGATTCACCTTTCGTGATTATGAGA
TGCTTTGGGCCCGCCAGGCTCCAGGGAAGGGTCTAGAGTGGGTCTCAGGT
ATTCTTCCGTCGGGTGGGCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCTGGT
TCGGGGAATGGGCCTATTCTTTTTGACTACTGGGGTCAGGGAACCCTGGT
CACCGTCTCGAGC

BMS2h-744 (SEQ ID NO: 873)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGGAGCATGATA
TGTTTTGGGTCCGCCAGGCTCCAGGGAAGGGTCTAGAGTGGGTCTCAGGG
ATTGGGGCTGAGGGTGTTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACCGACG
ATGTCTAATGGTTCTCAGTCGCGTTTTGACTACTGGGGTCAGGGAACCCT
GGTCACCGTCTCGAGC

BMS2h-745 (SEQ ID NO: 874)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTATTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-745-1 (SEQ ID NO: 875)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTTTCAGGT
ATTACTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAATTCGT

TABLE 2-continued

Human Anti-CD40L VH Domain Encoding Nucleotide Sequences

AATCTGCATTGGGATGTGGGGAGGCAGTTTGACTACTGGGGTCAGGGAAC
CCTGGTCACCGTCTCGAGC

BMS2h-745-10 (SEQ ID NO: 876)
GAGGTGCAGCTGTTGGAGTCTGGGGGAGGCTTGGTACAGCCTGGGGGGTC
CCTTCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTACTGAGGATGGTAATCGTACATACTACGCAGACTCCGTGAAGGGCCG
GTTCACCATCTCCCGCGACAATTCCAAGAACACGCTGTATCTGCAAATGA
ACAACCTGCGTGCCGAAGACACCGCGGTATATTACTGTGCGAAAATTCGT
AATCTGCATTGGGATGTGGGGAGGCAGTTTGACTACTGGGGTCAGGGAAC
CCTGGTCACCCGTCTCGAGC

BMS2h-745-11 (SEQ ID NO: 877)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGATCCGCCAGGCTCCAGGGAAGGGTCTAGAGTGGGTCTCAGGT
ATTACTGAGGATGGTAATCGTACATACTACGCAGACTCCGTGAAGGGCCG
GTTCACCATCTCCCGCGACAATTTCAAGAACACGCTGTATCTGCAGATGA
ACAGCCTGCGTGCCGAGGACACCGCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-745-12 (SEQ ID NO: 878)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTACTGAGGATGGTAATCGTACATACTACGCAGATTCCGTGAAGGGCCG
GTTCACCATCTCCCGCGACAATTCCATGAACACGCTGTATCTGCAAATGA
ACAGCCTGCGTGCCGAGGACACCGCGGTATATTACTGTGCGAAAATTCGT
AATCTGCATTGGGATGTGGGGAGGCAGTTTGTCTACTGGGGTCAGGGAAC
CCTGGTCACCGTCTCGAGC

BMS2h-745-13 (SEQ ID NO: 879)
GAGGTGCAGCTGTTGGAGTCTGGGGGAGGCTTGGTACAGCCTGGGGGGTC
CTTGCGTCTCTCCTGTGCAGCCTCCGGATTCACCTTTGATAACACTGAGA
TGGCTTGGATCCGCCAGGCTCCAGGGAAGGGTCTAGAGTGGGTCTCAGGT
ATTATTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-745-14 (SEQ ID NO: 880)
GAGGTGCAGCTGTTGGAGTCTGGGGGAGGCTTGGTACAGCCTGGGGGGTC
CCTGCGTCTCTCCTGTGCAGCCTCCGGGTTCACCTTTGATAATACTGAGA
TGGCTTGGATCCGCCAGGCTCCAGGGAAGGGTCTAGAGTGGGTCTCAGGT
ATTACTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-745-15 (SEQ ID NO: 881)
GAGGTGCAGCTGTTGGAGTCTGGGGGAGGCTTGGTACAGCCAGGGGGGTC
CCTGCGTCTCTCCTGTGCAGCCTCTGGATTCACCTTTGATAATACTGAGA
TGGCTTGGATCCGCCAGGCTCCAGGGAAGGGTCTAGAGTGGGTCTCAGGT
ATTACTGAGGATGGTAATCGTACATACTACGCAGACTCCGTGAAGGGCCG
GTTCACCATCTCCCGCGACAATTCCAAGAACGCGCTGTATCTGCAAATGA
ACAGCCTGCGTGCCGAGGACACCGCGGTATATTACTGTGCGAAAATTCGT
AATCTGCATTGGGATGTGGGGAGGCAGTTTGACTACTGGGGTCTGGGAAC
CCTGGTCACCGTCTCGAGC

BMS2h-745-16 (SEQ ID NO: 882)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTACTGAGGATGGTAATCGTACATACTACGCAGACTCCGTGAAGGGCCG
GTTCACCATCTCCCGCGACAATACCAAGAACACGCTGTATCTGCAAATGA
ACAGCCTGCGTGCCGAGGACACCGCGGTATATTACTGTGCGAAAATTCGT
AATCTGCATTGGGATGTGGGGAGGCAGTTTGTCTACTGGGGTCAGGGAAC
CCTGGTCACCGTCTCGAGC

BMS2h-745-17 (SEQ ID NO: 883)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCCTTGGATCCGCCAGGCTCCAGGGAAGGGTCTAGAGTGGGTCTCAGGT
ATTATTGAGGATGGTAATCGTACATACTACGCAGACTCCGTGAAGGGCCG
GTTCACCATCTCCCGCGACAATTCCAAGAACAGGCTGTATCTGCAAATGA
ACAGCCTGCGTGCCGAGGACACCGCGGTATATTACTGTGCGAAAATTCGT
AATCTGCATTGGGATGTGGGGAGGCAGTTTGACTACTGGGGTCAGGGCAC
CCTGGTCACCGTTTCGAGC

BMS2h-745-18 (SEQ ID NO: 884)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTACTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATCACTGTGCGAAAATTCGT
AATCTGCATTGGGATGTGGGGAGGCAGTTTGACTACTGGGGTCAGGGAAC
CCTCGTCACCGTCTCGAGC

BMS2h-745-19 (SEQ ID NO: 885)
GAGGTGCAGCTGTGTTGGAGTCTGGGGGAGGCTTGGTACAGCCTGAGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTATTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-745-2 (SEQ ID NO: 886)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTAGTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCAGAGGACTCCGCGGTATATTACTGTGCGAAAATTCGT
AATCTGCATTGGGATGTGGGGAGGCAGTTTGTCTACTGGGGTCAGGGAAC
CCTGGTCACCGTCTCGAGC

BMS2h-745-3 (SEQ ID NO: 887)
GAGGTGCAGCTGTTGGAGTCTGGGGGAGGCTTGGTAGAGCCTGGGGGGTC
CCTGCGTCTCTCCTGTGCAGCCTCCGGATTCACCTTTGATAATACTGAGA
TGGCTTGGGTCCGCCAGGCTCCTGGAAGGGTCTCGAGTGGGTCTCAGGT
ATTACTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-745-4 (SEQ ID NO: 888)
GAGGTGCAGCTGTTGGAGTCTGGGGGAGGCCTGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTAGTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATCACTGTGCGAAAATTCGT
AATCTGCATTGGGATGTGGGGAGGCAGTTTGACTACTGGGGTCAGGGAAC
CCTGGTCACCGTCTCGAGC

BMS2h-745-5 (SEQ ID NO: 889)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTACTGAGGATGGTAATCGTACATACTACGCTGACTCCGTGAAGGGCCG
GTTCATCATCTCCCGCGACAATTCCAAGAACACGCTGAATCTGCAAATGA
ACAGCCTGCGTGCCGAGGACACCGCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-745-6 (SEQ ID NO: 890)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGATCCGCCAGGCTCCAGGGAGGGGTCTAGAGTGGGTCTCAGGT
GTTACTGAGGATGGTAATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAATTCGT
AATCTGCATTGGGATGTGGGGAGGCAATTTGACTACTGGGGTCAGGGAAC
CCTGGTCACCGTCTCGAGC

TABLE 2-continued

Human Anti-CD40L VH Domain Encoding Nucleotide Sequences

BMS2h-745-7 (SEQ ID NO: 891)
GAGGTGCAGCTGTTGGAGTCAGGGGGAGGCTTGGTACAGCCTGGGGGGTC
CCTGCGTCTCTCCTGTGAAGCCTCCGGATTCACCTTTGATAATACTGAGA
TGGCTTGGATCCGCCAGGCTCCAGGGAAGGGTCTAGAGTGGGTCTCAGGT
ATTATTGAGGATGGTAATCGTACATACTACGCAGACTCCGTGAAGGGCCG
GTTCACCATCTCCCGCGACAATACCAAGAACACGCTGTATCTGCAAATGA
ACAGCCTGCGTGCCGAGGACACCGCGGTATATTATTGTGCGAAAATTCGT
AATCTGCATTGGGATGTGGGGAGGCAGTTTGACTACTGGGGTCAGGGAAC
CCTGGTCACCGTCTCGAGT

BMS2h-745-8 (SEQ ID NO: 892)
GAGGTGCAGCTGTTGGAGTCTGGGGGAGGCTTGGTACAGCCTGGGGGGTC
CCTGCGTCTCTCCTGTGCAGCCTCCGGATTCACCTTTGATAATACTGAGA
TGGCTTGGATCCGCCAGGCTCCAGGGAAGGGTCTAGAGTGGGTCTCAGGT
ATTACTGAGGATGGTGATCGTACATACTACGCAGACTCCGTGAAGGGCCG
GTTCACCATCTCCCGCGACAATTCCAAGAGCTCGCTGTATCTGCAAATGA
ACAGCCTGCGTGCCGAGGACACCGCGGTATATTACTGTGCGAAAATTCGT
AATCTGCATTGGGATGTGGGGAGGCAGTTTGACTACTGGGGTCAGGGAAC
CCTGGTCACCGTCTCCAGC

BMS2h-745-9 (SEQ ID NO: 893)
GAGGTGCAGCTGTTGGAGTCTGGGGGAGGCTCGGTACAGCCTGGGGGGTC
CCTGCGTCTCTCCTGTGCAGCCTCCGGATTCACCTTTGATAATACTGAGA
TGGCTTGGGTCCGCCAGGCTCCAGGGAAGGGTCTAGAGTGGGTCTCAGGT
ATTACTGAGGATGGTAATCGTACATACTACGCAGACTCCGTGAAGGGCCG
GTTCACCATCTCCCGCGACAATTCCAAGAACACTCTGTATCTGCAAATGA
ACAGCCTGCGTGCCGAGGACACCGCGGTATATTACTGTGCGAAAATTCGT
AATCTGCATTGGGATGTGGGGAGGCAGTTTGTCTACTGGGGTCAGGGAAC
CCTGGTCACCGTCTCGAGC

BMS2h-746 (SEQ ID NO: 894)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGTCGGCTGAGA
TGGGGTGGGTCCGCCAGGCTCCAGGGAAGGGTCTAGAGTGGGTCTCAGGT
ATTTCGAGGCCTGGTCAGGTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-747 (SEQ ID NO: 895)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGATGGTACTA
TGGGGTGGGCCCGCCAGGCTCCAGGGAAGGGTCTAGAGTGGGTCTCACTT
ATTTTGCCGTCGGGTAGTCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACATTCG
CTGACTAATCGTCCGTTTGACTACTGGGGTCAGGGAACCCTGGTCACCGT
CTCGAGC

BMS2h-748 (SEQ ID NO: 896)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAAGTATGATA
TGCGGTGGGCCCGCCAGGCTCCAGGGAAGGGTCTAGAGTGGGTCTCAGAT
ATTGATGCTGTTGGTACTCGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATACCGGGG
GGGACGTTTGACTACTGGGGTCAGGGAACCCTGGTCACCGTCTCGAGC

BMS2h-749 (SEQ ID NO: 897)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGATGTATGGTA
TGATGTGGGCCCGCCAGGCTCCAGGGAAGGGTCTAGAGTGGGTCTCATCT
ATTGAGGGTGCGGTCATGCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACTGCGGTATATTACTGTGCGATAGTGCTT
GGTATGTTTGACTACTGGGGTCAGGGAACCCTGGTCACCGTCTCGAGC

BMS2h-75 (SEQ ID NO: 898)
GAGGTGCAGCTGTTGGAGTCTGGGGGAGGCTTGGTACAGCCTGGGGGGTC
CCTGCGTCTCTCCTGTGCAGCCTCGGATTCACCTTTTTGCAGTATCCGA
TGGGTTGGGTCCGCCAGGCTCCAGGGAAGGGTCTAGAGTGGGTCTCAACT
ATTTCTCCTGTTGGTTTGACTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATTGTTT
GAGGGGTCGAGGATTCAGCGTGATGTGGGTTTTGACTACTGGGGTCAGGG
AACCCTGGTCACCGTCTCGAGC

BMS2h-750 (SEQ ID NO: 899)
GAGGTGCAGCTGTTGGAGTCTGGGGGGAGGCTTGGTACAGCCTGGGGGGTC
CCTGCGTCTCTCCTGTGCAGCCTCCGGATTCACCTTTGAGAAGTATCAGA
TGGGTTGGGCCCGCCAGGCTCCAGGGAAGGGTCTAGAGTGGGTCTCATCG
ATTCGGGGTCTGGTCTTGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTGCAT
ACTACGCTGCATACGGAGGTGATTGGGTTTGACTACTGGGGTCAGGGAAC
CCTGGTCACCGTCTCGAGC

BMS2h-751 (SEQ ID NO: 900)
GAGGTGCAGCTGTTGGAGTCTGGGGGAGGCTTGGTACAGCCGGGGGGGTC
CCTGCGTCTCTCCTGTGCAGCCTCCGGATTCACCTTTAGTCAGTATACGA
TGTATTGGGCCCGCCAGGCTCCAGGGAAGGGTCTAGAGTGGGTCTCAGAG
ATTTCTATAGTGGTTCTAATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATCGGGG
CTGCATTTTGACTACTGGGGTCAGGGAACCCTGGTCACCGTCTCGAGC

BMS2h-752 (SEQ ID NO: 901)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGATTATGCGA
TGGGTTGGGTCCGCCAGGCTCCAGGGAAGGGTCTGGAGTGGGTCTCACGT
ATTGGTGTGGAGGGTGGGGATACATACTACGCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTGTTG
CGGCTTTATCGTCTGGGGTTTGACTACTGGGGTCAGGGAACCCTGGTCAC
CGTCTCGAGC

BMS2h-753 (SEQ ID NO: 902)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTAAGTATGATA
TGACGTGGGTCCGCCAGGCTCCAGGGAAGGGTCTAGAGTGGGTCTCAAAG
ATTAATTCTGATGGTGGTCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGTTG
CATGGTAGGGGGTTTGTTATTTTTGACTACTGGGGTCAGGGAACCCTGGT
CACCGTCTCGAGC

BMS2h-754 (SEQ ID NO: 903)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGCGGTATGATA
TGGTGTGGGTCCGCCAGGCTCCAGGGAAGGGTCTAGAGTGGGTCTCACGG
ATTAATTCTATGGGTCTGGCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGATTAT
TCGGTTGCGCCGCATGGGTATCCTTTGGGTTTTGACTACTGGGGTCAGGG
AACCCTGGTCACCGTCTCGAGC

BMS2h-755 (SEQ ID NO: 904)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGGATTATTCGA
TGATGTGGGTCCGCCAGGCTCCAGGGAAGGGTCTAGAGTGGGTCTCAACG
ATTACTGATAATGGTACGTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACATATG
TCGCTTGCTACTTATCTGCAGTTTTTTGACTACTGGGGTCAGGGAACCCT
GGTCACCGTCTCGAGC

BMS2h-756 (SEQ ID NO: 905)
GAGGTGCAGCTGTTGGAGTCTGGGGGAGGCTTGGTACAGCCTGGGGGGTC
CCTGCGTCTCTCCTGTGCAGCCTCCGGATTCACCTTTATGGAGTATGATA
TGCTTTGGGTCCGCCAGGCTCCAGGGAAGGCTCTAGAGTGGGTCTCACGT
ATTTCGTCGGATGGTCTTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGGTG
AGTGCGCTTGCTCCTTTTGATATTGGTTTTGACTACTGGGGTCAGGGAAC
CCTGGTCACCGTCTCGAGC

BMS2h-757 (SEQ ID NO: 906)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGGAGTATAATA
TGGCTTGGGTCCGCCAGGCTCCAGGGAAGGGTCTGGAGTGGGTCTCAAGT
ATTAATTTTGCTGGTCGGACGACATACTACGCAGACTCCGTGAAGGGCCG

TABLE 2-continued

Human Anti-CD40L VH Domain Encoding
Nucleotide Sequences

GTTCACCATCTCCCGCGACAATTCCAAGAACACGCTGTATCTGCAAATGA
ACAGCCTGCGTGCCGAGGACACCGCGGTATATTACTGTGCGAAACTGTCT
CTTCCTTTTGGATATTTTTTCTTTTGACTACTGGGGTCAGGGAACCCTGGT
CACCGTCTCGAGC

BMS2h-758 (SEQ ID NO: 907)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTGATTATGGTA
TGAATTGGGTCCGCCAGGCTCCAGGGAAGGGTCTGGAGTGGGTCTCACAT
ATTTCTTCTAATGGTCGTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTAGT
GGTTATTTTGACTACTGGGGTCAGGGAACCCTGGTCACCGTCTCGAGC

BMS2h-758-1 (SEQ ID NO: 908)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTGATTATGGTA
TGAATTGGGTCCGCCAGGCTCCAGGGAAGGGTCTGGAGTGGGTCTCACAT
ATTTCTTCTAATGGTCGTTTTACATACTACGCAGACTCCGTGAAGGGCCG
GTTCACCATCTCCCGCGACAATTCCAAGAACATGCTGTATCTGCAATGA
ACAGCCTGCGTGCCGAGGACACCGCGGTATATTACTGTGCGAAACTAGT
GGTTATTATGAATACTGGGGTCAGGGAACCCTGGTCACCGTCTCGAGC

BMS2h-758-2 (SEQ ID NO: 909)
GAGGTGCAGCTGTTGGAGTCTGGGGGAGGCTTGGTACAGCCTGGGGGGTC
CCTGCGCCTCTCCTGTGCAGCCTCCGGATTCACCTTTGGTGATTATGGTA
TGAATTGGGTCCGCCAGGCTCCAGGGAAGGGTCTGGAGTGGGTCTCACAT
ATTTCTTCTAATGGTCGTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAACTAGT
GGTTATTTTGAATACTGGGGTCAGGGAACCCTGGTCACCGTCTCGAGC

BMS2h-758-3 (SEQ ID NO: 910)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTGATTATGGTA
TGAATTGGGTCCGCCAGGCCCCAGGGAAGGGTCTGGAGTGGGTCTCACAT
ATTTCTTCTAATGGTCGTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAACTAGT
AGTTATTTTGAATACTGGGGTCAGGGAACCCTGGTCACCGTCTCGAGC

BMS2h-758-4 (SEQ ID NO: 911)
GAGGTGCAGCTGTTGGAGTCTGGGGGAGGCTTGGTACAGCCTGGGGGGTC
CCTGCGTCTCTCCTGTGCAGCCTCCGGGTTCACCTTTGGTGATTATGGTA
TGAATTGGGTCCGCCAGGCTCCAGGGAAGGGTCTGGAGTGGGTCTCACAT
ATTTCTTCTAATGGTCGTTTTACATACTACGCAGACTCCGTGAAGGGCCG
GTTCACCATCTCCCGCGACAATTCCAAGAACACGCTGTGTTTCTGCAAATGA
ACAGCCTGCGTGCCGAGGACACCGCGGTATATTACTGTGCGAAACTAGT
GGTTATTATGAGTACTGGGGTCATGGAACCCTGGTCACCGTCTCGAGC

BMS2h-758-5 (SEQ ID NO: 912)
GAGGTGCAGCTGTTGGAGTCTGGGGGAGGCTTGGTCCAGCCTGGGGGGTC
CCTGCGTCTCTCCTGTGCTGCCTCCGGATTCGCCTTTGGTGATTATGGTA
TGAATTGGGTCCGCCAGGCTCCAGGGAAGGGTCTGGAGTGGGTCTCACAT
ATTTCTTCTAATGGTCGTTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTAGT
GGTTATTTTGAATACTGGGGTCAGGGAACCCTGGTCACCGTCTCGAGC

BMS2h-758-6 (SEQ ID NO: 913)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTGATTATGGTA
TGAATTGGGTCCGCCAGGCTCCAGGGAAGGGTCTGGAGTGGGTCTCACAT
ATTTCTTCTAATGGTCGTTTTATATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTAGT
GGTTACTTTGAATACTGGGGTCAGGGAACCCTGGTCACCGTCTCGAGC

BMS2h-759 (SEQ ID NO: 914)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGGAGTATGTTA
TGGGGTGGGTCCGCCAGGCTCCAGGGAAGGGTCTAGAGTGGGTCTCAACT
ATTAATGGTTTGGGTAATGTTACATACTACGCAGACTCCGTGAAGGGCCG
GTTCACCATCTCCCGCGACAATACCAAGAACACGCTGTATCTGCAAATGA
ACAGCCTGCGTGCCGAGGAGACCGCGGTATATTACTGTGCGGATACAGCTG
CCTAATTTTGACTACTGGGGTCAGGGAACCCTGGTCACCGTCTCGAGC

BMS2h-760 (SEQ ID NO: 915)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTAATGATGGGA
TGTGGTGGGTCCGCCAGGCTCCAGGGAAGGGTCTAGAGTGGGTCTCATTT
ATTAATGTTGATGGTAGGGAGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAATGGTCT
CCTGGGCGGGTTCAGTTTGACTACTGGGGTCAGGGAACCCTGGTCACCGT
CTCGAGC

BMS2h-761 (SEQ ID NO: 916)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTGGTTGGGATA
TGGCGTGGGTCCGCCAGGCTCCAGGGAAAGGGTCTAGAGTGGGTCTCAAGT
ATTGCTCATGAGGGTGGTGAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATATGTT
CCTGGGTCTCCTCTGTTTGACTACTGGGGTCAGAGAACCCTGGTCACCGT
CTCGAGC

BMS2h-762 (SEQ ID NO: 917)
GAGGTGCAGCTGTTGGAGTCTGGGGGAGGCTTGGTACAGCCTGGGGGGTC
CCTGCGTCTCTCCTGTGCAGCCTCCGGATTCACCTTTGATCAGGGTTGGA
TGTATTGGGTCCGCCAGGCTCCAGGGAAGGGTCTAGAGTGGGTCTCAGGG
ATTGGTTCGAATGGTCCTCGGACATCCTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCGGGG
GAGTATTTTGACTACTGGGGTCAGGGAACCCTGGTCACCGTCTCGAGC

BMS2h-763 (SEQ ID NO: 918)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGCAGAGTGATA
TGTGGTGGGTCCGCCAGGCTCCAGGGAAGGGTCTAGAGTGGGTCTCAGTT
ATTGGTAATAATGGTGAGTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATAAT
TGGCTGTTGTTTGACTACTGGGGTCAGGGAACCCTGGTCACCGTCTCGAG
C

BMS2h-764 (SEQ ID NO: 919)
GAGGTGCAGCTGTTGGAGTCTGGGGGAGGCTTGGTACAGCCTGGGGGGTC
CCTGCGTCTCTCCTGTGCAGCCTCCGGATTCACCTTTGATCTTAGTACTA
TGTATTGGGTCCGCCAGGCTCCAGGGAAGGGTCTAGAGTGGGTCTCAACT
ATTGGTGGGATGGTAGTCATACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGGAAGGTACG
CAGTATTTTGACTACTGGGGTCAGGGAACCCTGGTCACCGTCTCGAGC

BMS2h-765 (SEQ ID NO: 920)
GAGGTGCAGCTGTTGGAGTCTGGGGGAGGCTTGGTACAGCCTGGGGGGTC
CCTGCGTCTCTCCTGTGCAGCCTCCGGATTCACCTTTTCGGCGTATACGA
TGGAGTGGGTCCGCCAGGCTCCAGGGAAGGGTCTAGAGTGGGTCTCAAGT
ATTGGGGTTACGGGTTATGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTGGT
CAGGGTTTTGACTACTGGGGTCAGGGAACCCTGGTCACCGTCTCGAGC

BMS2h-766 (SEQ ID NO: 921)
GAGGTGCAGCTGTTGGAGTCTGGGGGAGGCTTGGTACAGCCTGGGGGGTC
CCTGCGTCTCTCCTGTGCAGCCTCCGGATTCACCTTTGGGGATTATGGGA
TGTCTTGGGTCCGCCAGGCTCCAGGGAAGGGTCTAGAGTGGGTCTCATAT
ATTGATCCTCTGGGTCGTCTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGATTTG
TCGTCGCTGCAGTATGGGGTGTCGCCTAATTTTGACTACTGGGGTCAGGG
AACCCTGGTCACCGTCTCGAGC

BMS2h-767 (SEQ ID NO: 922)
GAGGTGCAGCTGTTGGAGTCTGGGGGAGGCTTGGTACAGCCTGGGGGGTC
CCTGCGTCTCTCCTGTGCAGCCTCCGGATTCACCTTTTTTCATTATTCTA
TGAGTTGGGTCCGCCAGGCTCCAGGGAAGGGTCTAGAGTGGGTCTCATCT
ATTGGTCCGGTTGGTCGGGAGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAATGATT
CAGTCGCCGTTGTTTAAGGATTTTGACTACTGGGGTCAGGGAACCCTGGT
CACCGTCTCGAGC

TABLE 2-continued

Human Anti-CD40L VH Domain Encoding Nucleotide Sequences

BMS2h-768 (SEQ ID NO: 923)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGTGGTATGATA
TGTATTGGGTCCGCCAGGCTCCAGGGAAGGGTCTAGAGTGGGTCTCACGT
ATTGATAGTGGGGGTAATCAGACATACTACGCAGACTCCGTGAAGGGCCG
GTTCACCATCTCCCGCGACAATTCCAAGAACACGCTGTATCTGCAAATGA
ATAGCCTGCGTGCCGAGGACACCGCGGTATATTACTGTGCGGAAGCGTCG
CTTTTGGAAGTGGAGGTTGTTTGACTACTGGGGTCAGGGAACCCTGGTCAC
CGTCTCGAGC

BMS2h-77 (SEQ ID NO: 924)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGAGTATGTA
TGGCGTGGGTCCGCCAGGCTCCAGGGAAGGGTCTAGAGTGGGTCTCAACT
ATTTCTCCGCTGGGTATTTCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACATGCT
ACGTCTCAGGAGTCTTTGCGGTCTTTTGACTACTGGGGTCAGGGAACCCT
GGTCACCGTCTCGAGC

BMS2h-770 (SEQ ID NO: 925)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAAGTATGAGA
TGATGTGGGTCCGCCAGGCTCCAGGGAAGGGTCTAGAGTGGGTCTCAGCT
ATTAGTGGTAGTGGTGGTAGCACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGTCCT
CTGCCTGATGCGTTTTGGACTAGGGGTTTTGACTACTGGGGTCAGGGAAC
CCTGGTCACCGTCTCGAGC

BMS2h-771 (SEQ ID NO: 926)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTACTTATTCTA
TGGCGTGGGTCCGCCAGGCTCCAGGGAAGGGTCTAGAGTGGGTCTCAACT
ATTGATCGGCATGGTTTGGCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAACTCCT
GGTTCTTCTTGCAGACTGTTTTTGGCTACTGGGGTCAGGGAACCCTGGT
CACCGTCTCGAGC

BMS2h-772 (SEQ ID NO: 927)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGTCGTATCCTA
TGGGTTGGGTCCGCCAGGCTCCAGGGAAGGGTCTAGAGTGGGTCTCAAGT
ATTGATCATCATGGTCATTCGACATACTACGCAGACTCCGCGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTGCTT
AGGGTTTCGATGATTTTTGGTTTTGACTACTGGGGTCAGGGAACCCTGGT
CACCGTCTCGAGC

BMS2h-773 (SEQ ID NO: 928)
GAGGTGCAGCTGTTGGAGTCTGGGGGAGGCTTGGTACAGCCTGGGGGGTC
CCTGCGTCTCTCCTGTGCAGCCTCCGGATTCACCTTTGTGCAGTATGGGA
TGAGTTGGGTCCGCCAGGCTCCAGGGAAGGGTCTAGAGTGGGTCTCATGG
ATTAGTAGTAGTGGTACGTACATACTACGCAGACTCCGTGAAGGGCCG
GTTCACCATCTCCCGCGACAATTCCAAGAACACGCTGTATCTGCAAATGA
ACAGCCTACGTGCCGAGGACACCGCGGTATATTACTGTGCGAAACGTCT
AGGATGTTTGACTACTGGGGTCAGGGAACCCTGGTCACCGTCTCGAGC

BMS2h-774 (SEQ ID NO: 929)
GAGGTGCAGCTGTTGGAGTCTGGGGGAGGCTTGGTACAGCCTGGGGGGTC
CCTGCGTCTCTCCTGTGCGGCCTCCGGATTCACCTTTCGGGAGTATGATA
TGGGTTGGGTCCGCCAGGCTCCAGGGAAGGGTCTAGAGTGGGTCTCACTT
ATTTCGCCTCCTGGTCGTACTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGTTGTG
ATTCGGGTTATACGAATAGGTTTGACTACTGGGGTCAGGGAACCCTGGT
CACCGTCTCGAGC

BMS2h-775 (SEQ ID NO: 930)
GAGGTGCAGCTGTTGGAGTCTGGGGGAGGCTTGGTACAGCCTGGGGGGTC
CCTGCGTCTCTCCTGTGCAGCCTCCGGATTCACCTTTCCTAATTACGGGA
TGTTGTGGGTCCGCCAGGCTCCAGGGAAGGGTCTAGAGTGGGTCTCATCG
ATTAATTCTTCGGGTATGGAGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATTTTTT
CGTCTGAATGATCATAATTCTGTGTTTGGTTTTGACTACTGGGGTCAGGG
AACCCTGGTCACCGTCTCGAGC

BMS2h-776 (SEQ ID NO: 931)
GAGGTGCAGCTGTTGGAGTCTGGGGGAGGCTTGGTACAGCCTGGGGGGTC
CCTGCGTCTCTCCTGTGCAGCCTCCGGATTCACCTTTAAGGATTATAAGA
TGATGTGGATCCGCCAGGCTCCAGGGAAGGGTCTAGAGTGGGTCTCATCG
ATTGTTGGGTCTGGTTCGATGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGGGCCT
GGTTATTTTGACTACTGGGGTCAGGGAACCCTGGTCACCGTCTCGAGC

BMS2h-777 (SEQ ID NO: 932)
GAGGTGCAGCTGTTGGAGTCTGGGGGAGGCTTGGTACAGCCTGGGGGGTC
CCTGCGTCTCTCCTGTGCAGCCTCCGGATTCACCTTTCATAATTATGCTA
TGGGGTGGGTCCGCCAGGGCTCCAGGGAAGGGTCTAGAGTGGGTCTCAAGT
ATTGATGAGCATGGTACTATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATAGT
CTGGATCGGGTTTGGATTTTTGACTACTGGGGTCAGGGAACCCTGGTCAC
CGTCTCGAGC

BMS2h-778 (SEQ ID NO: 933)
GAGGTGCAGCTGTTGGAGTCTGGGGGGGGCTTGGTACAGCCTGGGGGGTC
CCTGCGTCTCTCCTGTGCAGCCTCCGGATTCACCTTTGCTGATTATCCGA
TGACTTGGGTCCGCCAGGCTCCAGGGAAGGGTCTAGAGTGGGTCTCAAGT
ATTTATTCTGCGGGTTCTCCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAACTTTAT
CATCGGGAGCCGATTCTTTTTGGGTTTGACTACTGGGGTCAGGGAACCCT
GGTCACCGTCTCGAGC

BMS2h-78 (SEQ ID NO: 934)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGAGGTATCAGA
TGGCGTGGGTCCGCCAGGCTCCGGGGAAGGGTCTAGAGTGGGTCTCAACG
ATTAGTTCTGATGGTGGGGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGGT
CATCGGTTTGACTACTGGGGTCAGGGAACCCTGGTCACCGTCTCGAGC

BMS2h-780 (SEQ ID NO: 935)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTTCTTATACTA
TGATGTGGGTCCGCCAGGCTCCAGGGAAGGGTCTAGAGTGGGTCTCAGAG
ATTGATCGGACGGGTGAGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAACCTGGG
TTTGCTTCTCTTCCTTTTGACTACTGGGGTCAGGGAACCCTGGTCACCGT
CTCGAGC

BMS2h-781 (SEQ ID NO: 936)
GAGGTGCAGCTGTTGGAGTCTGGGGGAGGCTTGGTACAGCCTGGGGGGTC
CCTGCGTCTCTCCTGTGCAGCCTCCGGATTCACCTTTACGGATTATACTA
TGTATTGGGTCCGCCAGGCTCCAGGGAAGGGTCTAGAGTGGGTCTCAAAG
ATTTCTCCGAGTGGTCGTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGATCCG
TTTGGGTTTGACTACTGGGGTCAGGGAACCCTGGTCACCGTCTCGAGC

BMS2h-782 (SEQ ID NO: 937)
GAGGTGCAGCTGTTGGAGTCTGGGGGAGGCTTGGTACAGCCTGGGGGGTC
CCTGCGTCTCTCCTGTGCAGCCTCCGGATTCACCTTTGATGATGCGGAGA
TGTTTTGGGTCCGCCAGGCTCCAGGGAAGGGTCTAGAGTGGGTCTCATCT
ATTGATGCTCGTGGTTTGACGACATACTACGCAGACCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGAAGCGACG
TCGGCTATGTATCCTTTTGACTACTGGGGTCAGGGAACCCTGGTCACCGT
CTCGAGC

BMS2h-783 (SEQ ID NO: 938)
GAGGTGCAGCTGTTGGAGTCTGGGGGAGGCTTGGTACAGCCTGGGGGGTC
CCTGCGTCTCTCCTGTGCAGCCTCCGGATTCACCTTTCGTGATTATGATA
TGGGTTGGGTCCGCCAGGCTCCAGGGAAGGGTCTAGAGTGGGTCTCAACT
ATTTCTCCTCTTGGTCATTTTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAATCTGGG

TABLE 2-continued

Human Anti-CD40L VH Domain Encoding Nucleotide Sequences

TTTCATGAGTATACTGAGGGGTTTGACTACTGGGGTCAGGGAACCCTGGT
CACCGTCTCGAGC

BMS2h-784 (SEQ ID NO: 939)
GAGGTGCAGCTGTTGGAGTCTGGGGGAGGCTTGGTACAGCCTGGGGGGTC
CCTGCGTCTCTCCTGTGCAGCCTCCGGATTCACCTTTGATCGTGCGGGTA
TGGGGTGGGTCCGCCAGGCTCCAGGGAAGGGTCTAGAGTGGGTCTCACTG
ATTGGGCGTGGTGGTGATATTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCCGGTATATTACTGTGCGAAAATTCGT
AATCTGCATTGGGATGTGGGGAGGCAGTTTGACTACTGGGGTCAGGGAAC
CCTGGTCACCGTCTCGAGC

BMS2h-80 (SEQ ID NO: 940)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTCGTTATCAGA
TGGCTTGGGTCCGCCAGGCTCCAGGGAAGGGTCTAGAGTGGGTCTCATCT
ATTTCTTCTGATGGTGGGGGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCGTCT
CGTCGGTTTGACTACTGGGGTCAGGGAACCCTGGTCACCGTCTCGAGC

BMS2h-81 (SEQ ID NO: 941)
GAGGTGCAGCTGTTGGAGTCTGGGGGAGGCTTGGTACAGCCTGGGGGTT
CCTGCGTCTCTCCTGTGCAGCCTCCGGATTCACCTTTGAGTTGTATCCGA
TGGCGTGGGTCCGCCAGGCTCCAGGGAAGGGTCTGGAGTGGGTCTCATCG
ATTTCTCCGGTTGGTTTTCTGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAGGGCAT
GAGGGGTCGTATACTCCGCGGTCGGCTTTTGACTACTGGGGTCAGGGAAC
CCTGGTCACCGTCTCGAGC

BMS2h-82 (SEQ ID NO: 942)
GAGGTGCAGCTGTTGGAGTCTGGGGGAGGCTTGGTACAGCCTGGGGGGTC
CCTGCGTCTCTCCTGTGCAGCCTCCGGATTCACCTTTGTGGCGTATCCTA
TGGCGTGGGTCCGCCAGGCTCCAGGGAAGGGTCTGGAGTGGGTCTCAACT
ATTGCGCCTCTGGGTGGTAATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACGTCCG
GAGGGGCTGCAGATTGATTCTCAGAATTTTGACTACTGGGGTCAGGGAAC
CCTGGTCACCGTCTCGAGC

BMS2h-83 (SEQ ID NO: 943)
GAGGTGCAGCTGTTGGAGTCTGGGGGAGGCTTGGTACAGCCTGGGGGGTC
CCTGCGTCTCTCCTGTGCAGCCTCCGGATTCACCTTTGCGTTGTATCAGA
TGGCTTGGGTCCGCCAGGCTCCAGGGAAGGGTCTAGAGTGGGTCTCATCG
ATTGATTCTTCTGGTAGTGATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACCTGAG
CGTGATTTTGACTACTGGGGTCAGGGAACCCTGGTCACCGTCTCGAGC

BMS2h-84 (SEQ ID NO: 944)
GAGGTGCAGCTGTTGGAGTCTGGGGGAGGCTTGGTACAGCCTGGGGGGTC
CCTGCGTCTCTCCTGTGCAGCCTCCGGATTCACCTTTAGGCAGTACCAGA
TGGCTTGGGCCCGCCAGGCTCCAGGGAAGGGTCTAGAGTGGGTCTCAACG
ATTGCGTCGGATGGTGTTTCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGTTGGT
CGTGATTTTGACTACTGGGGTCAGGGAACCCTGGTCACCGTCTCGAGC

BMS2h-85 (SEQ ID NO: 945)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCAGTATGATA
TGAGGTGGGTCCGCCAGGCTCCAGGGAAGGGTCTAGAGTGGGTCTCATGG
ATTGATGAGGCGGGTCATGAGACATACTACGCAGACTCCGTGAAGGGCCG
GTTCACCATCTCCCGCGACAATTCCAGGAACACGCTGTATCTGCAAATGA
ACAGCCTGCGTGCCGAGGACACCGCGGTATATTACTGTGCGAAAGGGATG
GATGGGTTTGACTACTGGGGTCAGGGAACCCTGGTCACCGTCTCGAGC

BMS2h-92 (SEQ ID NO: 946)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTGATTATCCGA
TGGGTTGGGTCCGCCAGGCTCCAGGGAAGGGTCTAGAGTGGGTCTCAACG
ATTTCTACGGGGGGTTTTTCGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGCGCGG

TATTATTATCTTAGTCAGATTAAGAATTTTGACTACTGGGGTCAGGGAAC
CCTGGTCACCGTCTCGAGC

BMS2h-93 (SEQ ID NO: 947)
GAGGTGCAGCTGTTGGAGTCTGGGGGAGGCTTGGTACAGCCTGGGGGGTC
CCTGCGTCTCTCCTGTGCAGCCTCCGGATTCACCTTTGATATTTATGGGA
TGACTTGGGTCCGCCAGGCTCCAGGGAAGGGTCTGGAGTGGGTCTCAAGT
ATTTTCGCCTCTTGGTCTTGTTACATACTACGCAGACCCCGTGAAGGGCCG
GTTCACCATCTCCCGCGACAATTCCAAGAACACGCTGTATCTGCAAATGA
ACAGCCTGCGTGCCGAGGACACCGGTATATTACTGTGCGAAACTGAAG
GAGCATGGGGATGTTCCTTTTGACTACTGGGGTCAGGGAACCCTGGTCAC
CGTCTCGAGC

BMS2h-94 (SEQ ID NO: 948)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGCTTTATCCGA
TGAGTTGGGTCCGCCAGGCTCCAGGGAAGGGTCTAGAGTGGGTCTCAACT
ATTTCTCCTACGGGTTTGTTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGGTATATTACTGTGCGAAATTTAAG
AGGGAGTGGGAAGACTGATGATACTAATTTTGACTACTGGGGTCAGGGAAC
CCTGGTCACCGTCTCGAGC

BMS2h-95 (SEQ ID NO: 949)
GAGGTGCAGCTGTTGGAGTCTGGGGGAGGCTTGGTACAGCCTGGGGGGTC
CCTGCGTCTCTCCTGTGCAGCCTCCGGATTCACCTTTCGGGAGTATGATA
TGCTGTGGGTCCGCCAGGCTCCAGGGAAGGGTCTAGAGTGGGTCTCAACG
ATTGTGGGGATGTAATGGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACAGGAT
CGTCAGTTTGACTACTGGGGTCAGGGAACCCTGGTCACCGTCTCGAGC

BMS2h-97 (SEQ ID NO: 950)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGAGTATGGTA
TGAGTTGGGTCCGCCAGGCTCCAGGGAAGGGTCTAGAGTGGGTCTCAACG
ATTTCGCCTATTGGTGTTACTACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAAATGCT
TATGATCGGAAGTCTAATTTTGACTACTGGGGTCAGGGAACCCTGGTCAC
CGTCTCGAGC

BMS2h-98 (SEQ ID NO: 951)
GAGGTGCAGCTGTTGGAGTCTGGGGGAGGCTTGGTACAGCCTGGGGGGTC
CCTGCGTCTCTCCTGTGCAGCCTCCGGATTCACCTTTGATCGGTATGTGA
TGGTGTGGGTCCGCCAGGCTCCAGGGAAGGATCTAGAGTGGGTCTCAGGT
ATTACTCCGAGTGGTAGGAGGACATACTACGCAGACTCCGTGAAGGGCCG
GTTCACCATCTCCCGCGACAATTCCAAGGACACGCTGTATCTGCAAATGA
ACAGCCTGCGTGCCGAGGACACCGCGGTATATTACTGTGCGAAAGTGTTG
GGGCGTCATTTTGATCCTCTTCTGCCTTCGTTTGACTACTGGGGTCAGGG
AACCCTGGTCACCGTCTCGAGC

BMS2h-99 (SEQ ID NO: 952)
GAGGTGCAGCTGTTGGAGTCTGGGGGAGGCTTGGTACAGCCTGGGGGGTC
CCTGCGTCTCTCCTGTGCAGCCTCCGGATTCACCTTTGAGGATTATGCTA
TGAGTTGGGTCCGCCAGGCTCCAGGGAAGGGTCTAGAGTGGGTCTCAACT
ATTACTCCGGGTGGTTTTTGGACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGCGAAAACGTCT
AGTGGGAGTTGCAGTTGGTTGAGGATTTTGACTACTGGGGTCAGGGAAC
CCTGGTCACCGTCTCGAGC

TABLE 3

Anti-human CD40L VK Domain Amino Acid Sequences

BMS2h-100 (SEQ ID NO: 953)
DIQMTQSPSS LSASVGDRVT ITCRASQNIK HSLRWYQQKP GKAPRLLIYH RSQLQSGVPS
RFSGSGSGTD FTLTISSLQP EDFATYYCQQ VRHRPYTFGQ GTKVEIKR

BMS2h-101 (SEQ ID NO: 954)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ VALFPYTFGQ GTKVEIKR

BMS2h-102 (SEQ ID NO: 955)
DIQMTQSPSS LSASVGDRVT ITCRASQHIG HHLRWYQQKP GKAPKLLIYH RSHLQSGVPS
RFSGSGSGTD FTLTISSLQP EDSATYYCQQ WDRPPYTFGQ GTKVEIKR

BMS2h-103 (SEQ ID NO: 956)
DIQMTQSPSS LSASVGDRVT ITCRASQAIG HRLRWYQQKP GKAPKLLIYH
RSKLQSGVPS RFSGSGSGTD FTLTISSLQP EDFATYYCQQ VRAVPYTFGQ GTKVEIKR

BMS2h-104 (SEQ ID NO: 957)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ VRFSPYTFGQ GTKVEIKR

BMS2h-105 (SEQ ID NO: 958)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ SYARPVTFGQ GTKVEIKR

BMS2h-106 (SEQ ID NO: 959)
DIQMTQSPSS LSASVGDRVT ITCRASQSIN HRLYWYQQKP GKAPKLLIYH RSRLQSGVPS
RFSGSGSGTD FTLTISSLQP EDFATYYCQQ YKVRPNTFGQ GTKVEIKR

BMS2h-107 (SEQ ID NO: 960)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ TYSSPHTFGQ GTKVEIKR

BMS2h-108 (SEQ ID NO: 961)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ RAVRPFTFGQ GTKVEIKR

BMS2h-109 (SEQ ID NO: 962)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ TYYRPLTFGQ GTKVEIKR

BMS2h-110 (SEQ ID NO: 963)
DIQMTQSPAS LSASVGDRVT ITCRASQDID PMLRWYQQKP GKAPKLLIYA GSILQSGVPS
RFSGSGSGTD FTLTISSLQP EDFATYYCQQ TSIRPYTFGQ GTKVEIKR

BMS2h-116 (SEQ ID NO: 964)
DIQMTQSPSS LSASVGDRVT ITCRASQPIG PDLLWYQQKP GKAPKLLIYQ TSILQSGVPS
RFSGSGSGTD FTLTISSLQP EDFATYYCQQ YWAFPVTFGQ GTKVEIKR

BMS2h-116-1 (SEQ ID NO: 965)
DIQMTQSPSS LSASVGDRVT ITCRASQPIG PDILWYQQKP GKAPKLLIYQ TSILQSGVPS
RFSGSESGTD FTLTISSLQP EDFATYYCQQ YWAFPVTFGQ GTKVEIKR

BMS2h-116-10 (SEQ ID NO: 966)
DIQITQSPSS LSASVGDRVT ITCRASQPIG PDLLWYQQKP GKAPKLLIYQ TSILRSGVPS
RFSGSGSGTD FTLTISSLQP EDLATYYCQQ YWAFPVTFGQ GTKVEIKR

BMS2h-116-11 (SEQ ID NO: 967)
DIQMTQSPSS LSASVGDRVT ITCRASQPIG PDLLWYQQKP GKAPKLLIYQ TSILRSGVPS
RFSGRGSGTD FTLTISSLQP EDFATYYCQQ YWAFPVTFGQ GTKVEIKR

BMS2h-116-12 (SEQ ID NO: 968)
DIQMTQSPSS LSASVGDRVT ITCRASQPIG PDLLWYQQKP GKAPKLLIYQ TSILRSGVPS
RFSGSGSGTD FTLTISSLQP EDFATYYCQQ YWTFPVTFGQ GTKVEIKR

BMS2h-116-13 (SEQ ID NO: 969)
DIQMTQSPSS LSASVGDRVT ITCRASQPIG PDLLWYQQKP GKAPKLLIYQ TSILRSGVPS
RFSGSGSETD FTLTISNLQP EDFATYYCQQ YWAFPVTFGQ GTKVVIKR

BMS2h-116-1312 (SEQ ID NO: 970)
DIQMTQSPSS LSASVGDRVT ITCRASQPIG PDLLWYQQKP GKAPKLLIYQ TSILRSGVPS
RFSGSGSETD FTLTISNLQP EDLATYYCQQ YWAFPVTFGK GTKVVIKR

BMS2h-116-1313 (SEQ ID NO: 971)
DIQMTQSPSS LSASVGDRVT ITCRASQPIG PDLLWYQQKP GKAPKLLIYQ TSILRSGVPS
RFSGSGSETD FTLTISNLQP EDFATYYCQQ YWAFPVTFGR GTKVVIKR

TABLE 3-continued

Anti-human CD40L VK Domain Amino Acid Sequences

BMS2h-116-1314 (SEQ ID NO: 972)
DIQMTQSPSS LSASVGDRVT ITCRASQPIG PDLLWYRQKP GKAPKLLIYQ TSILRSGVPS
RFSGSGSETD FTLTISNLQP EDFATYYCQQ YWAFPVTFGQ GTKVVIKR

BMS2h-116-1319 (SEQ ID NO: 973)
DIQMTQSPSS LSASVGDRVT ITCRASQPIG PDLLWYQQKP GKAPKLLIYQ TSIMRSGVPS
RFSGSGSETD FTLTISNLQP EDFATYYCQQ YWTFPVTFGQ GTKVEIKR

BMS2h-116-1320 (SEQ ID NO: 974)
DIQMTQSPSS LSAYVGDRVT ITCRASQPIG PDLLWYQQKP GKAPKLLIYQ TSILRSGVPS
RFSGSGSETD FTLTISNLQP EDFAKYYCQQ YWAFPVTFGQ GTKVVIKR

BMS2h-116-138 (SEQ ID NO: 975)
DIQMTQSPSS LSASVGDRVT ITCRASQPIG PDLLWYQQKP GKAPKLLIYQ TSILRSGVPS
RFSGSGSETD FTLTISNLQP VDFATYYCQQ YWAFPVTFGQ GTKVVIKR

BMS2h-116-14 (SEQ ID NO: 976)
DIQMTQSPSS LSASVGDRVT ITCRASQPIG PDLLWFQQKP GKAPKLLIYQ TSILQSGVPS
RFSGSESGTD FTLTISSLQP EDFATYYCQQ YWAFPVTFGQ GTKVEIKR

BMS2h-116-15 (SEQ ID NO: 977)
DIQMTQSPSS LSASVGDRVT ITCRASQPIG PDLLWYRQKP GKAPKLLIYQ TSILQSGVPS
RFSGSGSGTD FTLTISSLQP EDFATYYCQQ YWTFPVTFGQ GTKVEIKR

BMS2h-116-16 (SEQ ID NO: 978)
DIQMTQSPSS LSASVGDRVT ITCRASQPID PDLLWYQQKP GKAPKLLIYQ TSILQSGVPS
RFSGSGSGTV FTLTISSLQP EDFATYYCQQ YWAFPVTFGQ GTKVEIKR

BMS2h-116-17 (SEQ ID NO: 979)
DIQMTQSPSS LSASVGDRVT ITCRASQPIG PDLLWYQQKP GKAPKLLIYQ TSILRSGVPS
RFSGSGSGTD FTLTISSLQP EDFATYYCQQ YWAFPVTFGQ GTKVEIKR

BMS2h-116-2 (SEQ ID NO: 980)
DIQMTQSPSS LSASVGDRVT ITCRASQPIE PDLLWYQQKP GKAPKLLIYQ TSILQSGVPS
RFSGSGSGTD FTLTISSLQP EDFATYYCQQ YWASPVTFGQ GTKVEIKR

BMS2h-116-3 (SEQ ID NO: 981)
DIQMTQSPSS LSASVGDRVT ITCRASQPIG PDLLWYQQKP GKAPKLLIYQ
TSILQSGVPS RFSGSESGTD FTLTISSLQP EDIATYYCQQ YWAFPVTFGQ GTRVEIKR

BMS2h-116-4 (SEQ ID NO: 982)
DIQMTQSPSS LSASVGDRVT ITCRASQPIG PDLLWYQQKP GKAPKLLIYQ TSILQSGVPS
RFSGSESGTD FTLTISSLQP EDFATYYCQQ YWAFPVTFGQ GTKVEIKR

BMS2h-116-5 (SEQ ID NO: 983)
DIQMTQSPSS LSASVGDRVA ITCRASQPIG PDILWYQQKP GKAPKLLIYQ TSILRSGVPS
RFSGSGSGTD FTLTISSLQP EDSATYYCQQ YWAFPVTFGQ GTKVEIKR

BMS2h-116-6 (SEQ ID NO: 984)
DIQMTQSPSS LSASVGDRVT ITCRASQPIG PDLLWYQQKP GKAPKLLIYQ TSILRSGVPS
RFSGSGSVTD FTLTISSLQP EDFATYYCQQ YWAFPVTFGQ GTKVGIKR

BMS2h-116-7 (SEQ ID NO: 985)
DIQMTQSPSS LSASVGDRVT ITCRASQPID PDLLWYQQKP GKAPKLLIYQ TSILQSGVPS
RFSGSGSRTD FTLTISSLQP EDFATYYCQQ YWAFPVTFGQ GTKVEIKR

BMS2h-116-8 (SEQ ID NO: 986)
DIQMTQSPSS LSASVGDRVT ITCRASQPIG PDLLWYQQKP GKAPKLLIYQ TSILQSGVPS
RFSGSGSGTD FTLTISGLQP EDFATYYCQQ YWAFPVTFGQ GTKVEIKR

BMS2h-116-9 (SEQ ID NO: 987)
DIQMTQSPSS LSASVGDRVT ITCRASMPIG PDLLWYQQKP GKAPKLLIYQ TSILRSGVPS
RFSGSESGTD FTLTISSLQP EDFATYYCQQ YWAFPVTFGQ GTKVEIKR

BMS2h-141 (SEQ ID NO: 988)
DIQMTQSPSS LSASVGDRVT ITCRASQWIG DTLTWYQQKL GKAPKLLIYG GSELQSGVPP
RFSGSGSGTD FTLTISSLQP EDFATYYCQQ CISSPCTFGQ GTKVEIKR

BMS2h-142 (SEQ ID NO: 989)
DIQMTQSPSS LSASVGDRVT ITCRASQFIG DSLSWYQQKP GKAPKLLIYF SSILQSGVPS
RFSGSGSGTD FTLTISSLQP EDFATYYCQQ YHTSPTTFGR GTKVKIKR

BMS2h-143 (SEQ ID NO: 990)
DIQMTQSPSS LSASVGDRVT ITCRASQTIE TNLEWYQQKP GKAPKLLIYD SSQLQSGVPS
RFSGSGSGTD FTLTISSLQP EDLATYYCQQ YHGYPTTFGQ GTKVEIKR

TABLE 3-continued

Anti-human CD40L VK Domain Amino Acid Sequences

BMS2h-144 (SEQ ID NO: 991)
DIQMTQSPSS LSASVGDRVT ITCRASQMID QDLEWYQQKP GKAPKLLIYN ASWLQSGVPS
RFSGSGSGTD FTLTISSLQP EDFATYYCQQ YHGYPITFGQ GTKVEIKR

BMS2h-145 (SEQ ID NO: 992)
DIQMTQSPSS LSASVGDRVT ITCRASQTIY TSLSWYQQKP GKAPKLLIHY GSVLQSGVPS
RFSGSGSGTD FTLTISSLQP EDSATYYCQQ VHQAPTTFGQ GTKVEIKR

BMS2h-146 (SEQ ID NO: 993)
DIRMTQSPSS LSASVGDRVT ITCRASQWIG DSLAWYQQKP GKAPKLLIYG ISELQSGVPS
RFSGSGSGTD FTLTISSLQP EDSATYYCQL SSSMPHTFGQ GTKVEIKR

BMS2h-147 (SEQ ID NO: 994)
DIQMTQSPSS LSASVGDRVT ITCRASQEIE TNLEWYQQKP GKAPKLLIYD SSHLQSGVPS
RFSGSGSGTD FTLTISSLQP EDFATYYCQQ YHQNPPTFGQ GTKVEIKR

BMS2h-149 (SEQ ID NO: 995)
DIQMTQSPSS LSASVGDRVT ITCRASQWIG RQLVWYQQKP GKAPKLLIYG ATELQSGVPS
RFSGSGSGTD FTLTISSLQP EDFATYYCQQ QSKGPLTFGH GTKVEIKR

BMS2h-150 (SEQ ID NO: 996)
DIQMTQSPSS LSASVGDRVT ITCRASQGIG TDLNWYQQKP GKAPKLLIYM GSYLQSGVPS
RFSGSGSGTD FTLTISSLQP EDFATYYCQQ IYSFPITFGQ GTKVEIKR

BMS2h-154 (SEQ ID NO: 997)
DIQMTQSPSS LSASVGDRVT ITCRASQDIE EMLHWYQQKP GKAPKLLIYF GSLLQSGVPS
RFSGSRSGTD FTLTISSLQP EDFATYYCQQ HHTRPYTFGQ GTKVEIKR

BMS2h-155 (SEQ ID NO: 998)
DIQMTQSPSS LSASVGDRVT ITCRASQDIG MDLEWYQQIP GKVPKLLIYD ASYLQSGVPS
RFSGSGSGTD FTLTISSLQP EDFATYYCQQ YHKLPATFGQ GTKVEIKR

BMS2h-156 (SEQ ID NO: 999)
DIQMTQSPSS LSASVGDRVT ITCRASQDIM DNLEWYQQKP GKAPKLLIYA ASWLQSGVPS
RFSGSGSGTD FTLTISSLQP EDFATYYCQQ YHKLPVTFGQ GTKVEIKR

BMS2h-157 (SEQ ID NO: 1000)
DIQMTQSPSS LSASVGDRVT ITCRASQNIG EDLEWYQQKP GNAPKLLIYS ASHLQSGVPS
RFSGSGSGTD FTLTISSLQP EDFATYYCQQ YSSYPVTFGQ GTKVEIKR

BMS2h-158 (SEQ ID NO: 1001)
DIQMTQSPSS LSASVGDRVT ITCRASQPID EDLEWYQQKP GNAPKLLIYS ASYLQSGVPS
RFSGSGSGTD FTLTISRLQP EDFATYYCQQ YHLLPATFGQ GTKVEIKR

BMS2h-159 (SEQ ID NO: 1002)
DIQMIQSPSS LSASVGDRVT ITCRASQDIN EDLEWYQQKP GKAPKLLIYN ASMLQSGVPS
RFSGSGSGTD FTLTISSLQP KDFATYYCQQ YHTNPTTFGQ GTKVEIKR

BMS2h-160 (SEQ ID NO: 1003)
DIQMTQSPSS LSASVGDRVT ITCRASQDIE ADLEWYQQKP GKAPKLLIYH SSELQSGVPS
RFSGSGSGTD FTLTISSLQP EDFATYYCQQ YHMSPVTFGQ GTKVEIKR

BMS2h-161 (SEQ ID NO: 1004)
DIQMTQSPSS LSASVGDRVT ITCRASQDID SDLEWYQQKP GKAPMLLIYS SSDLQSGVPS
RFSGSGSGTD FTLTISSLQP EDFATYYCQQ YHSLPVTFGQ GTKVEIKR

BMS2h-162 (SEQ ID NO: 1005)
DIQMTQSPSS LSASVGDRVT ITCRASQDIS DDLEWYQQKP GKAPKLLIYN SSFLQSGVPS
RFSGSGSGAD FTLTISSLQP EDFATYYCQQ YHSLPVTFGQ GTKVEIKR

BMS2h-163 (SEQ ID NO: 1006)
DIQMTQSPSS LSASVGDRVT ITCRASQDIE GNLEWYQQKP GKAPKLLIYD SSQLQSGVPS
RFSGSGSGTD FTLTISSLQP EDFATYYCQQ YHHLPTTFGQ GTKVEIKR

BMS2h-164 (SEQ ID NO: 1007)
DIQMTQSPSS LSASVGDRVT ITCRASQSID TDLEWYQQKP GKAPKLLIYD GSWLQSGVPS
RFSGSGSGTD FTLTISSLQP EDFATYYCQQ YRWIPVTFGQ GTKVEIKR

BMS2h-165 (SEQ ID NO: 1008)
DIQMTQSPSS LSASVGDRVT ITCRASQSIS TDLEWYQQKL GKAPKLLIYD ASLLQSGVPS
RFSGSGSGTD FTLTISSLQP EDFATYYCQQ YSSLPVTFGQ GTKVEIKR

BMS2h-166 (SEQ ID NO: 1009)
DIQMTQSPSS LSASVGDRVT ITCRASQPIT TSLEWYQQKP GKAPKLLIYD ASMLQSGVPS
RFSGSGSGTD FTLTISSLQP EDFATYYCQQ YWVTPVTFGQ GTKVEIKR

TABLE 3-continued

Anti-human CD40L VK Domain Amino Acid Sequences

BMS2h-167 (SEQ ID NO: 1010)
DIQMTQSPSS LSASVGDRVT ITCRASQNIH TNLEWYQQKP GKAPKLLIYD GSMLQSGVPS
RFSGSGSGTD FTLTISSLQP EDFATYYCQQ YSANPVTFGQ GTKVGIKR

BMS2h-168 (SEQ ID NO: 1011)
DIQMTQSPSS LSASVGDRVT ITCRASQWIH TDLEWYQQKP GKAPKLLIYD GSMLQSGVPS
RFSGSGSGTD FTLTISSLQP EDFATYYCQQ YSVSPVTFGQ GTKVEIKR

BMS2h-169 (SEQ ID NO: 1012)
DIQMTQSPSS LSASVGDRVT ITCRASQSID NNLEWYQQKP GEAPKLLIYD GSLLQSGVPS
RFSGSGSGTD FTLTISSLQP EDFATYYCQQ YHLHPVTFGQ GTKVEIKR

BMS2h-170 (SEQ ID NO: 1013)
DIQMTQSPSS LSASVGDRVT ITCRASQDID TNLEWYQQKP GEAPKLLIYD RSTLQSGVPS
RFSGSGSGTD FTLTISSLQP EDFATYYCQQ YDSYPVTFGQ GTKVEIKR

BMS2h-171 (SEQ ID NO: 1014)
DIQMTQSPSS LSASVGDRVT ITCRASQSIE SNLEWYQQKP GKAPKLLIYN ASELQSGVPS
RFSGSGSGTD FTLTISSLRP EDFATYYCQQ YDQWPTTFGQ GTKVEIKR

BMS2h-172 (SEQ ID NO: 1015)
DIQMTQSPSS LSASVGDRVT ITCRASQAIG NTLRWYQQKP GKAPKLLIYL SSRLQSGVPS
RFSGSGSGTD FTLTISSLQP EDFATYYCQQ LKKPPYTFGQ GTKVEIKR

BMS2h-173 (SEQ ID NO: 1016)
DIQMTQSPSS LSASVGDRVT ITCRASQKIK NRLAWYQQKP GKAPKLLIYE VSHLQSGVPS
RFSGSGSGTD FTLTIGSLQP EDFATYYCQQ RRQSPYTFGQ GTKVEIKR

BMS2h-174 (SEQ ID NO: 1017)
DIQMTQSPSS LSASVGDRVT ITCRASEDIG EELFWYQQKP GKAPKLLIYS ASTLQSEVPS
RFSGSGSGTD FTLTISSLQH EDFATYYCQQ VYEWPYTFGQ GTKVEIKR

BMS2h-175 (SEQ ID NO: 1018)
DIQMTQSPSS LSASVGDRVT ITCRASQPIS GGLRWYQQKP GKAPKLLIYS TSMLQSGVPS
RFSGSGSGTD FTLTISSLQP EDFATYYCQQ LYSAPYTFGQ GTKVEIKR

BMS2h-305 (SEQ ID NO: 1019)
DIQMTQSPSS LSASVGDRVT ITCRASQDID QDLEWYQQKP GKAPKLLIYN VSLLQSGVPS
RFSGSGSGTD FTLTISSLQP EDFATYYCQQ YSMNPVTFGQ GTKVEIKR

BMS2h-306 (SEQ ID NO: 1020)
DIQMTQSPSS LSASVGDRVT ITCRASQDIG NQLKWYQQKP GKAPKLLIYQ ASGLQSGVPS
RFSGSGSGTD FTLTISSLQP EDFATYYCQQ YDLRPQTFGQ GTKVEIKR

BMS2h-307 (SEQ ID NO: 1021)
DIQMTQSPSF LSASVGDRVT ITCRASQKIS TSLEWYQQKP GKAPRLLIYD SSWLQSGVPS
RFSGSGSGTD FTLTISSLQP EDFATYYCQQ YEYNPITFGQ GTKVEIKR

BMS2h-33 (SEQ ID NO: 1022)
DIQMTQSPSS LSASVGDRVT ITCRASQTIG ESLHWYQQKP GKAPRLLIYF ASLLQSGVPS
RFSGSGSGTD FTLTISSLQP EDFATYYCQQ HHMLPSTFGQ GTKVEIKR

BMS2h-35 (SEQ ID NO: 1023)
DIQMTQSPSS LSASVGDRVT ITCRASQFIG DSLSWYQQKP GKAPKLLIYF SSILQSGVPS
RFSGSGSGTD FTLTISSLQP EDFATYYCQQ YMDIPITFGQ GTKVEIKR

BMS2h-36 (SEQ ID NO: 1024)
DIQMTQSPSS LSASVGDRVT ITCRASQDID HNLEWYQQKP GKAPKLLIYD SSMLQSGVPS
RFSGSGSGTD FTLTISSLQP EDFATYYCQQ YHSIPVTFGQ GTKVEIKR

BMS2h-37 (SEQ ID NO: 1025)
DIQMTQSPSS LSASVGDRVT ITCRASQQIE TNLEWYQQKP GKAPKLLIYD GSWLQSGVPS
RFSGSGSGTD FTLTISSLQP EDFATYYCQQ YHSLPATFGQ GTKVEIKR

BMS2h-38 (SEQ ID NO: 1026)
DIQMTQSPSS LSASVGDRVT ITCRASQDIG NNLEWYQQKP GKAPRLLIYH GSWLQSGVPS
RFSGSGSGTD FTLTISSLQP EDFATYYCQQ YDFNPTTFGQ GTKVEIKR

BMS2h-39 (SEQ ID NO: 1027)
DIQMTQSPSS LSASVGDCVT ITCRASQNID GLLWWYQQKP GKAPKLLIYA GSGLQSGVPS
RFSGSGSGTD FTLTISSLQP EDFATYYCQQ KAFEPFTFGQ GTKVEIKR

BMS2h-405 (SEQ ID NO: 1028)
DIQMTQTPSS LSASVGDRVT ITCRASQSIG HDLEWYQQKP GKAPKLLIYN VSWLQSGVPS
RFSGSGSGTD FTLTISSLQP EDFATYYCQQ YSHNPPTFGQ GTKVEIKR

TABLE 3-continued

Anti-human CD40L VK Domain Amino Acid Sequences

BMS2h-406 (SEQ ID NO: 1029)
DIQMTQSPSS LSASVGDRVT ITCRASQHIE NDLEWYQQKP GKAPKLLIYS ASHLQSGVPS
RFSGSGSGTD FTLTISSLQP EDFATYYCQQ YHLQPTTFGP GTKVEIKR

BMS2h-431 (SEQ ID NO: 1030)
DIQMTQSPSS LSASVGDRVT ITCRASQVIE GSLNWYQQKP GKAPKLLIYH RSILQSGVPS
RFSGRGSGTD FTLTISSLQP EDFATYYCQQ TYQLPLTFGQ GTKVEIKR

BMS2h-432 (SEQ ID NO: 1031)
DIQMTQSPSS LSASVGDRVT ITCRASRPIN GKLFWYQQKP GKAPKLLIAF ASALQSGVPS
RFSGSGSGTD FTLTISSLQP EDFATYYCVQ QAVYPITFGQ GTKVEIKR

BMS2h-433 (SEQ ID NO: 1032)
DIQMTQSPSS LSASVGDRVT ITCRASQAIE TNLEWYQQKP GKAPKLLIYD GSLLQSGVPS
RFSGRGSGTD FTLTISSLQP EDFATYYCQQ YHYQPATFGQ GTKVEIKR

BMS2h-434 (SEQ ID NO: 1033)
DIQMTQSPSS LSASVGDRVT ITCRASQDIE HDLEWYQQKP GKAPKLLIYS ASQLQSGVPS
RFSGSGSGTD FTLTISSLQP EDFATYYCQQ YQQPTTFGQ GTKVEIKR

BMS2h-435 (SEQ ID NO: 1034)
DIQMTQSPSS LSASVGDRVT ITCRASSQIE ESLWWYQQKP GKAPKLLIAD VSLLQSGVPS
RFSGSGSGTD FTLTISSLQP EDFATYYCAQ GVVEPRTFGQ GTKVEIKR

BMS2h-436 (SEQ ID NO: 1035)
DIQMTQSPSS LSASVGDRVT ITCRASQYIG LDLEWYQQKP GKAPKLLIYA ASWLQSGVPS
RFSGSGSGTD FTLTISSLQP EDFATYYCQQ YFRQPITFGQ GTKVEIKR

BMS2h-437 (SEQ ID NO: 1036)
DIQMTQSPSS LSASVGDRVT ITCRASTPIG TMLDWYQQKP GKAPKLLIGH SSWLQSGVPS
RFSGSGSGTD FTLTISSLQP EDFATYYCGQ HVRPPATFGQ GTKVEIKR

BMS2h-437-1 (SEQ ID NO: 1037)
DIQLTQSPTS LSATVGDRVT ITCRASTPIG TMLDWYQQKP GKAPKLLIGH SSWLQSGVPS
RFSGSGSGTD FTLTISSLQP EDFATYYCGQ HVRHPATFGQ GTKVEIKR

BMS2h-437-2 (SEQ ID NO: 1038)
DIQMTQSPSS LSASVGDRVT ITCRASTPIG TMLDWYQQKP GKAPKLLIGH SSWLQSGVPS
RFSGSGSGTD FTLTISSLQP EDFATYYCGQ HVRPPATFGQ GTKVGIKR

BMS2h-437-3 (SEQ ID NO: 1039)
DIQMTQSPSS LSASVGDRVT ITCRVSTPIG TMLDWYQQKP GKAPKLLIGH SSWLQSGVPP
RFSGSGSGTD FTLTISSLQP EDFATYYCGQ HVRPPATFGQ GTKVEIKR

BMS2h-437-4 (SEQ ID NO: 1040)
DIQMTQSPSS LSASVGDRVT ITCRASTPIG TMLDWYQQKP GKAPKLLIGH SSWLQSGVPS
RFSGCGSGTD FTLTISSLQP EDFATYYCGQ HVRPPATFGQ GTKVEIKR

BMS2h-437-5 (SEQ ID NO: 1041)
DIQMTQSPSS LSASVGDRVT ITCRASTPIG TMIDWYQQKP GKAPKLLIGH SSWLQSGVPS
RFSGSGSGTD FTLTISSLQP EDFATYYCGQ HVRPPATFGK GTKVEIKR

BMS2h-438 (SEQ ID NO: 1042)
DIQMTQSPSS LSASVGDRVT ITCRASQYID TNLEWYQQKP GKAPRLLIYD GSQLQSGVPS
RFSGSGSGTD FTLIISSLQP EDFATYYCQQ YQVVPVTFGQ GTKVEIKR

BMS2h-439 (SEQ ID NO: 1043)
DIQMTQSPSS LSASVGDRVT ITCRASQSIS SYLNWYQQKP GKAPRLLIVD SSGLQSGVPS
RFSGSGSGTD FTLTISSLQP EDFATYYCGQ DRWSPATFGQ GTKVEIKR

BMS2h-440 (SEQ ID NO: 1044)
DIQMTQSPSS LSASVGDRVT ITCRASSRIQ HMLSWYQQKP GKAPKLLIGG HSGLQSGVPS
RFSGSGSGTD FTLTISSLQP EDFATYYCAQ SCAWPLTFGQ GTKVEIKR

BMS2h-441 (SEQ ID NO: 1045)
DIQMTQSPSS LSASVGDRVT ITCRASRGID GDLWWYQQKP GKAPKLLIAD SSLLQSGVPS
RFSGSGSGTD FTLTISSLQP EDFATYYCGQ GAVRPMTFGQ GTKVEIKR

BMS2h-442 (SEQ ID NO: 1046)
DIQMTQSPSS LSASVGDRVT ITCRASRGID TDLWWYQQKP GKAPKLLIAD SSLLQSGVPS
RFSGSGSGTD FTLTISSLQP EDFATYYCGQ GAVRPMTFGQ GTKVEIKR

BMS2h-443 (SEQ ID NO: 1047)
DIQMTQSPSS LSASVGDRVT ITCRASYTIP VALDWYQQKP GKAPKLLIAD ASLLQSGVPS
RFSGSGSGTD FTLTISSLQP EDFATYYCAQ GWPGPQTFGQ GTKVEIKR

TABLE 3-continued

Anti-human CD40L VK Domain Amino Acid Sequences

BMS2h-444 (SEQ ID NO: 1048)
DIQMTQSPSS LSASVGDRVT ITCRASQSIA TDLEWYQQKP GKAPKLLIYD TSMLQSGVPS
RFSGSGSGTD FTLTISSLQP EDFATYYCQQ YSYNPSTFGQ GTKVEIKR

BMS2h-445 (SEQ ID NO: 1049)
DIQMTQSPSS LSASVGDRVT ITCRASVPIT EGLSWYQQKP GKAPKLLIQA NSWLQSGVPS
RFSGSGSGTD FTLTISSLQP EDFATYYCGQ WEHVPATFGQ GTKVEIKR

BMS2h-446 (SEQ ID NO: 1050)
DIQMTQSPSS LSASVGDRVT ITCRASSMIL YGLDWYQQKP GKAPKLLIGG TSALQSGVPS
RFSGSGSGTD FTLTISSLQP EDFATYYCGQ WETVPATFGQ GTKVEIKR

BMS2h-447 (SEQ ID NO: 1051)
DIQMTQSPSS LSASVGDRVT ITCRASQPIN GLLIWYQQKP GKAPKLLIYA MSSLQSGVPS
RFSGSGSGTD FTLTISSLQP EDFATYYCQQ LARIPFTFGQ GTKVGIKR

BMS2h-448 (SEQ ID NO: 1052)
DIQMTQSPSS LSASVGDRVT ITCRASQLIR TYLAWYQQKP GKAPKLLIYQ SSQLQSGVPS
RFSGSGSGTD FTLTISSLQP EDFATYYCQQ YNSYPDTFGQ GTKVEIKR

BMS2h-47 (SEQ ID NO: 1053)
DIQMTQSPSS LSASVGDRVT ITCRASQWIG DSLSWYQQKP GKAPKLLIYF GSYLQSGVPS
RFSGSGSGTD FTLTISSLQP EDFATYYCQQ YLHTPSTFGQ GTKVEIKR

BMS2h-484 (SEQ ID NO: 1054)
DIQMTQSPSS LSASVGDRVT ITCRASQDIE ADLEWYQQKP GKAPKLLIYH SSELQSGVPS
RFSGSGSGTD FTLTISSLQP EDFATYYCQQ YGFNPPTFGQ GTKVEIKR

BMS2h-485 (SEQ ID NO: 1055)
DIQMTQSPSS LSASVGDRVT ITCRASSPIE YGLDWYQQKP GKAPKLLIGG GSALQSGVPS
RFSGSGSGTD FTLTISSLQP EDFATYYCGQ WEVQPATFGQ GTKVEIKR

BMS2h-486 (SEQ ID NO: 1056)
DIQMTQSPSS LSASVGDRVT ITCRASQRID TDLEWYQQKP GKAPKLLIYD SSQLQSGVPS
RFSGSGSGTD FTLTISSLQP EDFATYYCQQ YHSAPATFGQ GTKVEIKR

BMS2h-487 (SEQ ID NO: 1057)
DIQMTQSPSS LSASVGDRVT ITCRASGWIG MSLEWHQQKP GKAPKLLIRG ASSLQSGVPS
RFSGSGSGTD FTLTISSLQP EDFATYYCSQ SRWPPVTFGQ GTKVEIKR

BMS2h-488 (SEQ ID NO: 1058)
DIQMTQSPSS LSASVGDRVT ITCRASRNIS NALSWYQQKP GKAPKLLILG ASWLQSGVPS
RFSGSGSGTD FTLTISSLQP EDFATYYCTQ VWDRPFTFGQ GTKVEIKR

BMS2h-489 (SEQ ID NO: 1059)
DIQMTQSPSS LSASVGDRVT ITCRASQDIM SALSWYQQKP GKAPKLLIYS TSILQSGVPS
RFSGSGSGTD FTLTISSLQP EDFATYYCQQ VYLLPVTFGQ GTKVEIKR

BMS2h-490 (SEQ ID NO: 1060)
DIQMTQSPSS LSASVGDRVT ITCRASQEIG IDLEWYQQKP GKAPKLLIYA ASYLQSGVPS
RFSSSGSGTD FTLTISSLQP EDFATYYCQQ YASNPPTFGR GTKVEIKR

BMS2h-491 (SEQ ID NO: 1061)
DIQMTQSPSS LSASVGDRVT ITCRASQMIG DWLNWYQQKP GKAPKLLIYR SSELQSGVPS
RFSGSGSGTD FTLTISSLQP EDFATYYCQQ LYFWPRTFGQ GTKVEIKR

BMS2h-492 (SEQ ID NO: 1062)
DIQMTQSPSS LSASVGDRVT ITCRASQAIE LNLEWYQQKP GKAPKLLIYD ASMLQSGVPS
RFSGSGSGTD FTLTISSLQP EDFATYYCQQ YDVYPPTFGQ GTKVEIKR

BMS2h-492-1 (SEQ ID NO: 1063)
DIQMTQSPSS LSASVGDRVT ITCRASQAIE HNLEWYQQKP GKAPKLLIYD ASMLQSGVPS
RFSGSGSGTD FTLTISSLQP EDLATYYCQQ YDAYPPTYGQ GTKVEIKR

BMS2h-492-2 (SEQ ID NO: 1064)
DIQMTQSPSS LSASVGDRVT ITCRASRAIE TNLEWYQQKP GKAPKLLFYD ASMLQSGVPS
RFGGSGSGTD FTLTISSLQP EDFATYYCLQ YDVYPPTFGQ GTKVEIKR

BMS2h-492-3 (SEQ ID NO: 1065)
DIQMTQSPSS LSATVGDRVT ITCRASQAIE TNLEWYQQKP GKAPKLLIYD ASMLQSGVPS
RFSGSGSGTD FTLTISSLQP EDFATYYCQQ YDAYPPTFGQ GTKVEIKR

BMS2h-492-4 (SEQ ID NO: 1066)
DIQMTQSPSS LSASVGDRVT ITCRASQAIE HNLEWYQQKP GKAPKLLIYD ASMLQSGVPS
RFSGRGSGTD FTLTISSLQP EDFATYYCQQ YDAYPPTFGQ GTKVEIKR

TABLE 3-continued

Anti-human CD40L VK Domain Amino Acid Sequences

BMS2h-492-5 (SEQ ID NO: 1067)
DIQMNQSPSS LSASVGDRVS ITCRASQAIE HNLEWYQQKP GKAPKLLIYD ASMLQSGVPS
RFSGSGSGTD FTLTISSLQP EDFATYYCQQ YDAYPPTFGQ GTKVEIKR

BMS2h-492-6 (SEQ ID NO: 1068)
DIQMTQSPSS LSASVGDRVT ITCRASQAIE SNLEWYQQKP GKAPKLLIYD ASMLQSGVPS
RFSGSGSGTD FTLTISSLQP EDFATYYCQQ YDVYPPTFGQ GTKVEIKR

BMS2h-492-7 (SEQ ID NO: 1069)
DIQMTQSPSS LSASVGDRVT ITCRASQAIE HNLEWYQQKP GKAPKLLIYD ASMLQSGVPS
RFSGSGSGTD FTLTISSLQP EDFATYYCQQ YDAYPPTFGQ GTKVEIKR

BMS2h-493 (SEQ ID NO: 1070)
DIQMTQSPSS LSASVGDRVT ITCRASQGID EDLEWYQQKP GKAPRLLIYS SSWLQSGVPS
RFSGSGSGTD FTLTISSLQP EDFATYYCQQ YFQYPPTFGQ GTKVEIKR

BMS2h-494 (SEQ ID NO: 1071)
DIQMTQSPSS LSASVGDRVT ITCRASQSID EDLEWYQQKP GKAPRLLIYS SSWLQSGVPS
RFSGSGSGTD FTLTISSLQP EDFATYYCQQ YFQYPPTFGQ GTKVEIKR

BMS2h-494-1 (SEQ ID NO: 1072)
DIQMTQSPSS LSASVGDRVT ITCRASQSID EDLEWYQQKP GKAPRLLIYS SSWLQSGVPS
RFSGSGSGTD FTLTISSLQP EDFATYYCQQ YSQYPPTFGQ GTKVEIKR

BMS2h-494-2 (SEQ ID NO: 1073)
DIQMTQSPSS LSASVGDRVT ITCRASQSIE EDLEWYQQKP GKAPRLLIYS SSWLQSGVPS
RFSGSGSGTD FTLTISSLQP EDFATYYCQQ YFQYPPTFGH GTKVEIKR

BMS2h-494-3 (SEQ ID NO: 1074)
DIQMTQSPSS LSASVGDRVT ITCRASQSID EDLEWYQQKP GKAPRLLIYS SSWLQSGVPS
RFSGSGSGTD FTLTISSLQP EDFATYFCQQ YFQYPPTFGQ GTKVEIKR

BMS2h-494-4 (SEQ ID NO: 1075)
EIQMTQSPSS LSASVGDRVT MTCRASQSID KDLEWYQQKP GKAPRLLIYS SSWLQRGVPS
RFSGSGSGTD FTLTISSLRP EDFATYYCQQ YFQYPPTLGQ GTKVEIKR

BMS2h-494-5 (SEQ ID NO: 1076)
DIQMTQSPSS LSASVGDRVT ITCRASQSID EDLEWYQQKP GKAPRLLIYS SSWLQSGVPS
RFSGSGSGTD FTLTISGLQP EDIATYYCKQ YSQYPPTFGQ GTKVEIKR

BMS2h-494-6 (SEQ ID NO: 1077)
DIQMTQSPPS LSASVGDRVT ITCRASQSID KDLEWYQQKP GKAPRLLIYS SSWLQRGVPS
RFSGSGSGTD FTLTISSLQP EDFATYHCQQ YFQYPPTFGQ GTKVEIKR

BMS2h-495 (SEQ ID NO: 1078)
DIQMTQSPSS LSASVGDRVT ITCRASEYIN AELAWYQQKP GKAPKLLIYG SSGLQSGVPS
RFSGSGSGTD FTLTISSLQP EDFATYYCLQ NAMWPITFGQ GTKVEIKR

BMS2h-496 (SEQ ID NO: 1079)
DIQMTQSPSS LSASVGDRVT ITCRASLDIN NGLIWYQQKP GKAPRLLILG ASGLQSGVPS
RFSGSGSGTD FTLTISSLQP EDFATYYCSQ VRSRPFTFGQ GTKVEIKR

BMS2h-497 (SEQ ID NO: 1080)
DIQMTQSPSS LSASVGDRVT ITCRASQDIL SALAWYQQKP GKAPKLLIYG SSVLQSGVPS
RFSGSGSGTD FTLTISSLQP EDFATYYCQQ NYSLPITFGQ GTKVEIKR

BMS2h-498 (SEQ ID NO: 1081)
DIQMTQSPSS LSASVGDRVT ITCRASSPIE SYLRWYQQKP GKAPKLLIRY VSVLQSGVPS
RFSGSGSGTD FTLTISSLQP EDFATYYCGQ WFRAPVTFGQ GTKVEIKR

BMS2h-499 (SEQ ID NO: 1082)
DIQMTQSPSS LSASVGDRVT ITCRVSESIN AELHWYQQKP GKAPKLLISG FSGLQSGVPS
RFSGSGSGTD FTLTISSLQP EDFATYYCVQ FAMWPFTFGQ GTKVEIKR

BMS2h-500 (SEQ ID NO: 1083)
DIQMTQSPSS LSASVGDRVT ITCRASMMIR FGLDWYQQKP GKAPKLLIGG GSSLQSGVPS
RFSGSGSGTD FTLTISSLQP EDFATYYCGQ HERWPATFGQ GTKVEIKR

BMS2h-501 (SEQ ID NO: 1084)
DIQMTQSPSS LSASVGDRVT ITCRASQSIG TLLRWYQQKP GKAPKLLIYL TSVLQSGVPS
RFSGSGSGTD FTLTISSLQP EDFATYYCQQ MVYRPYTFGQ GTKVEIKR

BMS2h-502 (SEQ ID NO: 1085)
DIQMTQSPSS LSASVGDRVT ITCRASQTIE TNLEWYQQKP GKAPKLLIYD SSQLQSGVPS
RFSGSGSGTD FTLTISSLQP EDFATYYCQQ YDKVPATFGQ GTKVEIKR

TABLE 3-continued

Anti-human CD40L VK Domain Amino Acid Sequences

BMS2h-503 (SEQ ID NO: 1086)
DIQMTQSPSS LSASVGDRVT ITCRASHHIQ RYLSWYQQKP GKAPKLLILW GSQLQSGVPS
RFSGSGSGTD FTLTISSLQP EDFATYYCGQ WWAPPPTFGQ GTKVEIKR

BMS2h-503-1 (SEQ ID NO: 1087)
DIQMTQSPSS LSASVGDRVT ITCRASHHIQ RYLSWYQQKP GKAPKLLILW GSQLQSGVPS
RFSGSGSGTD FTLTISSLQP EDFATYYCGQ WWAPPQTFGQ GTKVEIKR

BMS2h-503-2 (SEQ ID NO: 1088)
DIQMTQSPSS LSASVGDRVT ITCRASHDIQ RYLSWYQQKP GKAPKLLILW GSQLQSGVPS
RFSGSGSGTD FTLTISSLQP EDFATYYCGQ WWAPPQTFGQ GTKVEIKR

BMS2h-504 (SEQ ID NO: 1089)
DIQMTQSPSS LSASVGDRVT ITCRASQYID TNLEWYQQKP GKAPKLLIYD GSLLQSGVPS
RFSGSGSGTD FTLTISSLQP EDFATYYCGQ GAVVPVTFGQ GTKVEIKR

BMS2h-508 (SEQ ID NO: 1090)
DIQMTQSPSS LSASVGDRVT ITCRASQDIA FDLEWYQQKP GKAPKLLIYS ASMLQSGVPS
RFSGSGSGSD FTLTISSLQP EDFATYYCQQ YNLQPPTFGQ GTKVEIKR

BMS2h-509 (SEQ ID NO: 1091)
DIQMTQSPSS LSASVGDRVT ITCRASQNIA TLLRWYQQKP GKAPKLLIYA GSMLQSGVPS
RFSGSGSGTD FTLTISSLQP EDFATYYCQQ MWQRPYTFGQ GTKVEIKR

BMS2h-51 (SEQ ID NO: 1092)
DIQMTQSPSS LSASVGDRVT ITCRASQPIV DELDWYQQKP GKAPKLLIYA ASILQSGVPS
RFSGSGSGTD FTLTISSLQP EDFATYYCHQ WSTYPTTFGQ GTKVEIKR

BMS2h-510 (SEQ ID NO: 1093)
DIQMTQSPSS LSASVGDRVT ITCRASQSIS SYLNWYQQKP GKAPKLLIDG VSGLQSGVPS
RFSGSGSGTD FTLTISSLQP EDFATYYCGQ DWDWPRTFGQ GTKVEIKR

BMS2h-511 (SEQ ID NO: 1094)
DIQMTQSPSS LSASVGDRVT ITCRASRNIR DWLRWYQQKP GKAPKLLIDW GSVLQSGVPS
RFSGSGSGTD FTLTISSLQP EDFATYYCAQ TWDDPLTFGQ GTKVEIKR

BMS2h-511-1 (SEQ ID NO: 1095)
DIQMTQSPSS LSAFVGDRVT ITCRASRNIR DWLRWYQQKP GKAPKLLIDW GSELQSGVPS
RFSGSGSGTD FTLTISSLQP EDFATYYCAQ TWYDPLTFGH GTKVEIKR

BMS2h-512 (SEQ ID NO: 1096)
DIQMTQSPSS LSASVGDRVT ITCRASIDIH GGLTWYQQKP GKAPKLLIVG VSGLQSGVPS
RFSGSGSGTD FTLTISNLQP EDFATYYCAQ VWRRPFTFGQ GTKVEIKR

BMS2h-513 (SEQ ID NO: 1097)
DIQMTQSPSS LSASVGDRVT ITCRASQDIG SSLSWYQQKP GKAPKLLIYA SSLLQSGVPS
RFSGSGSGTD FTLTISSLQP EDFATYYCQQ TYALPVTFGQ GTKVEIKR

BMS2h-514 (SEQ ID NO: 1098)
DIQMTQSPSS LSASVGDRVT ITCRASQQIE TNLEWYQQKP GKAPKLLIYD GSWLQSGVPS
RFSGSGSGTD FTLTISSLQP EDFATYYCQQ YKYLPVTFGQ GTKVEIKR

BMS2h-52 (SEQ ID NO: 1099)
DIQMTQSPSS LSASVGDRVT ITCRASQDIG SALRWYQQKP GKAPKLLIYL GSDLQSGVPS
RFSGSGSGTD FTLTISSLQP EDFATYYCQQ TQYFPTTFGQ GTKVEIKR

BMS2h-53 (SEQ ID NO: 1100)
DIQMTQSPSS LSASVGDRVT ITCRASQAIY GGLRWYQQKP GKAPKLLIYG ESMLQSGVPS
RFSGSGSGTD FTLTISSLHP EDFATYYCQQ VYHKPFTFGQ GTKVEIKR

BMS2h-536 (SEQ ID NO: 1101)
DIQMTQSPSS LSASVGDRVT ITCRASQRIG VWLDWYQQKP GKAPKLLIYD GSFLQSGVPS
RFSGSGSGTD FTLTISSLQP EDFATYYCQQ TFSSPSTFGQ GTKVEIKR

BMS2h-537 (SEQ ID NO: 1102)
DIQMTQSPSS LSASVGDRVP ITCRASQWIG DELYWYQQKP GKAPKLLIYS SSTLQSGVPS
RFSGSGSGTD FTLTISSLQP EDFATYYCQQ SFQFPYTFGQ GTKVEIKR

BMS2h-538 (SEQ ID NO: 1103)
DIQMTQSPSS LSASVGDRVT ITCRASSNIT GPLEWYQQKP GKAPKLLIPG WSTLQSGVPS
RFSGSGSGTD FTLTISSLQP EDFATYYCGQ VWGEPVTFGQ GTKVEIKR

BMS2h-539 (SEQ ID NO: 1104)
DIQMTQSPSS LSASIGDRVT ITCRASQRIA YGLHWYQQKP GKAPRLLIGG RSGLQSGVPS
RFSGSGSGTD FTLTISSLQP EDFATYYCVQ PGMPPDTFGQ GTKVEIKR

TABLE 3-continued

Anti-human CD40L VK Domain Amino Acid Sequences

BMS2h-540 (SEQ ID NO: 1105)
DIQMTQSPSS LSASVGDRVT ITCRASKQIV GGLSWYQQKP GKAPKLLIGR HSGLQSGVPS
RFSGSGSGTD FTLTISSLQP EDFATYYCVQ GVWAPGTFGQ GTKVEIKR

BMS2h-541 (SEQ ID NO: 1106)
DIQMTQSPSS LSASVGDRVT ITCRASPAIA AKLDWYQQKP GKAPKLLIGA DSGLQSGVPS
RFSGSGSGTD FTLTISSLQP EDFATYYCGQ LWAGPPTFGQ GTKVEIKR

BMS2h-542 (SEQ ID NO: 1107)
DIQMTQSPSS LSASVGDRVT ITCRASRTIA DGLDWYQQKP GKAPKLLIGA YSGLQSGVPS
RFSGSGSGTD FTLTISSLQP EDFATYYCGQ LWEGPPTFGQ GTKVEIKR

BMS2h-543 (SEQ ID NO: 1108)
DIQMTQSPSS LSASVGDRVT ITCRASQRIY GFLDWYQQKP GKAPKLLIYV SSLQSGVPS
RFSGSGSGTD FTLTISSLQP EDFATYYCQQ TLAWPFTFGQ GTKVEIKR

BMS2h-544 (SEQ ID NO: 1109)
DIQMTQSPSS LSASVGDRVT ITCRASQDIR DWLMWYQQKP GKAPKLLIYW GSFLQSGVPS
RFSGSGSGTD FTLTISSLQP EDFATYYCQQ LYDTPYTFGQ GTKVEIKR

BMS2h-545 (SEQ ID NO: 1110)
DIQMTQSPSS LSASVGDRVT ITCRASQNIN TGLDWYQQKP GKAPKLLIYD SSALQSGVPS
RFSGSGSGTD FTLTISSLQP EDFATYYCQQ TSYYPYTFGQ GTKVEIKR

BMS2h-546 (SEQ ID NO: 1111)
DIQMTQSPSS LSASVGDRVT ITCRASQKIF GWLDWYQQKP GKAPKLLIYG TSKLQSGVPS
RFSGSGSGTD FTLTISSLQP EDFATYYCQQ VYSLPYTFGQ GTKVEIKR

BMS2h-547 (SEQ ID NO: 1112)
DIQMTQSPSS LSASVGDRVT ITCRASSNIG ADLDWYQQKP GKAPKLLIGG ASGLQSGVPS
RFSGSGSGTD FTLTISSLQP EDFATYYCGQ LWNGPPTFGQ GTKVEIKR

BMS2h-548 (SEQ ID NO: 1113)
DIQMTQSPSS LSASVGDRVT ITCRASSPIY DGLDWYQQKP GKAPKLLISG ASWLQSGVPS
RFSGSGSGTD FTLTISSLQP EDFATYYCGQ LWLGPPTFGQ GTKVEIKQ

BMS2h-549 (SEQ ID NO: 1114)
DIQMTQSPSS LSASVGDRVT ITCRASSRIY NGLHWYQQKP GKAPKLLIGG RSGLQSGVPS
RFSGSGSGTD FTLTISSLQP EDFATYYCAQ VGEAPSTFGQ GTKVEIKR

BMS2h-550 (SEQ ID NO: 1115)
DIQMTQSPSS LSASVGDRVT ITCRASRFIN EELDWYQQKP GKAPKLLISW SSWLQSGVPS
RFSGSGSGTD FTLTISSLQP EDFATYYCVQ PGGGPGTFGQ GTKVEIKR

BMS2h-551 (SEQ ID NO: 1116)
DIQMTQSPSS LSASVGDRVT ITCRASRDIL DELDWYQQKP GKAPRLLIGG GSGLQSGVPS
RFSGSGSGTD FTLTISSLQP EDFATYYCGQ LWHGPPTFGQ GTKVEIKR

BMS2h-552 (SEQ ID NO: 1117)
DIQMTQSPSS LSASVGDRVT ITCRASSPIY TGLHWYQQKP GKAPKLLIGG RSGLQSGVPS
RFSGSGSGTD FTLTISSLQP EDFATYYCMQ VGTAPATFGQ GTKVEIKR

BMS2h-585 (SEQ ID NO: 1118)
DIRMTQSPSS LSASVGDRVT ITCRASQNIS RRLLWYQQKP GKAPKLLIYS SSRLQSGVPS
RFGGSGSGTD FTLTISSLQP EDFATYYCQQ TYSYPHTFGQ GTKVEIKR

BMS2h-604 (SEQ ID NO: 1119)
DIQMTQSPSS LSASVGDRVT ITCRASSPIP QDLYWYQQKP GKAPKLLIVG ISQLQSGVPS
RFSGSGSGTD FTLTISSLQP EDFATYYCGQ LWSAPATFGQ GTKVEIKR

BMS2h-605 (SEQ ID NO: 1120)
DIQMTQSPSS LSASVGDRVT ITCRASKSID GMLDWYQQKP GKAPKLLIPG FSGLQSGVPS
RFSGSGSGTD FTLTISSLQP EDFATYYCGQ SVEAPWTFGQ GTKVEIKR

BMS2h-606 (SEQ ID NO: 1121)
DIQMTQSPSS LSASVGDRVT ITCRASRYIA HPLDWYQQKP GKAPKLLIPG SSVLQSGVPS
RFSGSGSGTD FTLTISSLQP EDFATYYCGQ SVVVPWTFGQ GTKVEIKR

BMS2h-607 (SEQ ID NO: 1122)
DIQMTQSPSS LSASVGDRVT ITCRASRTIE GGLDWYQQKP GKAPKLLIMG GSGLQSGVPS
RFSGSGSGTD FTLTISSLQP EDFATYYCGQ LWVGPPTFGQ GTKVEIKR

BMS2h-608 (SEQ ID NO: 1123)
DIQMTQSPSS LSASVGDRVT ITCRASKFIR DELYWYQQKP GKAPRLLIGG SSLLQSGVPS
RFSGSGSGTD FTLTISSLQP EDFATYYCGQ LWRAPATFGQ GTKVEIKR

TABLE 3-continued

Anti-human CD40L VK Domain Amino Acid Sequences

BMS2h-609 (SEQ ID NO: 1124)
DIQMTQSPSS LSASVGDRVT ITCRASKPIY GGLEWYQQKP GKAPRLLIGG GSVLQSGVPS
RFSGSGSGTD FTLTISSLQP EDFATYYCGQ VWGGPVTFGQ GTKVEIKR

BMS2h-610 (SEQ ID NO: 1125)
DIRMTQSPSS LSASVGDRVT ITCRASRPIS GCLDWYQQKP GKAPKLLIDG ASGLQSGVPS
RFSGSGSGTD FTLTISSLQP EDFATYYCGQ WWEYPPTFGQ GTKVEIKR

BMS2h-611 (SEQ ID NO: 1126)
DIQMTQSPSS LSASVGDRVT ITCRASKPIV RDLEWYQQKP GKAPKLLIHG VSTLQSGVPS
RFSGSGSGTD FTLTISSLQP EDFATYYCGQ LEAAPATFGQ GTKVEIKR

BMS2h-612 (SEQ ID NO: 1127)
DIQMTQSPSS LSASVGDRVT ITCRASRDIG DWLYWYQQKP GKAPRLLIVW ASVLQSGVPS
RFSGSGSGTD FTLTISSLQP EDFATYYCAQ WGTPPTTFGQ GTKVEIKR

BMS2h-613 (SEQ ID NO: 1128)
DIQMTQSPSS LSASVGDRVT ITCRASNRIE YGLDWYQQKP GKAPKLLISG SSRLQSGVPS
RFSSSGSGTD FTLTISSLQP EDFATYYCGQ LEAAPATFGQ GTKVEIKR

BMS2h-614 (SEQ ID NO: 1129)
DIQMTQSPSS LSASVGDRVT ITCRASRNIG HFLDWYQQKP GKAPKLLILG GSSLQSGVPS
RFSGSGSGTD FTLTISSLQP EDFATYYCGQ LVEPPATFGQ GTKVEIKR

BMS2h-615 (SEQ ID NO: 1130)
DIQMTQSPSS LSASVGDRVT ITCRASSSIY SDLYWYQQKP GKAPKLLIDG WSGLQSGVPS
RFSGSGSGTD FTLTISSLQP EDFATYYCGQ LHRAPATFGQ GTKVEIKR

BMS2h-616 (SEQ ID NO: 1131)
DIQMTQSPSS LSASVGDRVT ITCRASRFIT DRLDWYQQKP GKAPKLLIGG VSGLQSGVPS
RFSGSGSGTD FTLTISSLQP EDFATYYCGQ SSELPWTFGQ GTKVEIKR

BMS2h-617 (SEQ ID NO: 1132)
DIQMTQSPSS LSASVGDRVT ITCRASRKIG SELYWYQQKP GKAPKLLIGG RSRLQSGVPS
RFSGSGSGTD FTLTISSLQP EDFATYYCGQ LWEPPATFGQ GTKVEIKR

BMS2h-618 (SEQ ID NO: 1133)
DIQMTQSPSS LSASVGDRVT ITCRASRNIG NGLDWYQQKP GKAPKLLIGE GSRLQSGVPS
RFSGSGSGTD FTLTISSLQP EDFATYYCGQ LWHTPPTFGQ GTKVEIKR

BMS2h-619 (SEQ ID NO: 1134)
DIQMTQSPSS LSASVGDRVT ITCRASRNIY GWLSWYQQKP GKAPRLLIGG WSGLQSGVPS
RFSGSGSGTD FTLTISSLQP EDFATYYCAQ DYTLPGTFGQ GTKVEIKR

BMS2h-730 (SEQ ID NO: 1135)
DIQMTQSPSS LSASVGDRVT ITCRASQDIK DWLHWYQQKP GKAPKLLIYF ASGLQSGVPS
RFSGSGSGTD FTLTISSLQP EDSATYYCQQ HYSTPYTSGQ GTKVEIKR

BMS2h-731 (SEQ ID NO: 1136)
DIQMTQSPPS LSASVGDRVT ITCRASQLIS SHLDWYQQKP GKAPKLLVYD ASELQSGVPS
RFSGSGSGTD FTLTISSLQP EDFATYYCQQ HRSLPFTFGQ GTKVEIKR

BMS2h-732 (SEQ ID NO: 1137)
DIQMTQSPSS LSASVGDRVT ITCRASQWIG GALAWYQQKP GKAPRLLIYQ ISVLQSGIPS
RFSGSGSGTD FTLTISSLQP EDFATYYCQQ YIRSPFTFGQ GTKVEIKR

BMS2h-733 (SEQ ID NO: 1138)
DIQMTQSPSS LSASVGDRVT ITCRASQSIG AALNWYQQKP GKAPKLLIYG LSSLQSGVPS
RFSGSGSGTD FTLTISSLQP EDFATYYCQQ LFRLPLTFGQ GTKVEIKR

BMS2h-734 (SEQ ID NO: 1139)
DIQMTQSPSS LSASVGDRVT ITCRASQPIG GRLVWYQQKP GKAPKLLIYG SSILQSGVPS
RFSGSGSGTD FTLTISSLQP EDFATYYCQQ YAEAPITFGQ GTKVEIKR

BMS2h-735 (SEQ ID NO: 1140)
DIQMTQSPSS LSASVGDRVT ITCRASQNIG SSLIWYQQKP GKAPTLLIYY SSKLQSGVPS
RFSGSGSGTD FTLTISSLQP EDFATYYCQQ SLSSPYTVGQ GTKVEIKR

BMS2h-736 (SEQ ID NO: 1141)
DIQMTQSPSS LSASVGDRVT ITCRASQWIG SELAWYQQKP GKAPKLLIYW TSNLQSGVPS
RFSGSGSGTD FTLTISNLQP EDFATYYCQQ ILETPLTFGQ GTKVEIKR

BMS2h-737 (SEQ ID NO: 1142)
DIQMTQSPSS LSASVGDRVT ITCRASQKIW DALYWYQQKP GKAPKLLIYR GSILQSGVPS
RFSGSGSGTD FTLTISSLQP EDFATYYCQQ FYRWPHTFGQ GTKVEIKR

TABLE 3-continued

Anti-human CD40L VK Domain Amino Acid Sequences

BMS2h-738 (SEQ ID NO: 1143)
DIQMTQSPSS LSASVGDRVT ITCRASQHIE DSLRWYQQKP GKAPKLLIYY GSVLQSGVPS
RFSGSGSGTD FTLTISSLQP EDFATYYCQQ MYKFPITFGQ GTKVEIKR

BMS2h-739 (SEQ ID NO: 1144)
DIQTTQSPSS LSASVGDRVT ITCRASQRIN SSLLWYQQKP GKAPKLLIYD TSTLQSGVPS
RFSGSRSGTD FTLTISSLQP EDFATYYCQQ IWGSPPTFGQ GTKVEIKR

BMS2h-740 (SEQ ID NO: 1145)
DIQMTQSPSS LSASVGDRVT ITCRASQSIP VGLNWYQQKP GKAPRLLIYS GSTLQSGVPS
RFSGSGSGTD FTLTISSLQP EDFATYYCQQ DWYYPNTFGQ GTKVEIKR

BMS2h-785 (SEQ ID NO: 1146)
DIQMTQSPSS LSASVGDRVT ITCRASQPIY GWLNWYQQKP GKAPKLLIYL TSGLQSGVPS
RFSGSGSGTD FTLTISSLQP EDFATYYCQQ IHSSPFTFGQ GTKVEIKR

BMS2h-8 (SEQ ID NO: 1147)
DIQMTQSPSS LSASVGDRVT ITCRASQFID TSLEWYQQKP GKAPKLLIYD GSHLQSGVPS
RFSGSGSGTD FTLTISSLQP EDLATYYCQQ YWVLPLTFGQ GTKVEIKR

BMS2h-86 (SEQ ID NO: 1148)
DIQMTQSPSS LSASVGDRVT ITCRASQDIG DALFWYQQKP GKAPKLLIYY SSMLQSGVPS
RFSGGGSGTD FTLTISSLQP EDFATYYCQQ RHSTPATFGQ GTKVEIKR

BMS2h-87 (SEQ ID NO: 1149)
DIQMTQSPSS LSASVGDRVT ITCRASQDID ESLMWYQQKP GKAPRLLIYG VSYLQSGVPS
RFSGSGSGTD FTLTISSLQP EDFATYYCQQ RWKAPFTFGQ GTKVEIKR

BMS2h-88 (SEQ ID NO: 1150)
DIQMTQSPSS LSASVGDRVT ITCRASQEIV EDLYWYQQKP GKAAKLLIYG ASWLQSGVPS
RFSGSGSGTD FTLTISSLQP EDFATYYCQQ TRRRPYTFGQ GTKVEIKR

BMS2h-89 (SEQ ID NO: 1151)
DIQMTQSPAS LSASVGDRVT ITCRASQDID PMLRWYQQKP GKAPKLLIYA GSILQSGVPS
RFSGSGSGTD FTLTISSLQP EDFATYYCQQ TLVTPYTFGQ GTKVEIKR

BMS2h-90 (SEQ ID NO: 1152)
DIQMTQSPSS LSASVGDRVT ITCRASQSIS DALFWYQQKP GKAPRLLIYY GSVLQSGVPS
RFSGSGSGTD FTLTISSLQP EDFATYYCQQ RFQEPVTFGQ GTKVEIKR

BMS2h-91 (SEQ ID NO: 1153)
DIQMTQSPSS LSASVGDRVT ITCRASQQIS DELNWYQQKP GKAPKLLIYA VSILQSGVPS
RFSGSGSGTD FTLTISSLQP EDFATYYCQQ WLSFPSTFGQ GTKVEIKR

TABLE 4

Human Anti-CD40L VK Domain
Encoding Nucleotide Sequences

BMS2h-100 (SEQ ID NO: 1154)
GACATCCAGATGACCCAGTCTCCATCCTCCCTGTCTGCATCTGTAGGAGA
CCGTGTCACCATCACTTGCCGAGCAAGTCAGAATATTAAGCATTCGTTAC
GGTGGTACCAGCAGAAACCAGGGAAAGCCCCTAGGCTCCTGATCTATCAT
CGTTCCCAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGGTTAGGCATCGTCCTTATACGTTCGGCCAA
GGGACCAAGGTGGAAATCAAACGG

BMS2h-101 (SEQ ID NO: 1155)
GACATCCAGATGACCCAGTCTCCATCCTCTCTGTCTGCATCTGTAGGAGA
CCGTGTCACCATCACTTGCCGGGCAAGTCAGGCTATTGGGCATCGGTTAC
GTTGGTATCAGCAGAAACCAGGGAAAGCCCCTAAGCTCCTGATCTATCAT
CGGTCCAAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGGTTGCTTTGTTTCCCTATACGTTCGGCCAA
GGGACCAAGGTGGAAATCAAACGG

BMS2h-102 (SEQ ID NO: 1156)
GACATCCAGATGACCCAGTCTCCATCCTCCCTGTCTGCATCTGTAGGAGA
CCGTGTCACCATCACTTGCCGGGCAAGTCAGCATATTGGTCATCATTTAA
AGGTCCCATTTGCAAAGTGGGGTCCCATCACGTTTCAGTGGCAGTGGATC
TGGGACAGATTTCACTCTCACCATCAGCAGTCTGCAACCTGAAGATTCTG
CTACGTACTACTGTCAACAGTGGGATAGGCCGCCTTATACGTTCGGCCAA
GGGACCAAGGTGGAAATCAAACGG

BMS2h-103 (SEQ ID NO: 1157)
GACATCCAGATGACCCAGTCCCCATCCTCCCTGTCTGCATCTGTAGGAGA
CCGTGTCACCATCACTTGCCGGGCAAGTCAGGCTATTGGGCATCGGTTAC
GTTGGTATCAGCAGAAACCAGGGAAAGCCCCTAAGCTCCTGATCTATCAT
CGGTCCAAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGGTGCGGGCTGTGCCTTATACGTTTGGCCAA
GGGACCAAGGTGGAAATTAAACGG

BMS2h-104 (SEQ ID NO: 1158)
GACATCCAGATGACCCAGTCTCCATCCTCCCTGTCTGCATCTGTAGGAGA
CCGTGTCACCATCACTTGCCGGGCAAGTCAGGCTATTGGGCATCGGTTAC
GTTGGTATCAGCAGAAACCAGGGAAAGCCCCTAAGCTCCTGATCTATCAT
CGGTCCAAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGGTTCGTTTTTCTCCTTATACGTTCGGCCAA
GGGACCAAGGTGGAAATCAAACGG

BMS2h-105 (SEQ ID NO: 1159)
GACATCCAGATGACCCAGTCTCCATCCTCCCTGTCTGCATCTGTAGGAGA
CCGTGTCACCATCACTTGCCGGGCAAGTCAGGCTATTGGGCATCGGTTAC
GTTGGTATCAGCAGAAACCAGGGAAAGCCCCTAAGCTCCTGATCTATCAT

TABLE 4-continued

Human Anti-CD40L VK Domain Encoding Nucleotide Sequences

CGGTCCAAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTCTTATGCTAGGCCTGTGACGTTCGGCCAA
GGGACCAAGGTGGAAATCAAACGG

BMS2h-106 (SEQ ID NO: 1160)
GACATCCAGATGACCCAGTCTCCATCCTCCCTGTCTGCATCTGTAGGAGA
CCGTGTCACCATCACTTGCCGGGCAAGTCAAAGTATTAATCATAGGTTAT
ATTGGTACCAGCAGAAACCAGGGAAAGCCCCTAAGCTCCTGATCTATCAT
CGGTCCAGGTTGCAAAGTGGGGTCCCATCACGTTTCAGTGGCAGTGGATC
TGGGACAGATTTCACTCTCACCATCAGCAGTCTGCAACCTGAGGATTTTG
CTACGTACTACTGTCAACAGTATAAGGTTAGGCCTAATACGTTCGGCCAA
GGGACCAAGGTGGAAATCAAACGG

BMS2h-107 (SEQ ID NO: 1161)
GACATCCAGATGACCCAGTCTCCATCCTCCCTGTCTGCATCTGTAGGAGA
CCGTGTCACCATCACTTGCCGGGCAAGTCAGGCTATTGGGCATCGGTTAC
GTTGGTATCAGCAGAAACCAGGGAAAGCCCCTAAGCTCCTGATTTATCAG
CGGTCCAAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGACTTATTCGTCCTCATACGTTCGGCCAA
GGGACCAAGGTGGAAATCAAACGG

BMS2h-108 (SEQ ID NO: 1162)
GACATCCAGATGACCCAGTCTCCATCCTCCCTGTCTGCATCTGTAGGAGA
CCGTGTCACCATCACTTGCCGGGCAAGTCAGGCTATTGGGCATCGGTTAC
GTTGGTATCAGCAGAAACCAGGGAAAGCCCCTAAGCTCCTGATCTATCAT
CGGTCCAAGTTGCAAAGTGGGGTCCCATCACGTTTCAGTGGCAGTGGATC
TGGGACAGATTTCACTCTCACCATCAGCAGTCTACAACCTGAAGATTTTG
CTACGTACTACTGTCAACAGAGGGCGGTGAGGCCTTTTACGTTCGGCCAA
GGGACCAAAGTGGAAATCAAACGG

BMS2h-109 (SEQ ID NO: 1163)
GACATCCAGATGACCCAGTCTCCATCCTCCCTGTCTGCATCTGTAGGAGA
CCGTGTCACCATCACTTGCCGGGCAAGTCAGGCTATTGGGCATCGGTTAC
GTTGGTATCAGCAGAAACCAGGGAAAGCCCCTAAGCTCCTGATCTATCAT
CGGTCCAAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGACTTATTATCGTCCTCTTACGTTCGGCCAA
GGGACCAAGGTGGAAATCAAACGG

BMS2h-110 (SEQ ID NO: 1164)
GACATCCAGATGACCCAGCCTCCATCCTCCCTGTCTGCATCTGTAGGAGA
CCGTGTCACCATCACTTGCCGGGCAAGTCAGGATATTGATCCTATGTTAA
GGTGGTACCAGCAGAAACCAGGGAAAGCCCCTAAGCTCCTGATCTATGCG
GGTTCCATTTTGCAAAGTGGGGTCCCATCACGTTTCAGTGGCAGTGGATC
TGGGACAGATTTCTCACCATCAGCAGTCTGCAACCTGAAGATTTTG
CTACGTACTACTGTCAACAGACTAGTATTAGGCCTTATACGTTCGGCCAA
GGGACCAAGGTGGAAATCAAACGG

BMS2h-116 (SEQ ID NO: 1165)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGAAATCAAACGG

BMS2h-116-1 (SEQ ID NO: 1166)
GACATCCAGATGACCCAGTCTCCATCCTCCCTGTCTGCATCTGTAGGAGA
CCGTGTCACCATCACTTGCCGGGCAAGTCAGCCTATTGGTCCTGATATAC
TGTGGTACCAGCAGAAACCAGGGAAAGCCCCTAAGCTCCTGATCTATCAG
ACGTCCATCTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGAAATCAAACGG

BMS2h-116-10 (SEQ ID NO: 1167)
GACATCCAGATAACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATATTGCGAAGTGGAGTCCCATCACGTTTCAGTGGCAGTGGGTC
TGGGACAGATTTCACTCTCACCATCAGCAGTCTGCAACCTGAAGATCTTG
CTACGTACTACTGTCAACAGTATTGGGCTTTTCCTGTGACGTTCGGCCAA
GGGACCAAGGTGGAAATCAAACGG

BMS2h-116-11 (SEQ ID NO: 1168)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTTCTGATCTATCAG
ACGTCCATTTTGCGAAGTGGGGTCCCATCACGTTTCAGTGGCAGAGGATC
TGGGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGAAATCAAACGG

BMS2h-116-12 (SEQ ID NO: 1169)
GACATCCAGATGACCCAGTCTCCATCCTCCCTGTCTGCATCTGTAGGAGA
CCGTGTCACCATCACTTGCCGGGCAAGTCAACCTATTGGTCCTGATTTAC
TGTGGTACCAGCAGAAACCAGGGAAAGCCCCTAAGCTCTTGATCTATCAG
ACGTCCATTTTGCGAAGTGGGGTCCCATCACGTTTCAGTGGCAGCGGATC
TGGGACTGATTTCACTCTCACCATCAGCAGTCTGCAACCTGAAGATTTTG
CTACGTACTACTGTCAACAGTATTGGACTTTTCCTGTGACGTTCGGCCAA
GGGACCAAGGTGGAAATCAAACGG

BMS2h-116-13 (SEQ ID NO: 1170)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACAGGGAAAGCCCCTAAGCTCCTGATCTATCAG
ACGTCCATTTTGCGAAGTGGGGTCCCATCACGTTTCAGTGGCAGTGGATC
TGAGACAGATTTCACTCTCACCATCAGCAATCTGCAACCTGAAGATTTTG
CTACGTACTACTGTCAACAGTATTGGGCTTTTCCTGTGACGTTCGGCCAA
GGGACCAAGGTGGTAATCAAACGG

BMS2h-116-1312 (SEQ ID NO: 1171)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATTTTGCGAAGTGGGGTCCCATCACGTTTCAGTGGCAGTGGATC
TGAGACAGATTTCACTCTCACCATCAGCAATCTGCAACCTGAAGATCTTG
CTACGTACTACTGTCAACAGTATTGGGCTTTTCCTGTGACGTTCGGCAAA
GGGACCAAGGTGGTAATCAAACGG

BMS2h-116-1313 (SEQ ID NO: 1172)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATTTTGCGAAGTGGGGTCCCATCACGTTTCAGTGGCAGTGGATC
TGAGACAGATTTCACTCTCACCATCAGCAATCTGCAACCTGAAGATTTTG
CTACGTACTACTGTCAACAGTATTGGGCTTTTCCTGTGACGTTCGGCCGA
GGGACCAAGGTGGTAATCAAACGG

BMS2h-116-1314 (SEQ ID NO: 1173)
GACATCCAGATGACCCAGTCTCCATCCTCCCTGTCTGCATCTGTAGGAGA
CCGTGTCACCATCACTTGCCGAGCAAGTCAGCCTATTGGTCCTGATTTAC
TGTGGTACCGGCAGAAACCAGGGAAAGCCCCTAAGCTCCTGATCTATCAG
ACGTCCATTTTGCGAAGTGGTGTCCCATCACGTTTCAGTGGCAGTGGATC
TGAGACAGATTTCACTCTCACCATCAGCAATCTGCAACCTGAAGATTTTG
CTACGTACTACTGTCAACAGTATTGGCTTTTCCTGTGACGTTCGGCCAA
GGGACCAAGGTGGTAATCAAACGG

BMS2h-116-1319 (SEQ ID NO: 1174)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATTATGCGAAGTGGGGTCCCATCACGTTTCAGTGGCAGTGGATC
TGAGACAGATTTCACTCTCACCATCAGCAATCTGCAACCTGAAGATTTTG
CTACGTACTACTGTCAACAGTATTGGACTTTTCCTGTGACGTTCGGCCAA
GGGACCAAGGTGGAAATCAAACGG

BMS2h-116-1320 (SEQ ID NO: 1175)
GACATCCAGATGACCCAGTCTCCATCCTCCCTGTCTGCATATGTAGGAGA
CCGTGTCACCATCACTTGCCGGGCAAGTCAGCCTATTGGTCCTGATTTAC
TTTGGTACCAGCAGAAACCAGGGAAAGCCCCTAAGCTCCTGATCTATCAG
ACGTCCATTTTGCGAAGTGGGGTCCCATCACGTTTCAGTGGCAGTGGATC
TGAGACAGATTTCACCCTCACCATCAGCAATCTGCAACCTGAAGATTTTG
CTAAGTACTACTGTCAACAGTATTGGCTTTTCCTGTGACGTTCGGCCAA
GGGACCAAGGTGGTGATCAAACGG

BMS2h-116-138 (SEQ ID NO: 1176)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATTTTGCGAAGTGGGGTCCCATCACGTTTCAGTGGCAGTGGATC

TABLE 4-continued

Human Anti-CD40L VK Domain
Encoding Nucleotide Sequences

TGAGACAGATTTCACTCTCACCATCAGCAATCTGCAACCTGTAGATTTTG
CTACGTACTACTGTCAACAGTATTGGGCTTTTCCTGTGACGTTCGGCCAA
GGGACCAAGGTAGTAATCAAACGG

BMS2h-116-14 (SEQ ID NO: 1177)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTTCCAGCAGAAACCAGGGAAAGCCCCTAAGCTCCTGATCTATCAG
ACGTCCATTTTGCAAAGTGGGGTCCCATCACGTTTCAGTGGCAGTGAATC
TGGGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGAAATCAAACGG

BMS2h-116-15 (SEQ ID NO: 1178)
GACATCCAGATGACCCAGTCTCCATCCTCCCTGTCTGCATCTGTAGGAGA
CCGTGTCACCATCACTTGCCGGGCAAGTCAGCCTATCGGTCCTGATTTAC
TGTGGTACCGGCAGAAACCAGGGAAAGCCCCTAAGCTCCTGATCTATCAG
ACGTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTGGACTTTTCCTGTGACGTTCGGCCAA
GGGACCAAGGTGGAAATCAAACGG

BMS2h-116-16 (SEQ ID NO: 1179)
GACATCCAGATGACCCAGTCTCCATCCTCCCTGTCTGCATCTGTAGGAGA
CCGTGTCACCATCACTTGCCGGGCAAGTCAGCCTATTGATCCTGACTTAC
TGTGGTACCAGCAGAAACCAGGTAAAGCCCCTAAGCTCCTGATCTATCAG
ACGTCCATTTTGCAAAGTGGGGTCCCATCACGTTTCAGTGGCAGTGGATC
TGGGACAGTTTTCACTCTCACCATCAGCAGTCTGCAACCTGAAGATTTTG
CTACGTACTACTGTCAACAGTATTGGGCATTTCCTGTGACGTTCGGCCAA
GGGACCAAGGTGGAAATCAAACGG

BMS2h-116-17 (SEQ ID NO: 1180)
GACATCCAGATGACCCAGTCTCCATCCTCCCTGTCTGCATCAGTAGGAGA
CCGTGTCACCATCACTTGCCGGGCAAGTCAGCCTATTGGTCCTGATTTAC
TGTGGTACCAGCAGAAGCCAGGGAAAGCCCCTAAGCTCCTGATCTATCAG
ACGTCCATTTTGCGAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGAAATCAAACGG

BMS2h-116-2 (SEQ ID NO: 1181)
GACATCCAGATGACCCAGTCTCCATCATCCCTGTCTGCATCTGTAGGAGA
CCGTGTCACCATCACTTGCCGGGCAAGTCAGCCTATTGAACCTGATTTAC
TGTGGTACCAGCAGAAACCAGGGAAAGCCCCTAAGCTCCTGATCTATCAG
ACGTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTGGGCTTCTCCTGTGACGTTCGGCCAA
GGGACCAAGGTGGAAATCAAACGG

BMS2h-116-3 (SEQ ID NO: 1182)
GACATCCAGATGACCCAGTCACCATCCTCCCTGTCTGCATCTGTAGGAGA
CCGTGTCACCATCACTTGCCGGGCTAGTCAGCCTATTGGTCCTGATTTAC
TGTGGTACCAGCAGAAACCAGGGAAAGCCCCTAAGCTCCTGATCTATCAG
ACGTCCATTTTGCAAAGTGGGGTCCCATCACGTTTCAGCGGCAGTGGATC
CGGGACAGATTTCACTCTCACCATCAGCAGTCTGCAACCTGAAGATATTG
CAACGTACTACTGTCAACAGTATTGGGCTTTTCCTGTGACGTTCGGCCAA
GGGACCAGGGTGGAAATCAAACGG

BMS2h-116-4 (SEQ ID NO: 1183)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATTTTGCAAAGTGGGGTCCCTTCACGTTTCAGTGGCAGTGAATC
TGGGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGAAATCAAACGG

BMS2h-116-5 (SEQ ID NO: 1184)
GACATCCAGATGACCCAGTCTCCATCCTCCCTGTCTGCATCTGTAGGAGA
CCGTGTCGCCATCACTTGCCGGGCAAGTCAGCCTATTGGTCCTGATATAC
TGTGGTACCAGCAGAAACCAGGGAAAGCCCCTAAGCTCCTGATCTATCAG
ACGTCCATTTTGCGAAGTGGGGTCCCATCACGTTTCAGTGGCAGTGGATC
TGGGACAGATTTCACTCTCACCATCAGCAGTCTGCAACCTGAAGATTCTG
CTACGTACTACTGTCAACAGTATTGGGCTTTTCCTGTGACGTTCGGTCAA
GGGACCAAGGTGGAAATCAAACGG

TABLE 4-continued

Human Anti-CD40L VK Domain
Encoding Nucleotide Sequences

BMS2h-116-6 (SEQ ID NO: 1185)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATTTTGCAAGTGGGGTCCCTCACGTTTCAGTGGCAGTGGATC
TGTGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGGAATCAAGCGG

BMS2h-116-7 (SEQ ID NO: 1186)
GACATCCAGATGACCCAGTCTCCATCCTCCCTGTCTGCATCTGTAGGAGA
CCGTGTCACCATCACTTGCCGGGCAAGTCAGCCTATTGATCCTGATTTAC
TGTGGTACCAGCAGAAACCAGGGAAAGCCCCTAAGCTCCTGATCTATCAG
ACGTCCATTTTGCAAAGTGGGGTCCCATCACGTTTCAGTGGCAGTGGATC
TAGGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGAAATCAAACGG

BMS2h-116-8 (SEQ ID NO: 1187)
GACATCCAGATGACCCAGTCTCCATCCTCCCTGTCTGCATCTGTAGGAGA
CCGTGTCACCATCACTTGCCGGGCAAGTCAGCCTATTGGTCCTGATTTAC
TGTGGTACCAGCAGAAACCAGGGAAAGCCCCTAAGCTCCTGATCTATCAG
ACGTCCATTTTGCAAAGTGGGGTCCCATCACGTTTCAGTGGCAGTGGATC
TGGGACAGATTTCACTCTCACCATCAGCGGTCTGCAACCTGAAGATTTTG
CTACGTACTACTGTCAGCAGTATTGGGCTTTTCCTGTGACGTTCGGCCAA
GGGACCAAGGTGGAAATCAAACGG

BMS2h-116-9 (SEQ ID NO: 1188)
GACATCCAGATGACCCAGTCTCCATCCTCCCTGTCTGCATCTGTAGGAGA
CCGTGTCACCATCACTTGCCGGGCAAGTATGCCTATTGGTCCTGATTTAC
TGTGGTACCAGCAGAAACCAGGGAAAGCCCCTAAGCTCCTGATCTATCAG
ACGTCCATTTTGCGAAGTGGGGTCCCATCACGTTTCAGTGGCAGTGAATC
TGGGACAGATTTCACTCTCACCATCAGCAGTCTGCAACCTGAAGATTTTG
CTACGTACTACTGTCAACAGTATTGGGCTTTTCCTGTGACGTTCGGCCAA
GGGACCAAGGTGGAAATCAAACGG

BMS2h-141 (SEQ ID NO: 1189)
GACATCCAGATGACCCAGTCTCCATCCTCCCTGTCTGCATCTGTAGGAGA
CCGTGTCACCATCACTTGCCGGGCAAGTCAGTGGATTGGGGATACGTTAA
CGTGGTACCAGCAGAAACTAGGGAAAGCCCCTAAGCTCCTGATCTATGGT
GGTTCCGAGTTGCAAAGTGGGGTCCCACCACGTTTCAGTGGCAGTGGATC
TGGGACAGATTTCACTCTCACCACATCAGCAGTCTGCAACCTGAAGATTTTG
CTACGTACTACTGTCAACAGTGTATTAGTAGTCCTTGTACGTTCGGCCAA
GGGACCAAGGTGGAAATCAAACGG

BMS2h-142 (SEQ ID NO: 1190)
GACATCCAGATGACCCAGTCTCCATCCTCCCTGTCTGCATCTGTAGGAGA
CCGTGTCACCATCACTTGCCGGGCAAGTCAGTTTATTGGTGATTCTTTAT
CTTGGTACCAGCAGAAACCAGGGAAAGCCCCTAAGCTCCTGATCTATTTT
TCTTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATACTTCGCCTACTACGTTCGGCCGA
GGGACCAAGGTGAAAATCAAACGG

BMS2h-143 (SEQ ID NO: 1191)
GACATCCAGATGACCCAGTCTCCATCCTCCCTGTCCGCATCTGTAGGAGA
CCGTGTCACCATCACTTGCCGGGCAAGTCAGACTATTGAGACTAATTTAG
AGTGGTACCAGCAGAAACCAGGGAAAGCCCCTAAGCTCCTGATCTATGAT
TCTTCCAGTTGCAAAGTGGGGTCCCATCACGTTTCAGTGGCAGTGGATC
TGGGACAGATTTTACTCTCACCATCAGCAGTCTGCAACCTGAAGATTTAG
CTACGTACTACTGTCAACAGTATCATGGGTATCCTACGACGTTCGGCCAA
GGGACCAAGGTGGAAATCAAACGG

BMS2h-144 (SEQ ID NO: 1192)
GACATCCAGATGACCCAGTCTCCATCCTCCCTGTCTGCATCTGTAGGAGA
CCGTGTCACCATCACTTGCCGGGCAAGTCAGATGATTGATCAGGATTTAG
AGTGGTACCAGCAGAAACCAGGGAAAGCCCCTAAGCTCCTGATCTATAAT
GCGTCCTGGTTGCAAAGTGGGGTCCCATCACGTTTCAGCGGCAGTGGATC
TGGGACAGATTTCACTCTCACCATCAGCAGTCTGCAACCTGAAGATTTTG
CTACGTACTACTGTCAACAGTATCATGGTTATCCTATTACGTTCGGCCAA
GGGACCAAGGTGGAAATCAAACGG

BMS2h-145 (SEQ ID NO: 1193)
GACATCCAGATGACCCAGTCTCCATCCTCCCTGTCTGCATCTGTAGGAGA
CCGTGTCACCATCACTTGCCGGGCAAGTCAGACGATTTATACTTCGTTAA
GTTGGTATCAGCAGAAACCAGGGAAAGCCCCTAAGCTCCTGATCCATTAT

TABLE 4-continued

Human Anti-CD40L VK Domain Encoding Nucleotide Sequences

GGTTCCGTGTTGCAAAGTGGGGTCCCATCACGTTTCAGTGGCAGTGGATC
TGGGACAGATTTCACTCTCACCATCAGCAGTCTGCAACCTGAAGATTCTG
CTACGTACTACTGTCAACAGGTTCATCAGGCTCCTACGACGTTCGGCCAA
GGGACCAAGGTGGAAATCAAACGG

BMS2h-146 (SEQ ID NO: 1194)
GACATCCGGATGACCCAGTCTCCATCCTCCCTGTCTGCATCTGTAGGAGA
CCGTGTCACCATCACTTGCCGGGCAAGTCAGTGGATTGGGGATTCTTTAG
CGTGGTACCAGCAGAAGCCAGGGAAAGCCCCTAAGCTCCTGATCTATGGT
ATTTCCGAGTTGCAAAGTGGGGTCCCATCACGTTTCAGTGGCAGTGGATC
TGGGACAGATTTCACTCTCACCATCAGCAGTCTGCAACCTGAAGATTCTG
CTACGTACTACTGTCAACTGTCTAGTAGTATGCCTCATACGTTCGGCCAA
GGGACCAAGGTGGAAATCAAACGG

BMS2h-147 (SEQ ID NO: 1195)
GACATCCAGATGACCCAGTCTCCATCCTCCCTGTCTGCATCTGTAGGAGA
CCGTGTCACCATCACTTGCCGGGCAAGTCAGGAGATTGAGACGAATTTAG
AGTGGTACCAGCAGAAACCAGGGAAAGCCCCTAAGCTCCTGATCTATGAT
TCGTCCCATTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATCAGAATCCTCCGACGTTCGGCCAA
GGAACCAAGGTGGAAATCAAACGG

BMS2h-149 (SEQ ID NO: 1196)
GACATCCAGATGACCCAGTCTCCATCCTCCCTGTCTGCATCTGTAGGAGA
CCGTGTCACCATCACTTGCCGGGCAAGTCAGTGGATTGGGGCAGTTAG
TTTGGTACCAGCAGAAACCAGGGAAAGCCCCTAAGCTCCTGATCTATGGG
GCGACCGAGTTGCAAAGTGGGGTCCCATCACGTTTTAGTGGCAGTGGATC
TGGGACAGATTTCACTCTCACCATCAGCAGTCTGCAACCTGAAGATTTTG
CTACGTACTACTGTCAACAGCAGTCGAAGGGTCCTCTTACGTTCGGCCAT
GGGACCAAGGTGGAAATCAAACGG

BMS2h-150 (SEQ ID NO: 1197)
GACATCCAGATGACCCAGTCTCCATCCTCCCTGTCTGCATCTGTAGGAGA
CCGTGTCACCATCACTTGCCGGGCAAGTCAGGGGATTGGTACTGATTTAA
ATTGGTATCAGCAGAAACCAGGGAAAGCCCCTAAGCTCCTGATCTATATG
GGTTCCTATTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGATTTATTCTTTTCCTATTACGTTCGGCCAA
GGGACCAAGGTGGAAATCAAACGG

BMS2h-154 (SEQ ID NO: 1198)
GACATCCAGATGACCCAGTCTCCATCCTCCCTGTCTGCATCTGTAGGAGA
CCGTGTCACCATCACTTGCCGGGCAAGTCAGGATATTGAGGAGATGTTAC
ATTGGTATCAGCAGAAACCAGGGAAAGCCCCTAAGCTCCTGATCTATTTT
GGTTCCCTGTTGCAAAGTGGGGTCCCATCACGTTTCAGTGGCAGTAGATC
TGGGACAGATTTCTCTCACCATCAGCAGTCTGCAACCTGAAGATTTTG
CTACGTACTACTGTCAACAGCATCATACTCGTCCTTATACGTTCGGCCAA
GGGACCAAGGTGGAAATCAAACGG

BMS2h-155 (SEQ ID NO: 1199)
GACATCCAGATGACCCAGTCTCCATCCTCCCTGTCTGCATCTGTAGGAGA
CCGTGTCACCATCACTTGCCGGGCAAGTCAGGATATTGGGATGGATTTAG
AGTGGTACCAGCAGATACCAGGGAAAGTCCCTAAGCTCCTGATCTATGAT
GCGTCCTATTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATAAGCTTCCTGCGACGTTTGGCCAA
GGGACCAAGGTGGAAATCAAACGG

BMS2h-156 (SEQ ID NO: 1200)
GACATCCAGATGACCCAGTCTCCATCCTCCCTGTCTGCATCTGTAGGAGA
CCGTGTCACCATCACTTGCCGGGCAAGTCAGGATATTATGGATAATTTAG
AGTGGTATCAGCAGAAACCAGGGAAAGCCCCTAAGCTCCTGATCTATGCG
GCGTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATAAGTTGCCTGTGACGTTCGGCCAA
GGGACCAAGGTGGAAATCAAACGG

BMS2h-157 (SEQ ID NO: 1201)
GACATCCAGATGACCCAGTCTCCATCCTCCCTGTCTGCATCTGTAGGAGA
CCGTGTCACCATCACTTGCCGAGCAAGTCAGAATATTGGGGAGGATTTAG
AGTGGTACCAGCAGAAACCAGGGAAAGCCCCTAAGCTCCTGATCTATAGT
GCGTCCCATTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTCTAGTTATCCTGTTACGTTCGGCCAA
GGGACCAAGGTGGAAATCAAACGG

BMS2h-158 (SEQ ID NO: 1202)
GACATCCAGATGACCCAGTCTCCATCCTCCCTGTCTGCATCCGTAGGAGA
CCGTGTCACCATCACTTGCCGGGCAAGTCAGCCGATTGATGAGGATTTAG
AGTGGTACCAGCAGAAACCAGGGAATGCCCCTAAGCTCCTGATCTATAGT
GCGTCCTATTTGCAAAGTGGGGTCCCATCACGTTTCAGTGGCAGTGGATC
TGGGACAGATTTCACTCTCACCATCAGCAGACTGCAACCTGAAGATTTTG
CTACGTACTACTGTCAACAGTATCATCTTCTGCCTGCTACGTTCGGCCAA
GGGACCAAGGTGGAAATCAAACGG

BMS2h-159 (SEQ ID NO: 1203)
GACATCCAGATGATCCAGTCTCCATCCTCCCTGTCTGCATCTGTAGGAGA
CCGTGTCACCATCACTTGCCGGGCAAGTCAGGATATTAATGAGGATTTAG
AGTGGTATCAGCAGAAACCAGGGAAAGCCCCTAAGCTCCTGATCTATAAT
GCTTCCATGTTGCAAAGCGGGGTCCCATCACGTTTCAGTGGCAGTGGATC
TGGGACAGATTTCACTCTCACCATCAGCAGTCTGCAACCTAAAGATTTTG
CTACGTACTACTGTCAACAGTATCATACTAATCCTACTACGTTCGGCCAA
GGGACCAAGGTGGAAATCAAACGG

BMS2h-160 (SEQ ID NO: 1204)
GACATCCAGATGACCCAGTCTCCATCCTCCCTGTCTGCATCTGTAGGAGA
CCGTGTCACCATCACTTGCCGGGCAAGTCAGGATATTGAGGCGGATTTAG
AGTGGTACCAGCAGAAACCAGGGAAAGCCCCTAAGCTCCTGATCTATCAT
TCTTCCGAGTTGCAAAGTGGGGTCCCATCACGTTTCAGTGGAAGTGGATC
TGGGACAGATTTCACTCTCACCATCAGCAGTCTGCAACCTGAAGATTTTG
CTACGTACTACTGTCAACAGTATCATATGTCGCCTGTGACGTTCGGCCAA
GGGACCAAGGTGGAAATCAAACGG

BMS2h-161 (SEQ ID NO: 1205)
GACATCCAGATGACCCAGTCTCCATCCTCCCTGTCTGCATCTGTAGGAGA
CCGTGTCACCATCACTTGCCGGGCAAGTCAGGATATTGATAGTGATTTAG
AGTGGTACCAGCAGAAACCAGGGAAAGCCCCTATGCTCCTGATCTATTCT
TCGTCCGATTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATAGTCTGCCTGTTACGTTCGGCCAA
GGGACCAAGGTGGAAATCAAACGG

BMS2h-162 (SEQ ID NO: 1206)
GACATCCAGATGACCCAGTCTCCATCCTCCCTGTCTGCATCTGTAGGAGA
CCGTGTCACCATCACTTGCCGGGCAAGTCAGGATATTTCGGATGATTTAG
AGTGGTACCAGCAGAAACCAGGGAAAGCCCCTAAGCTCCTGATCTATAAT
TCGTCCTTTTTGCAAAGTGGGGTCCCATCACGTTTCAGTGGCAGTGGATC
TGGGGCAGATTTCACTCTCACCATCAGCAGTCTGCAACCTGAAGATTTTG
CTACGTACTACTGTCAACAGTATCATAGTTTGCCTGTTACGTTCGGCCAA
GGGACCAAGGTGGAAATCAAACGG

BMS2h-163 (SEQ ID NO: 1207)
GACATCCAGATGACCCAGTCTCCATCCTCCCTGTCTGCATCTGTAGGAGA
CCGTGTCACCATCACTTGCCGGGCAAGTCAGGATATTGAGGGTAATTTAG
AGTGGTACCAGCAGAAACCAGGGAAAGCCCCTAAGCTCCTGATCTATGAT
TCGTCCCAGTTGCAAAGTGGGGTCCCATCACGTTTCAGTGGCAGTGGGTC
TGGGACAGATTTCACTCTCACCATCAGCAGTCTGCAACCTGAAGATTTTG
CTACGTACTACTGTCAACAGTATCATCATCTTCCTACGACGTTCGGCCAA
GGGACCAAGGTGGAAATCAAACGG

BMS2h-164 (SEQ ID NO: 1208)
GACATCCAGATGACCCAGTCTCCATCCTCCCTGTCTGCATCTGTAGGAGA
CCGTGTCACCATCACTTGCCGGGCAAGTCAGAGTATTGATACGGATTTAG
AGTGGTATCAGCAGAAACCAGGGAAAGCCCCTAAGCTCCTGATCTATGAT
GGGTCCTGGTTGCAAAGTGGGGTCCCATCACGTTTCAGTGGCAGTGGATC
TGGGACAGATTTTACTCTCACCATCAGCAGTCTGCAACCTGAAGATTTTG
CTACGTACTACTGTCAACAGTATCGGTGGATTCCTGTTACGTTCGGCCAA
GGGACCAAGGTGGAAATCAAACGG

BMS2h-165 (SEQ ID NO: 1209)
GACATCCAGATGACCCAGTCTCCATCCTCCCTGTCTGCATCTGTAGGAGA
CCGTGTCACCATCACTTGCCGGGCAAGTCAGAGTATTAGTACTGATTTAG
AGTGGTACCAGCAGAAACTAGGGAAAGCCCCTAAGCTCCTGATCTATGAT
GCTTCCTTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTCGAGTCTGCCTGTTACGTTCGGCCAA
GGGACCAAGGTGGAAATCAAACGG

BMS2h-166 (SEQ ID NO: 1210)
GACATCCAGATGACCCAGTCTCCATCCTCCCTGTCTGCATCTGTAGGAGA
CCGTGTCACCATCACTTGCCGGGCAAGTCAGCCTATTACGACGTCTTTAG
AGTGGTACCAGCAGAAACCAGGGAAAGCCCCTAAGCTCCTGATCTATGAT
GCGTCCATGTTGCAAAGTGGGGTCCCATCACGTTTCAGTGGCAGTGGATC

TABLE 4-continued

Human Anti-CD40L VK Domain
Encoding Nucleotide Sequences

TGGGACAGATTTCACTCTCACCATCAGCAGTCTGCAACCTGAAGATTTTG
CTACGTACTACTGTCAACAGTATTGGGTTACGCCTGTTACGTTCGGCCAA
GGGACCAAGGTGGAAATCAAACGG

BMS2h-167 (SEQ ID NO: 1211)
GACATCCAGATGACCCAGTCTCCATCCTCCCTGTCTGCATCTGTAGGAGA
CCGTGTCACCATCACCTGCCGGGCAAGTCAGAATATTCATACGAATTTAG
AGTGGTATCAGCAGAAACCAGGGAAAGCCCCTAAGCTCCTGATCTATGAT
GGTTCCATGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTCGGTAATCCTGTTACGTTCGGCCAA
GGGACCAAGGTGGAATCAAACGG

BMS2h-168 (SEQ ID NO: 1212)
GACATCCAGATGACCCAGTCTCCATCCTCCCTGTCTGCATCTGTAGGAGA
CCGTGTCACCATCACTTGCCGGGCAAGTCAGTGGATTCATACGGATTTAG
AGTGGTATCAGCAGAAACCAGGGAAAGCCCCTAAGCTCCTGATCTATGAT
GGTTCCATGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATAGTGTGTCGCCTGTTACGTTCGGCCAA
GGGACCAAGGTGGAAATCAAACGG

BMS2h-169 (SEQ ID NO: 1213)
GACATCCAGATGACCCAGTCTCCATCCTCCCTGTCTGCATCTGTAGGAGA
CCGTGTCACCATCACTTGCCGGGCAAGTCAGAGTATTGATAATAATTTAG
AGTGGTACCAGCAGAAACCAGGGAAAGCCCCTAAGCTCCTGATCTATGAT
GGGTCCCTTTTGCAAAGTGGGGTCCCATCACGTTTCAGTGGCAGTGGATC
TGGGACAGATTTCACTCTTACCATCAGCAGTCTGCAACCTGAAGATTTTG
CTACGTACTACTGTCAACAGTATCATCTTCATCCTGTTACGTTCGGCCAA
GGGACCAAGGTGGAAATCAAACGG

BMS2h-170 (SEQ ID NO: 1214)
GACATCCAGATGACCCAGTCTCCATCCTCCCTGTCTGCATCTGTAGGAGA
CCGTGTCACCATCACTTGCCGGGCAAGTCAGGATATTGATACGAATTTAG
AGTGGTATCAGCAGAAACCAGGGAAGCCCCTAAGCTCCTGATCTATGAT
CGTTCCACGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATGATTCTTATCCTGTGACGTTCGGCCAA
GGGACCAAGGTGGAAATCAAACGG

BMS2h-171 (SEQ ID NO: 1215)
GACATCCAGATGACCCAGTCTCCATCCTCCCTGTCTGCATCTGTAGGAGA
CCGTGTCACCATCACTTGCCGGGCAAGTCAGTCATTGAGTCTAATTTAG
AGTGGTACCAGCAGAAACCAGGGAAAGCCCCTAAGCTCCTGATCTATAAT
GCGTCCGAGTTGCAAAGTGGGGTCCCATCACGTTTCAGTGGCAGTGGATC
TGGGACAGATTTCACTCTCACCATCAGCAGTCTGCGACCTGAAGATTTTG
CTACGTACTACTGTCAACAGTATGATCAGTGGCCTACGACGTTCGGCCAA
GGGACCAAGGTGGAAATCAAACGG

BMS2h-172 (SEQ ID NO: 1216)
GACATCCAGATGACCCAGTCTCCATCCTCCCTGTCTGCATCTGTAGGAGA
CCGTGTCACTATCACTTGCCGGGCAAGTCAGGCTATTGGTAATACTTTAC
GGTGGTACCAGCAGAAACCAGGGAAAGCCCCTAAGCTCCTGATCTATCTT
AGTTCCAGGTTGCAAAGTGGGGTCCCATCACGTTTCAGTGGCAGTGGATC
TGGGACAGATTTTACTCTCACCATCAGCAGTCTGCAACCTGAAGATTTTG
CTACGTACTACTGTCAACAGCTGAAGAAGCCTCCTTATACGTTCGGCCAA
GGGACCAAGGTGGAAATCAAACGG

BMS2h-173 (SEQ ID NO: 1217)
GACATCCAGATGACCCAGTCTCCATCCTCCCTGTCTGCATCTGTAGGAGA
CCGTGTCACCATCACTTGCCGGGCAAGTCAGAAGATTAAGAATCGGTTAG
CGTGGTACCAGCAGAAACCAGGGAAAGCCCCTAAGCTCCTGATCTATGAG
GTTTCCCATTTGCAAAGTGGGGTCCCATCACGTTTCAGTGGCAGTGGATC
TGGGACAGATTTCACTCTCACCATCGGCAGTCTGCAACCTGAAGATTTTG
CTACGTACTACTGTCAACAGAGGAGGCAGTCGCCTTATACGTTCGGCCAA
GGGACCAAGGTGGAAATCAAACGG

BMS2h-174 (SEQ ID NO: 1218)
GACATCCAGATGACCCAGTCTCCATCCTCCCTGTCTGCATCTGTAGGAGA
CCGTGTCACCATCACTTGCCGGGCAAGTGAGGATATTGGGGAGGAGTTAT
TTTGGTATCAGCAGAAACCAGGGAAAGCCCCTAAGCTCCTGATCTATTCG
GCGTCCACGTTGCAAAGTGAGGTCCCATCACGTTTCAGTGGCAGTGGATC
TGGGACAGATTTCACTCTCACCATCAGCAGTCTGCAACATGAAGATTTTG
CTACGTACTACTGTCAACAGGTTTATGAGTGGCCTTATACGTTCGGCCAA
GGGACCAAGGTGGAAATCAAACGG

BMS2h-175 (SEQ ID NO: 1219)
GACATCCAGATGACCCAGTCTCCATCCTCCCTGTCTGCATCTGTAGGAGA
CCGTGTCACCATCACTTGCCGGGCAAGTCAGCCTATTTCTGGGGGTTTAA
GGTGGTACCAGCAGAAACCAGGGAAACCCCTAAGCTCCTGATCTATTCT
ACTTCCATGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGCTTTATTCTGCTCCTTATACGTTCGGCCAA
GGGACCAAGGTGGAAATCAAACGG

BMS2h-305 (SEQ ID NO: 1220)
GACATCCAGATGACCCAGTCTCCATCCTCCCTGTCTGCATCTGTAGGAGA
CCGTGTCACCATCACTTGCCGGGCAAGTCAGGATATTGATCAGGATTTAG
AGTGGTACCAGCAGAAACCAGGGAAAGCCCCTAAGCTCCTGATCTATAAT
GTTTCCCTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTCTATGAATCCTGTTACGTTCGGCCAA
GGGACCAAGGTGGAAATCAAACGG

BMS2h-306 (SEQ ID NO: 1221)
GACATCCAGATGACCCAGTCTCCATCCTCCCTGTCTGCATCTGTAGGAGA
CCGTGTCACCATCACTTGCCGGGCAAGTCAGGATATTGGGAATCAGTTAA
AGTGGTACCAGCAGAAACCAGGGAAAGCCCCTAAGCTCCTGATCTATCAG
GCTTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATGATTTGAGGCCTCAGACGTTCGGCCAA
GGGACCAAGGTGGAAATCAAACGG

BMS2h-307 (SEQ ID NO: 1222)
GACATCCAGATGACCCAGTCTCCATCCTTCCTGTCTGCATCTGTAGGTGA
CCGTGTCACCATCACTTGCCGGGCGAGTCAGAAGATTTCTACGTCTTTAG
AGTGGTATCAGCAGAAACCAGGGAAAGCCCCTAGGCTCCTGATCTATGAT
TCTTCCTGGTTGCAAAGTGGGGTCCCATCACGTTTCAGTGGCAGTGGATC
TGGGACAGATTTCACTCTCACCATTAGCAGTCTGCAACCTGAAGATTTTG
CTACGTACTACTGTCAACAGTATGAGTATAATCCTATTACGTTCGGCCAA
GGGACCAAGGTGGAAATCAAACGG

BMS2h-33 (SEQ ID NO: 1223)
GACATCCAGATGACCCAGTCTCCATCCTCCCTGTCTGCATCTGTAGGAGA
CCGTGTCACCATCACTTGCCGGGCAAGTCAGACGATTGGGGAGAGTTTAC
ATTGGTACCAGCAGAAACCAGGGAAAGCCCCTAGGCTCCTGATCTATTTT
GCTTCCCTGTTGCAAAGTGGGGTCCCATCGCGTTTCAGTGGCAGTGGATC
TGGGACAGATTTTACTCTCACCATCAGCAGTCTGCAACCTGAAGATTTTG
CTACGTACTACTGTCAACAGCATCATATGCTTCCTTACGTTCGGCCAA
GGGACCAAGGTGGAAATCAAACGG

BMS2h-35 (SEQ ID NO: 1224)
GACATCCAAATGACCCAGTCTCCATCCTCCCTGTCTGCATCTGTAGGAGA
CCGTGTCACCATCACTTGCCGGGCAAGTCAGTTTATTGGTGATTCTTTAT
CTTGGTACCAGCAGAAACCAGGGAAAGCCCCTAAGCTCCTGATCTATTTT
TCTTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATATGGATATTCCTATTACGTTCGGCCAA
GGGACCAAGGTGGAAATCAAACGG

BMS2h-36 (SEQ ID NO: 1225)
GACATCCAGATGACCCAGTCTCCATCCTCCCTGTCTGCATCTGTAGGAGA
CCGTGTCACCATCACTTGCCGGGCAAGTCAGGATATTGATCATAATTTAG
AGTGGTATCAGCAGAAACCAGGGAAAGCCCCTAAGCTCCTGATCTATGAT
AGTTCCATGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATTCTATTCCTGTTACGTTCGGCCAA
GGGACCAAGGTGGAAATCAAACGG

BMS2h-37 (SEQ ID NO: 1226)
GACATCCAGATGACCCAGTCTCCATCCTCCCTGTCTGCATCTGTAGGAGA
CCGTGTCACCATCACTTGCCGGGCAAGTCAGCAGATTGAGACGAATTTAG
AGTGGTACCAGCAGAAACCAGGGAAAGCCCCTAAGCTCCTGATCTATGAT
GGTTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATAGTTTGCCTGCTACGTTCGGCCAA
GGGACCAAGGTGGAAATCAAACGG

BMS2h-38 (SEQ ID NO: 1227)
GACATCCAGATGACCCAGTCTCCATCCTCCCTGTCTGCATCTGTAGGAGA
CCGTGTCACCATCACTTGCCGGGCAAGTCAGGATATTGGTAATAATTTAG
AGTGGTACCAGCAGAAACCAGGGAAAGCCCCTAGGCTCCTGATCTATCAT

TABLE 4-continued

Human Anti-CD40L VK Domain
Encoding Nucleotide Sequences

GGGTCCTGGTTGCAAAGTGGGGTCCCATCGCGTTTCAGTGGCAGTGGATC
TGGGACAGATTTCACTCTTACCATCAGCAGTCTGCAACCTGAAGATTTTG
CTACGTACTACTGTCAACAGTATGATTTTAATCCTACTACGTTCGGCCAA
GGGACCAAGGTGGAAATCAAACGG

BMS2h-39 (SEQ ID NO: 1228)
GACATCCAGATGACCCAGTCTCCATCCTCCCTGTCTGCATCTGTAGGAGA
CTGTGTCACCATCACTTGCCGGGCAAGTCAGAATATTGATGGTCTGTTAT
GGTGGTATCAGCAGAAACCAGGGAAAGCCCCTAAGCTCCTGATCTATGCG
GGGTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGAAGGCTTTTGAGCCTTTTACGTTCGGCCAA
GGGACCAAGGTGGAAATCAAACGG

BMS2h-405 (SEQ ID NO: 1229)
GACATCCAGATGACCCAGACTCCATCCTCCCTGTCTGCATCTGTAGGAGA
CCGTGTCACCATCACTTGCCGGGCAAGTCAGAGTATTGGTCATGATTTAG
AGTGGTACCAGCAGAAACCAGGGAAAGCCCCTAAGCTCCTGATCTATAAT
GTGTCCTGGTTGCAAAGTGGGGTCCCATCACGTTTCAGTGGCAGTGGATC
TGGGACAGATTTTACTCTCACCATCAGCAGTCTGCAACCTGAAGATTTTG
CTACGTACTACTGTCAACAGTATAGTCATAATCCTCCTACGTTCGGCCAA
GGGACCAAGGTGGAAATCAAACGG

BMS2h-406 (SEQ ID NO: 1230)
GACATCCAGATGACCCAGTCTCCATCCTCCCTGTCTGCATCTGTAGGAGA
CCGTGTCACTATCACTTGCCGGGCAAGTCAGCATATTGAGAATGATTTAG
AGTGGTACCAGCAGAAACCAGGGAAAGCCCCTAAGCTCCTGATCTATTCT
GCTTCCCATTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATCTTCAGCCTACGACGTTCGGCCCA
GGGACCAAGGTGGAAATCAAACGG

BMS2h-431 (SEQ ID NO: 1231)
GACATCCAGATGACCCAGTCTCCATCCTCCCTGTCTGCATCTGTAGGAGA
CCGTGTCACTATCACTTGCCGGGCAAGTCAGGTTATTGAGGGTAGTTTAA
ATTGGTACCAGCAGAAACCAGGGAAAGCCCCTAAGCTCCTGATCTATCAT
AGGTCCATTTTGCAAAGTGGGGTCCCATCACGTTTCAGTGGCCGTGGATC
TGGGACAGATTTCACTCTCACCATCAGCAGTCTGCAACCTGAAGATTTTG
CTACGTACTGTCAACAGACTTATCAGCTTCCTTTTGACGTTCGGCCAA
GGGACCAAGGTGGAAATCAAACGG

BMS2h-432 (SEQ ID NO: 1232)
GACATCCAGATGACCCAGTCTCCATCCTCCCTGTCTGCATCTGTAGGAGA
CCGTGTCACCATCACTTGCCGGGCAAGTCGTCCTATTAATGGTAAGTTAT
TTTGGTACCAGCAGAAACCAGGCAAAGCCCCTAAGCTCCTGATCGCGTTT
GCTTCCGCTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGTGCAGCAGGCTGTGTATCCTATTACGTTCGGCCAA
GGGACCAAGGTGGAAATCAAACGG

BMS2h-433 (SEQ ID NO: 1233)
GACATCCAGATGACCCAGTCTCCATCCTCCCTGTCTGCATCTGTAGGAGA
CCGTGTCACCATCACTTGCCGGGCAAGTCAGGCTATTGAGACGAATTTAG
AGTGGTATCAGCAGAAACCAGGGAAAGCCCCTAAGCTCCTGATCTATGAT
GGGTCCCTTTTGCAAAGTGGGGTCCCATCACGTTTCAGTGGCAGAGGATT
TGGGACAGATTTCACTCTCACCATCAGCAGTCTGCAACCTGAAGATTTTG
CTACGTACTACTGTCAACAGTATCATTATCAGCCTGCGACGTTCGGCCAA
GGGACCAAGGTGGAAATCAAACGG

BMS2h-434 (SEQ ID NO: 1234)
GACATCCAGATGACCCAGTCTCCATCCTCCCTGTCTGCATCTGTAGGAGA
CCGTGTCACCATCACTTGCCGGGCAAGTCAGGATATTGAGCATGATTTAG
AGTGGTACCAGCAGAAACCAGGGAAAGCCCCTAAGCTCCTGATCTATTCG
GCGTCCCAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCAGCAGCAGCTACTACGTTCGGCCAA
GGGACCAAGGTGGAAATCAAACGG

BMS2h-435 (SEQ ID NO: 1235)
GACATCCAGATGACCCAGTCTCCATCCTCCCTGTCTGCATCTGTAGGAGA
CCGTGTCACCATCACTTGCCGGGCAAGTTCGCAGATTGAGGAGTCTTTAT
GGTGGTACCAGCAGAAACCAGGGAAAGCCCCTAAGCTCCTGATCGCGGAT
GTTTCCCTGTTGCAAAGTGGAGTCCCATCACGTTTCAGTGGCAGTGGATC
TGGGACAGATTTCACTCTCACCATCAGCAGTCTGCAACCTGAAGATTTTG
CTACGTACTACTGTGCTCAGGGTGTGGTGGAGCCTCGACGTTCGGCCAA
GGGACCAAGGTGGAAATCAAACGG

BMS2h-436 (SEQ ID NO: 1236)
GACATCCAGATGACCCAGTCTCCATCCTCCCTGTCTGCATCTGTAGGAGA
CCGTGTCACCATCACTTGCCGGGCAAGTCAGTATATTGGTCTGGATTTAG
AGTGGTATCAGCAGAAACCAGGGAAAGCCCCTAAGCTCCTGATCTATGCT
GCTTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTTTGGCAGCCTATTACGTTCGGCCAA
GGGACCAAGGTGGAAATCAAACGG

BMS2h-437 (SEQ ID NO: 1237)
GACATCCAGATGACCCAGTCTCCATCCTCCCTGTCTGCATCTGTAGGAGA
CCGTGTCACCATCACTTGCCGGGCAAGTACGCCGATTGGTACTATGTTAG
ATTGGTACCAGCAGAAACCAGGGAAAGCCCCTAAGCTCCTGATCGGGCAT
TCGTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGCATGTGCGTCCTCCTGCGACGTTCGGCCAA
GGGACCAAGGTGGAAATCAAACGG

BMS2h-437-1 (SEQ ID NO: 1238)
GACATCCAGTTGACCCAGTCTCCAACCTCCCTGTCTGCAACTGTAGGAGA
CCGTGTCACCATCACTTGCCGGGCAAGTACGCCGATTGGTACTATGTTAG
ATTGGTACCAGCAGAAACCTGGGAAAGCCCCTAAGCTCCTGATCGGGCAT
TCGTCCTGGTTGCAAAGTGGGGTCCCATCACGTTTCAGTGGCAGTGGATC
TGGGACTGATTTCACTCTCACCATCAGCAGTCTGCAACCTGAAGATTTTG
CTACGTACTACTGTGGGCAGCATGTGCGTCATCCTGCGACGTTCGGCCAA
GGGACCAAGGTGGAAATCAAGCGG

BMS2h-437-2 (SEQ ID NO: 1239)
GACATCCAGATGACCCAGTCTCCATCCTCCCTGTCTGCATCTGTAGGAGA
CCGTGTCACCATCACTTGCCGGGCAAGTACGCCGATTGGTACTATGTTAG
ATTGGTACCAGCAGAAACCAGGGAAAGCCCCTAAGCTCCTGATCGGGCAT
TCGTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGACAGCATGTGCGTCCTCCTGCGACGTTCGGCCAA
GGGACCAAGGTGGGAATCAAACGG

BMS2h-437-3 (SEQ ID NO: 1240)
GACATCCAGATGACCCAGTCTCCGTCCTCCCTGTCTGCATCTGTAGGAGA
CCGTGTCACCATCACTTGCGGGGTAAGTACGCCGATTGGTACTATGTTAG
ATTGGTACCAGCAGAAACCAGGGAAAGCCCCTAAGCTCCTGATCGGGCAT
TCGTCCTGGTTGCAAAGTGGGGTCCCACCACGTTTCAGTGGCAGCGGATC
TGGGACAGATTTCACTCTCACCATCAGCAGTCTGCAACCTGAAGATTTTG
CTACGTACTACTGTGGGCAGCATGTGCGTCCTCCTGCGACGTTCGGCCAA
GGGACCAAGGTGGAAATCAAACGG

BMS2h-437-4 (SEQ ID NO: 1241)
GACATCCAGATGACCCAGTCTCCATCCTCCCTGTCTGCATCTGTAGGAGA
CCGTGTCACCATCACTTGCCGGGCAAGTACGCCGATTGGTACTATGTTAG
ATTGGTACCAGCAGAAACCAGGGAAAGCCCCTAAGCTCCTGATCGGGCAT
TCGTCCTGGTTGCAAAGTGGGGTCCCATCACGTTTCAGTGGCTGTGGATC
TGGGACAGATTTCACTCTCACCATCAGCAGTCTGCAACCTGAAGATTTTG
CTACGTACTACTGTGGGCAGCATGTGCGTCCTCCTGCGACGTTCGGCCAA
GGGACCAAGGTGGAAATCAAACGG

BMS2h-437-5 (SEQ ID NO: 1242)
GACATCCAGATGACCCAGTCTCCATCCTCCCTGTCTGCATCTGTAGGAGA
CCGTGTCACCATCACTTGCCGGGCAAGTACGCCGATTGGTACTATGATAG
ATTGGTACCAGCAGAAACCAGGGAAAGCCCCTAAGCTCCTGATCGGGCAT
TCGTCCTGGTTGCAAAGTGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGCATGTGCGTCCTCCTGCGACGTTCGGCAAA
GGGACCAAGGTGGAAATCAAACGG

BMS2h-438 (SEQ ID NO: 1243)
GACATCCAGATGACCCAGTCTCCATCCTCCCTGTCTGCATCTGTAGGAGA
CCGTGTCACCATCACATGCCGGGCAAGTCAGTATATTGATACTAATTTAG
AGTGGTACCAGCAGAAACCAGGGAAAGCCCCTAGGCTCCTGATCTATGAT
GGTTCCCAGTTGCAAAGTGGGGTCCCATCACGTTTCAGTGGCAGTGGATC
TGGGACAGATTTCACTCTCATCATCAGCAGTCTGCAACCTGAAGATTTTG
CTACGTACTACTGTCAACAGTATCAGGTTGTGCCTGTTACGTTCGGCCAA
GGGACCAAGGTGGAAATCAAACGG

BMS2h-439 (SEQ ID NO: 1244)
GACATCCAGATGACCCAGTCTCCATCCTCCCTGTCTGCATCTGTAGGAGA
CCGTGTCACCATCACTTGCCGGGCAAGTCAGAGCATTAGCAGCTATTTAA
ATTGGTACCAGCAGAAACCAGGGAAAGCCCCTAGGCTCCTGATCGTGGAT
TCTTCCGGGTTGCAAAGTGGGGTCCCATCACGTTTCAGTGGCAGTGGATC

TABLE 4-continued

Human Anti-CD40L VK Domain
Encoding Nucleotide Sequences

TGGGACAGATTTCACTCTCACCATCAGCAGTCTGCAACCTGAAGATTTTG
CTACGTACTACTGTGGTCAGGATCGTTGGTCTCCTGCTACGTTCGGCCAA
GGGACCAAGGTGGAAATCAAACGG

BMS2h-440 (SEQ ID NO: 1245)
GACATCCAGATGACCCAGTCTCCATCCTCCCTGTCTGCATCTGTAGGAGA
CCGTGTCACCATCACTTGCCGGGCAAGTTCGCGGATTCAGCATATGTTAT
CTTGGTACCAGCAGAAACCAGGGAAAGCCCCTAAGCTCCTGATCGGTGGG
CATTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAATCGTGTGCGTGGCCTCTGACGTTCGGCCAA
GGGACCAAGGTGGAAATCAAACGG

BMS2h-441 (SEQ ID NO: 1246)
GACATCCAGATGACCCAGTCTCCATCCTCCCTGTCTGCATCTGTAGGAGA
CCGTGTCACCATCACTTGCCGGGCAAGTAGGGGTATTGATGGTGATTTAT
GGTGGTACCAGCAGAAACCAGGGAAAGCCCCTAAGCTCCTGATCGCGGAT
TCTTCCCTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGGGGGCTGTTCGGCCTATGACGTTCGGCCAA
GGGACCAAGGTGGAAATCAAACGG

BMS2h-442 (SEQ ID NO: 1247)
GACATCCAGATGACCCAGTCTCCATCCTCCCTGTCTGCATCTGTAGGAGA
CCGTGTCACCATCACTTGCCGGGCAAGTAGGGGTATTGATACTGATTTAT
GGTGGTACCAGCAGAAACCAGGGAAAGCCCCTAAGCTCCTGATCGCGGAT
TCTTCCCTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGGGGGCTGTTCGGCCTATGACGTTCGGCCAA
GGGACCAAGGTGGAAATCAAACGG

BMS2h-443 (SEQ ID NO: 1248)
GACATCCAGATGACCCAGTCTCCATCCTCCCTGTCTGCATCTGTAGGAGA
CCGTGTCACCATCACTTGCCGGGCAAGTTATACTATTCCGGTTGCTTTAG
ATTGGTACCAGCAGAAACCAGGGAAAGCCCCTAAGCTCCTGATCGCTGAT
GCGTCCTTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGGGTTGGCCGGGGCCTCAGACGTTCGGCCAA
GGGACCAAGGTGGAAATCAAACGG

BMS2h-444 (SEQ ID NO: 1249)
GACATCCAGATGACCCAGTCTCCATCCTCCCTGTCTGCATCTGTAGGAGA
CCGTGTCACCATCACTTGCCGGGCAAGTCAGATTATTGCGACGGACTTAG
AGTGGTATCAGCAGAAACCAGGGAAAGCCCCTAAGCTCCTGATCTATGAT
ACTTCCATGTTGCAAAGCGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATAGTTATAATCCTTCGACGTTCGGCCAA
GGGACCAAGGTGGAAATCAAACGG

BMS2h-445 (SEQ ID NO: 1250)
GACATCCAGATGACCCAGTCTCCATCCTCCCTGTCTGCATCTGTAGGAGA
CCGTGTCACCATCACTTGCCGGGCAAGTGTGCCTATTACTGAGGGTTTAT
CGTGGTACCAGCAGAAACCAGGGAAAGCCCCTAAGCTCCTGATCCAGGCT
AATTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTGGGAGCATGTTCCTGCGACGTTCGGCCAA
GGGACCAAGGTGGAAATCAAACGG

BMS2h-446 (SEQ ID NO: 1251)
GACATCCAGATGACCCAGTCTCCATCCTCCCTGTCTGCATCTGTAGGAGA
CCGTGTCACCATCACTTGCCGGGCAAGTAGTATGATTCTTTATGGTTTAG
ATTGGTACCAGCAGAAACCAGGGAAAGCCCCTAAGCTCCTGATCGGTGGT
ACTTCCGCGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTGGGAGACGGTTCCTGCTACGTTCGGCCAA
GGGACCAAGGTGGAAATCAAACGG

BMS2h-447 (SEQ ID NO: 1252)
GACATCCAGATGACCCAGTCTCCATCCTCCCTGTCTGCATCTGTAGGAGA
CCGTGTCACCATCACTTGCCGGGCAAGTCAGCCTATTAATGGGCTTTTAA
TTTGGTATCAGCAGAAACCAGGGAAAGCCCCTAAGCTCCTGATCTATGCG
ATGTCCAGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTTGGCTCGGATTCCTTTTACGTTCGGCCAA
GGGACCAAGGTGGGAATCAAACGG

BMS2h-448 (SEQ ID NO: 1253)
GACATCCAGATGACCCAGTCTCCATCCTCCCTGTCTGCATCTGTAGGAGA
CCGTGTCACCATCACTTGCCGAGCAAGTCAGCTGATTCGGACTTATTTAG
CGTGGTACCAGCAGAAACCAGGGAAAGCCCCTAAGCTCCTGATCTATCAG
TCTTCTCAGTTGCAAAGTGGTGTCCCATCACGTTTCAGTGGCAGTGGATC
TGGGACAGATTTCACTCTCACCATCAGCAGTCTGCAACCTGAAGATTTTG
CTACGTACTACTGTCAACAGTATAATTCTTATCCTGATACGTTCGGCCAA
GGGACCAAGGTGGAAATCAAACGG

BMS2h-47 (SEQ ID NO: 1254)
GACATCCAGATGACCCAGTCTCCATCCTCCCTGTCTGCATCTGTAGGAGA
CCGTGTCACCATCACTTGCCGGGCAAGTCAGTGGATTGGGGATTCGTTAA
GTTGGTACCAGCAGAAACCAGGGAAAGCCCCTAAGCTCCTGATCTATTTT
GGTTCCTATTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATTTGCATACTCCTTCGACGTTCGGCCAA
GGGACCAAGGTGGAAATCAAACGG

BMS2h-484 (SEQ ID NO: 1255)
GACATCCAGATGACCCAGTCTCCATCCTCCCTGTCTGCATCTGTAGGAGA
CCGTGTCACCATCACTTGCCGGGCAAGTCAGGATATTGAGGCGGATTTAG
AGTGGTACCAGCAGAAACCAGGGAAAGCCCCTAAGCTCCTGATCTATCAT
TCTTCCGAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATGGTTTTAATCCTCCTACGTTCGGCCAA
GGGACCAAGGTGGAAATCAAACGG

BMS2h-485 (SEQ ID NO: 1256)
GACATCCAGATGACCCAGTCTCCATCCTCCCTGTCTGCATCTGTAGGAGA
CCGTGTCACCATCACTTGCCGGGCAAGTTCTCCTATTGAGTATGGTTTAG
ATTGGTACCAGCAGAAACCAGGGAAAGCCCCTAAGCTCCTGATCGGGGGG
GGGTCCGCGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGAGGTTCAGCCTGCTACGTTCGGCCAA
GGGACCAAGGTGGAAATCAAACGG

BMS2h-486 (SEQ ID NO: 1257)
GACATCCAGATGACCCAGTCTCCATCCTCCCTGTCTGCATCTGTAGGAGA
CCGTGTCACCATCACTTGCCGGGCAAGTCAGCGGATTGATACTGATTTAG
AGTGGTACCAGCAGAAACCAGGGAAAGCCCCTAAGCTCCTGATCTATGAT
AGTTCACAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATCATAGTGCGCCTGCGACGTTCGGCCAA
GGGACCAAGGTGGAAATCAAACGG

BMS2h-487 (SEQ ID NO: 1258)
GACATCCAGATGACCCAGTCTCCATCCTCCCTGTCTGCATCTGTAGGAGA
CCGTGTCACCATCACTTGCCGGGCAAGTGGGTGGATTGGTATGTCTTTAG
AGTGGCACCAGCAGAAACCAGGGAAAGCCCCTAAGCTCCTGATCCGTGGG
GCTTCCTCTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTAGTCAGTCTCGGTGGCCGCCTGTGACGTTCGGCCAA
GGGACCAAGGTGGAAATCAAACGG

BMS2h-488 (SEQ ID NO: 1259)
GACATCCAGATGACCCAGTCTCCATCCTCCCTGTCTGCATCTGTAGGAGA
CCGTGTCACCATCACTTGCCGGGCAAGTCGTAATATTTCGAATGCTTTAT
CGTGGTACCAGCAGAAACCAGGGAAAGCCCCTAAGCTCCTGATCCTTGGG
GCTTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTACTCAGGTGTGGGATAGGCCTTTTACGTTCGGCCAA
GGGACCAAGGTGGAAATCAAACGG

BMS2h-489 (SEQ ID NO: 1260)
GACATCCAGATGACCCAGTCTCCATCCTCCCTGTCTGCATCTGTAGGAGA
CCGTGTCACCATCACTTGCCGGGCAAGTCAGGATATTATGTCGGCTTTAT
CTTGGTATCAGCAGAAACCAGGGAAAGCCCCTAAGCTCCTGATCTATTCT
ACTTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGGTTTATTTGCTGCCTGTTACGTTCGGCCAA
GGGACCAAGGTGGAAATCAAACGG

BMS2h-490 (SEQ ID NO: 1261)
GACATCCAGATGACCCAGTCTCCATCCTCCCTGTCTGCATCTGTAGGAGA
CCGTGTCACCATCACTTGCCGGGCAAGTCAGGAGATTGGGATTGATTTAG
AGTGGTATCAGCAGAAACCAGGGAAAGCCCCTAAGCTCCTGATCTATGCT

TABLE 4-continued

Human Anti-CD40L VK Domain Encoding Nucleotide Sequences

GCTTCTTATTTGCAAAGTGGGGTCCCATCACGTTTCAGTAGCAGTGGATC
TGGGACAGATTTCACTCTCACCATCAGCAGTCTGCAACCTGAAGATTTTG
CTACGTACTACTGTCAACAGTATGCTTCTAATCCTCCTACGTTCGGCCGA
GGGACCAAGGTGGAAATCAAACGG

BMS2h-491 (SEQ ID NO: 1262)
GACATCCAGATGACCCAGTCTCCATCCTCCCTGTCTGCATCTGTAGGAGA
CCGTGTCACCATCACTTGCCGGGCAAGTCAGATGATTGGGGATTGGTTAA
ATTGGTACCAGCAGAAACCAGGGAAAGCCCCTAAACTCCTGATCTATCGT
AGTTCCGAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTTGTATTTTTGGCCTCGTACGTTCGGCCAA
GGGACCAAGGTGGAAATCAAACGG

BMS2h-492 (SEQ ID NO: 1263)
GACATCCAGATGACCCAGTCTCCATCCTCCCTGTCTGCATCTGTAGGAGA
CCGTGTCACCATCACTTGCCGGGCAAGTCAGGCGATTGAGCTTAATTTAG
AGTGGTACCAGCAGAAACCAGGGAAGGCCCCTAAGCTCCTGATCTATGAT
GCTTCCATGTTGCAAAGCGGGGTCCCATCACGTTTCAGTGGCAGTGGATC
TGGGACAGATTTCACTCTCACCATTAGCAGTCTGCAACCTGAAGATTTTG
CTACGTACTACTGTCAACAGTATGATGTTTATCCTCCTACGTTCGGCCAA
GGGACCAAGGTGGAAATCAAACGG

BMS2h-492-1 (SEQ ID NO: 1264)
GACATCCAGATGACCCAGTCTCCATCCTCCCTGTCTGCATCTGTAGGAGA
CCGTGTCACCATCACTTGCCGGCCAAGTCAGGCGATTGAGCATAATTTAG
AGTGGTACCAGCAGAAGCCAGGGAAGGCCCCTAAGCTCCTGATCTATGAT
GCTTCCATGTTGCAAAGCGGGGTCCCATCACGTTTCAGTGGCAGTGGATC
TGGGACAGATTTCACTCTCACCATTAGCAGTCTCCAACCTGAAGATTTAG
CTACGTACTACTGTCAACAGTATGATGCTTATCCTCCTACGTACGGCCAA
GGGACCAAGGTGGAAATCAAACGG

BMS2h-492-2 (SEQ ID NO: 1265)
GACATCCAGATGACACAGTCTCCATCCTCCCTGTCCGCATCTGTAGGAGA
CCGTGTCACCATCACTTGCCGGGCAAGTCGGGCGATAGAGACTAATTTAG
AGTGGTACCAGCAGAAACCAGGGAAGGCCCCTAAGCTCCTGTTCTATGAT
GCTTCCATGTTGCAAAGCGGGGTCCCATCACGTTTCGGTGGCAGTGGATC
TGGGACAGATTTCACTCTCACCATTAGCAGTCTGCAACCTGAAGATTTTG
CTACGTACTACTGTACAGTATGATGTTTATCCTCCTACGTTCGGCCAA
GGGACCAAGGTGGAAATCAAACGG

BMS2h-492-3 (SEQ ID NO: 1266)
GACATCCAGATGACCCAGTCTCCATCCTCCCTGTCTGCAACTGTAGGAGA
CCGTGTCACCATCACTTGTCGTGCAAGTCAGGCGATTGAGACTAATTTAG
AGTGGTACCAGCAGAAACCAGGGAAGGCCCCTAAGCTCCTGATCTATGAT
GCTTCCATGTTGCAAAGCGGGGTCCCATCACGTTTCAGTGGCAGTGGATC
TGGGACAGACTTCACTCTCACCATTAGCAGTCTGCAACCTGAAGATTTTG
CTACGTACTACTGTCAACAGTATGATGCTTATCCTCCTACGTTCGGCCAA
GGGACCAAGGTGGAAATCAAACGG

BMS2h-492-4 (SEQ ID NO: 1267)
GACATCCAGATGACCCAGTCTCCATCCTCCCTGTCTGCATCTGTAGGAGA
CCGTGTCACCATCACTTGCCGGGCAAGTCAGGCGATTGAGCATAACTTAG
AGTGGTACCAGCAGAAACCAGGGAAGGCCCCTAAGCTCCTGATCTATGAT
GCTTCCATGTTGCAAAGCGGGGTCCCATCACGTTTCAGTGGCAGTGGATC
TGGGACAGATTTCACTCTCACCATTAGCAGTCTGCAACCTGAAGATTTTG
CTACGTACTACTGTCAACAGTATGATGCTTATCCTCCTACGTTCGGCCAA
GGGACCAAGGTGGAAATCAAACGG

BMS2h-492-5 (SEQ ID NO: 1268)
GACATCCAGATGAACCAGTCTCCATCCTCCCTGTCTGCATCTGTAGGAGA
CCGTGTCTCCATCACTTGCAGGGCAAGTCAGGCTATTGAGCATAATTTAG
AGTGGTACCAGCAGAAACCAGGGAAGGCCCCTAAGCTCCTGATCTATGAT
GCTTCCATGTTGCAAAGCGGGGTCCCATCACGCGTTCAGTGGCAGTGGATC
TGGGACAGATTTCACTCTCACCATTAGCAGTCTGCAACCTGAAGATTTTG
CTACGTACTACTGTCAACAGTATGATGCTTATCCTCCTACGTTCGGCCAA
GGGACCAAGGTGGAAATCAAACGG

BMS2h-492-6 (SEQ ID NO: 1269)
GACATCCAGATGACCCAGTCTCCATCCTCCCTGTCTGCATCTGTAGGAGA
CCGTGTCACCATCACTTGCCGGGCAAGTCAGGCGATTGAGTCTAATTTAG
AGTGGTACCAGCAAAAACCAGGGAAGGCCCCTAAGCTCCTGATCTATGAT
GCTTCCATGTTGCAAAGCGGGGTCCCATCACGTTTCAGTGGCAGTGGATC
TGGGACAGATTTCACTCTCACCATTAGCAGTCTGCAACCTGAAGATTTTG
CTACGTACTACTGTCAACAGTATGATGTTTATCCTCCTACGTTCGGCCAA
GGGACCAAGGTGGAAATCAAACGG

BMS2h-492-7 (SEQ ID NO: 1270)
GACATCCAGATGACCCAGTCTCCATCCTCCCTGTCTGCATCTGTAGGAGA
CCGTGTCACCATCACTTGCCGTGCAAGTCAGGCGATTGAGCATAATTTAG
AGTGGTACCAGCAGAAACCAGGGAAGGCCCCTAAGCTCCTGATCTATGAT
GCTTCCATGTTGCAAAGCGGGGTCCCATCACGTTTCAGTGGCAGTGGATC
TGGGACAGATTTCACTCTCACCATTAGCAGTCTGCAACCTGAAGATTTTG
CTACGTACTACTGTCAACAGTATGATGCTTATCCTCCTACGTTCGGCCAA
GGGACCAAGGTGGAAATCAAACGG

BMS2h-493 (SEQ ID NO: 1271)
GACATCCAGATGACCCAGTCTCCATCCTCCCTGTCTGCATCTGTAGGAGA
CCGTGTCACCATCACTTGCCGGGCAAGTCAGGGTATTGATGAGGATTTAG
AGTGGTACCAGCAGAAACCAGGGAAAGCCCCTAGGCTCCTGATCTATTCT
AGTTCCTGGTTGCAAAGTGGGGTCCCATCACGTTTCAGTGGGAGTGGATC
TGGGACAGATTTCACTCTCACCATCAGCAGTCTGCAACCTGAAGATTTTG
CTACGTACTACTGTCAACAGTATTTTCAGTATCCTCCGACGTTCGGCCAA
GGGACCAAGGTGGAAATCAAACGG

BMS2h-494 (SEQ ID NO: 1272)
GACATCCAGATGACCCAGTCTCCATCCTCCCTGTCTGCATCTGTAGGAGA
CCGTGTCACCATCACTTGCCGGGCAAGTCAGAGTATTGATGAGGATTTAG
AGTGGTACCAGCAGAAACCAGGGAAAGCCCCTAGGCTCCTGATCTATTCT
AGTTCCTGGTTGCAAAGTGGGGTCCCATCACGTTTCAGTGGGAGTGGATC
TGGGACAGATTTCACTCTCACCATCAGCAGTCTGCAACCTGAAGATTTTG
CTACGTACTACTGTCAACAGTATTTTCAGTATCCTCCGACGTTCGGCCAA
GGGACCAAGGTGGAAATCAAACGG

BMS2h-494-1 (SEQ ID NO: 1273)
GACATCCAGATGACCCAGTCTCCATCCTCCCTGTCCGCATCTGTAGGAGA
CCGTGTCACCATCACTTGCCAGGGCAAGTCAGAGTATTGATGAGGATTTAG
AGTGGTACCAGCAGAAACCAGGGAAAGCCCCTAGGCTCCTGATCTATTCT
AGTTCCTGGTTGCAAAGTGGGGTCCCATCACGTTTCAGTGGGAGTGGATC
TGGGACAGATTTCACTCTCACCATCAGCAGTCTGCAACCTGAAGATTTTG
CTACGTACTACTGTCAACAGTATTCTCAGTATCCTCCGACGTTCGGCCAA
GGGACCAAGGTGGAAATCAAACGG

BMS2h-494-2 (SEQ ID NO: 1274)
GACATCCAGATGACCCAGTCTCCATCCTCCCTGTCTGCATCTGTAGGAGA
CCGTGTCACCATCTTGCCGGGCAAGTCAGAGTATTGAAGAGGATTTAG
AGTGGTACCAGCAGAAACCAGGGAAAGCCCCTAGGCTCCTGATCTATTCT
AGTTCCTGGTTGCAAAGCGGGGTCCCATCACGTTTCAGTGGGAGTGGCTC
TGGGACAGATTTCACTCTCACCATCAGCAGTCTGCAACCTGAAGATTTTG
CTACGTACTACTGTCAACAGTATTTTCAGTATCCTCCGACGTTCGGCCAT
GGGACCAAGGTGGAAATCAAACGG

BMS2h-494-3 (SEQ ID NO: 1275)
GACATCCAGATGACCCAGTCTCCATCCTCCCTGTCTGCATCTGTAGGAGA
CCGTGTCACCATCACTTGCCGGGCAAGTCAGAGTATTGATGAGGATTTAG
AGTGGTACCAGCAGAAACCAGGGAAAGCCCCTAGGCTCCTGATCTATTCT
AGTTCCTGGTTGCAAAGTGGGGTCCCATCACGTTTCAGTGGGAGTGGATC
TGGGACAGATTTCACTCTCACCATCAGCAGTCTGCAACCTGAAGATTTTG
CTACGTACTTCTGTCAACAGTATTTTCAGTATCCTCCGACGTTCGGCCAA
GGGACCAAGGTGGAAATCAAACGG

BMS2h-494-4 (SEQ ID NO: 1276)
GAGATCCAGATGACCCAGTCTCCATCCTCCCTGTCTGCATCTGTAGGAGA
CCGTGTCACCATGACTTGCCGGGCAAGTCAGAGTATTGATAAGGATTTAG
AGTGGTACCAGCAGAAACCAGGGAAAGCCCCTAGGCTCCTGATCTATTCT
AGTTCCTGGTTGCAAAGAGGGGTCCCATCACGTTTCAGTGGGAGTGGATC
TGGGACAGATTTCACTCTCACCATCAGCAGTCTGCAACCTGAAGATTTTG
CTACGTACTACTGTCAACAGTATTTTCAGTATCCTCCGACGTTGGGCCAA
GGGACCAAGGTGGAAATCAAACGG

BMS2h-494-5 (SEQ ID NO: 1277)
GACATCCAGATGACCCAGTCTCCATCCTCCCTGTCTGCATCTGTAGGAGA
CCGAGTCACCATCACTTGCCGGGCAAGTCAGAGTATTGATGAGGATTTAG
AGTGGTACCAGCAGAAACCAGGGAAAGCCCCTAGGCTCCTGATCTATTCT
AGTTCCTGGTTGCAAAGTGGGGTCCCATCACGTTTCAGTGGGAGTGGATC
TGGGACAGATTTCACTCTCACCATCAGCGGTCTGCAACCTGAAGATATCG
CTACGTACTACTGTAAACAGTATTCTCAGTATCCTCCGACGTTCGGCCAA
GGGACCAAGGTGGAAATCAAACGG

BMS2h-494-6 (SEQ ID NO: 1278)
GACATCCAGATGACCCAGTCCCCACCCTCCCTGTCTGCATCTGTAGGAGA
CCGTGTCACCATCACTTGCCGGGCAAGTCAGAGTATTGATAAGGATTTAG
AGTGGTACCAGCAGAAACCAGGGAAAGCCCCTAGGCTCCTGATCTATTCT
AGTTCCTGGTTGCAAAGAGGGGTCCCATCACGTTTCAGTGGGAGTGGATC

TABLE 4-continued

Human Anti-CD40L VK Domain
Encoding Nucleotide Sequences

TGGGACAGATTTCACTCTCACCATCAGCAGTCTGCAACCTGAAGATTTTG
CTACGTACCACTGTCAACAGTATTTTCAGTATCCTCCGACGTTCGGCCAA
GGGACCAAGGTGGAAATCAAACGG

BMS2h-495 (SEQ ID NO: 1279)
GACATCCAGATGACCCAGTCTCCATCCTCCCTGTCTGCATCTGTAGGAGA
CCGTGTCACCATCACTTGCCGGGCAAGTGAGTATATTAATGCTGAGTTAG
CTTGGTATCAGCAGAAACCAGGGAAAGCCCCTAAGCTCCTGATCTATGGG
AGTTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCTGCAGAATGCGATGTGGCCTATTACGTTCGGCCAA
GGGACCAAGGTGGAAATCAAACGG

BMS2h-496 (SEQ ID NO: 1280)
GACATCCAGATGACCCAGTCTCCATCCTCCCTGTCTGCATCTGTAGGAGA
CCGTGTCACCATCACTTGCCGGGCAAGTCTGGATATTAATAATGGTTTAA
TTTGGTACCAGCAGAAACCAGGGAAAGCCCCTAGGCTCCTGATCTTGGGT
GCGTCCGGTTTGCAAAGTGGGGTCCCATCACGTTTCAGTGGCAGTGGATC
TGGGACAGATTTCACTCTCACCATCAGCAGTCTGCAAGCTGAAGATTTTG
CTACGTACTACTGTTCGCAGGTGCGTTCTCGGCCTTTTACGTTCGGCCAA
GGGACCAAGGTGGAAATCAAACGG

BMS2h-497 (SEQ ID NO: 1281)
GACATCCAGATGACCCAGTCTCCATCCTCCCTGTCTGCATCTGTAGGAGA
CCGTGTCACCATCACTTGCCGGGCAAGTCAGGATATTCTGAGTGCGTTAG
CTTGGTATCAGCAGAAACCAGGGAAAGCCCCTAAGCTCCTGATCTATGGG
AGTTCCGTTTTGCAAAGTGGGGTCCCATCACGTTTCAGTGGCAGTGGATC
AGGGACAGATTTCACTCTCACCATCAGCAGTCTGCAACCTGAAGATTTTG
CTACGTACTACTGTCAACAGAATTATAGTCTTCCTATTACGTTCGGCCAA
GGGACCAAGGTGGAAATCAAACGG

BMS2h-498 (SEQ ID NO: 1282)
GACATCCAGATGACCCAGTCTCCATCCTCCCTGTCTGCATCTGTAGGAGA
CCGTGTCACCATCACTTGCCGGGCAAGTTCTCCTATTGAGTCGTATTTAA
GGTGGTACCAGCAGAAACCAGGGAAAGCCCCTAAGCTCCTGATCAGGTAT
GTGTCCGTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTGGTTTCGGGCGCCTGTTACGTTCGGCCAA
GGGACCAAGGTGGAAATCAAACGG

BMS2h-499 (SEQ ID NO: 1283)
GACATCCAGATGACCCAGTCTCCATCCTCCCTGTCTGCATCTGTAGGAGA
CCGTGTCACCATCACTTGCCGGGTAAGTGAGTCTATTAATGCTGAGTTAC
ATTGGTACCAGCAGAAACCAGGGAAAGCCCCTAAGCTCCTGATCTCTGGG
TTTTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGTGCAGTTTGCGATGTGGCCTTTTACGTTCGGCCAA
GGGACCAAGGTGGAAATCAAACGG

BMS2h-500 (SEQ ID NO: 1284)
GACATCCAGATGACCCAGTCTCCATCCTCCCTGTCTGCATCTGTAGGAGA
CCGTGTCACCATCACTTGCCGGGCAAGTATGATGATTAGGTTTGGGTTAG
ATTGGTACCAGCAGAAACCAGGGAAAGCCCCTAAGCTCCTGATCGGTGGT
GGGTCCTCTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGCATGAGCGGTGGCCTGCTACGTTCGGCCAA
GGGACCAAGGTGGAAATCAAACGG

BMS2h-501 (SEQ ID NO: 1285)
GACATCCAGATGACCCAGTCTCCATCCTCCCTGTCTGCATCTGTAGGAGA
CCGTGTCACCATCACTTGCCGGGCAAGTCAGAGTATTGGTACTCTTTTAC
GTTGGTATCAGCAGAAACCAGGGAAAGCCCCTAAGCTCCTGATCTATCTT
ACTTCCGTTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGATGGTTTATCGTCCTTATACGTTCGGCCAA
GGGACCAAGGTGGAAATCAAACGG

BMS2h-502 (SEQ ID NO: 1286)
GACATCCAGATGACCCAGTCTCCATCCTCCCTGTCTGCATCTGTAGGAGA
CCGTGTCACCATCACTTGCCGGGCAAGTCAGACTATTGAGACTAATTTAG
AGTGGTACCAGCAGAAACCAGGGAAAGCCCCTAAGCTCCTGATCTATGAT
TCTTCCCAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATGATAAGGTTCCTGCGACGTTCGGCCAA
GGGACCAAGGTGGAAATCAAACGG

BMS2h-503 (SEQ ID NO: 1287)
GACATCCAGATGACCCAGTCTCCATCCTCCCTGTCTGCATCTGTAGGAGA
CCGTGTCACCATCACTTGCCGGGCAAGTCATCATATTCAGAGGTATTTAT
CGTGGTACCAGCAGAAACCAGGGAAAGCCCCTAAGCTCCTGATCCTTTGG
GGTTCCCAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTGGTGGGCTCCTCCTCCGACGTTCGGCCAA
GGGACCAAGGTGGAAATCAAACGG

BMS2h-503-1 (SEQ ID NO: 1288)
GACATCCAGATGACCCAGTCTCCATCCTCCCTGTCTGCATCTGTAGGAGA
CCGTGTCACCATCACTTGCCGGGCAAGTCATCATATTCAGAGGTATTTAT
CGTGGTACCAGCAGAAACCAGGGAAAGCCCCTAAGCTCCTGATCCTTTGG
GGTTCCCAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTGGTGGGCTCCTCCTCAGACGTTCGGCCAA
GGGACCAAGGTGGAAATCAAACGG

BMS2h-503-2 (SEQ ID NO: 1289)
GACATCCAGATGACCCAGTCTCCATCCTCCCTGTCTGCATCTGTAGGAGA
CCGTGTCACCATCACTTGCCGGGCAAGTCATGATATTCAGAGGTATTTAT
CGTGGTACCAGCAGAAACCAGGGAAAGCCCCTAAGCTCCTGATCCTTTGG
GGTTCCCAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTGGTGGGCTCCTCCTCAGACGTTCGGCCAA
GGGACCAAGGTGGAAATCAAACGG

BMS2h-504 (SEQ ID NO: 1290)
GACATCCAGATGACCCAGTCTCCATCCTCCCTGTCTGCATCTGTAGGAGA
CCGTGTCACCATCACATGCCGGGCAAGTCAGTATATTGATACTAATTTAG
AGTGGTACCAGCAGAAACCAGGGAAAGCCCCTAAGCTCCTGATCTATGAT
GGTTCCCTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGGGGCTGTTGTGCCTGTTACGTTCGGCCAA
GGGACCAAGGTGGAAATCAAACGG

BMS2h-508 (SEQ ID NO: 1291)
GACATCCAGATGACCCAGTCTCCATCCTCCCTGTCTGCATCTGTAGGAGA
CCGTGTCACCATCACTTGCCGGGCAAGTCAGGATATTGCTTTTGATTTAG
AGTGGTATCAGCAGAAACCAGGGAAAGCCCCTAAGCTCCTGATCTATTCG
GCGTCCATGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATAATCTTCAGCCTCCTACGTTCGGCCAA
GGGACCAAGGTGGAAATCAAACGG

BMS2h-509 (SEQ ID NO: 1292)
GACATCCAGATGACCCAGTCTCCATCCTCCCTGTCTGCATCTGTAGGAGA
CCGTGTCACCATCACTTGCCGGGCAAGTCAGAATATTGCTACGCTGTTAC
GTTGGTACCAGCAGAAACCAGGGAAAGCCCCTAAGCTCCTGATCTATGCT
GGTTCCATGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGATGTGGCAGCGTCCTTATACGTTCGGCCAA
GGGACCAAGGTGGAAATCAAACGG

BMS2h-51 (SEQ ID NO: 1293)
GACATCCAGATGACCCAGTCTCCATCCTCCCTGTCTGCATCTGTAGGAGA
CCGTGTCACCATCACTTGCCGGGCAAGTCAGCCTATTGTTGATGAGTTAG
ATTGGTACCAGCAGAAACCAGGGAAAGCCCCTAAGCTCCTGATCTATGCT
GCGTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCATCAGTGGTCTACTTATCCTACGACGTTCGGCCAA
GGGACCAAGGTGGAAATTAAACGG

BMS2h-510 (SEQ ID NO: 1294)
GACATCCAGATGACCCAATCTCCATCCTCCCTGTCTGCATCTGTAGGAGA
CCGTGTCACCATCACTTGCCGGGCAAGTCAGAGCATTAGCAGCTATTTAA
ATTGGTACCAGCAGAAACCAGGGAAAGCCCCTAAGCTCCTAATCGATGGT
GTTTCCGGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGGATTGGGATTGCCTCGTACGTTCGGCCAA
GGGACCAAGGTGGAAATCAAACGG

BMS2h-511 (SEQ ID NO: 1295)
GACATCCAGATGACCCAGTCTCCATCCTCCCTGTCTGCATCTGTAGGAGA
CCGTGTCACCATCACTTGCCGGGCAAGTAGGAATATTCGTGATTGGTTAC
GGTGGTACCAGCAGAAACCAGGGAAAGCCCCTAAGCTCCTGATCGATTGG

TABLE 4-continued

Human Anti-CD40L VK Domain Encoding Nucleotide Sequences

GGGTCCGTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCTCAGACGTGGGATGATCCTCTGACGTTCGGCCAA
GGGACCAAGGTGGAAATCAAACGG

BMS2h-511-1 (SEQ ID NO: 1296)
GACATCCAGATGACCCAGTCTCCATCCTCCCTGTCTGCATTTGTAGGAGA
CCGTGTCACCATCACTTGCCGGGCAAGTAGGAATATTCGTGATTGGTTAC
GGTGGTACCAACAGAAACCAGGGAAAGCCCCTAAGCTCCTGATCGATTGG
GGGTCCGAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCTCAGACGTGGTATGATCCTCTGACGTTCGGCCAC
GGGACCAAGGTGGAAATCAAACGG

BMS2h-512 (SEQ ID NO: 1297)
GACATCCAGATGACCCAGTCTCCATCCTCCCTGTCTGCATCTGTAGGAGA
CCGTGTCACCATCACTTGCCGGGCAAGTATTGATATTCATGGTGGTTTAA
CTTGGTACCAGCAGAAACCAGGGAAAGCCCCTAAGCTCCTGATCGTGGGG
GTTTCCGGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGTGCGCAGGTGTGGCGTAGGCCTTTTACGTTCGGCCAA
GGGACCAAGGTGGAAATCAAACGG

BMS2h-513 (SEQ ID NO: 1298)
GACATCCAGATGACCCAGTCTCCATCCTCCCTGTCTGCATCTGTAGGAGA
CCGTGTCACCATCACTTGCCGGGCAAGTCAGGATATTGGGAGTTCGTTAT
CTTGGTATCAGCAGAAACCAGGGAAAGCCCCTAAGCTCCTGATCTATGCT
TCTTCCCTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGACTTATGCTCTTCCTGTTACGTTCGGCCAA
GGGACCAAGGTGGAAATCAAACGG

BMS2h-514 (SEQ ID NO: 1299)
GACATCCAGATGACCCAGTCTCCATCCTCCCTGTCTGCATCTGTAGGAGA
CCGTGTCACCATCACTTGCCGGGCAAGTCAGCAGATTGAGACGAATTTAG
AGTGGTATCAGCAGAAACCAGGGAAAGCCCCTAAGCTCCTGATCTATGAT
GGTTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATAAGTATCTGCCTGTGACGTTCGGCCAA
GGGACCAAGGTGGAAATCAAACGG

BMS2h-52 (SEQ ID NO: 1300)
GACATCCAGATGACCCAGTCTCCATCCTCCCTGTCTGCATCTGTAGGTGA
CCGTGTCACCATCACTTGCCGGGCAAGTCAGGATATTGGGTCTGCGTTAA
GGTGGTATCAGCAGAAACCAGGGAAAGCCCCTAAGCTCCTGATCTATTTG
GGTTCCGATTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGACAGTATTTTCCTACGACGTTCGGCCAA
GGGACCAAGGTGGAAATCAAACGG

BMS2h-53 (SEQ ID NO: 1301)
GACATCCAGATGACCCAGTCTCCATCCTCCCTGTCTGCATCTGTAGGAGA
CCGTGTCACCATCACTTGCCGGGCAAGTCAGGCGATTTATGGGGGGTTAC
GGTGGTACCAGCAGAAACCAGGGAAAGCCCCTAAGCTCCTGATCTATGGG
GAGTCCATGTTGCAAAGTGGGGTCCCATCACGTTTCAGTGGCAGTGGATC
TGGGACAGATTTCACTCTCACCATCAGCAGTCTGCATCTGAAGATTTTG
CTACGTACTACTGTCAACAGGTTTATCATAAGCCTTTTACGTTCGGCCAA
GGGACCAAGGTGGAAATCAAACGG

BMS2h-536 (SEQ ID NO: 1302)
GACATCCAGATGACCCAGTCTCCATCCTCCCTGTCTGCATCTGTAGGAGA
CCGTGTCACCATCACGTGCCGGGCAAGTCAGCGTATTGGGGTGTGGTTAG
ATTGGTATCAGCAGAAACCAGGGAAAGCCCCTAAGCTCCTGATCTATGAT
GGTTCCTTTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGACTTTTTGAGTCCTTCTACGTTCGGCCAA
GGGACCAAGGTGGAAATCAAACGG

BMS2h-537 (SEQ ID NO: 1303)
GACATCCAGATGACCCAGTCTCCATCCTCCCTGTCTGCATCTGTAGGAGA
CCGTGTCCCCATCACTTGCCGGGCAAGTCAGTGGATTGGGGATGAGTTAT
ATTGGTATCAGCAGAAACCAGGGAAAGCCCCTAAGCTCCTGATCTATAGT
TCTTCCACTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTCGTTTCAGTTTCCTTATACGTTCGGCCAA
GGGACCAAGGTGGAAATCAAACGG

BMS2h-538 (SEQ ID NO: 1304)
GACATCCAGATGACCCAGTCTCCATCCTCCCTGTCTGCATCTGTAGGAGA
CCGTGTCACCATCACTTGCCGGGCAAGTAGTAATATTACGGGGCCGTTAG
AGTGGTACCAGCAGAAACCAGGGAAAGCCCCTAAGCTCCTGATCCCTGGT
TGGTCCACTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGTCAGGTGTGGGGGGAGCCTGTTACGTTCGGCCAA
GGGACCAAGGTGGAAATCAAACGG

BMS2h-539 (SEQ ID NO: 1305)
GACATCCAGATGACCCAGTCTCCATCCTCCCTGTCTGCGTCTATAGGAGA
CCGTGTCACCATCACTTGCCGGGCAAGTCAGCGTATTGCTTATGGTTTAC
ATTGGTACCAGCAGAAACCAGGGAAAGCCCCTAAGCTCCTGATCGGGGGG
CGGTCCGGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGTGCAGCCTGGGATGCCGCCTGATACGTTCGGCCAA
GGGACCAAGGTGGAAATCAAACGG

BMS2h-540 (SEQ ID NO: 1306)
GACATCCAGATGACCCAGTCTCCATCCTCCCTGTCTGCATCTGTAGGAGA
CCGTGTCACCATCACTTGCCGGGCAAGTAAGCAGATTGTTGGTGGTTTAT
CTTGGTACCAGCAGAAACCAGGGAAAGCCCCTAAGCTCCTGATCGGGCGT
CATTCTGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGTGCAGGGGGTTTGGGCTCCTGGGACGTTCGGCCAA
GGGACCAAGGTGGAAATCAAACGG

BMS2h-541 (SEQ ID NO: 1307)
GACATCCAGATGACCCAGTCTCCATCCTCCCTGTCTGCATCTGTAGGAGA
CCGTGTCACCATCACTTGCCGGGCAAGTCCTGCTATTGCTGCTAAGTTAG
ATTGGTACCAGCAGAAACCAGGGAAAGCCCCTAAGCTCCTGATCGTGCG
GATTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGTCAGCTGTGGGCGGGGCCTCCGACGTTCGGCCAA
GGGACCAAGGTGGAAATCAAACGG

BMS2h-542 (SEQ ID NO: 1308)
GACATCCAGATGACCCAGTCTCCATCCTCCCTGTCTGCATCTGTAGGAGA
CCGTGTCACCATCACTTGCCGGGCAAGTCGTACTATTGCTGATGGGTTAG
ATTGGTACCAGCAGAAACCAGGGAAAGCCCCTAAGCTCCTGATCGGGGCG
TATTCCGGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGCTTTGGGAGGGTCCTCCGACGTTCGGCCAA
GGGACCAAGGTGGAAATCAAACGG

BMS2h-543 (SEQ ID NO: 1309)
GACATCCAGATGACCCAGTCTCCATCCTCCCTGTCTGCATCTGTAGGAGA
CCGTGTCACCATCACTTGCCGGGCAAGTCAGAGGATTTATGGGTTTTAG
ATTGGTATCAGCAGAAACCAGGGAAAGCCCCTAAGCTCCTGATCTATGGG
GTGTCCTCGTTGCAAAGTGGGGTCCCATCACGTTTTAGTGGCAGCGGATC
TGGGACAGATTTCACTCTCACCATCAGCAGTCTGCAACCTGAAGATTTTG
CTACGTACTACTGTCAACAGACTTTGGCGTGGCCTTTTACGTTCGGCCAA
GGGACCAAGGTGGAAATCAAACGG

BMS2h-544 (SEQ ID NO: 1310)
GACATCCAGATGACCCAGTCTCCATCCTCCCTGTCTGCATCTGTAGGAGA
CCGTGTCACCATCACTTGCCGGGCAAGTCAGGATATTCGGGATTGGTTAA
TGTGGTACCAGCAGAAACCAGGGAAAGCCCCTAAGCTCCTGATCTATTGG
GGTTCCTTTTTGCAAAGTGGGTCCCATCACGTTTCAGTGGCAGTGGATC
TGGGACAGATTTCACTCTCACCATCAGCAGTCTGCAACCTGAAGATTTTG
CTACGTACTACTGTCAACAGCTGTATGATACTCCTTATACGTTCGGCCAA
GGGACCAAGGTGGAAATCAAACGG

BMS2h-545 (SEQ ID NO: 1311)
GACATCCAGATGACCCAGTCTCCATCCTCCCTGTCTGCATCTGTAGGAGA
CCGTGTCACCATCACTTGCCGGGCAAGTCAGAATATTAATACGGGTTTAG
ATTGGTATCAGCAGAAACCAGGGAAAGCCCCTAAGCTCCTGATCTATGAT
AGTTCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGACGTCGTATTATCCTTATACGTTCGGCCAA
GGGACCAAGGTGGAAATCAAACGG

BMS2h-546 (SEQ ID NO: 1312)
GACATCCAGATGACCCAGTCTCCATCCTCCCTGTCTGCATCTGTAGGAGA
CCGTGTCACCATCACTTGCCGGGCAAGTCAGAAGATTTTGGTTGGTTAG
ATTGGTACCAGCAGAAACCAGGGAAAGCCCCTAAGCTCCTGATCTATGGG
ACTTCCAAGTTGCAAAGTGGGGTCCCATCACGTTTCAGTGGCAGTGGATC

TABLE 4-continued

Human Anti-CD40L VK Domain
Encoding Nucleotide Sequences

TGGGACAGATTTCACTCTCACCATCAGCAGTCTGCAACCTGAAGATTTTG
CTACGTACTACTGTCAACAGGTTTATTCGCTTCCTTATACGTTCGGCCAA
GGGACCAAGGTGGAAATCAAACGG

BMS2h-547 (SEQ ID NO: 1313)
GACATCCAGATGACCCAGTCTCCATCCTCCCTGTCTGCATCTGTAGGAGA
CCGTGTCACCATCACTTGCCGGGCAAGTTCGAATATTGGGGCGGATTTAG
ATTGGTACCAGCAGAAACCAGGGAAAGCCCCTAAGCTCCTGATCGGGGGG
GCGTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGCTGTGGAATGGGCCTCCTACGTTCGGCCAA
GGGACCAAGGTGGAAATCAAACGG

BMS2h-548 (SEQ ID NO: 1314)
GACATCCAGATGACCCAGTCTCCATCCTCCCTGTCTGCATCTGTAGGAGA
CCGTGTCACCATCACTTGCCGGGCAAGTAGTCCGATTTATGATGGTTTAG
ATTGGTACCAGCAGAAACCAGGGAAAGCCCCTAAGCTCCTGATCTCTGGT
GCTTCCTGGTTGCAAAGTGGGGTCCCATCACGTTCAGTGGCAGTGGATC
TGGGACAGATTTCACTCTCACCATCAGCAGTCTGCAACCTGAAGATTTTG
CTACGTACTACTGTGGTCAGTTGTGGTTGGGTCCTCCGACGTTCGGCCAA
GGGACCAAGGTGGAAATCAAACAG

BMS2h-549 (SEQ ID NO: 1315)
GACATCCAGATGACCCAGTCTCCATCCTCCCTGTCTGCATCTGTAGGAGA
CCGTGTCACCATCACTTGCCGGGCAAGTTCGCGTATTTATAATGGTTTAC
ATTGGTACCAGCAGAAACCAGGGAAAGCCCCTAAGCTCCTGATCGGTGGT
CGGTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCTCAGGTGGGGGAGGCTCCTTCTACGTTCGGCCAA
GGGACCAAGGTGGAAATCAAACGG

BMS2h-550 (SEQ ID NO: 1316)
GACATCCAGATGACCCAGTCTCCATCCTCCCTGTCTGCATCTGTAGGAGA
CCGTGTCACCATCACTTGCCGGGCAAGTAGGTTTATTAATGAGGAGTTAG
ATTGGTACCAGCAGAAACCAGGGAAAGCCCCTAAGCTCCTGATCTCGTGG
TCTTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGTGCAGCCGGGGGTGGTCCTGGGACGTTCGGCCAA
GGGACCAAGGTGGAAATCAAACGG

BMS2h-551 (SEQ ID NO: 1317)
GACATCCAGATGACCCAGTCTCCATCCTCCCTGTCTGCATCTGTAGGAGA
CCGTGTCACCATCACTTGCCGGGCAAGTAGGGATATTCTGGATGAGTTAG
ATTGGTACCAGCAGAAACCAGGGAAAGCCCCTAGGCTCCTGATCGGTGGG
GGGTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGTCAGCTGTGGCATGGGCCTCCGACGTTCGGCCAA
GGGACCAAGGTGGAAATCAAACGG

BMS2h-552 (SEQ ID NO: 1318)
GACATCCAGATGACCCAGTCTCCATCCTCCCTGTCTGCATCTGTAGGAGA
CCGTGTCACCATCACTTGCCGGGCAAGTAGTCCTATTTATACGGTTTAC
ATTGGTACCAGCAGAAACCAGGGAAAGCCCCTAAGCTCCTGATCGGTGGG
CGGTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTATGCAGGTTGGGACGGCTCCTGCTACGTTCGGCCAA
GGGACCAAGGTGGAAATCAAACGG

BMS2h-585 (SEQ ID NO: 1319)
GACATCCGGATGACCCAGTCTCCATCCTCCCTGTCTGCATCTGTAGGAGA
CCGTGTCACCATCACTTGCCGGGCAAGTCAGAATATTTCTAGGCGGTTAC
TGTGGTACCAGCAGAAACCAGGGAAAGCCCCTAAGCTCCTGATCTATTCT
TCTTCCCGGTTCAAAGTGGGGTCCCATCACGTTTCGGTGGCAGTGGATC
TGGGACGGATTTCACTCTCACCATCAGCAGTCTGCAACCTGAAGATTTTG
CTACGTACTACTGTCAACAGACGTATACCTCATACGTTCGGCCAA
GGGACCAAGGTGGAAATCAAACGG

BMS2h-604 (SEQ ID NO: 1320)
GACATCCAGATGACCCAGTCTCCATCCTCCCTGTCTGCATCTGTAGGAGA
CCGTGTCACCATCACTTGCCGGGCAAGTAGTCCGATTCCGCAGGATTTAT
ATTGGTACCAGCAGAAACCAGGGAAAGCCCCTAAGCTCCTGATCGTTGGG
ATTTCCCAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTTGTGGAGTGCGCCTGCTACGTTCGGCCAA
GGGACCAAGGTGGAAATCAAACGG

BMS2h-605 (SEQ ID NO: 1321)
GACATCCAGATGACCCAGTCTCCATCCTCCCTGTCTGCATCTGTAGGAGA
CCGTGTCACCATCACTTGCCGGGCAAGTAAGTCTATTGATGGGATGTTAG
ATTGGTACCAGCAGAAACCAGGGAAAGCCCCTAAGCTCCTGATCCCTGGT
TTTTCCGGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTCGGTTGAGGCGCCTTGGACGTTCGGCCAA
GGGACCAAGGTGGAAATCAAACGG

BMS2h-606 (SEQ ID NO: 1322)
GACATCCAGATGACCCAGTCTCCATCCTCCCTGTCTGCATCTGTAGGAGA
CCGTGTCACCATCACTTGCCGGGCAAGTCGGTATATTGCTCATCCTTTAG
ATTGGTACCAGCAGAAACCAGGGAAAGCCCCTAAGCTCCTGATCCCGGGT
TCGTCCGTTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGTCAGTCGGTTGTGGTGCCTTGGACGTTCGGCCAA
GGGACCAAGGTGGAAATCAAACGG

BMS2h-607 (SEQ ID NO: 1323)
GACATCCAGATGACCCAGTCTCCATCCTCCCTGTCTGCATCTGTAGGAGA
CCGTGTCACCATCACTTGCCGGGCAAGTCGGACGATTGAGGGTGGTTTAG
ATTGGTACCAGCAGAAACCAGGGAAAGCCCCTAAGCTCCTGATCATGGGG
GGTTCCGGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTTGTGGGTGGGTCCTCCTACGTTCGGCCAA
GGGACCAAGGTGGAAATCAAACGG

BMS2h-608 (SEQ ID NO: 1324)
GACATCCAGATGACCCAGTCTCCATCCCTGTCTGCATCTGTAGGAGA
CCGTGTCACCATCACTTGCCGGGCAAGTAAGTTTATTAGGGATGAGTTAT
ATTGGTACCAGCAGAAACCAGGGAAAGCCCCTAGGCTCCTGATCGGTGGT
TCGTCCTTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGCAGTGGCGGGCGCCTGCGACGTTCGGCCAA
GGGACCAAGGTGGAAATCAAACGG

BMS2h-609 (SEQ ID NO: 1325)
GACATCCAGATGACCCAGTCTCCATCCTCCCTGTCTGCATCTGTAGGAGA
CCGTGTCACCATCACTTGCCGGGCAAGTAAGCCGATTTATGGTGGTTTAG
AGTGGTACCAGCAGAAACCAGGGAAAGCCCCTAGGCTCCTGATCGGGGGG
GGTTCCGTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGGTGTGGGGGGGTCCTGTTACGTTCGGCCAA
GGGACCAAGGTGGAAATCAAACGG

BMS2h-610 (SEQ ID NO: 1326)
GACATCCGGATGACCCAGTCTCCATCCTCCCTGTCTGCATCTGTAGGAGA
CCGTGTCACCATCACTTGCCGGGCAAGTCGGCCGATTAGTGGTTGTTTAG
ATTGGTACCAGCAGAAACCAGGGAAAGCCCCTAAGCTCCTGATCGATGGG
GCTTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTGGTGGGAGTATCCTCCTACGTTCGGCCAA
GGGACCAAGGTGGAAATCAAACGG

BMS2h-611 (SEQ ID NO: 1327)
GACATCCAGATGACCCAGTCTCCATCCTCCCTGTCTGCATCTGTAGGAGA
CCGTGTCACCATCACTTGCCGGGCAAGTAAGCCTATTGTGAGGGATTAG
AGTGGTACCAGCAGAAACCAGGGAAAGCCCCTAAGCTCCTGATCCATGGT
GTGTCCACGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGCTTGAGGCGGCGCCTGCGACGTTCGGCCAA
GGGACCAAGGTGGAAATCAAACGG

BMS2h-612 (SEQ ID NO: 1328)
GACATCCAGATGACCCAGTCTCCATCCTCCCTGTCTGCATCTGTAGGAGA
CCGTGTCACCATCACTTGCCGGGCAAGTCGGGATATTGGTGATTGGTTAT
ATTGGTACCAGCAGAAACCAGGGAAAGCCCTAGGCTCCTGATCGTTGGG
GCGTCCGTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGTGGGGACTCCTCCTACGACGTTCGGCCAA
GGGACCAAGGTGGAAATCAAACGG

BMS2h-613 (SEQ ID NO: 1329)
GACATCCAGATGACCCAGTCTCCATCCTCCCTGTCTGCATCTGTAGGAGA
CCGTGTCACCATCACTTGCCGGGCAAGTAATCGTATTGAGTATGGTTTAG
ATTGGTACCAGCAGAAACCAGGGAAAGCCCCTAAGCTCCTGATCTCGGGG

TABLE 4-continued

Human Anti-CD40L VK Domain
Encoding Nucleotide Sequences

TCTTCCCGTTTGCAAAGTGGGGTCCCATCACGTTTCAGTAGCAGTGGATC
TGGGACAGATTTCACTCTCACCATCAGCAGTCTGCAACCTGAAGATTTTG
CTACGTACTACTGTGGGCAGCTTGAGGCGGCGCCTGCGACGTTCGGCCAA
GGGACCAAGGTGGAAATCAAACGG

BMS2h-614 (SEQ ID NO: 1330)
GACATCCAGATGACCCAGTCTCCATCCTCCCTGTCTGCATCTGTAGGAGA
CCGTGTCACCATCACTTGCCGGGCAAGTCGGAATATTGGGCATTTTTTAG
ATTGGTACCAGCAGAAACCAGGGAAAGCCCCTAAGCTCCTGATCTTGGGG
GGGTCCTCGTTTGCAAAGTGGGGTCCCATCACGTTTCAGTGGCAGCGGGTC
TGGGACAGATTTCACTCTCACCATCAGCAGTCTGCAACCTGAAGATTTTG
CTACGTACTACTGTGGGCAGTTGGTGGAGCCTCCTGCGACGTTCGGCCAA
GGGACCAAGGTGGAAATCAAACGG

BMS2h-615 (SEQ ID NO: 1331)
GACATCCAGATGACCCAGTCTCCATCCTCCCTGTCTGCATCTGTAGGAGA
CCGTGTCACCATCACTTGCCGGGCAAGTTCGAGTATTTATAGTGATTTAT
ATTGGTACCAGCAGAAACCAGGGAAAGCCCCTAAGCTCCTGATCGATGGG
TGGTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGCTGCATCGTGCTCCTGCGACGTTCGGCCAA
GGGACCAAGGTGGAAATCAAACGG

BMS2h-616 (SEQ ID NO: 1332)
GACATCCAGATGACCCAGTCTCCATCCTCCCTGTCTGCATCTGTAGGAGA
CCGTGTCACCATCACTTGCCGGGCAAGTAGGTTTATTACTGATCGTTTAG
ATTGGTACCAGCAGAAACCAGGGAAAGCCCCTAAGCTCCTGATCGGTGGT
GTTTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGAGTTCGGAGTTGCCTTGGACGTTCGGCCAA
GGGACCAAGGTGGAAATCAAACGG

BMS2h-617 (SEQ ID NO: 1333)
GACATCCAGATGACCCAGTCTCCATCCTCCCTGTCTGCATCTGTAGGAGA
CCGTGTCACCATCACTTGCCGGGCAAGTCGTAAGATTGGTAGTGAGTTAT
ATTGGTACCAGCAGAAACCAGGGAAAGCCCCTAAGCTCCTGATCGGTGGT
AGGTCCCGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGTTGTGGGAGCCTCCTGCGACGTTCGGCCAA
GGGACCAAGGTGGAAATCAAACGG

BMS2h-618 (SEQ ID NO: 1334)
GACATCCAGATGACCCAGTCTCCATCCTCCCTGTCTGCATCTGTAGGAGA
CCGTGTCACCATCACTTGCCGGGCAAGTAGGAATATTGGTAATGGTTTAG
ATTGGTACCAGCAGAAACCAGGGAAAGCCCCTAAGCTCCTGATCGGGGAG
GGGTCCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGGGCAGCTTTGGCATACTCCTCCTACGTTCGGCCAA
GGGACCAAGGTGGAAATCAAACGG

BMS2h-619 (SEQ ID NO: 1335)
GACATCCAGATGACCCAGTCTCCATCCTCCCTGTCTGCATCTGTAGGAGA
CCGTGTCACCATCACTTGCCGGGCAAGTCGGAATATTTATGGTTGGTTAT
CGTGGTACCAGCAGAAACCAGGGAAAGCCCCTAGGCTCCTGATCGGTGGG
TGGTCCGGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGGATTATACGTTGCCTGGTACGTTCGGCCAA
GGGACCAAGGTGGAAATCAAACGG

BMS2h-730 (SEQ ID NO: 1336)
GACATCCAGATGACCCAGTCTCCATCCTCCCTGTCTGCATCTGTAGGAGA
CCGTGTCACCATCACTTGCCGGGCAAGTCAGGATATTAAGGATTGGTTAC
ATTGGTACCAGCAGAAACCAGGGAAAGCCCCTAAGCTCCTGATCTATTTT
GCGTCCGGTTTGCAAAGTGGGGTCCCATCACGTTTCAGTGGCAGTGGATC
TGGGACAGATTTCACTCTCACCATCAGCAGTCTGCAACCTGAAGATTCTG
CTACGTACTACTGTCAACAGCATTATAGTACGCCTTATACGTCCGGCCAA
GGGACCAAGGTGGAAATCAAACGG

BMS2h-731 (SEQ ID NO: 1337)
GACATCCAGATGACCCAGTCTCCACCCTCCCTGTCTGCATCTGTAGGAGA
CCGTGTCACCATCACTTGCCGGGCAAGTCAGTTGATTTCTTCTCATTTAG
ATTGGTACCAGCAGAAACCAGGGAAAGCCCCTAAGCTCCTGATCTATGAT
GCTTCCGAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGCATCGCAGTCTGCCTTTTACGTTCGGCCAA
GGGACCAAGGTAGAAATCAAACGG

BMS2h-732 (SEQ ID NO: 1338)
GACATCCAGATGACCCAGTCTCCATCCTCCCTGTCTGCATCTGTAGGAGA
CCGTGTCACCATCACTTGCCGGGCAAGTCAGTGGATTGGTGGGCGTTAG
CGTGGTACCAGCAGAAACCAGGGAAAGCCCCTAGGCTCCTTATCTATCAG
ATTTCCGTTTGCAAAGTGGGATCCCATCACGTTTCAGTGGCAGTGGATC
TGGGACAGATTTCACTCTCACCATCAGCAGTCTGCAACCTGAAGATTTTG
CTACGTACTACTGTCAACAGTATATTCGGTCTCCTTTTACGTTCGGCCAA
GGGACCAAGGTGGAAATCAAACGG

BMS2h-733 (SEQ ID NO: 1339)
GACATCCAGATGACCCAGTCTCCATCCTCCCTGTCTGCATCTGTAGGAGA
CCGTGTCACCATCACTTGCCGGGCAAGTCAGAGTATTGGGGCGGCGTTAA
ATTGGTATCAGCAGAAACCAGGGAAAGCCCCTAAGCTCCTGATCTATGGT
CTGTCCTCTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGCTGTTTAGGCTTCCTTTTGACGTTCGGCCAA
GGGACCAAGGTGGAAATCAAACGG

BMS2h-734 (SEQ ID NO: 1340)
GACATCCAGATGACCCAGTCTCCATCCTCCCTGTCTGCATCTGTAGGAGA
CCGTGTCACCATCACTTGCCGGGCAAGTCAGCCTATTGGGGGTCGTTTAG
TGTGGTACCAGCAGAAACCAGGGAAAGCCCCTAAGCTCCTGATCTATGGG
TCTTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTATGCTGAGGCTCCTATTACGTTCGGCCAA
GGGACCAAGGTGGAAATCAAACGG

BMS2h-735 (SEQ ID NO: 1341)
GACATCCAGATGACCCAGTCTCCATCCTCCCTGTCTGCATCTGTAGGAGA
CCGTGTCACCATCACTTGCCGGGCAAGTCAGAATATTGGGTCTAGTTTAA
TTTGGTACCAGCAGAAACCAGGGAAAGCCCCTACGCTCCTGATCTATTAT
TCGTCCAAGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTCTTTGTCGAGTCCTTATACGGTCGGCCAA
GGGACCAAGGTGGAAATCAAACGG

BMS2h-736 (SEQ ID NO: 1342)
GACATCCAGATGACCCAGTCTCCATCCTCCCTGTCTGCATCTGTAGGAGA
CCGTGTCACCATCACTTGCCGGGCAAGTCAGTATTGGGAGTGAGTTAG
CGTGGTATCAGCAGAAACCAGGGAAAGCCCCTAAGCTCCTGATCTATTGG
ACGTCCAATTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGTCAACAGATTCGGAGACTCCTTTGACGTTTGGCCAA
GGGACCAAGGTGGAAATCAAACGG

BMS2h-737 (SEQ ID NO: 1343)
GACATCCAGATGACCCAGTCTCCATCCTCCCTGTCTGCATCTGTAGGAGA
CCGTGTCACCATCACTTGCCGGGCAAGTCAGAAGATTTGGGATGCTTTAT
ATTGGTATCAGCAGAAACCAGGGAAAGCCCCTAAGCTCCTGATCTATCGT
GGGTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTTTTATCGGTGCCTCATACGTTCGGCCAA
GGGACCAAGGTGGAAATCAAACGG

BMS2h-738 (SEQ ID NO: 1344)
GACATCCAGATGACCCAGTCTCCATCCTCCCTGTCTGCATCTGTAGGAGA
CCGTGTCACCATCACTTGCCGGGCAAGTCAGCATATTGAGGATTCTTTAC
GGTGGTACCAGCAGAAACCAGGGAAAGCCCCTAAGCTCCTGATCTATTAT
GGTTCCGTGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGATGTATAAGTTTCCTATTACGTTCGGCCAA
GGGACCAAGGTGGAAATCAAACGG

BMS2h-739 (SEQ ID NO: 1345)
GACATCCAGACGACCCAGTCTCCATCCTCCCTGTCTGCATCTGTAGGAGA
CCGTGTCACCATCACTTGCCGGGCAAGTCAGCGGATTAATTCTTCTTTAC
TGTGGTACCAGCAGAAACCAGGGAAAGCCCCTAAGCTCCTGATCTATGAT
ACTTCCGTTTGCAAAGTGGGGTCCCATCACGTTTCAGTGGCAGTAGATC
TGGGACAGATTTCACTCTCACCATCAGCAGTCTGCAACCTGAAGATTTCG
CTACGTACTACTGTCAACAGATTTGGGGTTCGCCTCCTACGTTCGGCCAG
GGGACCAAGGTGGAAATCAAACGG

BMS2h-740 (SEQ ID NO: 1346)
GACATCCAGATGACCCAGTCTCCATCCTCCCTGTCTGCATCTGTAGGAGA
CCGTGTCACCATCACTTGCCGGGCAAGTCAGTCGATTCCTGTTGGTTTAA
ATTGGTACCAGCAGAAACCAGGGAAAGCCCCTAGGCTCCTGATCTATTCT
GGGTCCACTTTGCAAAGTGGGGTCCCATCACGTTTCAGTGGCAGTGGATC

TABLE 4-continued

Human Anti-CD40L VK Domain
Encoding Nucleotide Sequences

TGGGACAGATTTCACTCTCACCATCAGCAGTCTGCAACCTGAAGATTTTG
CTACGTACTACTGTCAACAGGATTGGTATTATCCTAATACGTTCGGCCAA
GGGACCAAGGTGGAAATCAAACGG

BMS2h-785 (SEQ ID NO: 1347)
GACATCCAGATGACCCAGTCTCCATCCTCCCTGTCTGCATCTGTAGGAGA
CCGTGTCACCATCACTTGCCGGGCAAGTCAGCCTATTTATGTTGGTTAA
ATTGGTATCAGCAGAAACCAGGGAAAGCCCCTAAGCTCCTGATCTATTTG
ACGTCCGGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGATTCATAGTTCTCCTTTTACGTTCGGCCAA
GGGACCAAGGTGGAAATCAAACGG

BMS2h-8 (SEQ ID NO: 1348)
GACATCCAGATGACCCAGTCTCCATCCTCCCTGTCTGCATCTGTAGGAGA
CCGTGTCACCATCACTTGCCGGGCAAGTCAGTTTATTGATACGTCGTTAG
AGTGGTATCAGCAGAAACCAGGGAAAGCCCCTAAGCTCCTGATCTATGAT
GGGTCCCATTTGCAAAGTGGGGTCCCATCACGTTTCAGTGGCAGTGGATC
TGGGACAGATTTCACTCTCACCATCAGCAGTCTGCAACCTGAAGATTTAG
CTACGTACTACTGTCAACAGTATTGGGTTCTTCCTCTGACGTTCGGCCAA
GGGACCAAGGTGGAAATCAAACGG

BMS2h-86 (SEQ ID NO: 1349)
GACATCCAGATGACCCAGTCTCCATCCTCCCTGTCTGCATCTGTAGGAGA
CCGTGTCACCATCACTTGCCGGGCAAGTCAGGATATTGGGGATGCTTTAT
TTTGGTACCAGCAGAAACCAGGGAAAGCCCCTAAGCTCCTGATCTATTAT
TCTTCCATGTTGCAAAGTGGGGTCCCATCACGTTTCAGTGGCGGTGGATC
TGGGACAGATTTCACTCTCACCATCAGCAGTCTGCAACCTGAAGATTTTG
CTACGTACTACTGTCAACAGCGGCATAGTACTCCTGCTACGTTCGGCCAA
GGGACCAAGGTGGAAATCAAACGG

BMS2h-87 (SEQ ID NO: 1350)
GACATCCAGATGACCCAGTCTCCATCCTCCCTGTCTGCATCTGTAGGAGA
CCGTGTCACCATCACTTGCCGGGCAAGTCAGGATATTGATGAGTCTTTAA
TGTGGTACCAGCAGAAACCAGGGAAAGCCCCTAGGCTCCTGATCTATGGG
GTGTCCTATTTGCAAAGTGGGGTCCCATCACGTTTCAGTGGCAGTGGATC
TGGGACAGATTTCACTCTCACCATCAGCAGTCTGCAACCTGAAGATTTCG
CTACGTACTACTGTCAACAGCGGTGGAAGGCTCCTTTTACGTTCGGCCAA
GGGACCAAGGTGGAAATCAAACGG

BMS2h-88 (SEQ ID NO: 1351)
GACATCCAGATGACCCAGTCTCCATCCTCCCTGTCTGCATCTGTAGGAGA
CCGTGTTACCATCACTTGCCGGGCAAGTCAGGAGATTGGAAGGATTTAT
ATTGGTATCAGCAGAAACCAGGGAAAGCCGCTAAGCTCCTGATCTATGGT
GCGTCCTGGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGACGCGTAGGCGTCCTTATACGTTCGGCCAA
GGGACCAAGGTGGAAATCAAACGG

BMS2h-89 (SEQ ID NO: 1352)
GACATCCAGATGACCCAGTCTCCAGCCTCCCTGTCTGCATCTGTAGGAGA
CCGTGTCACCATCACTTGCCGGGCAAGTCAGGATATTGATCCTATGTTAA
GGTGGTACCAGCAGAAACCAGGGAAAGCCCCTAAGCTCCTGATCTATGCG
GGTTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGACGGTGGTGACTCCTTATACGTTCGGCCAA
GGGACCAAGGTGGAAATCAAACGG

BMS2h-90 (SEQ ID NO: 1353)
GACATCCAGATGACCCAGTCTCCATCCTCCCTGTCTGCATCTGTAGGAGA
CCGTGTCACCATCACTTGCCGGGCAAGTCAGTCGATTTCGGATGCGTTAT
TTTGGTACCAGCAGAAACCAGGGAAAGCCCCTAGGCTCCTGATCTATTAT
GGTTCCGTTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGCGTTTTCAGGAGCCTGTGACGTTCGGCCAA
GGGACCAAGGTGGAAATCAAACGG

BMS2h-91 (SEQ ID NO: 1354)
GACATCCAGATGACCCAGTCTCCATCCTCCCTGTCCGCATCTGTAGGAGA
CCGTGTCACCATCACTTGCCGGGCAAGTCAGCAGATTAGTGATGAGTTAA
ATTGGTATCAGCAGAAACCAGGGAAAGCCCCTAAGCTCCTGATCTATGCT
GTGTCCATTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTCAACAGTGGTTGAGTTTTCCTTCGACGTTTGGCCAA
GGGACCAAGGTGGAAATCAAACGG

Example 1

Generation of Human Anti-CD40L Variable Domains BMS2h-2 Through BMS2h-785

The following example describes the generation of the 2h lineage of anti-human CD40L variable domains, designated BMS2h-2 through BMS2h-785. Following recombinant expression of a repertoire of single immunoglobulin variable domains on the surface of phage, selection is performed by contacting the phage repertoire with immobilized target antigen, washing to remove unbound phage, and propagating the bound phage. This process is frequently referred to as "panning." It is applicable to the screening of single immunoglobulin variable domains, as well as other antibody fragments that can be expressed on a display library, e.g., scFv, Fab, and Fab'. Alternatively, phage may be pre-selected for the expression of properly folded member variants by panning against an immobilized generic ligand (e.g., protein A or protein L) that is only bound by folded members. This has the advantage of reducing the proportion of non-functional members, thereby increasing the proportion of members likely to bind a target antigen. Pre-selection with generic ligands is taught in WO 99/20749, for example. The screening of phage antibody libraries is generally described, for example, by Harrison et al., *Meth. Enzymol.* 267: 83-109 (1996).

Screening is commonly performed using purified antigen immobilized on a solid support, for example, plastic tubes or wells, or on a chromatography matrix, for example Sepharose™ (Pharmacia). Screening or selection can also be performed on complex antigens, such as the surface of cells (Marks et al., *BioTechnology* 11: 1145 (1993); de Kruif et al., *Proc. Natl. Acad. Sci. USA* 92: 3938 (1995)). Another alternative involves selection by binding biotinylated antigen in solution, followed by capture on streptavidin-coated beads.

dAb Selection for Clone BMS2h-719 and BMS2h-7xx Series:

Three rounds of selection using decreasing concentrations of antigen (500 nM at round 1; 50 nM at round 2; 50 nM or 5 nM at round 3 depending on the library output used) were performed in parallel against biotinylated (1.2 moles biotin/mole CD40L) human CD40L monomer triple mutant (T211E, S222Y, H224K, [108-261] Construct #7) provided by Bristol-Myers Squibb. Phage from the naïve 4G and 6G Domantis dAb libraries were combined into the pools a) to g) indicated below before initiating selections:

a) 4G VH CDR3 lengths between 7-10 amino acids.
b) 4G VH CDR3 lengths between 11-15 amino acids.
c) 4G VH CDR3 lengths between 7-15 amino acids.
d) 4G VK
e) 6G VH CDR3 lengths between 7-9
f) 6G VH CDR3 lengths between 10-15
g) 6G VK Each round of selection involved adding the desired concentration of biotinylated CD40L to a mixture of 200 µl of phage (from one of the naïve library pools indicated above, or subsequent selection output phage) and 1000 µl of 2% MPBS (Phosphate Buffered Saline) containing 2% (w/v) Marvel [Premier Foods, UK]) and incubating at room temperature for 1 hour by mixing end-over-end. The biotinylated antigen phage complex was then captured by adding 100 µl of resuspended Dynabeads M-280 Streptavidin [Invitrogen, UK] and incubated for 5 minutes with mixing end-over-end at room temperature. The Dynabeads were then recovered using a KingFisher magnetic separator

[Thermo Fisher Scientific, UK] and washed 7×1 ml PBST (PBS containing 0.1% (v/v) polyoxyethylenesorbitan 20 monolaurate [Sigma-Aldrich, UK]) followed by 1×1 ml PBS. Bound phage retained on the washed Dynabeads were eluted by incubation with 500 μl of trypsin-PBS (50 μl of 10 mg/ml trypsin [Sigma-Aldrich, UK] dissolved in 50 mM Tris-HCl pH 7.4, 1 mM $CaCl_2$ added to 450 μl PBS). The phage-containing solution was recovered and 250 μl used to infect 1.75 ml of logarithmic growth phase E. coli TG1 (at an $OD_{600}$ of 0.4) for 30 minutes at 37° C. The E. coli TG1 phage infected culture was centrifuged at 11,600 g in a micro centrifuge for 1 minute and the resulting cell pellet resuspended in 1 ml 2×TY (16 g Tryptone, 10 g Yeast Extract and 5 g NaCl in 1 liter, autoclaved for 15 minutes at 121° C.) and plated onto a 9 cm Petri dish containing TYE media supplemented with 15 μg/ml tetracycline. The plates were incubated overnight at 37° C. then 2 ml of 2×TY supplemented with 15% glycerol was added to each plate and cells loosened with a glass spreader and mixed thoroughly. Fifty microliters of the scraped bacteria was used to inoculate 50 ml of 2×TY supplemented with 15 μg/ml tetracycline and grown overnight at 37° C. with shaking at 250 rpm. The overnight culture was centrifuged at 3,300 g for 15 min to pellet the bacteria. To precipitate phage, 10 ml PEG/NaCl (20% Polyethylene glycol 8000, 2.5 M NaCl) was added to 40 ml supernatant. The phage/PEG solution was mixed and left on ice for 1 h, then spun at 3,300 g for 30 min at 4° C. and the supernatant discarded. The pellet was resuspended in 2 ml PBS and spun at 11,600 g for 10 min in a micro centrifuge to remove the remaining bacterial debris. The resultant supernatant containing phage was then used for the next round of selection against the appropriate concentration of biotinylated CD40L monomer triple mutant antigen.

Phage ELISA

Monoclonal phage ELISAs were carried out following selection rounds 2 and 3. All washes were performed using 3 washes of 250 μl PBST followed by 3 washes of 250 μl PBS. The plates were coated overnight at 4° C. with 50 μl/well of 1 μg/ml NeutrAvidin [Thermo Scientific, UK] in 0.2M carbonate-bicarbonate buffer, pH 9.4. The plates were washed and then blocked with 2% MPBS for 1 hour at room temperature. The plates were then washed and incubated with 50 μl/well of ~1.0 μg/ml biotinylated human CD40L monomer triple mutant in 2% MPBS. The plates were washed and 25 μl/well phage supernatants added to an equal volume of 2% MPBS and incubated for 1 hour at room temperature. The plates were washed and bound phage detected with 50 μl/well anti-M13-HRP conjugate [GE Healthcare, UK] diluted 1:5000 in 2% MPBS and incubated for 1 hour at room temperature. The plates were washed and the ELISA developed using 50 μl/well SureBlue 1-Component TMB MicroWell Peroxidase solution [KPL Inc, USA]. The colorimetric reaction was stopped by the addition of an equal volume of 1 M HCl and the ELISA plate read at 450 nm. Specific phage were identified by comparison to wells coated with NeutrAvidin but without biotinylated CD40L monomer triple mutant.

Recovery of dAb Genes from MidiPrep pDOM4 Plasmid

The dAb V-genes from the following round 3 outputs were recovered by DNA restriction enzyme digestion of the phage vector pDOM4:

a) 4G VH CDR3 lengths between 7-10 amino acids (50 nM antigen concentration).
b) 4G VH CDR3 lengths between 11-15 amino acids (50 nM antigen concentration).
c) 4G VH CDR3 lengths between 11-15 amino acids (5 nM antigen concentration).
d) 4G VH CDR3 lengths between 7-15 amino acids (50 nM antigen concentration).
e) 4G VK (50 nM antigen concentration).
f) 4G VK (5 nM antigen concentration).
g) 6G VH CDR3 lengths between 7-9 (50 nM antigen concentration).
h) 6G VH CDR3 lengths between 10-15 (5 nM antigen concentration).

Approximately 20 μg of MidiPrep [Qiagen, UK] DNA was digested with SalI and NotI as follows: 20 μl DNA (~1 μg/μl) was mixed with 1.5 μl SalI (20 U/μl) [NEB, UK] and 3 μl NotI (10 U/μl) [NEB, UK], 4 μl Buffer 3 [NEB, UK], 0.4 μl BSA (10 mg/ml) [NEB, UK] and tissue culture grade water [Sigma, UK] added to 40 μl. Samples were incubated for 5 hours at 37° C. in an air incubator following which the digested dAb genes were isolated by running the digestion mix on a 2% agarose gel [E-gel, Invitrogen, UK], the appropriate DNA bands excised and cleaned using a PCR purification kit [Qiagen, UK]. The purified V-genes were ligated into a SalI and NotI double digested pDOM5 expression vector.

Soluble dAb ELISA

Binding dAbs were identified as follows. Ninety-six individual colonies containing dAb V-genes cloned into the soluble dAb expression vector pDOM5 were picked from each output into 200 μl Terrific Broth containing OnEx Autoinduction media [Novagen, UK] and incubated overnight at 37° C. with shaking at 250 rpm in Costar 96 Well Cell Culture Clusters [Corning Incorporated, USA] sealed with a gas permeable adhesive plastic strip. The cultures were centrifuged to pellet the cells and the supernatants assayed by antigen binding ELISA for dAbs that bound to CD40L monomer triple mutant and IZ-CD40L mutant (CD40L containing an isoleucine zipper trimerization domain, supplied by Bristol-Myers Squibb). MaxiSorp 96 well immunoplates [Nunc, USA] were coated overnight at 4° C. with 50 μl/well of 1 μg/ml NeutrAvidin in 0.2 M carbonate-bicarbonate buffer, pH 9.4. All washes were as described for the phage ELISA. The plates were blocked for 1 hour at room temperature with 200 μl of PBS containing 1% Tween 20. The plate was then washed and incubated for 1 hour at room temperature with 50 μl/well of 1 μg/ml biotinylated human CD40L monomer triple mutant in PBST or 1 μg/ml biotinylated human IZ-CD40L mutant in PBST (both antigens supplied by Bristol-Myers Squibb). The ELISA plate was washed and dAb-containing culture supernatant clarified by centrifugation at 1,800 g for 10 min at 4° C., then added to the ELISA plate (30 μl/well) to which was added an equal volume of PBST. The plates were incubated for 1 hour at room temperature and then washed. Bound dAb was detected by adding 50 μl/well 9E10 [anti-myc IgG, Sigma-Aldrich, UK] diluted 1:2000 in PBST and incubating for 1 hour at room temperature; the ELISA plate was then washed and 50 μl/well anti-mouse Fc-HRP [Sigma-Aldrich, UK] diluted 1:2000 in PBST added and incubated for 1 hour at room temperature. The plates were washed and the ELISA developed by adding 50 μl/well SureBlue 1-Component TMB MicroWell Peroxidase solution [KPL Inc, USA] and the colour allowed to develop. The colourimetric reaction was stopped by the addition of an equal volume of 1 M HCl and the ELISA plate read at 450 nm. Antigen binding dAbs were identified by comparison of the signal intensity from human CD40L monomer triple mutant and human IZ-CD40L mutant wells with control wells not containing antigen.

Expression & Purification of dAb at 50 ml Scale

Unique dAbs were identified by DNA sequencing ELISA positive clones. The unique dAbs identified were expressed as follows in 250 ml baffled flasks, to which was added:
 a) 50 ml of Terrific Broth [Sigma-Aldrich, UK].
 b) 100 µg/ml carbenicillin [Sigma-Aldrich, UK].
 c) 1 drop of antifoam A204 [Sigma-Aldrich, UK].
 d) Novagen Overnight Express Autoinduction Kit [Novagen, UK].

A bacterial scrape from a fresh confluent 9 cm diameter agar plate or from a glycerol stock of the desired dAb clone was used to inoculate the Terrific Broth, then the flask sealed with Milliwrap PTFE membrane [Millipore, UK], and incubated for 48 hrs, 250 rpm shaking at 30° C. The bacterial overnight culture was clarified by centrifugation and the VH or VK dAb purified using Streamline Protein A [GE Healthcare, UK] or Protein L agarose [generated in-house] respectively. The resulting purified proteins were assayed by RBA to determine which clones could inhibit the binding of CD40L for CD40.

CD40L Bead Receptor Binding Assay

Inhibitory dAbs were initially identified by screening purified dAb in a CD40L bead receptor binding assay (RBA). Sphero streptavidin polystyrene beads (0.5% w/v, 6.7 µm diameter) [Saxon, Europe] were prepared and washed according to the manufacturer's instructions. The beads were then pelleted at 11,600 g for 1 minute, the supernatant discarded and the beads resuspended in 1 ml PBS by vortexing. The washing step was repeated twice more, the supernatant discarded and the beads resuspended in 1 ml (0.5 mg/ml) of biotinylated human IZ-CD40L in PBS and incubated overnight at room temperature with end-over-end rotation. Following incubation, the beads were pelleted and washed three times with 1 ml PBS as before and then resuspended in 0.5 ml PBS containing 0.1% bovine serum albumin (BSA). The antigen coated beads were then diluted 1:10 in PBS containing 0.1% BSA prior to use. The reagents for the RBA assay were added as follows to duplicate wells in a 384-well black sided clear bottomed FMAT plate [Applied Biosystems, UK]:
 a) 12.5 µl dAb protein or buffer control. The dAb titration starting concentration was typically 10 µM (final concentration) which was diluted 1:3.3 (i.e., 30 µl sample added to 70 µl PBS containing 0.1% BSA) to produce an 8-point titration effect curve.
 b) 12.5 µl CD40-Fc [supplied by Bristol-Myers Squibb, USA; lot CY24Feb06-1] at 0.2 µg/ml (for a final concentration of 0.05 µg/ml) diluted in PBS containing 0.1% BSA.
 c) 12.5 µl Mixture of mouse anti-human Fc [Sigma-Aldrich, UK] at 2 µg/ml (for a final concentration of 0.5 µg/ml) and goat anti-mouse Alexa Fluor 647 [Invitrogen, UK] at 1 µg/ml (for a final concentration of 0.25 µg/ml) diluted in PBS containing 0.1% BSA.
 d) 12.5 µl IZ-CD40L coated beads described above were added to the centre of the well so they did not disperse to the edge of the well.

Following addition of the reagents to the 384 well plate, it was incubated at room temperature for 6 hours in the dark and then read in an AB8200 FMAT system [Applied Biosystems, UK].

Example 2 dAb Selection for Clone BMS2h-572

Three rounds of selection using decreasing concentrations of antigen (300 nM at round 1; 30 nM at round 2; 3 nM at round 3) were performed in parallel against biotinylated (1.42 moles biotin/mole trimer) human isoleucine zipper-CD40L (IZ-hCD40L) provided by Bristol-Myers Squibb. Phage from the naïve 4G and 6G Domantis dAb libraries were combined into the pools a) to h) indicated below before initiating selections:
 a) 4G VH CDR3 lengths between 7-9 amino acids.
 b) 4G VH CDR3 lengths between 10-12 amino acids.
 c) 4G VH CDR3 lengths between 13-15 amino acids.
 d) 4G VK
 e) 6G VH CDR3 lengths between 7-9
 f) 6G VH CDR3 lengths between 10-12
 g) 6G VH CDR3 lengths between 13-15
 h) 6G VK Each round of selection involved adding the desired concentration of biotinylated CD40L to a mixture of phage (from one of the naïve library pools indicated above, or subsequent selection output phage) in 1000 µl of 2% MPBS (Phosphate Buffered Saline containing 2% (w/v) Marvel [Premier Foods, UK]) and incubating at room temperature for 1 hour by mixing end-over-end. The biotinylated antigen phage complex was then captured by adding 100 µl of resuspended Dynabeads M-280 Streptavidin [Invitrogen, UK] (rounds 1 and 3) or 50 µl of M-280 tosylactivated Dynabeads (Invitrogen) that had been coupled with NeutrAvidin [Thermo Fisher Scientific, UK] (round 2) and incubated for 5 minutes with mixing end-over-end at room temperature. The Dynabeads were then recovered using a KingFisher magnetic separator [Thermo Fisher Scientific, UK] and washed 7×1 ml PBST (PBS containing 0.1% (v/v) polyoxyethylenesorbitan 20 monolaurate [Sigma-Aldrich, UK]) followed by 1×1 ml PBS. Bound phage retained on the washed Dynabeads were eluted by incubation with 500 µl of trypsin-PBS (50 µl of 10 mg/ml trypsin [Sigma-Aldrich, UK] dissolved in 50 mM Tris-HCl pH 7.4, 1 mM $CaCl_2$ added to 450 µl PBS). The phage-containing solution was recovered and 250 µl used to infect 1.75 ml of logarithmic growth phase E. coli TG1 (at an $OD_{600}$ of 0.4) for 30 minutes at 37° C. The E. coli TG1 phage infected culture was centrifuged at 11,600 g in a micro centrifuge for 1 minute and the resulting cell pellet resuspended in 1 ml 2×TY (16 g Tryptone, 10 g Yeast Extract and 5 g NaCl in 1 liter, autoclaved for 15 minutes at 121° C.) and plated onto a 9 cm Petri dish containing TYE media supplemented with 15 µg/ml tetracycline. The plates were incubated overnight at 37° C. then 2 ml of 2×TY supplemented with 15% glycerol was added to each plate and cells loosened with a glass spreader and mixed thoroughly. Fifty microliters of the scraped bacteria was used to inoculate 50 ml of 2×TY supplemented with 15 µg/ml tetracycline and grown overnight at 37° C. with shaking at 250 rpm. The overnight culture was centrifuged at 3,300 g for 15 min to pellet the bacteria. To precipitate phage, 10 ml PEG/NaCl (20% Polyethylene glycol 8000, 2.5 M NaCl) was added to 40 ml supernatant. The phage/PEG solution was mixed and left on ice for 1 h, then spun at 3,300 g for 30 min at 4° C. and the supernatant discarded. The pellet was resuspended in 2 ml PBS and spun at 11,600 g for 10 min in a micro centrifuge to remove the remaining bacterial debris. The resultant supernatant containing phage was then used for the next round of selection against the appropriate concentration of biotinylated IZ-hCD40L.

Phage ELISA

Monoclonal phage ELISAs were carried out following selection rounds 2 and 3. All washes were performed using 3 washes of 250 µl PBST followed by 3 washes of 250 µl PBS. The plates were coated overnight at 4° C. with 50 µl/well of 1 µg/ml IZ-hCD40L in PBS. The plates were washed and then blocked with 2% MPBS for 1 hour at room temperature. The plates were washed and 25 µl/well phage supernatants added to an equal volume of 2% MPBS and incubated for 1 hour at room temperature. The plates were washed and bound phage detected with 50 µl/well anti-M13-HRP conjugate [GE Healthcare, UK] diluted 1:5000 in 2% MPBS and incubated for 1 hour at room temperature. The plates were washed and the ELISA developed using 50 µl/well SureBlue 1-Component TMB MicroWell Peroxidase solution [KPL Inc, USA]. The colorimetric reaction was stopped by the addition of an equal volume of 1 M HCl and the ELISA plate read at 450 nm. Specific phage were identified by comparison to wells that were not coated with antigen but otherwise identically treated.

Recovery of dAb Genes from pDOM4 Plasmid

The dAb V-genes from round 2 and 3 outputs were recovered by SalI and NotI restriction enzyme digestion of the phage vector pDOM4 and ligated into a SalI and NotI double digested pDOM5 expression vector.

Soluble dAb ELISA

Binding dAbs were identified as follows. Ninety-six individual colonies containing dAb V-genes cloned into the soluble dAb expression vector pDOM5 were picked from each output into 200 µl Terrific Broth containing OnEx Autoinduction media [Novagen, UK] and incubated overnight at 37° C. with shaking at 250 rpm in Costar 96 Well Cell Culture Clusters [Corning Incorporated, USA] sealed with a gas permeable adhesive plastic strip. The cultures were centrifuged to pellet the cells and the supernatants assayed by antigen binding ELISA for dAbs that bound to IZ-hCD40L. MaxiSorp 96 well immunoplates [Nunc, USA] were coated overnight at 4° C. with 50 µl/well of 1 µg/ml IZ-hCD40L in PBS. All washes were as described for the phage ELISA. The plates were blocked for 1 hour at room temperature with 200 µl of PBS containing 1% Tween 20. The ELISA plate was washed and dAb-containing culture supernatant clarified by centrifugation at 1,800 g for 10 min at 4° C., then added to the ELISA plate (30 µl/well) to which was added an equal volume of PBST. The plates were incubated for 1 hour at room temperature and then washed. Bound dAb was detected by adding 50 µl/well 9E10 [anti-myc IgG, Sigma-Aldrich, UK] diluted 1:2000 in PBST and incubating for 1 hour at room temperature; the ELISA plate was then washed and 50 µl/well anti-mouse Fc-HRP [Sigma-Aldrich, UK] diluted 1:2000 in PBST added and incubated for 1 hour at room temperature. The plates were washed and the ELISA developed by adding 50 µl/well SureBlue 1-Component TMB MicroWell Peroxidase solution [KPL Inc, USA] and the colour allowed to develop. The colorimetric reaction was stopped by the addition of an equal volume of 1 M HCl and the ELISA plate read at 450 nm. Antigen binding dAbs were identified by comparison of the signal intensity from IZ-hCD40L wells with control wells not containing antigen.

Example 3

Identification of Clones BMS2h-503-1, BMS2h-719-2, and BMS2h-572-6

BMS2h-503, BMS2h-719 and BMS2h-572 dAbs were subjected to error-prone affinity maturation to generate BMS2h-503, BMS2h-719 and BMS2h-572 lineages, respectively. This was performed using random mutagenesis where on average 3.6 amino acid changes were introduced per dAb. Phage libraries (average size 6×10$^8$) were selected using biotinylated monomeric and trimeric human CD40L with alternating streptavidin/neutravidin bead capture of the antigen (as described). Three rounds of selections using decreasing concentrations of antigen (100 nM at round 1; 10 nM at round 2; 1 nM at round 3) were performed. Sequencing was used to monitor diversity following each selection round. Selection outputs (round 2 selected on CD40L trimer for BMS2h-572; round 3 selected on CD40L trimer for BMS2h-503 and round 3 selected on CD40L monomer for BMS2h-719) were sub-cloned into soluble expression vector pDOM13 (no C terminal tag) (as described) and screened as monoclonal bacterial micro-culture supernatants by BIAcore for improved off-rates compared to parental clones on both monomeric and trimeric CD40L. Identified improved variants were DNA sequenced and unique dAbs expressed, purified and then assayed using the BMS2h bead RBA as well as cellular CD40L driven assays (as described). As a result, BMS2h-503-1 (sequence listed in TABLE 3), BMS2h-719-2 and BMS2h-572-6 dAbs (sequences listed in TABLE 1) were identified. Activities of these dAbs are listed in TABLE 5 below.

Formatting BMS2h-503-1, BMS2h-719-2 and BMS2h-572-6 as Fc Fusions

BMS2h-572-6, BMS2h-503-1 and BMS2h-719-2 dAbs were cloned into pDOM38 vector containing Fc tail derived from human IgG1 to create DMS0502, DMS0500 and DMS0501, respectively. BMS2h-572-6, BMS2h-503-1 and BMS2h-719-2 dAbs were also cloned into pDOM38 vector containing Fc tail derived from human IgG4 to create DMS0505, DMS0506 and DMS0504, respectively. The constructs were transiently expressed in HEK293 cells and the proteins were purified using Protein A. Purified Fc fusions were analysed by Biacore for binding to monomeric and trimeric CD40L as well as in various cell assays (as described).

Identification of Clones BMS2h-572-608, BMS2h-572-614 and BMS2h-572-619

BMS2h-572-6 dAb was subjected to affinity maturation using doped oligo approach. Four doped libraries were constructed for this dAb:
Library 1-5 residues in CDR1 diversified
Library 2-6 residues in CDR2 diversified
Library 3-13 residues in CDR2 diversified
Library 4-7 residues in CDR3 diversified
In each library, diversification was performed using nnS codons where n retained a large fraction of the parent base (85%) and split the rest between the equimolar amounts of the remaining three bases (5% each) and S stood for G or C. Phage libraries (average size 8×10$^8$) were selected using biotinylated monomeric and trimeric human CD40L with alternating streptavidin/neutravidin bead capture of the antigen (as described). Libraries 2 and 3 were pulled together during the selection process. Three rounds of selections using decreasing concentrations of antigen (50 nM at round 1; 5 nM at round 2; 1 nM at round 3 with 200 fold excess of competitor—non biotinylated CD40L trimer) were performed. Sequencing was used to monitor diversity following each selection round. Selection outputs (rounds 2 and 3) were sub-cloned into soluble expression vector pDOM13 (no C terminal tag) (as described) and screened as monoclonal bacterial micro-culture supernatants by BIAcore for improved off-rates compared to parental clones on both monomeric and trimeric CD40L. Identified improved variants were DNA sequenced and unique dAbs expressed, purified and then assayed using the BMS2h bead RBA as well as cellular CD40L driven assays (as described). As a result, BMS2h-572-608, BMS2h-572-614 and BMS2h-572-619 dAbs were identified.

Construction of Clone BMS2h-572-633

Sequence analysis revealed that all of the amino acid differences between BMS2h-572-608 and the parental dAb BMS2h-572-6 were located in CDR1 and the differences between BMS2h-572-614 and parental dAb BMS2h-572-6 were located in CDR3. Both matured dAbs shared CDR2 with the parental dAb BMS2h-572-6. This created an opportunity to construct a combination mutant which had CDR1 of BMS2h-572-608 and CDR3 of BMS2h-572-614. Firstly, CDR1 region of BMS2h-572-608 was PCR amplified. Secondly, CDR2+CDR3 fragment of BMS2h-572-614 was PCR amplified. This was followed by SOE PCR assembly of the two fragments to create a combination mutant BMS2h-572-633. The assembled dAb PCR product was cloned into soluble expression vector pDOM13 (no C terminal tag), sequence verified, expressed, purified and then assayed using the BMS2h bead RBA as well as cellular CD40L driven assays (as described).

Formatting BMS2h-572-633 as Fc Fusion

BMS2h-572-633 dAb was cloned into pDOM38 vector containing Fc tail derived from human IgG1 to create DMS0507. The construct was transiently expressed in HEK293 cells and the protein was purified using Protein A. Purified Fc fusion was analysed by Biacore for binding to monomeric and trimeric CD40L as well as in various cell assays (as described).

Example 4

CD40L Activity Cell Assays

Anti-human CD40L dAbs were assayed functionally for their ability to antagonize CD40L activities. The CD40L activities tested were B cell proliferation and cytokine production by hCD40L-driven activation of primary monocytes-derived dendritic cells (DCs). Unless otherwise noted, all assays were performed in RPMI media supplemented with 10% fetal calf serum (FCS). The results of various assays, described in detail below, are shown in TABLE 5 and TABLE 6.

Soluble 1Z-hCD40L-Driven Primary Human B Cell Proliferation:

$1 \times 10^5$ tonsillar human B cells were incubated with 0.6 μg/ml of IZ-hCD40L along with varying titration of dAb or mAb in a final volume of 200 μl/well in a 96-well round bottom plate. The plates were incubated at 37° C. for 72 hours following which thymidine ($^3$H; 0.5 μci/well) was added for 6 hours. B cell proliferation was quantified based on thymidine incorporation. All assays, unless otherwise noted, were performed in RPMI media supplemented with 10% fetal calf serum (FCS).

CHO-hCD40L-Driven Primary Human B Cell Proliferation:

CHO cells were transfected with human CD40L to generate a stable cell line expressing high levels of CD40L on the cell surface. CHO-CD40L cells were irradiated at 10,000 Rads before incubation with human B cells. $1 \times 10^5$ tonsillar human B cells were incubated with $1 \times 10^3$ CHO-CD40L cells (1:100 ratio of CHO-CD40L: human B cells) along with varying titration of dAb or mAb in a final volume of 200 μl/well in a 96-well round bottom plate. The plates were incubated at 37° C. for 72 hours following which thymidine ($^3$H; 0.5 μci/well) was added for 6 hours. B cell proliferation was quantified based on thymidine incorporation. All assays, unless otherwise noted, were performed in RPMI media supplemented with 10% fetal calf serum (FCS).

Primary T Cell-Driven Human B Cell Proliferation:

T cells were isolated from human peripheral blood mononuclear cells (PBMCs) and enriched using via sheep red blood cell (SRBC) affinity. Enriched human T cells were cultured with PM-LCLs (EBV-transformed B cell line; irradiated at 10,000 Rads) at a 5:1 ratio (T:LCL) for 6 days at 37° C. to generate a population of allogeneic T cells. At day 6, the expanded T cells were isolated and irradiated at 3000 Rads, and then cultured ($5 \times 10^4$ T cells/well) with primary human tonsillar B cells ($1 \times 10^5$ B cells/well) at a 1:2 ratio in 96-well flat bottom plated coated with anti-CD3 mAb (OKT3). Varying titrations of dAbs/mAbs were added to each well; the final volume in each well was 200 μl. Test plates were incubated at 37° C. for 3 days. Human B cell proliferation was determined via the addition of thymidine ($^3$H; 0.5 μci/well) to the cultures for the last 18 hours. All assays, unless otherwise noted, were performed in RPMI media supplemented with 10% fetal calf serum (FCS). In some instances, the supernatant was harvested and measured for the presence of IL-6.

CHO-hCD40L-Driven Activation of Primary Human Monocytes-Derived Dendritic Cells (DCs):

Human PBMCs were enriched for monocytes by depleting T cells via SRBC resetting. The monocyte-enriched PBMCs were cultured with 10 ng/ml GM-CSF and 5 ng/ml IL-4 in 6-well plates for six days at 37° C. The cultured plates were replenished with fresh media (with GM-CSF and IL-4) on days 2 and 5. The immature DCs were used in cell assays on day 6. $8 \times 10^4$ immature DCs were cultured with $4 \times 10^3$ CHO-hCD40L cells (irradiated at 10,000 Rads) along with varying titrations of dAbs/mAbs in a 96-well flat bottom plate. After 24 hours, supernatants were harvested and tested for the presence of various cytokines (IL-12, TNF, IL-23). DC activation was determined by the levels of cytokine production. All assays, unless otherwise noted, were performed in RPMI media supplemented with 10% fetal calf serum (FCS).

TABLE 5

Potency of Monomeric dAb Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|
| 2h116-13 | 130.0 ± 40.0 | 1300.0, 700.0 | | 888.0, >2000.0, 1000.0 |
| 2h116-1312 | 23.0 ± 3.0 | 530.0 ± 300.0 | 234 ± 46 | 112.0 ± 47.0 |
| 2h116-1313 | 29.0 ± 4.0 | 211.0, 334.0 | 258 ± 79 | 136.0 ± 51.0 |
| 2h116-1314 | 41.0 ± 10.0 | 1300.0, 4400.0 | 1687 ± 1150 | 664.0 ± 353.0 |
| 2h116-1319 | 180.0 ± 57.0 | >7000.0 | | |
| 2h116-1320 | 20.0 ± 7.0 | 138.0 ± 60.0 | 191 ± 72 | 32.0 ± 10.0 |
| 2h437 | 5700.0 ± 1800 | | | |
| 2h437-4 | 203.0 ± 90.0 | >7000.0 | | 1329.0 ± 412.0 |
| 2h492 | >7000.0 | | | |
| 2h492-3 | 1100.0 ± 400.0 | >7000.0 | | |
| 2h492-4 | 1700.0 ± 900.0 | >7000.0 | | |
| 2h492-5 | 2300.0 ± 700.0 | | | |
| 2h492-6 | 6300.0 ± 1400.0 | | | |
| 2h492-7 | 1900.0 ± 600.0 | | | |
| 2h494 | 6100.0 ± 1200.0 | | | |
| 2h494-2 | 4800.0 ± 2300.0 | | | |
| 2h494-3 | >7000.0 | | | |
| 2h494-4 | 590.0 ± 250.0 | >7000.0 | | |
| 2h494-6 | 2000.0 ± 2100.0 | >7000.0 | | |
| 2h503 | 4200.0 ± 316.0 | >7000.0 | | |
| 2h503-1 | 24.0 ± 2.0 | 2300.0 ± 700.0 | | 756.0 ± 333.0 |
| 2h503-104 | 16.0, 19.0 | | | |
| 2h503-2 | 44.0 ± 6.0 | 3000.0 ± 1000.0 | | 1562.0 ± 96.0 |
| 2h572 | >7000.0 | | | |
| 2h572-6 | 208.0 ± 73.0 | >7000.0 | >7000.0 | >2000.0, 608.0 ±260.0 |
| 2h572-604 | 254.0, 354.0 | >700.0 | | 387.0 |
| 2h572-608 | 96.0 ± 19.0 | | >7000.0 | 152.0 ± 61.0 |
| 2h572-610 | 109.0 ± 34.0 | | >7000.0 | 207.0 ± 87.0 |
| 2h572-614 | 93.0 ± 53.0 | | >7000.0 | 135.0 ± 54.0 |
| 2h572-616 | 204.0, 340.0 | | >7000.0 | 608.0 ± 136.0 |
| 2h572-617 | 157.0, 189.0 | | >7000.0 | 338.0 ± 101.0 |
| 2h572-619 | 90.0 ± 62.0 | 421.0, 1496.0 | >7000.0 | 188.0 ± 41.0 |
| 2h572-622 | 301.0, 293.0 | | >7000.0 | 281.0 ± 127.0 |
| 2h572-623 | 181.0, 261.0 | | >7000.0 | 280.0 ± 73.0 |
| 2h572-630 | 103.0 ± 71.0 | | | 246.0 ± 240.0 |
| 2h572-631 | 108.0 ± 77.0 | | | 230.0 ± 200.0 |
| 2h572-632 | 117.0 ± 91.0 | | | 241.0 ± 190.0 |
| 2h572-633 | 20.0 ± 15.0 | | | 53.0 ± 60.0 |
| 2h572-634 | 31.0 ± 18.0 | | | 77.0 ± 67.0 |
| 2h572-635 | 29.0 ± 19.0 | | | 52.0 ± 26.0 |
| 2h572-9 | 324.0, 243.0 | | | >2000.0 |
| 2h572-11 | 140.0 ± 33.0 | >7000.0 | | 671.0 ± 165.0 |
| 2h572-12 | 79.0, 76.0 | | | 225.0, >2000.0 |
| 2h572-14 | 134.0 ± 12.0 | >7000.0 | | 882.0 ± 310.0 |
| 2h572-15 | 168.0 ± 67.0 | >7000.0 | | 876.0 ± 391.0 |
| 2h572-22 | 357.0, 305.05 | | | |
| 2h702 | >7000.0 | | | |
| 2h703 | >7000.0 | | | |
| 2h706 | >7000.0 | | | |
| 2h707 | >7000.0 | | | |
| 2h710 | >7000.0 | | | |
| 2h712 | >7000.0 | | | |
| 2h717 | >7000.0 | | | |
| 2h719 | 600.0 ± 640.0 | | | 134.0, 646.0 |
| 2h719-2 | 82.0 ± 39.0 | >7000.0 | | 196.0 ± 150.0 |
| 2h719-202 | 29.0 ± 12.0 | | | 79.0 ± 29.0 |
| 2h719-203 | 81.0, 96.0 | | | |
| 2h719-213 | 62.0, 98.0 | | | |
| 2h719-214 | 66.0, 89.0 | | | |
| 2h719-215 | 92.0, 91.0 | | | |
| 2h719-218 | 57.0, 60.0 | | | |
| 2h719-225 | 253.0, 198.0 | | | 176.0 ± 84.0 |
| 2h719-226 | 164.0, 247.0 | | | 812.0 ± 53.0 |
| 2h719-12 | 358.0 ± 159.0 | | | 266.0 ± 66.0 |
| 2h719-13 | 50.0 ± 8.0 | 659.0, 683.0, 4450.0, 1750.0 | | 219.0 ± 88.0 |
| 2h719-17 | 132.0 ± 50.0 | 236.0, 268.0 | | 113.0 ± 49.0 |
| 2h719-19 | 138.0 ± 31.0 | 202.0, >7000.0, >7000.0, 3800.0, 5400.0 | | 184.0 ± 99.0 |

TABLE 5-continued

Potency of Monomeric dAb Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|
| 2h722 | >7000.0 | | | |
| 2h723 | >7000.0 | | | |
| 2h725 | 6400.0 ± 1200.0 | | | |
| 2h725-2 | >7000.0 | | | |
| 2h725-9 | >7000.0 | | | |
| 2h725-19 | >7000.0 | | | |
| 2h726 | >7000.0 | | | |
| 2h730 | >7000.0 | | | |
| 2h731 | 5800.0 ± 2500.0 | | | |
| 2h744 | >7000.0 | | | |
| 2h745 | 6400.0, 3500.0, >7000.0 | | | |
| 2h745-1 | >7000.0 | | | |
| 2h745-2 | >7000.0 | | | |
| 2h745-9 | >7000.0 | | | |
| 2h745-13 | >7000.0 | | | |
| 2h745-14 | >7000.0 | | | |
| 2h746 | >7000.0 | | | |
| 2h747 | >7000.0 | | | |
| 2h752 | >7000.0 | | | |
| 2h754 | 6600.0 ± 900.0 | | | |
| 2h757 | 6400.0 ± 800.0 | | | |
| 2h758 | 5900.0 ± 1500.0 | | | |
| 2h758-1 | >7000.0 | | | |
| 2h758-2 | >7000.0 | | | |
| 2h758-3 | >7000.0 | | | |
| 2h758-4 | >7000.0 | | | |
| 2h758-5 | >7000.0 | | | |
| 2h765 | >7000.0 | | | |
| 2h766 | >7000.0 | | | |
| 2h774 | >7000.0 | | | |
| 2h775 | >7000.0 | | | |
| 2h780 | >7000.0 | | | |
| 2h781 | >7000.0 | | | |
| 2h782 | >7000.0 | | | |
| 2h783 | >2000.0 | | | |
| 2h784 | >4700.0 | | | |
| 2h785 | 3700.0, >7000.0 | | | |

TABLE 6

Potency of Fc*-formatted Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | T-B cell MLR IL-6 EC50 (nM) | CHO-hCD40L-driven DC Activation IL-12 EC50 (nM) | CHO-hCD40L-driven DC Activation IL-6 EC50 (nM) | CHO-hCD40L-driven DC Activation IL-23 EC50 (nM) | CHO-hCD40L-driven DC Activation TNF EC50 (nM) |
|---|---|---|---|---|---|---|---|---|
| 2h116-1320-Fc | 13.0 ± 2.0 | >130.0 | 244.0 ± 112.0 | | 14.0 ± 11.0 | | | |
| 2h503-1 Fc | 4.0 ± 0.5 | 60.0 ± 20.0 | 45 ± 6 | | 2.8 ± 2.0 | | | |
| 2h503-1 IgG1 | 4.5 ± 1.0 | 67.0 ± 40.0 | 39.5 ± 12.04 | | 1.4 ± 0.7 | | | |
| 2h503-1 IgG4 | 2.5 ± 1.0 | 69.0 ± 50.0 | 48.3 ± 8.8 | | 18.1 ± 6.4 | | | |
| 2h572-6 Fc | 0.6 ± 0.4 | 3.0 ± 1.0 | 1.9 ± 0.7 | | 0.22 ± 0.18 | | | |
| 2h572-6 IgG1 | 1.0 ± 0.4 | 10.0 ± 5.0 | 3.1 ± 1.4 | 2.9 ± 1.7 | 0.58 ± 0.36 | | | |
| 2h572-6 IgG4 | 0.9 ± 0.2 | 11.0 ± 5.0 | 3.2 ± 1.5 | 1.3 ± 0.5 | 1.1 ± 0.5 | | | |
| 2h572-6-CT Long Fc | 1.0 ± 0.5 | 6.0 ± 6.0 | 13.6 ± 9.2 | 8.1 ± 3.1 | 3.0 ± 1.9 | | | |
| 2h572-633 Fc | 3.5 ± 0.6 | 3.0 ± 3.0 | 0.15 ± 0.02 | 0.11 ± 0.02 | 0.34 ± 0.17 | | | |
| 2h572-634 Fc | 3.0 ± 0.0 | 3.5 ± 3.0 | 0.23 ± 0.08 | 0.19 ± 0.03 | 0.42 ± 0.05 | | | |
| 2h572-635 Fc | 2.0 ± 0.8 | 2.5 ± 1.0 | 0.16 ± 0.09 | 0.11 ± 0.02 | 0.445 ± 0.14 | | | |
| 2h572-619-Ctshort Fc | 1.5 ± 0.6 | 2.0 | 0.40 ± 0.1 | 0.3 ± 0.07 | 1.8 ± 1.3 | | | |
| 2h572-619-Ctlong Fc | 1.6 ± 0.5 | 2.0 ± 1.0 | 0.72 ± 0.45 | 0.43 ± 0.12 | 1.4 ± 0.6 | 1.5 ± 0.36 | 1.5 ± 0.46 | 2.0 ± 0.7 |
| 2h572-619-N297Qshort Fc | 0.9 ± 0 | 1.0 ± 0.6 | 0.226, 0.216 | 0.1, 0.1 | 1.2 ± 0.6 | | | |

TABLE 6-continued

Potency of Fc*-formatted Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | T-B cell MLR IL-6 EC50 (nM) | CHO-hCD40L-driven DC Activation IL-12 EC50 (nM) | CHO-hCD40L-driven DC Activation IL-6 EC50 (nM) | CHO-hCD40L-driven DC Activation IL-23 EC50 (nM) | CHO-hCD40L-driven DC Activation TNF EC50 (nM) |
|---|---|---|---|---|---|---|---|---|
| 2h572-619-N297Qlong Fc | 0.98 ± 0.05 | 2.0 ± 0.0 | 0.480, 0.474 | 0.22, 0.11 | 1.1 ± 0.23 | | | |
| 2h572-608-N297Qshort Fc | 1.0 ± 0.05 | 2.0 ± 0.0 | | | 0.93 ± 0.4 | | | |
| 2h572-608-CT Long Fc | 2.0 ± 1.0 | 2.0 ± 1.0 | 0.468 ± 0.156 | 0.38 ± 0.06 | 1.6 ± 0.74 | | | |
| 2h572-614-CT Long Fc | 2.0 ± 1.0 | 2.0 ± 0.5 | 0.283 ± 0.038 | 0.25 ± 0.02 | 1.4 ± 0.68 | | | |
| 2h572-633-CT Long Fc | 3.0 ± 0.7 | 1.0 ± 1.0 | 0.174 ± 0.077 | 0.13 ± 0.07 | 1.9 ± 1.3 | 1.3 ± 0.3 | 1.2 ± 0.3 | 1.7 ± 0.43 |
| 2h572-633-CT-Fc SP5 | 5.0 ± 0.5 | 1.0 ± 0.5 | 0.161 ± 0.053 | 0.13 ± 0.04 | 2.3 ± 1.5 | 1.5 ± 0.7 | | 2.9 ± 1.3 |
| 2h572-634-CT Long Fc | 2.0 ± 1.0 | 1.0 ± 0.6 | 0.162 ± 0.029 | 0.13 ± 0.02 | 1.5 ± 0.91 | | | |
| 2h572-635-CT Long Fc | 3.0 ± 1.0 | 2.0 ± 0.6 | 0.149 ± 0.014 | 0.13 ± 0.01 | 1.6 ± 0.93 | | | |
| 2h719-2 Fc | 1.0 ± 0 | 0.7 ± 0.4 | 6 ± 1.4 | | 0.13 ± 0.08 | | | |
| 2h719-2 IgG1 | 1.0 ± 0.5 | 6.0 ± 0.3 | 13.8 ± 10.6 | 2.2 ± 1.3 | 0.35 ± 0.23 | | | |
| 2h719-2 IgG4 | 1.5 ± 0.6 | 16.0 ± 13.0 | 15.9 ± 10.9 | 2.1 ± 0.7 | 1.1 ± 0.48 | | | |
| 2h719-202-N297Qshort Fc | 1.8 ± 0.5 | 1.7 ± 0.7 | | | 0.66 ± 0.26 | | | |
| 2h719-202-CT Long Fc | 3.0 ± 1.0 | 2.5 ± 0.6 | 1.7 ± 0.7 | 1.3 ± 0.3 | 3.1 ± 2.0 | | | |

*FIG. 3 provides sequences of various Fc domains. FIG. 4 shows examples of various Fc-formatted dAbs.

Example 5

Binding Kinetics and CD40L Affinity of Various Antibodies

BMS-986004 is a dimeric fusion protein, composed of a modified Fc fragment of IgG1 linked to the C-terminus of the dAb BMS2h-572-633. Surface plasmon resonance (SPR) was used to characterize the kinetics and affinity of BMS-986004 or the monovalent component domain antibody BMS2h-572-633 binding to CD40L. The BMS-986004 values were compared to those for the benchmark antibodies 5c8-IgG1 and 5c8-CT and the monovalent component 5c8 FAB fragment. The SPR experiments utilized a hCD40L construct containing an N-terminal isoleucine zipper motif (IZ-hCD40L) which facilitates the specific assembly of the CD40L molecule into the native trimeric form. A biotinylated version of IZ-hCD40L (biot-IZ-hCD40L) with equivalent binding activity was also utilized for some SPR experiments.

The monovalent BMS2h-572-633 domain antibody binds biot-IZ-hCD40L with a Kd of 7.8 nM, compared to an affinity of 5.4 nM for the monovalent 5c8 FAB fragment, TABLE 7. Because BMS-986004 is bivalent, and the IZ-hCD40L target is trivalent, the SPR binding data are influenced by avidity regardless of whether CD40L target is on the chip surface or in solution. To estimate the avidity-influenced binding affinity, the SPR data for BMS-986004 binding to a biot-IZ-hCD40L surface was fitted to a 1:1 Langmuir model, suggesting a dissociation constant of less than 1 nM, TABLE 7. Similar results were obtained for 5c8-IgG1 and 5c8-CT.

TABLE 7

IZ-hCD40L kinetic and affinity values as determined using SPR (Biacore)

| Anti-CD40L Ab | Temperature (° C.) | Model | ka (M−1s−1) | kd (s−1) | Kd (nM) |
|---|---|---|---|---|---|
| BMS-986004 | 25 | 1:1 Langmuir | 2.3E+06* | 2.6E−04* | 0.11* |
| 2h572-633 | 25 | 1:1 Langmuir | 1.0E+06 | 8.1E−03 | 7.8 |
| 5c8-IgG1 | 25 | 1:1 Langmuir | 5.4E+05* | 2.3E−04* | 0.42* |
| 5c8-CT | 25 | 1:1 Langmuir | 5.8E+05* | 1.3E−04* | 0.22* |
| 5c8 FAB fragment | 25 | 1:1 Langmuir | 1.4E+05 | 7.6E−04 | 5.4 |

*Value is influenced by avidity due to analyte bivalency.

Figure 5:
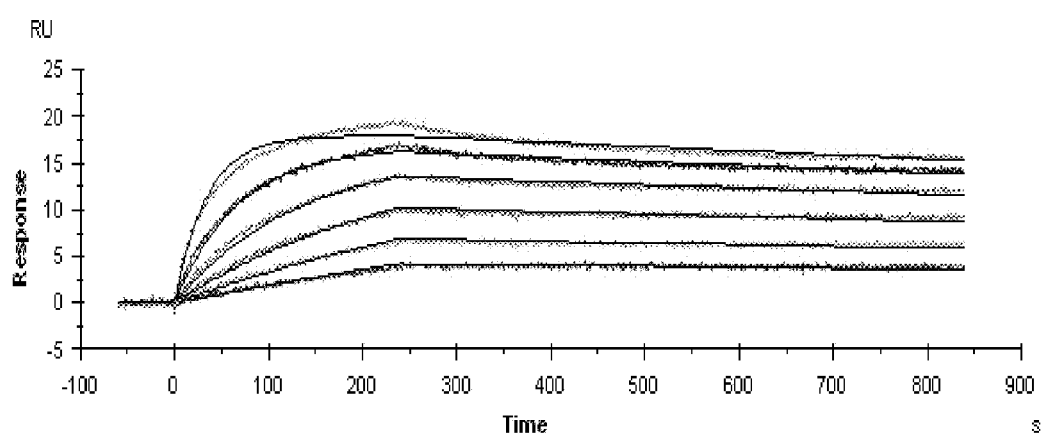
FIG. 5 depicts SPR sensorgram data for the binding of 12.5-0.39 nM BMS-986004 (2:1 dilution series) to biot-IZ-hCD40L captured on a streptavidin SPR sensor chip at 25° C. Colored lines show the double-referenced sensorgram data, and black lines show the 1:1 Langmuir fit to the data, with an avidity-influenced apparent Kd value of 0.11 nM.

FIG. 5 shows SPR sensorgram data for the binding of 12.5-0.39 nM BMS-986004 (2:1 dilution series) to biot-IZ-hCD40L captured on a streptavidin SPR sensor chip at 25° C. Colored lines show the double-referenced sensorgram data, and black lines show the 1:1 Langmuir fit to the data, with an avidity-influenced apparent Kd value of 0.11 nM.

Figure 6:
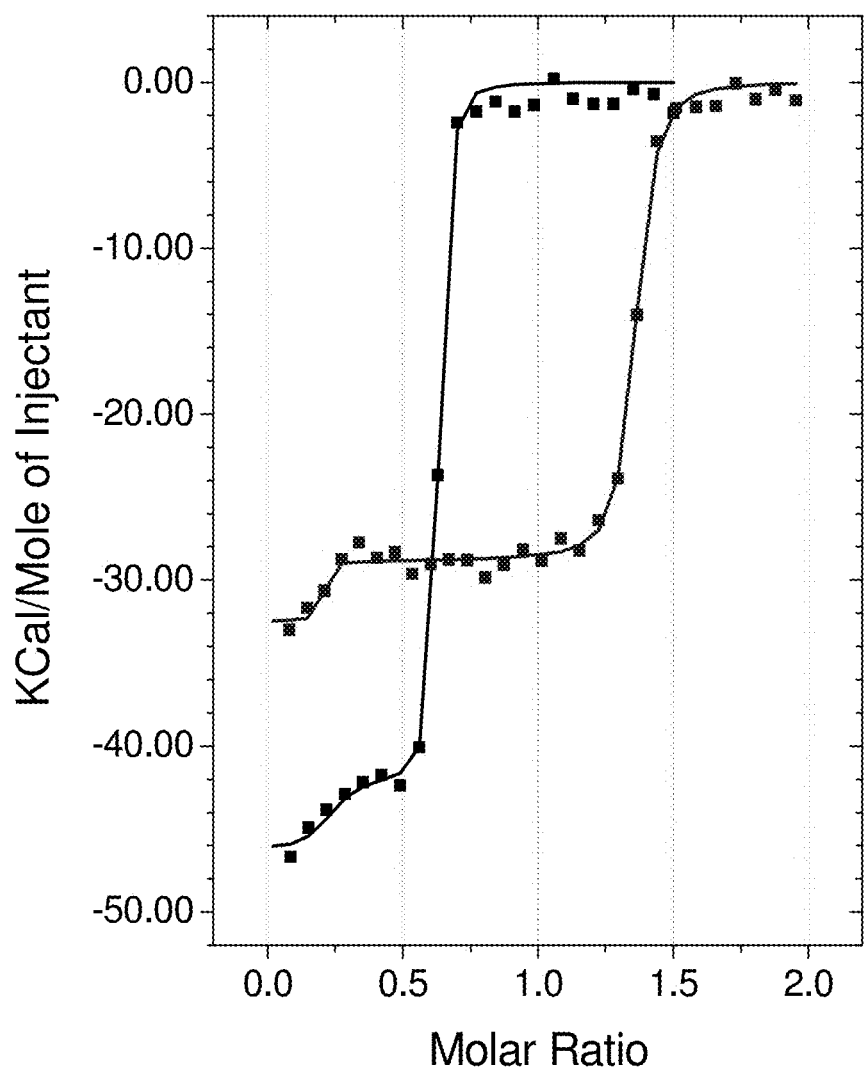
FIG. 6 shows ITC data for titrations of 19 µM IZ-hCD40L into 2 µM BMS-986004 (black) or 18 µM BMS-986004 into 2 µM IZ-hCD40L (blue). The molar ratio (apparent stoichiometry) is defined per mole of IZ-hCD40L trimer and per mole of bivalent BMS-986004 Fc-dimer. Molar ratio values obtained as the equivalence points on the abscissa suggest more than one mole of BMS-986004 can bind per mole of IZ-hCD40L trimer; however, an exact structural model for the complex cannot be determined from the ITC data alone. Squares represent the integrated heat of binding data and solid lines represent the best fit to a "2 sets of sites model."

The affinity and thermodynamics of BMS-986004 binding to CD40L were also characterized in solution using isothermal titration calorimetry (ITC) at temperatures ranging from 15-37° C. These data suggested the presence of multiple thermodynamically distinct binding modes (FIG. 6) with Kd values for the different modes beyond the high-affinity limit of detection (Kd<2 nM) (TABLE 8), consistent with the SPR data. The affinity of the monovalent 5c8 FAB fragment for IZ-hCD40L as determined by ITC (3.5 nM) was also consistent with the value determined by SPR.

TABLE 8

IZ-hCD40L affinity as determined using ITC

| Molecule in the ITC syringe | Molecule in the ITC cell | Kd (nM) |
|---|---|---|
| BMS-986004 | IZ-hCD40L | <2 |
| 5c8-CT | IZ-hCD40L | <2 |
| IZ-hCD40L | BMS-986004 | <2 |
| IZ-hCD40L | 5c8-CT | <2 |
| IZ-hCD40L | 5c8 FAB fragment | 3.5 |

Example 6

Fc Receptor Affinity of Various Antibodies

The Fc-domain of BMS-986004 (termed "CT") was engineered from a wild type IgG1 Fc domain to retain the ability to bind FcRn, but to disrupt the binding to Fcγ receptors. To confirm that the engineered molecule has the desired Fc receptor binding profile, the binding affinities of BMS-986004 for human FcRn, and the human Fcγ receptors CD64 (FcγRI), CD32a (FcγRIIa), CD32b/c (FcγRIIb/c), CD16a (FcγRIIIa), CD16b (FcγRIIIb) were measured using SPR, in comparison to 5c8-IgG1 and 5c8-CT. For these experiments, BMS-986004 was captured via the domain antibody domains on a biot-IZ-hCD40L sensor surface, and the soluble Fc receptor proteins were tested for binding to the exposed Fc domain. Likewise, 5c8-IgG1 and 5c8-CT were captured on a biot-IZ-hCD40L surface via the FAB domains, with soluble FcR binding.

BMS-986004 bound FcRn with Kd of 670 nM at pH 6.0 which is the relevant pH for binding within the endosome, TABLE 9. However, binding was significantly reduced (Kd>5000 nM) at neutral pH suggesting efficient release of from FcRn under these conditions. BMS-986004 bound CD64 with a Kd of 0.6 nM, and had a statistically weak affinity for CD32a, CD32b/c, CD16a and CD16b (Kd>3000 nM). Both 5c8-IgG1 and 5c8-CT had a similar FcRn affinity as BMS-986004. 5c8-CT, which has the identical "CT" Fc region as BMS-986004, also had a similar FcγR binding properties as BMS-986004, whereas 5c8-IgG1, which has a wild type IgG1 Fc domain, bound more strongly to FcγRs, TABLE 9.

TABLE 9

Fc receptor affinity as determined using SPR (Biacore).

| Sample | pH | BMS-986004 Kd (nM) | 5c8-IgG1 Kd (nM) | 5c8-CT Kd (nM) |
|---|---|---|---|---|
| hFcRn | 6 | 670 | 590 | 720 |
| hFcRn | 7.1 | >5000 | >5000 | >5000 |
| CD64 | 7.1 | 0.6 | <0.05 | 0.9 ± 0.4 |
| CD32a | 7.1 | >3000 | ~$10^{-7}$ M* | >3000 |
| CD32b/c | 7.1 | >3000 | >3000 | >3000 |
| CD16a | 7.1 | >3000 | 240 ± 40 | >3000 |
| CD16b | 7.1 | >3000 | >3000 | >3000 |

*CD32a binding to 5c8-IgG1 was biphasic. Kd was estimated as ~$10^{-7}$ M based on steady state fit to dominant binding even. This Kd is in range of literature reported KD for CD32a binding to IgG1.

Example 7

In-Vitro Cell-Based Assays

The potency of BMS-986004 was evaluated in various primary immune cell assays to ensure robust potency across different cell types. The primary human B cell proliferation assays were conducted two ways, as described in detail above in Example 4: (1) recombinant CD40L trimer was used to drive B cell proliferation; and (2) CHO cells expressing CD40L on the membrane (CHO-CD40L) were utilized to induce B cell proliferation. The utility of CHO-CD40L cells was particularly important to ensure that signals from membrane-bound CD40L were inhibited equally well when compared to the soluble CD40L trimer. The CHO-CD40L cells were also used to drive the activation of primary human DCs differentiated from culturing PBMC-derived monocytes in presence of GM-CSF and IL-4. Similarly, the T-B MLR assay measured B cell activation driven by CD40L present on activated T cells. In all of the above described primary assays, BMS-986004 was equipotent to the benchmark 5c8 mAb: potencies ranged from was single-digit nM to sub-nM, depending on the assay (TABLE 10).

TABLE 10

Potency of BMS-986004 in Various Primary Cell Assays

| mAb/dAb-Fc | Trimer B cell Assay EC50 (nM) | CHO-CD40L B Cell Assay EC50 (nM) | T-B MLR EC50 (nM) | T-B MLR IL-6 EC50 (nM) | CHO-CD40L DC Assay IL-12 EC50 (nM) | CHO-CD40L DC Assay IL-6 EC50 (nM) | CHO-CD40L DC Assay TNF-a EC50 (nM) |
|---|---|---|---|---|---|---|---|
| 5c8 | 8.0 ± 3.0 | 2.0 ± 2.0 | 0.54 ± 0.37 | 0.23 ± 0.09 | 2.0 ± 1.5 | | |
| 5c8-IgG1 | 5.0 ± 1.0 | 2.0 ± 2.0 | 0.34 ± 0.13 | 0.21 ± 0.06 | 0.92 ± 0.94 | 0.73 ± 0.5 | 2.3 ± 1.3 |
| BMS-986004 | 5.0 ± 0.5 | 1.0 ± 0.5 | 0.16 ± 0.05 | 0.13 ± 0.04 | 3.1 ± 1.6 | 1.9 ± 0.6 | 3.6 ± 1.1 |

Example 8

Assessment of Whole Blood Receptor Occupancy (RO)

A receptor occupancy method was developed to measure CD40L target engagement by BMS-986003 in cynomolgus whole blood samples and, subsequently, in BMS-986004 in human whole blood samples. BMS-986003 is a dAb which shares the same amino acid sequence as BMS-986004, except for a non-native glycine residue at its amino-terminus.

Occupancy is measured on CD4+ T cells by flow cytometry using an anti-CD40L mAb that competes for binding to CD40L with BMS-986003/BMS-986004, and is cross-reactive with human and cynomolgus CD40L. In the presence of bound dAb, the anti-CD40L detection mAb is blocked from binding to CD40L in a concentration-dependent manner, providing a measure of target occupancy. Given that basal CD40L is expressed at low levels on resting T cells in peripheral blood, RO was assessed in both unstimulated blood samples and in samples where phytohemagglutinin (PHA) was used to induce up-regulation of CD40L on the T cell surface. Binding potency curves were generated following ex vivo whole blood treatment with BMS-986003 and BMS-986004. The average $EC_{50}$ and $EC_{90}$ values obtained are shown in TABLE 11.

TABLE 11

Binding Potency of BMS-986003 and BMS-986004 on CD4+ T-cells in ex vivo Whole Blood Receptor Occupancy Assay

|  | n | Average $EC_{50}$, nM | Average $EC_{90}$, nM |
|---|---|---|---|
| BMS-986003 |  |  |  |
| Human (basal) | 1 | 0.9 | 3 |
| Human (PHA-induced) | 6 | 0.8 | 9 |
| Cyno (basal) | 3 | 0.6 | 3 |
| Cyno (PHA-induced) | 3 | 0.4 | 2 |
| BMS-986004 |  |  |  |
| Human (basal) | 3 | 0.4 | 3 |
| Human (PHA-induced) | 3 | 0.7 | 5 |

The target binding potency in whole blood for BMS-986003 and BMS-986004 closely correlates between human and cynomolgus monkey. The $EC_{50}$ values for BMS-986003 and BMS-986004 are also similar when bound to basal and PHA-induced CD40L. Additionally, these values are comparable to those obtained in human in vitro cell based assays (see TABLE 10). Based on the measured $EC_{90}$ values, full target saturation in peripheral blood should be achieved at concentrations ≤10 nM.

To support the preclinical PK/PD profile of BMS-986003 and BMS-986004, RO was assessed in both the cynomolgus KLH study (immunization with keyhole limpet hemocyanin) with BMS-986003 and the IV bridging study with BMS-986004. Further details of these findings can be found in Examples below.

Example 9

In Vivo Pharmacology

To show efficacy of a CD40L dAb in mouse disease models, a mouse CD40L dAb 2m126-24 was formatted with mouse IgG1 Fc with D265A point mutation to further lower the Fc effector function. This mouse surrogate dAb 2m126-24-Fc shows potency comparable to BMS-986004 and MR-1, a hamster anti-mouse CD40L antibody (TABLE 12).

Inhibition of KLH Induced Antibody Response by the Mouse CD40L dAb

Figure 7:
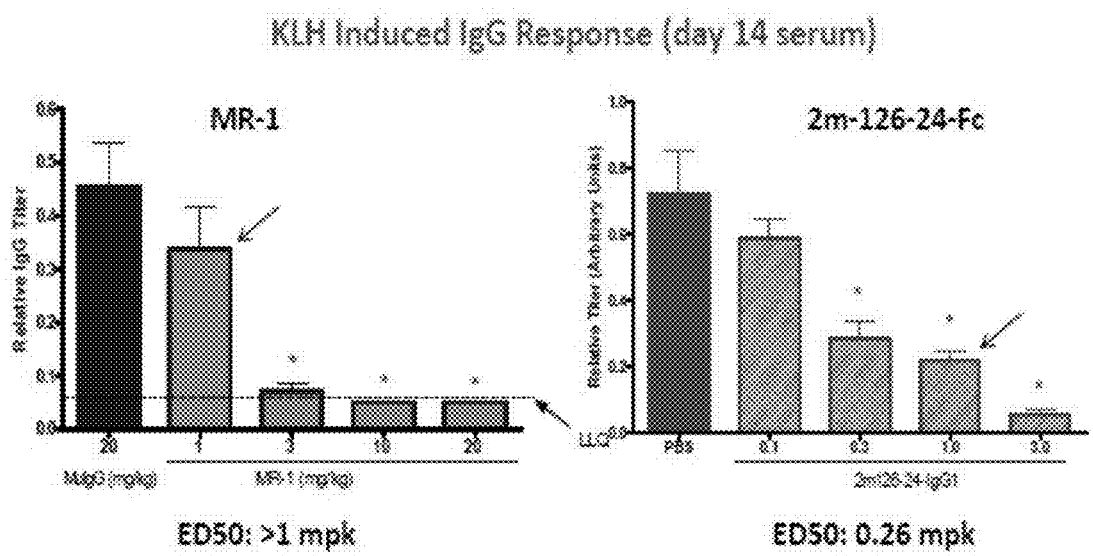
FIG. 7 shows in vivo efficacy of mouse CD40L surrogate dAb-Fc (KLH-induced antibody response.

Female BALB/c mice were injected intraperitoneally (i.p.) with 250 µg KLH on day 0. Mice were dosed subcutaneously (s.c.) with MR-1 or BMS-2m-126-24-Fc at indicated doses on day −1 and day 6. Blood was collected and the serum was analyzed for anti-KLH IgM on day 7 and IgG on day 14 by ELISA. Serum from BALB/c mice collected on day 14 after immunization with KLH was pooled and used as a positive comparator, and the data is expressed as a ratio of the titre of the test serum to the titre of the pooled BALB/c serum. As shown in FIG. 7, BMS-2m-126-24-Fc demonstrated a dose dependent suppression of IgG titers with maximal effect shown at 3 mg/kg, with ED50 calculated to be 0.26 mg/kg. Both the CD40L dAb and the antibody were tested at 1 mg/kg, showing 70% vs. 30% reduction in IgG response, respectively. Similar exposure of the dAb and the antibody were observed at 1 mg/kg, suggesting that the dAb is slightly more potent than the antibody at suppressing KLH-induced IgG response. In conclusion, the CD40L dAb has demonstrated at least the same level of efficacy as the anti-CD40L antibody at inhibiting a T cell dependent antibody response.

Inhibition of TNBS-Induced Colitis by the Mouse CD40L dAb

Figure 8:
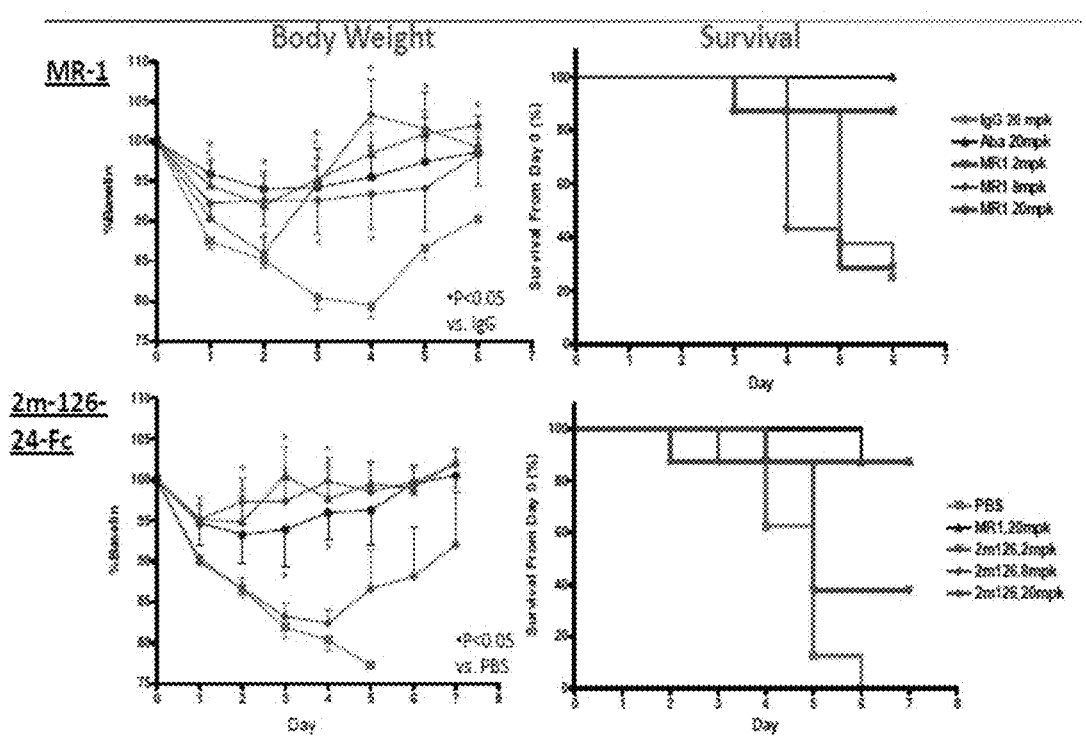
FIG. 8 demonstrates that mouse dAb BMS-2m-126-24-Fc and antibody MR-1 inhibit TNBS-induced colitis in mice.

Male SJL/J mice were intrarectally administered with 2.5 mg Trinitrobenzene sulfonic acid (TNBS) in 50% EtOH via a catheter inserted 4 cm distal to the anus. Mice were dosed once s.c. with MR-1 or BMS-2m-126-24-Fc at indicated doses 4 hours prior to TNBS injection. FIG. 8 presents the changes in the mean body weight and the percent survival of groups of mice treated with PBS/IgG or varying dose levels of MR-1 or the dAb. Abatacept was used as a positive control (20 mg/kg, i.p. every other day). A typical profile of TNBS-induced colitis was shown in the IgG control group: loss of body weight, peaking at day 3-4; colitis-related death occurring at day 3 and beyond; and the survived mice showing signs of recovery after day 4. Treatment with the CD40L dAb or the antibody (both tested at 2, 8 and 20 mg/kg) caused a dose-dependent inhibition of the body-weight loss and the increase in survival rate; both compounds at 8 mg/kg yielded a degree of efficacy that is comparable to that of Abatacept at 20 mg/kg. In conclusion, the mouse CD40L dAb BMS-2m-126-24-Fc has demonstrated comparable efficacy to the anti-CD40L antibody MR-1 in an acute TNBS-induced colitis model.

TABLE 12

In vitro Potency Comparison

|  | mAb/dAb-Fc | Trimer B cell Assay EC50 (nM) | CHO-CD40L B cell Assay EC50 (nM) | CHO-CD40L DC Assay IL-6 EC50 (nM) |
|---|---|---|---|---|
| Human | 5c8 | 8.0 ± 3.0 | 2.0 ± 2.0 |  |
|  | BMS-986004 | 5.0 ± 0.5 | 1.0 ± 0.5 | 1.9 ± 0.6 |
| Mouse | 2m126-24-Fc | 4.7 ± 0.9 | 0.4 ± 0.06 | 0.5 ± 0.2 |
|  | MR-1 (mAb) | 1.7 ± 0.4 | 0.6 ± 0.2 | 0.6 ± 0.3 |

Figure 9:
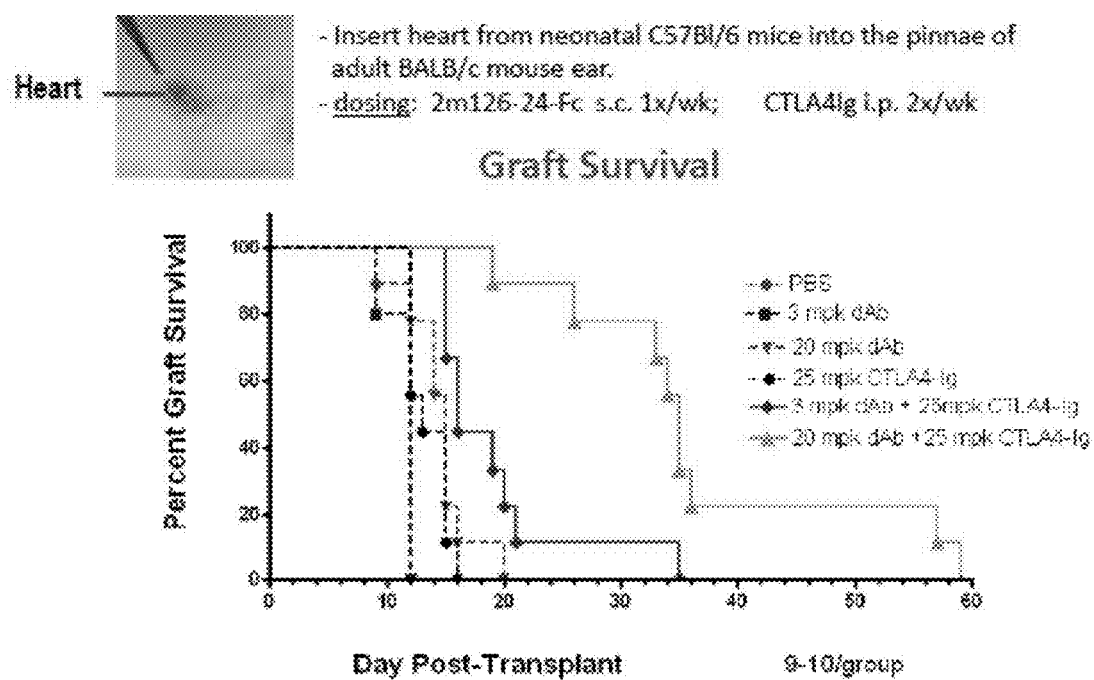
FIG. 9 shows that BMS-2m-126-24-Fc and CTLA4-Ig work synergistically to prolong the survival of cardiac allografts.

Synergistic Effect Between CTLA4 Ig and the Mouse CD40L dAb in a Mouse "Heart-to-Ear" Transplant Model Heart grafts from neonatal (48-72 hrs) C57B1/6 mice were implanted into a subcutaneous pocket created in the ear pinnae of BALB/c mice. Mice were treated with CTLA4-Ig (i.p. 2×/wk), BMS-2m126-24-Fc (s.c. 1×/wk), or combination of both at indicated doses, with first dosing initiated the day prior to transplantation. Time to rejection was defined by the absence of cardiac contractility for three consecutive days as assessed daily by the electrocardiogram (ECG) device of allograft. As expected, without any treatment, C57BL/6 mice that received the neonatal BALB/c heart rejected the graft shortly thereafter, with median survival time (MST) of 12 days. The monotherapy with 3, 20 mg/kg of the dAb or 25 mg/kg of CTLA4-Ig had no or little impact on prolonging the survival of the allograft (MST: 12, 15 and 13 days respectively). However, in the groups treated with combination of 20 mg/kg of the dAb and 25 mg/kg of CTLA4-Ig, the graft survival was significantly prolonged showing MST of 35 days (FIG. 9). This data has provided rationale for combining CD40L dAb with belatacept in human renal transplant patients. Future transplant studies in non-human primates will further define the dose level and assess the potential effect on tolerance induction with CD40L dAb BMS-986004.

Example 10

In Vivo Nonclinical Pharmacokinetics (PK) and Pharmacodynamics (PD)

Various in vivo studies were conducted to characterize the PK and PD of BMS-986004, BMS-986003, and a mouse CD40L dAb-Fc surrogate BMS-2m-126-24-CT, in the nonclinical setting. The key findings are summarized below.

ELISA to Measure BMS-986004 dAb

Enzyme-linked immunosorbency assay (ELISA)-based bioanalytical methods were developed to support the PK studies, acute and chronic efficacy studies in mice, and exploratory PK/PD studies employing cynomolgus monkeys. In all cases, whole blood was obtained and plasma prepared in the presence of EDTA, the samples were then subjected to ELISA analysis.

Plasma concentrations of BMS-986004 were measured with an ELISA assay that utilized human CD40L antigen to capture the analyte from test samples. Test samples were thawed at 4° C., mixed well and diluted 1:100 in assay diluent composed of 1×PBS, 0.05% Tween-20, and 1% BSA (PTB). Subsequent dilutions of the sample were made using 1% normal monkey plasma/PTB as diluent. This allowed the test analyte to be assayed at several dilutions ($10^2$-$10^5$) while keeping the sample matrix at 1%.

Recombinant trimeric human CD40L was obtained from Protein Structure and Science (PSS), LVL and was bound to 96 well plates at a final concentration of 2 μg/mL. Test samples, quality control (QC) samples and the standards were detected with affinity-purified rabbit anti-heavy chain (Vh) domain framework polyclonal antibody (Covance Research Products, Denver, Pa.) diluted to a concentration of 0.25 μg/ml in PTB, followed by horseradish peroxidase-labeled donkey anti-rabbit polyclonal secondary antibody (Jackson Immunoresearch, West Grove, Pa.) with substrate (TMB—tetramethylbenzidine) added, and the enzymatic reaction stopped with 1 M phosphoric acid. Absorbance was measured at a wavelength of 450 nm. The analysis of BMS-986004 in test samples was conducted using a standard curve. Standard curve calibrators prepared on the day of each run in 1% monkey plasma were used to define the dynamic range of the bioanalytical method. The range of resulting standard curve in 100% plasma was 10-1200 ng/mL. The reference standard for BMS-986004 was obtained from Biologics Process and Product Development (BPPD), HPW. The reference standard material was representative of the manufacturing batch and was used in the study protocol. Standard curves and QCs were evaluated using criteria for accuracy and precision of ≤20% which was considered to be acceptable for assay performance. Test samples were quantified using a 4-parameter logistic fit regression model weighted by reciprocal concentration (1/x) derived from the calibrators.

Performance of the QC samples, measured by the deviation of the calculated concentration from its nominal value indicated the reference material was stable in neat monkey plasma at concentrations of 30-1000 ng/ml when stored at −70° C. for over 2 months.

ELISA to Measure a Mouse Surrogate dAb

Mouse CD40L-specific dAb BMS-2m-126-24-CT was measured in mouse plasma samples to provide exposure data in support of several acute and chronic efficacy studies as well as PK assessment.

While the assay format for mouse dAbs was quite similar to that for human dAbs in monkey samples, there were a few differences. The mouse plasma matrix was diluted to 1:10 (10%) in assay diluent, and all subsequent dilutions of test samples were made using 10% mouse matrix. Likewise, all standards and QCs were also incubated on ELISA plates in 10% mouse plasma. The concentration of BMS-2m-126-24-CT in test samples from mice was measured using mouse CD40L to capture the analyte. As the mouse dAb has Vk framework, all test samples, QCs, and the standards were detected with affinity purified rabbit anti-kappa (Vk) domain polyclonal antibody (Covance Research Products, Denver, Pa.) diluted to a concentration of 0.5 μg/mL in PTB. The rest of the assay and analysis procedure was similar to the procedure for the analysis of human CD40L dAbs. Acceptance criteria for back-calculated concentrations of standards and QCs were also similar to those for human CD40L dAbs. The quantitative range of BMS-2m-126-24-CT as determined from the standard curve was 12.5 to 600 ng/mL in neat sample matrix.

Nonclinical Pharmacokinetics

TABLE 13 summarizes the PK parameters for BMS-986004, BMS-986003, and BMS-2m-126-24-CT in nonclinical animal species.

TABLE 13

Single-dose PK Parameters (mean ± SD) from Two Nonclinical Animal Species

| Species | dAb | Route | Dose (mg/kg) | Cmax (μM) | Tmax (h) | AUC0-inf (μM · h) | T½ (h) | CLTp (mL/h/kg) | Vss (L/kg) | F (%) |
|---|---|---|---|---|---|---|---|---|---|---|
| Mouse | BMS-2m-126-24-CT | IV | 1 (N = 3) | — | — | 6.9 | 101 | 1.85 | 0.26 | — |
| | | SC | 1 (N = 3) | 0.063 | 24 | 10 | 100 | — | — | 100 |
| | | | 10 (N = 3) | 0.68 | 24 | 114 | 120 | — | — | 100 |
| Monkey | BMS-986003 | IV | 2 (N = 2) | — | — | 40 | 106 | 0.67 | 0.067 | — |
| | | SC | 0.2 (N = 4) | 0.019 ± 0.004 | 60 ± 72 | 4.0 ± 2.7 | 85 ± 29 | — | — | 88 |
| | | | 2 (N = 4) | 0.22 ± 0.075 | 33 ± 43 | 29.7 ± 4.9 | 68 ± 11 | — | — | 74 |
| | | | 20 (N = 4) | 1.48 ± 0.34 | 11 ± 9 | 175 ± 27 | 105 ± 18 | — | — | 44 |
| | BMS-986004 | IV | 11 (N = 4) | — | — | 241 ± 18 | 124 ± 12 | 0.59 ± 0.04 | 0.098 ± 0.01 | — |
| | 5c8-IgG1 | IV | 20 (N = 4) | — | — | 1800 ± 74 | 400 | 0.074 | 0.042 | — |

Figure 11A:
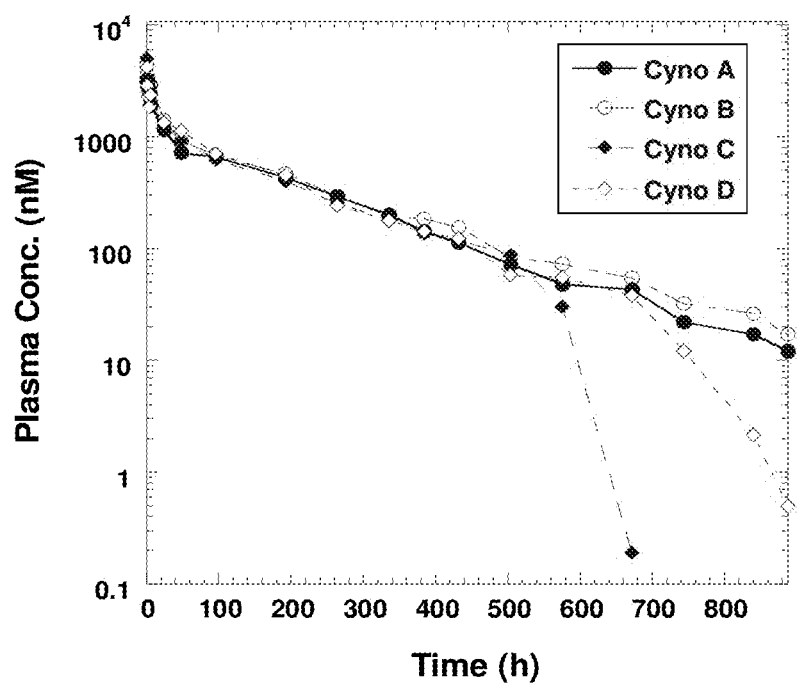
FIG. 11A shows plasma concentration vs. time profile of BMS-986004 after IV dosing of 11 mg/kg in monkeys.
Figure 11B:
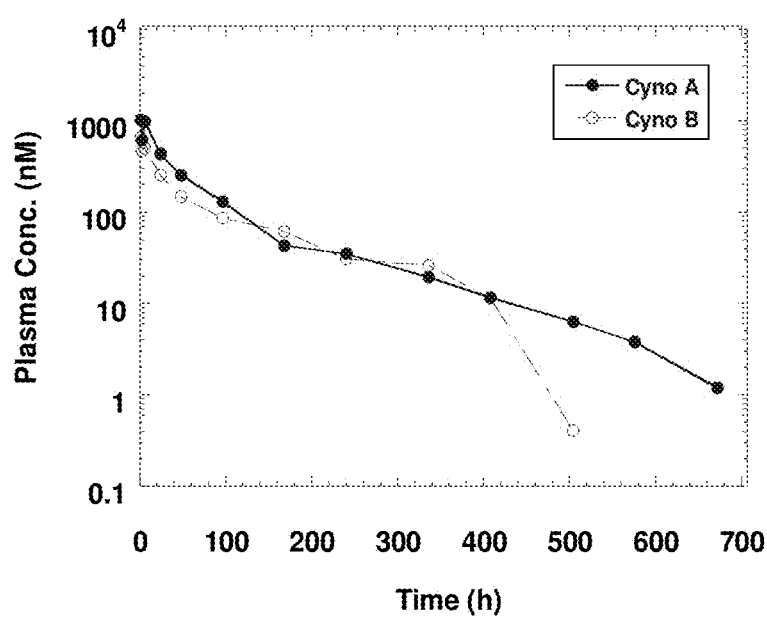
FIG. 11B demonstrates plasma concentration vs. time profiles of BMS-986003 after IV dosing of 2 mg/kg in monkeys.

BMS-986004 and BMS-986003 exhibited comparable PK profiles in monkeys (FIG. 11A and FIG. 11B). After IV administration, the plasma concentrations of BMS-986004 and BMS-986003 exhibited a bi-exponential decline up to 504 and 408 h, respectively. Accelerated clearance was observed afterward in 50% of monkeys enrolled in both studies. Immunogenicity testing of the plasma samples collected at 38 d after BMS-986004 treatment suggested that all monkeys developed anti-drug antibody (ADA); and that the monkeys with higher ADA levels showed faster clearance. Although no immunogenicity test was conducted for the IV PK study with BMS-986003, a similar level of immunogenicity was observed in monkeys after subcutaneous dosing with BMS-986003 in the PK/PD study, suggesting both proteins were immunogenic in monkeys. The terminal half-life (T½) of 124 and 106 h for BMS-986004 and BMS-986003 was, therefore, determined using the exposures collected up to two weeks (336 h) only. The steady-state volume of distribution (Vss) of BMS-986004 and BMS-986003 was 0.098 and 0.074 L/kg, respectively. The values are greater than the plasma volume (0.06 L/kg) but less than the volume of extracellular fluid (0.2 L/kg), suggesting that the proteins largely reside in the extracellular space. The total body plasma clearance (CLTp) of BMS-986004 and BMS-986003 was 0.59 and 0.65 mL/h/kg, respectively.

The PK parameters of BMS-986004 in monkeys were compared to those of abatacept, a similar size protein (78.5 vs 78-kDa BMS-986004, based on amino acid sequence), with the same modified human IgG1 Fc format. As expected, the parameters of BMS-986004 were nearly identical with those of abatacept (CLTp of 0.6 mL/h/kg, Vss of 0.087 L/kg, T½ of 5 d), suggesting the humans PK of BMS-986004 and abatacept is likely to be similar.

Figure 12:
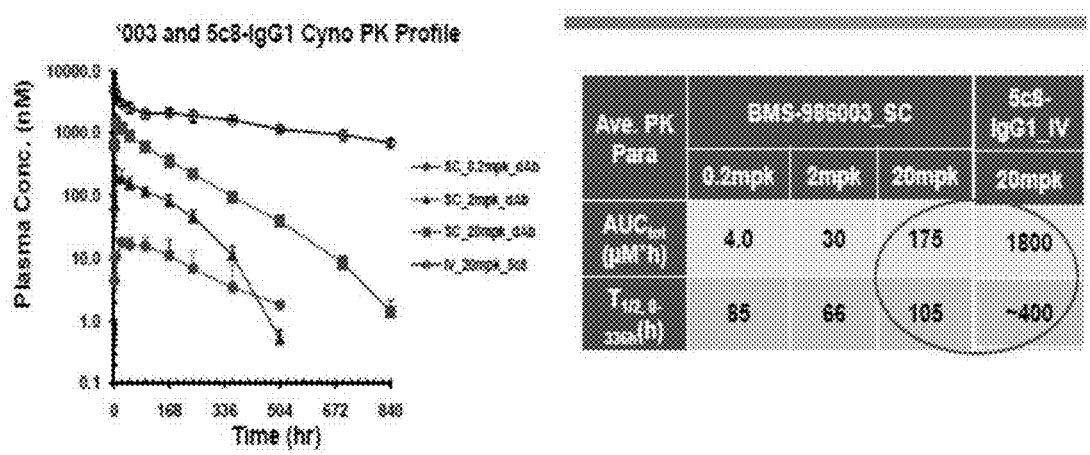
FIG. 12 presents plasma concentrations vs. time profiles of BMS-986003 (after SC dosing at 0.2, 2 and 20 mg/kg in monkeys) and of 5c8 IgG1 (after IV dosing at 20 mg/kg in monkeys).

The absorption of BMS-986003 after subcutaneous (SC) administration was evaluated in the monkey PK/PD study. The monkeys were administered with BMS-986003 as single subcutaneous doses of 0 (vehicle control), 0.2, 2 and 20 mg/kg, at 24 h prior to the immunization with keyhole limpet hemocyanin (KLH), a T cell-dependent antigen. After dosing, BMS-986003 was slowly absorbed, with a Tmax ranging from 6-96 h (FIG. 12). The exposure of BMS-986003 appeared to be less than dose-proportional across all dose levels. With a dose ratio of 1:10:100, the average Cmax and AUC0-inf ratios were 1:12:80 and 1:7:44, respectively. With the exposure following the IV dose (2 mg/kg) as reference, and assuming linear PK after IV dosing, the SC bioavailability of BMS-986003 was 88%, 74%, and 44% at 0.2, 2, and 20 mg/kg, respectively. The terminal T½ was confounded by the immunogenicity observed with most of the monkeys at 2 to 5 weeks after dosing. Therefore, the T½ was estimated to be 85, 66, and 105 h at 0.2, 2 and 20 mg/kg, respectively.

The PK of 5c8-IgG1, an anti-human CD40L monoclonal antibody used as a positive control in the PK/PD study, was evaluated after IV administration at 20 mg/kg (FIG. 12). 5c8-IgG1 exhibited 10-fold higher plasma exposures and 4-fold longer T½ when compared to BMS-986003 given SC at the same dose (TABLE 13).

Figure 13:
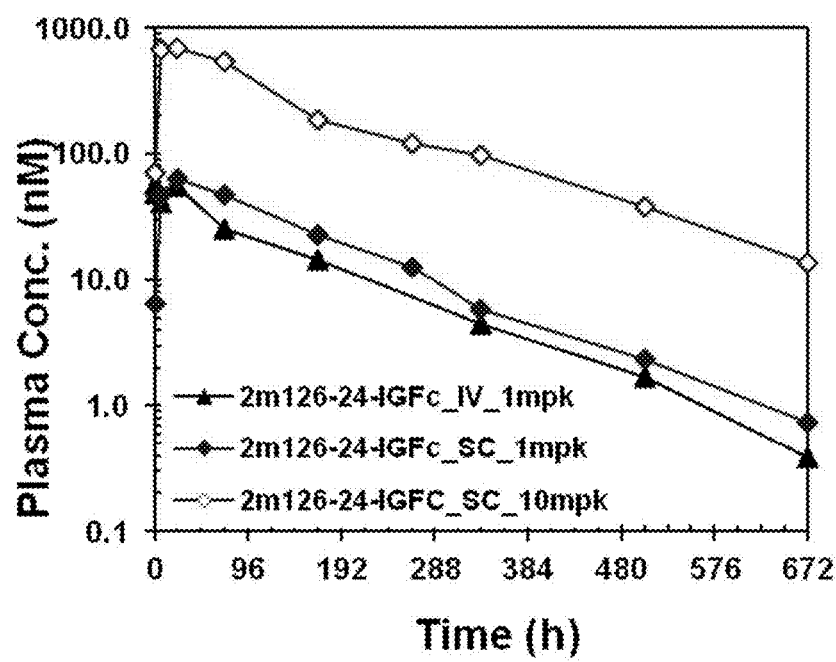
FIG. 13 shows plasma concentrations vs. time profiles of BMS-2m-126-24-CT after 1 mg/kg IV and SC dosing, and 10 mg/kg SC dosing to mice.

The PK of the mouse surrogate dAb-Fc fusion protein, BMS-2m-126-24-CT, was evaluated in mice following single IV and SC administration (TABLE 13). After a single IV (1 mg/kg), the plasma concentrations followed a monoexponential decline with a terminal T½ of 101 h (FIG. 13). The CLTp was 1.85 mL/h/kg; and the Vss was at 0.26 L/kg, indicating extracellular distribution. After single SC doses of 1 and 10 mg/kg, BMS-2m-126-24-CT was slowly absorbed with a Tmax of 24 h. The systemic exposures increased in a dose-proportional manner. With a dose ratio of 1:10, the Cmax and AUC0-inf increased in the proportion of 1:11. The terminal T½ was 100 and 120 h at 1 and 10 mg/kg, respectively. The ratio of the dose-adjusted exposure (AUC0-inf) after SC and IV administration was greater than 1, suggesting complete absorption after SC administration.

Pharmacokinetic/Pharmacodynamic Modeling

The PD of BMS-986003 was measured as the suppression of anti-KLH antibody response in the PK/PD study. BMS-986003 suppressed 70% the antibody response to KLH $$\left(\% \text{ response suppressed} = \left(1 - \frac{AUEC_{0-1008h\ IgG\ titers} \text{treated group}}{AUEC_{0-1008h\ IgG\ titers} \text{vehicle group}}\right) * 100\right)$$

at the highest dose of 20 mg/kg. Marginal (15%) and no suppression of the antibody response occurred at 2 and 0.2 mg/kg. In comparison, 5c8-IgG1 exhibited 10-fold higher plasma exposures and 4-fold longer T½ than BMS-986003 at the same dose level (20 mg/kg). As a result, 5c8-IgG1 suppressed 97% anti-KLH antibody response. In order to compare the in vivo potency between BMS-986003 and 5c8-IgG1, PK/PD modeling was performed using SAAM II (version 1.2.1, Seattle, Wash.). The plasma concentrations of BMS-986003 following SC administration were described using a first-order absorption kinetics coupled with a 2-compartment model, where the elimination occurred in both central and peripheral compartments. Because of complications from immunogenicity and possible nonlinear absorption, the PK data were fitted individually at each dose.

For 5c8-IgG1, a two-compartment model with central elimination was used. The anti-KLH antibody response, expressed as the average value of IgG titers, was modeled using a 6-compartment signal transduction model. The kinetics of KLH in the body was assumed to be a 1-compartment model. The inhibition of the IgG production by BMS-986003 and 5c8-IgG1 was described using an Imax model, with a maximum inhibition equal to 100%. As shown in FIG. 14, the model-fitted curves were able to describe both the PK and PD profile. The plasma IC50 of BMS-986003 and 5c8-IgG1 for the suppression of KLH-induced IgG production was estimated to be 74±14 and 60±18 nM, respectively. These results demonstrated that the potency of these two molecules was comparable in vivo.

The CD40L receptor occupancy (RO) of BMS-986004 was measured in the IV PK study. Following IV administration of 11 mg/kg, the RO of BMS-986004 on the peripheral-blood mononuclear cells (PBMC) was time- and concentration-dependent. PK/PD modeling was performed to estimated an RO EC50. The plasma concentrations were modeled using a modified two-compartment model with an additional ADA-mediated first order elimination constant introduced at 504 h after dosing; and the RO was modeled using an Emax model $$\left( RO\ \% = \frac{Emax^* \cdot Cp^\gamma}{EC50^\gamma + Cp^\gamma} \right).$$

Figure 15:
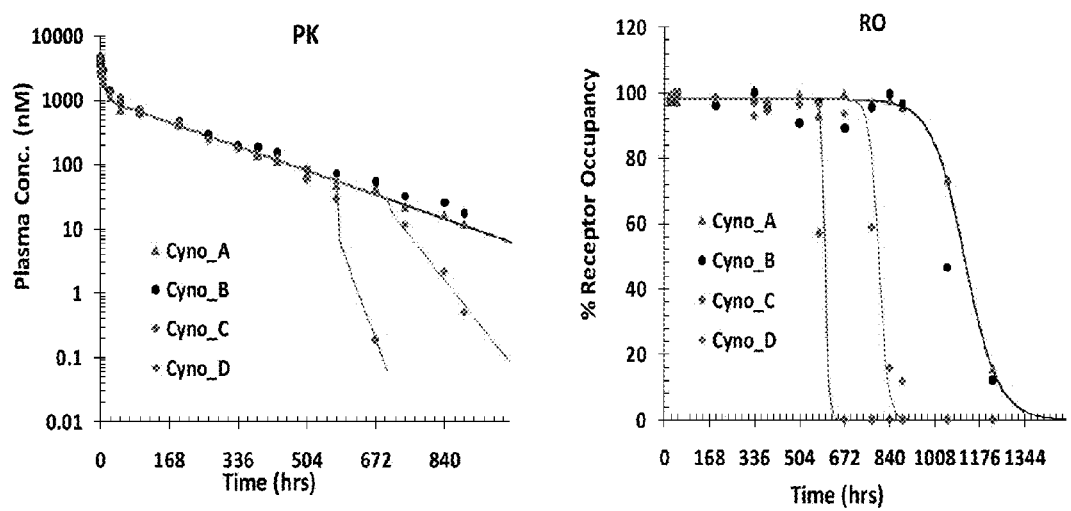
FIG. 15 shows PK/PD modeling of BMS-986004 plasma exposures and ex vivo RO on peripheral blood mononuclear cells (PBMC).

As shown in FIG. 15, the fitted curves were able to describe both exposure and RO, with an estimated RO EC50 of 3.4±0.3 nM and the γ (hill factor) of 3.1±0.1. In comparison, the RO EC50 was ~22-fold lower than the anti-KLH antibody response IC50 of 74±14 nM, suggesting that >95% RO is required in order to achieve appreciable (>50%) anti-KLH antibody suppression.

Example 11

Nonclinical Toxicology Single-Dose PK/PD Study

The objectives of this study were to 1) determine the tolerability of BMS-986003, including its potential immunogenicity, when given subcutaneously as a single dose to monkeys; 2) evaluate its PD (e.g., inhibition of the antibody response to T-cell-dependent antigen) and PK profiles; 3) evaluate the receptor occupancy of BMS-986003 and peripheral T-cell counts following subcutaneous dosing; and 4) aid dose selection for renal transplant studies and first-in-human dosing.

BMS-986003 was administered s.c. in the posterior thorax as single doses of 0 (vehicle control), 0.2, 2, or 20 mg/kg to groups of 2 cynomolgus monkeys per sex. An additional two monkeys/sex received a single intravenous dose of 20 mg/kg 5c8-IgG1, a monoclonal antibody to human CD40L that was used as a positive control in this study. All doses were administered at 2 mL/kg in the vehicle (PBS; pH 7.2). To assess the effects on the T-cell dependent antibody response, animals were immunized at approximately 24 hours after dosing with test article or immediately after dosing the positive control with 10 mg of KLH by intramuscular injection (posterior quadriceps or caudal thigh). Criteria for evaluation included survival, PK, immunogenicity, PD (inhibition of the antibody response to the T-cell-dependent antigen, KLH), clinical signs, body weights, food consumption, peripheral-blood immunophenotyping, receptor occupancy, and clinical-pathology evaluations (hematology, serum chemistry, and coagulation). Animals were returned to stock following a 6-week post-dose observation period.

At doses ≤20 mg/kg, BMS-986003 was slowly absorbed (Tmax=6-96 h) and Cmax and AUCtot values increased in a less than dose-proportional manner across all dose groups and there were no apparent gender differences. The T½ values estimated ranged from 69-104 h across all doses. BMS-986003 was substantially immunogenic; all monkeys developed a positive anti-drug antibody (ADA) response during the 6-week post-dose period. At 0.2 and 2 mg/kg, the mean group total ADA response peaked at Day 22 at mean group end point titers (EPT) of 4203 and 6469, respectively. At 20 mg/kg, the ADA response, while positive, was somewhat delayed and partially suppressed, consistent with target pharmacology, peaking at Day 36 at a mean group EPT of 1828. Further characterization of the antibodies demonstrated the majority of binding to the dAb (non-Fc) portion of the molecule and these antibodies were shown to block the binding of BMS-986003 to CD40L in 2 different immunoassay formats suggesting that the ADA were neutralizing. In addition, the formation of ADA appeared to accelerate the elimination of BMS-986003 in several monkeys.

Mean PK parameters for BMS-986003 are presented in TABLE 14.

TABLE 14

Pharmacokinetic Summary

| Mean Parameter | BMS-986003 SC | | | 5C8-IgG1 IV |
|---|---|---|---|---|
| | 0.2 mg/kg (N = 4) | 2 mg/kg (N = 4) | 20 mg/kg (N = 4) | 20 mg/kg (N = 4) |
| Gender | Male/Female | Male/Female | Male/Female | Male/Female |
| AUC(0-inf) μg · h/mL | 219/407 | 2165/2477 | 14195/13114 | 267750/272250 |
| CLTp mL/h/kg | Not applicable | Not applicable | Not applicable | ND/0.074 |
| T½ h | 69/101 | 68/69 | 107/104 | ND/400 |
| Cmax μg/mL | 69/101 | 45/49 | 88/91 | Not applicable |
| Tmax h | 24/96 | 51/15 | 6/15 | Not applicable |

Molecular weight used for conversion was 78104 Da for BMS-986003, 150000 Da for 5c8-IgG1 mAb.
ND = not determined,;
AUCextra for males was above 20%, therefore the T½ was not reported.

There were no BMS-986003- or 5c8-IgG1-related clinical observations or effects on body weights or clinical pathology parameters except 1 male treated with 5c8-IgG1 had decreased red blood cells (0.74×control), hemoglobin (0.73× predose), and hematocrit (0.75×predose) on Day 8, and 3 of 4 monkeys receiving 5c8-IgG1 had decreased lymphocytes (0.53× to 0.65×predose) on Day 8, suggestive of lymphocyte depletion.

CD40L receptor occupancy was generally time- and dose-dependent and more sustained following administration of 20 mg/kg BMS-986003, consistent with higher and more sustained exposures at this dose and PD activity. For BMS-986003, mean peak receptor occupancy on peripheral-blood mononuclear cells (PBMC) was achieved at 24 hrs (97%), 6 hrs (99%) or 48 hrs (99%) post-dose, decreasing to <90% occupancy at 240, 360, or 696 hrs and to <50% occupancy at 360, 696, or 1032 hrs, at 0.2, 2, or 20 mg/kg, respectively. In comparison, for 5c8-IgG1 at 20 mg/kg, mean peak receptor occupancy on PBMC was achieved at 48 hours 100%), and was sustained at ≥97% for the entire study (1032 hr or through Day 44).

BMS-986003 suppressed the antibody response to KLH only at the high dose of 20 mg/kg. On Days 8-30 at 20 mg/kg, there was a 69 to 83% suppression of the geometric group mean antibody response to KLH, relative to the control group, with a peak suppression of 83% occurring on Day 16. No suppression of the antibody response occurred at 0.2 or 2 mg/kg BMS-986003. These data demonstrate that BMS-986003 at a sustained receptor occupancy of >90% for at least 1 month and at sustained plasma concentrations above ~10 µg/mL through Day 11 is able to inhibit a T-cell dependent antibody response in cynomolgus monkeys. For the positive control antibody, 5c8-IgG1, suppression of 74-97% of the geometric group mean antibody response to KLH occurred on Days 8-30, with peak suppression of 97% by Day 16 which was generally sustained through Day 30.

No biologically relevant BMS-986003 related changes in absolute numbers of B cells (CD45+, CD20+, CD3−), total T (CD45+, CD3+) cells, helper T (CD45+, CD3+, CD4+, CD8−) cells, cytotoxic T (CD45+, CD3+, CD4−, CD8+) cells, or natural killer (CD45+, CD3−, CD16+) cells occurred during the study, which confirmed lack of any Fc effector function. However, on Day 8, 3 of 4 monkeys treated with 20 mg/kg 5c8-IgG1 had decreased T-lymphocytes (0.53×-0.66×predose), both helper T-cell (0.64× to 0.77×predose) and cytotoxic (0.40× to 0.61×predose) T-cell populations, suggestive of depletion.

In conclusion, BMS-986003 administered as single SC doses of 0.2, 2, or 20 mg/kg (AUC≤14195 µg*hr/mL) was well tolerated in cynomolgus monkeys with no adverse drug-related effects. The positive control, 5c8-IgG1, at a dose of 20 mg/kg, resulted in complete, sustained inhibition of the antibody response to KLH and sustained receptor occupancy of nearly 100% through 30 days post-dose. Mild depletion of T-cells was also noted by Day 8 in monkeys receiving 5c8-IgG1 (0.40× to 0.77×predose), which was not observed with BMS-986003. BMS-986003 was able to suppress an antibody response to KLH at 20 mg/kg (peak suppression of 83%) following KLH immunization on Day 1 and had sustained receptor occupancy of ≥90% through Day 22 and ≥50% through Day 29. Similar dampening of the immunogenicity to BMS-986003 occurred at 20 mg/kg. However, lower BMS-986003 doses of 0.2 and 2 mg/kg did not suppress the antibody response to KLH or the anti-drug antibody response. The lack of pharmacology at the lower doses also correlated with decreasing receptor occupancy (i.e., <90% by Day 11 [0.2 mg/kg] or 16 [2 mg/kg]; <50% by Day 16 [0.2 mg/kg] or 30 [2 mg/kg]) and accelerated clearance, presumably due to the formation of ADA. The inhibition of TDAR is consistent with the mechanism of action of this compound and was not considered adverse.

Example 12

Evaluation of the Risk for TE/Thrombosis

It has been hypothesized that the TE associated with administration of the anti-CD40L monoclonal antibodies is mediated by anti-CD40L mAb-CD40L immune complex (IC)-mediated cross linking of platelets, facilitated by IC binding to FcgRIIa, an IgG Fc receptor, causing activation and aggregation (FIG. 10). Blocking the interaction of Fc moiety of IgG with FcgRIIa is, therefore, expected to mitigate platelet cross linking and thrombosis. The following methods and approaches were designed to evaluate the risk of TE and/or thrombosis.

In Vitro Platelet Activation Assays

Several in vitro assays were conducted to test the hypothesis that platelets are activated by CD40L mab/sCD40L IC in a FcgRIIa-dependent manner. The positive control 5c8-IgG1 was used to validate the assays prior to testing BMS-986003 and BMS-986004. Blood from human donors or mice expressing hFcgRIIa receptor on platelets were used for these studies. Platelet activation was detected by flow cytometry using antibodies against the well-validated platelet activation markers P-selectin (CD62P) and PAC-1 (activated GPIIb/IIIa). Briefly, blood was diluted 1:25 in modified Tyrodes-HEPES containing 1 mM CaC12 to which detection antibodies and test reagents was added, incubated, and analyzed for platelet activation. Initial experiments determined that sCD40L or 5c8IgG1 alone did not activate platelets, but different immune complex ratios of 1:1 to 1:8 of 5c8:sCD40L significantly activated platelets. Subsequent experiments used 5c8-IgG1 or 5c8-mIgG2a IC, mostly at a 1:3 molar ratio of 5c8:sCD40L.

Platelet Activation by 5c8/sCD40L IC can be Blocked by Anti-FcgRIIa Antibody

Figure 16:
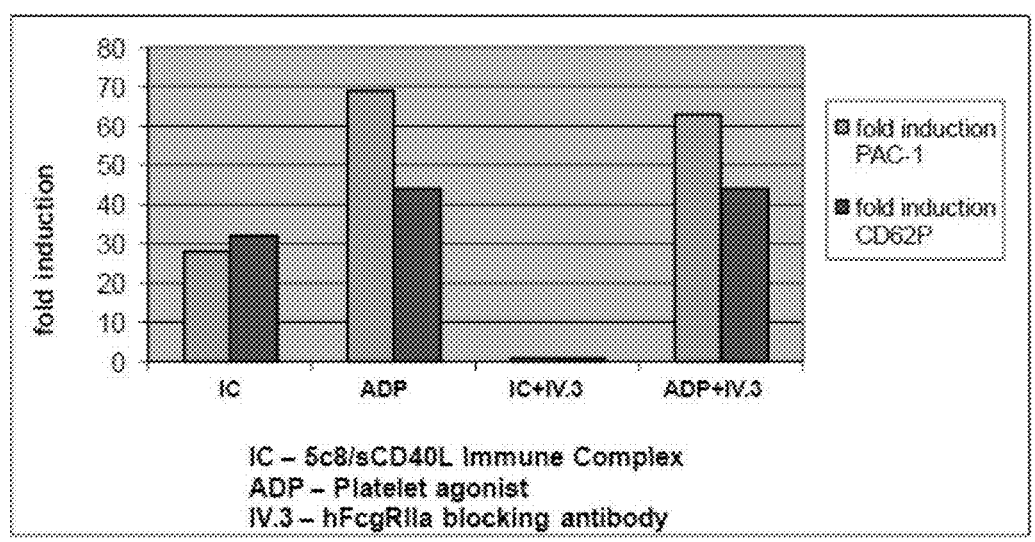
FIG. 16 demonstrates that IV.3 blocks 5c8/sCD40L IC-mediated activation of platelets in human blood.

Studies were conducted with the FcgRIIa blocking antibody IV.3 to test whether activation of platelets by 5c8/sCD40L IC was indeed FcgRIIA-mediated. Blood from human donors was pre-incubated with 0.5 µg/µl of the FcgRIIa blocking antibody IV.3 prior to dilution and incubation with detection antibodies as described above. Adenosine diphosphate (ADP), a platelet activator via a different mechanism, was used as a positive control. As illustrated in FIG. 16, platelet activation by 5c8/sCD40 IC was completely blocked by IV.3, while activation by ADP was not inhibited by the blocking antibody, indicating that activation by the IC is FcgRIIa-mediated.

Selection of Inert Fc Tails

Figure 17:
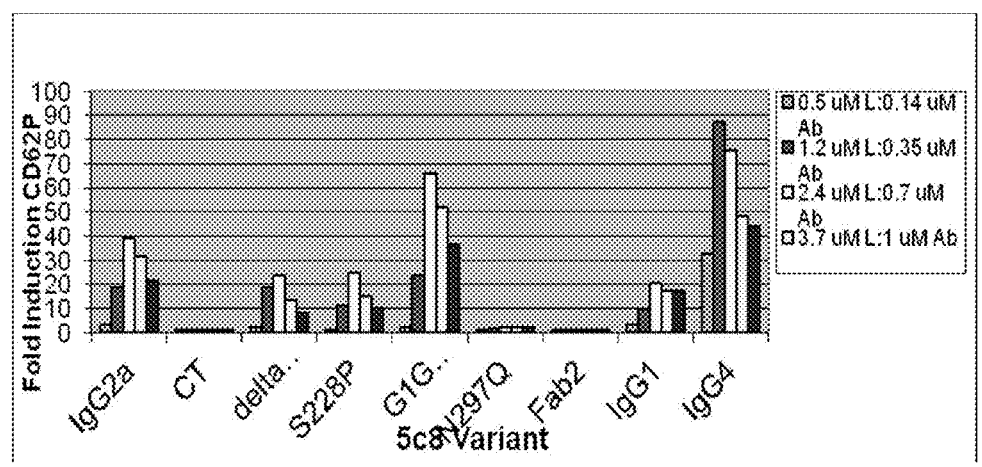
FIG. 17 shows the effect of Fc variants on platelet activation in human blood.

A requirement for potential candidate molecules was absence of binding to FcgRIIa to prevent potential platelet activation. Several 5c8 constructs containing different mutations derived from IgG1 (e.g. 5c8-CT and N297Q) or IgG4 (e.g., 5c8-S228P) were expressed and screened for Fc tails that did not activate platelets using different molar ratios of sCD40L to mAbs. Wild-type and most mutated constructs activated platelets except for 5c8-CT and 5c8-N297Q (FIG. 17). Absence of Fc (5c8-Fab2) also did not activate platelets further confirming that IC-platelet activation is Fc-mediated. The CT tail was chosen to format the dAb candidates BMS-986003 and BMS-986004.

Effect of FcgRIIa Polymorphism on Platelet Activation

Figure 18:
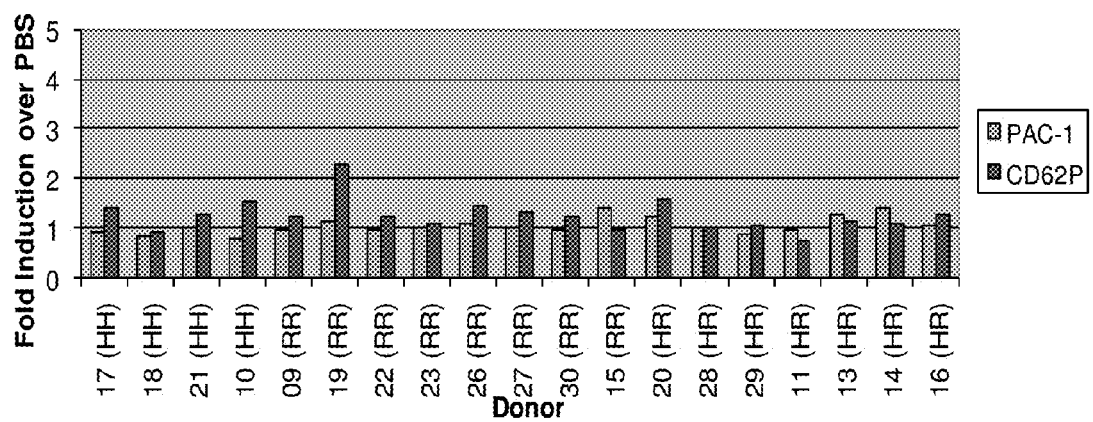
FIG. 18 demonstrates activation of platelets with 5c8-CT/sCD40L IC in blood from human donors genotyped for FcgRIIa polymorphism.

The gene for FcgRIIa is variable at codon 131, resulting in His-Arg (CAT/CGT) polymorphism. The genotype distribution in approximately 100 individuals with about equal distribution of Caucasians and African Americans was A/A (His homozygous; 14%), A/G (His/Arg heterozygous; 60%), and G/G (Arginine homozygous; 26%) for Caucasian Americans and A/A (30%), A/G (51%), and G/G (19%) for African-Americans. Reilly et al., *Clin. Diagn. Lab. Immunol.* 1: 640-644 (1994). Fc-dependent platelet aggregation was noted in samples from R131 individuals when treated with anti-CD9 in mIgG2 or mIgG1 Fc format, while platelets from H131 individuals aggregated only with anti-CD9 as mIgG2 format; this suggests that Fc-dependent aggregation with an IgG1 mAb could potentially segregate a patient population into low and high responders, which has previously been reported with this polymorphism. Tomiyama et al., *Blood* 80: 2261-2268 (1992). To address any potential differences in platelet activation with the IgG1 and CT Fc tail, 19 donors were genotyped for hFcgRIIa polymorphism and samples tested for platelet activation. The donor pool polymorphism (RR; 42%, HH; 21%, HR; 37%) was sufficient to evaluate any potential differences in platelet activation to the IgG1 format. Representative of literature reports, platelet activation with 5c8-IgG1/sCD40L IC was similar across all genotyped individuals. No activation was found with 5c8-CT/sCD40L IC (FIG. 18), suggesting no or minimal risk of increased TE in a patient population with an antibody formatted with the CT tail.

BMS-986004: Platelet Activation in Human Blood Donors

Figure 19:
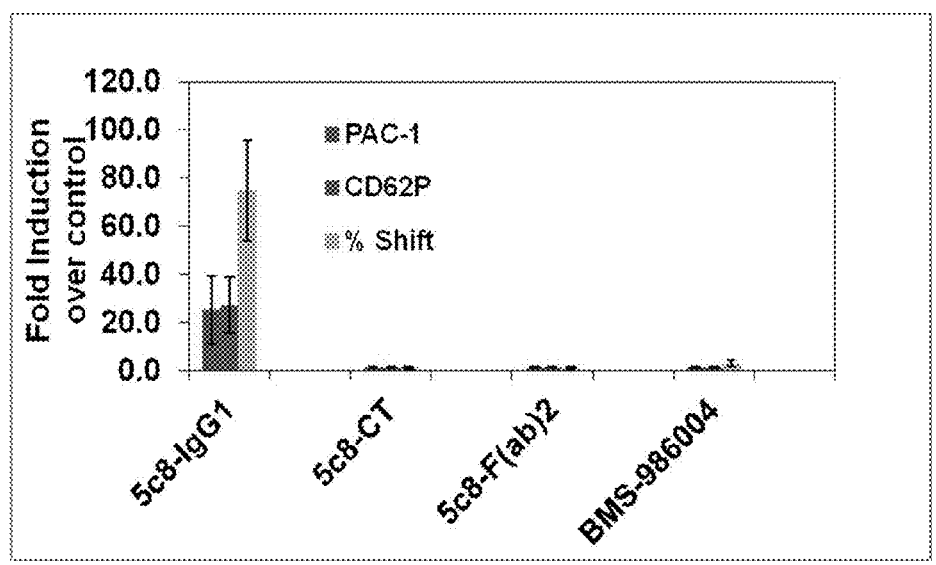
FIG. 19 diagrams platelet activation by various antibodies in blood from human donors.

The experiments described above using 5c8, supported selection of the CT-tail as the best format for BMS-986004 (also called BMS2h-572-633-CT-L2). Blood obtained from 6 donors was treated with 5c8-IgG1, 5c8-CT, F(ab)$_2$, and BMS-986004. Platelets were activated by 5c8-IgG1 but not by any of the other constructs, including BMS-986004 (FIG. 19), suggesting that this dAb has no or low risk for causing platelet activation and TE in clinical studies.

BMS-986003: Platelet Activation in Blood from Mice Expressing hFcgRIIa

Figure 20:
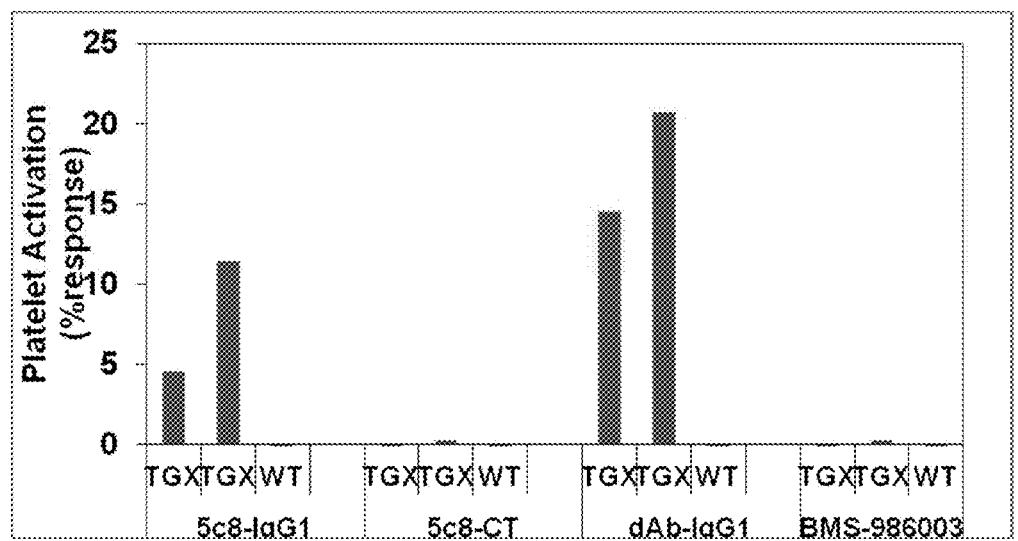
FIG. 20 shows levels of platelet activation by various antibodies, including BMS-986003, in hFcgRIIa-expressing transgenic mice.

To further confirm that activation of platelets by anti-CD40L antibodies was mediated by FcgRIIa receptor, blood from transgenic mice expressing the human receptor (R131 genotype) was treated with 5c8-IgG1, 5c8-IgG2a, dAb-IgG1, 5c8-CT, and BMS-986003 (also called BMS-2h572-633-CT). Platelets were specifically activated by 5c8-IgG1, 5c8-IgG2a, and dAb-IgG1/sCD40L IC in blood from mice expressing hFcgRIIa, but not wild-type littermates. 5c8-CT and BMS-986003 did not activate platelets, further confirming a low risk for TE with the presently disclosed antibodies (FIG. 20).

Example 13

Epitope Binding Experiments

Figure 25:
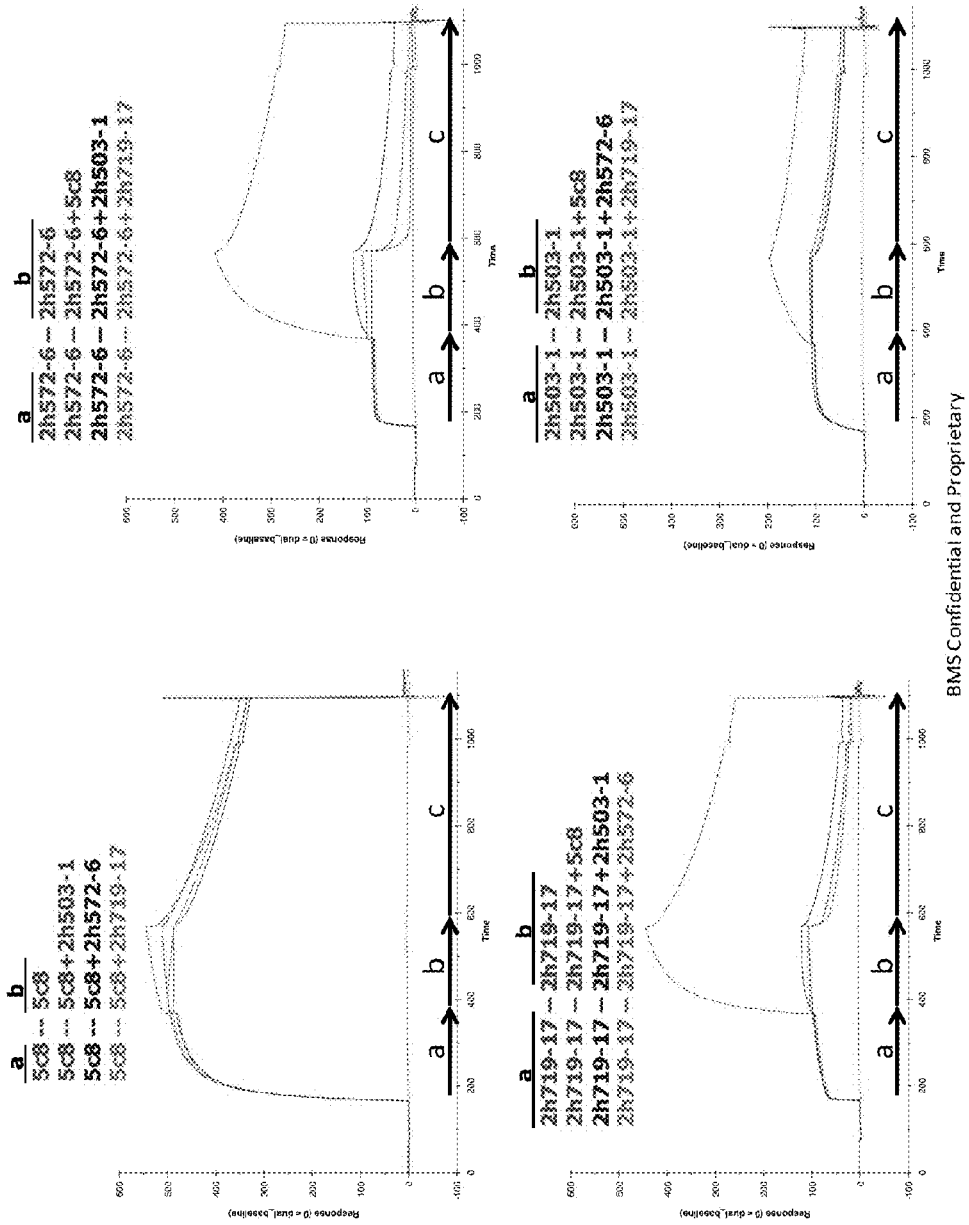
FIG. 25 shows SPR sensorgram data for binding experiments using monovalent dAbs BMS2h-503-1, BMS2h-572-6, BMS2h-719-17, and monovalent Fab fragment of 5c8, where the indicated molecules compete with each other for binding to CD40L (biotinylated IZ-hCD40L).

FIG. 25 shows SPR sensorgram data for experiments designed to test whether or not monovalent dAb molecules BMS2h-503-1, BMS2h-572-6, BMS2h-719-17, and the monovalent anti-CD40L 5c8 Fab fragment compete with each other for binding to CD40L. Experiments were performed using biotinylated CD40L (biot-IZ-hCD40L) that was captured on a streptavidin sensor chip surface. The tests involved the sequential injection of a specified molecule (phase "a"), immediately followed by injection of the same molecule in the presence of a second specified molecule (phase "b"), followed by dissociation (phase "c"). Competition for binding is identified as a reduction (blocking) of the binding signal for the second molecule in the presence of the first, with the level of blocking being governed by the association and dissociation kinetics of each molecule. For each pair of molecules tested, the binding of the second molecule was shown to be reduced when the first molecule was present. These result suggest that BMS2h-503-1, BMS2h-572-6, BMS2h-719-17, and 5c8 Fab compete with each other for binding to biot-IZ-hCD40L.

Figure 26:
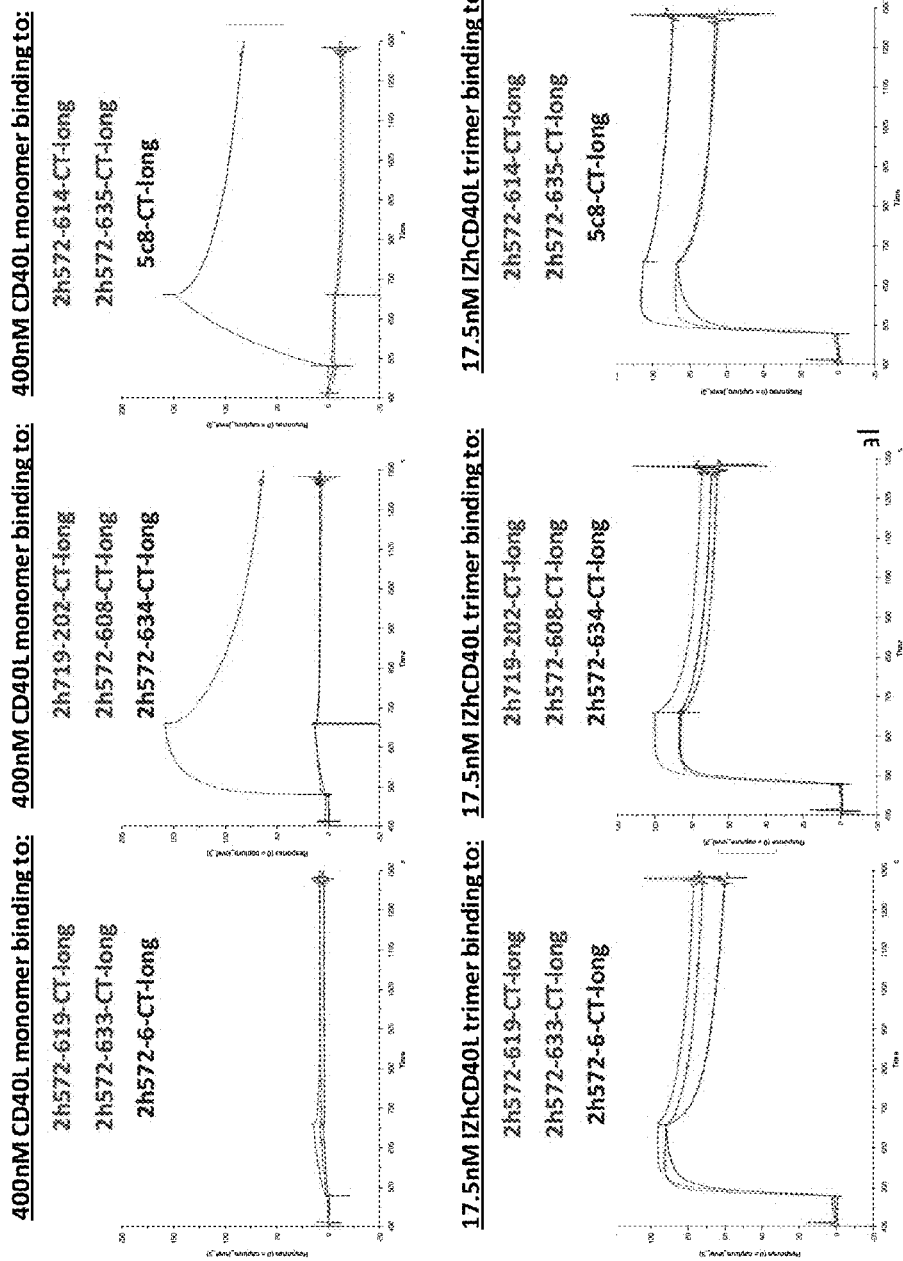
FIG. 26 shows SPR sensorgram data for experiments testing the binding of BMS2h-572-619-CT-long, BMS2h-572-633-CT-long, BMS2h-572-6-CT-long, BMS2h-719-202-CT-long, BMS2h-572-608-CT-long, BMS2h-572-634-CT-long, BMS2h-572-614-CT-long, BMS2h-572-635-CT-long, and 5c8-CT-long molecules to either CD40L monomer (upper 3 panels) or CD40L trimer (lower 3 panels).

FIG. 26 shows SPR sensorgram data for binding of the indicated dAb-CT-long and the 5c8-CT-long molecules to either human CD40L monomer (triple CD40L mutant (T211E, S222Y, H224K, [108-261])) or to CD40L trimer (IZ-hCD40L). The dAb-CT-long and the 5c8-CT-long molecules were captured via their "CT-long" Fc-domain on an immobilized anti-human IgG Fc (Biacore, GE Healthcare) antibody sensor chip surface. The data in the top 3 panels show that human CD40L monomer binds specifically to BMS2h-719-202-CT-long and 5c8-CT-long, but does not bind to any of the indicated dAb-CT-long molecules that contain dAbs from the BMS2h-572-6 lineage. In contrast, the bottom 3 panels show that CD40L trimer (IZ-hCD40L) binds strongly to all the tested dAb-CT-long molecules from the BMS2h-572-6 lineage, as well as to BMS2h-719-202-CT-long and 5c8-CT-long. These results suggest that the molecules from the BMS2h-572-6xx-CT-long lineage are specific for an epitope that is only present on the CD40L trimer and not present on monomeric human CD40L, whereas BMS2h-719-202-CT-long and 5c8-CT-long bind to an epitope that is present on both the CD40L monomer and trimer.

Although the present embodiments have been described in detail with reference to examples above, it is understood that various modifications can be made without departing from the spirit of these embodiments, and would be readily known to the skilled artisan.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09765150B2). An electronic copy of the "Sequence Listing" will also be available from the USPTO upon request and payment of the fee set forth in 37 CFR 1.19(b)(3).

What is claimed is:

1. An isolated antibody polypeptide comprising a first variable domain that specifically binds human CD40L, wherein CD40L comprises the amino acid sequence of SEQ ID NO: 1, wherein the first variable domain comprises
   (a) a CDR1 region having a sequence Trp-$X_1$-Leu-Met-Gly (SEQ ID NO: 2), wherein $X_1$ is Glu or Gln,
   (b) a CDR2 region having a sequence Gly-Ile-Glu-Gly-Pro-Gly-Asp-Val-Thr-Tyr-Tyr-Ala-Asp-Ser-Val-Lys-Gly (SEQ ID NO: 3), and
   (c) a CDR3 region having a sequence Lys-$X_2$-$Y_2$-$Z_2$-Ser-Asp-Tyr (SEQ ID NO: 4), wherein $X_2$ is Asp or Glu, $Y_2$ is Ala or Ser, and $Z_2$ is Lys, Asn, or Arg.

2. The antibody polypeptide of claim 1, wherein the first variable domain comprises the amino acid sequence of:
BMS2h-572-10 (SEQ ID NO: 225), BMS2h-572-11 (SEQ ID NO: 226), BMS2h-572-12 (SEQ ID NO: 227), BMS2h-572-14 (SEQ ID NO: 229), BMS2h-572-15 (SEQ ID NO: 230), BMS2h-572-22 (SEQ ID NO: 237), BMS2h-572-23 (SEQ ID NO: 238), BMS2h-572-6 (SEQ ID NO: 243), BMS2h-572-604 (SEQ ID NO: 247), BMS2h-572-607 (SEQ ID NO: 250), BMS2h-572-608 (SEQ ID NO: 251), BMS2h-572-609 (SEQ ID NO: 252), BMS2h-572-610 (SEQ ID NO: 253), BMS2h-572-611 (SEQ ID NO: 254), BMS2h-572-612 (SEQ ID NO: 255), BMS2h-572-613 (SEQ ID NO: 256), BMS2h-572-614 (SEQ ID NO: 257), BMS2h-572-616 (SEQ ID NO: 259), BMS2h-572-619 (SEQ ID NO: 262), BMS2h-572-630 (SEQ ID NO: 271), BMS2h-572-631 (SEQ ID NO: 272), BMS2h-572-632 (SEQ ID NO: 273), BMS2h-572-633 (SEQ ID NO: 274), BMS2h-572-634 (SEQ ID NO: 275), BMS2h-572-635 (SEQ ID NO: 276), BMS2h-572-8 (SEQ ID NO: 278), or BMS2h-572-9 (SEQ ID NO: 279).

3. The antibody polypeptide of claim 1, wherein the first variable domain comprises the amino acid sequence of BMS2h-572-633 (SEQ ID NO: 274).

4. The antibody polypeptide of claim 1, wherein the antibody polypeptide is a domain antibody (dAb).

5. The antibody polypeptide of claim 1, wherein the antibody polypeptide is a fusion polypeptide comprising the first variable domain and an Fc domain.

6. The antibody polypeptide of claim 5, wherein the fusion polypeptide comprises an IgG4 Fc domain.

7. The antibody polypeptide of claim 5, wherein the fusion polypeptide comprises an IgG1 Fc domain.

8. The antibody polypeptide of claim 5, wherein the fusion polypeptide comprises a CT-Long domain (amino acids 139 to 370 of SEQ ID NO: 1362).

9. The antibody polypeptide of claim 5, wherein the fusion polypeptide comprises a CT-short domain (amino acids 138 to 362 of SEQ ID NO: 1363).

10. The antibody polypeptide of claim 5, wherein the fusion polypeptide comprises a N297Q Long Fc domain (amino acids 139 to 370 of SEQ ID NO: 1364).

11. The antibody polypeptide of claim 5, wherein the fusion polypeptide comprises a N297Q Short Fc domain (amino acids 138 to 362 of SEQ ID NO: 1365).

12. The antibody polypeptide of claim 1, wherein the antibody polypeptide further comprises a second variable domain that specifically binds a second antigen, wherein the second antigen is an antigen other than human CD40L.

13. The antibody polypeptide of claim 12, wherein the second antigen is a cluster of differentiation (CD) molecule or a Major Histocompatibility Complex (MHC) Class II molecule.

14. The antibody polypeptide of claim 12, wherein the second antigen is serum albumin (SA).

15. A pharmaceutical composition comprising a therapeutically-effective amount of the antibody polypeptide of claim 1 and a pharmaceutically acceptable carrier.

16. The pharmaceutical composition of claim 15, further comprising an immunosuppressive/immunomodulatory and/or anti-inflammatory agent.

17. A method of antagonizing CD40L activity in a patient with an immune disease in need of such treatment, comprising administering to the patient a therapeutically effective amount of the pharmaceutical composition of claim 15.

18. The method of claim 17, wherein the isolated antibody polypeptide is administered in combination with an immunosuppressive/immunomodulatory and/or anti-inflammatory agent.

19. The method of claim 17, wherein the immune disease is an autoimmune disease or a graft-related disease.

20. The method of claim 17, wherein the immune disease is a graft-related disease.

21. The method of claim 20, wherein the graft-related disease comprises solid organ, tissue and/or cell transplant rejection.

22. The method of claim 20, wherein the graft-related disease is graft versus host disease (GVHD).

23. The method of claim 20, wherein the graft-related disease is an acute transplant rejection.

24. The method of claim 20, wherein the graft-related disease is a chronic transplant rejection.

25. The method of claim 20, wherein the isolated antibody polypeptide is co-administered with a CTLA4 mutant molecule.

26. The method of claim 25, wherein the CTLA4 mutant molecule is L104EA29Y-Ig (belatacept).

27. The method of claim 17, wherein the immune disease is selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, AIDS, atopic allergy, bronchial asthma, eczema, leprosy, schizophrenia, inherited depression, chronic fatigue syndrome, Alzheimer's disease, Parkinson's disease, myocardial infarction, stroke, autism, epilepsy, Arthus's phenomenon, anaphylaxis, alcohol addiction, and drug addiction.

28. The method of claim 17, wherein the immune disease is selected from the group consisting of myasthenia gravis, idiopathic thrombocytopenic purpura, and systemic sclerosis.

29. An isolated antibody polypeptide comprising a first variable domain, wherein said antibody polypeptide specifically binds human CD40L, wherein CD40L comprises the amino acid sequence of SEQ ID NO: 1, wherein the antibody polypeptide competes with the binding of BMS2h-572-633, and wherein the antibody polypeptide inhibits binding of CD40L to CD40 with an EC50 of 100 pM to 100 nM.

30. The isolated antibody polypeptide of claim 29, wherein the first variable domain comprises the amino acid sequence of one of the antibody polypeptides selected from the lineage group consisting of BMS2h-572, BMS2h-719, BMS2h-503, and BMS2h-116.

31. The isolated antibody polypeptide of claim 30, wherein the first variable domain comprises an amino acid sequence at least 95% identical to BMS2h-572-6, BMS2h-572-608, BMS2h-572-614, BMS2h-572-619, BMS2h-572-633, BMS2h-572-634, BMS2h-572-635, BMS2h-719-2, BMS2h-719-202, BMS2h-719-203, BMS2h-719-213, BMS2h-719-214, BMS2h-719-215, BMS2h-719-218, BMS2h-719-225, BMS2h-503-1, BMS2h-503-2, BMS2h-116-1312, BMS2h-116-1313, or BMS2h-116-1320.

32. The isolated antibody polypeptide of claim 31, wherein the first variable domain comprises the amino acid sequence of BMS2h-572-6, BMS2h-572-608, BMS2h-572-614, BMS2h-572-619, BMS2h-572-633, BMS2h-572-634, BMS2h-572-635, BMS2h-719-2, BMS2h-719-202, BMS2h-719-203, BMS2h-719-213, BMS2h-719-214, BMS2h-719-215, BMS2h-719-218, BMS2h-719-225, BMS2h-503-1, BMS2h-503-2, BMS2h-116-1312, BMS2h-116-1313, or BMS2h-116-1320.

33. The antibody polypeptide of claim 5, wherein the amino acid sequence of the fusion polypeptide is set forth in SEQ ID NO: 1355.

34. The antibody polypeptide of claim 5, wherein the fusion polypeptide comprises the first variable domain consisting of the amino acid sequence of BMS2h-572-633 (SEQ ID NO: 274) and an Fc domain consisting of the amino acid sequence of amino acids 139 to 370 of SEQ ID NO: 1362.

35. The antibody polypeptide of claim 34, wherein the first variable domain and the Fc domain are linked by an amino acid sequence selected from the group consisting of: AS, AST, TVAAPS (SEQ ID NO: 13), TVA, ASTSGPS (SEQ ID NO: 14) and (GGGGS)$_n$ (SEQ ID NO: 12) wherein n is 1, 2, 3, 4, or 5.

36. The pharmaceutical composition of claim 15, comprising the antibody polypeptide of claim 34.

37. The pharmaceutical composition of claim 15, comprising the antibody polypeptide of claim 35.

\* \* \* \* \*